(12) United States Patent
Altman et al.

(10) Patent No.: US 9,545,369 B2
(45) Date of Patent: *Jan. 17, 2017

(54) STABLE SILK PROTEIN FRAGMENT COMPOSITIONS

(71) Applicant: Silk Therapeutics, Inc., Medford, MA (US)

(72) Inventors: Gregory H. Altman, Arlington, MA (US); Rebecca L. Horan, Arlington, MA (US); Rachel Lee Dow, Medford, MA (US); Rachel M. Lind, Somers, NY (US); Dylan S. Haas, Yorktown Heights, NY (US)

(73) Assignee: Silk Therapeutics, Inc., Medford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/877,907

(22) Filed: Oct. 7, 2015

(65) Prior Publication Data

US 2016/0022563 A1    Jan. 28, 2016

Related U.S. Application Data

(63) Continuation of application No. 14/503,021, filed on Sep. 30, 2014, now Pat. No. 9,187,538.

(60) Provisional application No. 61/884,820, filed on Sep. 30, 2013, provisional application No. 62/000,928, filed on May 20, 2014, provisional application No. 62/036,450, filed on Aug. 12, 2014.

(51) Int. Cl.

| | | |
|---|---|---|
| A61K 9/08 | (2006.01) |
| A61K 8/02 | (2006.01) |
| A61K 38/01 | (2006.01) |
| A61K 8/64 | (2006.01) |
| C07K 1/12 | (2006.01) |
| C07K 14/435 | (2006.01) |
| A61K 38/00 | (2006.01) |
| A61K 8/98 | (2006.01) |
| A61K 8/27 | (2006.01) |
| A61K 8/29 | (2006.01) |
| A61K 8/67 | (2006.01) |
| A61K 8/73 | (2006.01) |
| A61K 8/97 | (2006.01) |
| A61Q 17/04 | (2006.01) |
| A61Q 19/00 | (2006.01) |
| A61Q 19/08 | (2006.01) |
| A45D 33/00 | (2006.01) |
| A61Q 19/02 | (2006.01) |
| A61K 8/92 | (2006.01) |
| A61K 8/04 | (2006.01) |
| A61K 8/19 | (2006.01) |
| A61K 8/365 | (2006.01) |
| A61K 8/49 | (2006.01) |

(52) U.S. Cl.
CPC ............... *A61K 8/64* (2013.01); *A45D 33/00* (2013.01); *A61K 8/02* (2013.01); *A61K 8/0216* (2013.01); *A61K 8/042* (2013.01); *A61K 8/19* (2013.01); *A61K 8/27* (2013.01); *A61K 8/29* (2013.01); *A61K 8/365* (2013.01); *A61K 8/4953* (2013.01); *A61K 8/676* (2013.01); *A61K 8/735* (2013.01); *A61K 8/922* (2013.01); *A61K 8/97* (2013.01); *A61K 8/987* (2013.01); *A61K 9/08* (2013.01); *A61K 38/00* (2013.01); *A61K 38/012* (2013.01); *A61Q 17/04* (2013.01); *A61Q 19/00* (2013.01); *A61Q 19/007* (2013.01); *A61Q 19/02* (2013.01); *A61Q 19/08* (2013.01); *C07K 1/12* (2013.01); *C07K 14/43586* (2013.01); *A61K 2800/591* (2013.01); *A61K 2800/72* (2013.01); *A61K 2800/74* (2013.01); *A61K 2800/75* (2013.01)

(58) Field of Classification Search
None
See application file for complete search history.

(56) References Cited

U.S. PATENT DOCUMENTS

| 26,501 A | 12/1859 | Kendrick et al. |
|---|---|---|
| 64,499 A | 5/1867 | Daubert |
| 445,875 A | 2/1891 | Brickell |
| 687,221 A | 11/1901 | Gaff et al. |
| 5,902,932 A | 5/1999 | Bills et al. |
| 6,432,910 B2 * | 8/2002 | Nakagawa ............ A61L 15/50 428/96 |
| 7,632,873 B2 | 12/2009 | Mougin |

(Continued)

FOREIGN PATENT DOCUMENTS

| WO | 2012/145739 | 10/2012 |
|---|---|---|
| WO | 2014/011644 | 1/2014 |
| WO | 2014/145002 | 9/2014 |

OTHER PUBLICATIONS

Wang, Q., et al. Biomacromolecules (2012), 14; pp. 285-289.*

(Continued)

*Primary Examiner* — Kevin S Orwig
(74) *Attorney, Agent, or Firm* — Morgan Lewis & Bockius LLP

(57) ABSTRACT

A composition is disclosed that includes pure silk fibroin-based protein fragments that are substantially devoid of sericin, wherein the composition has an average weight average molecular weight ranging from about 17 kDa to about 38 kDa, wherein the composition has a polydispersity of between about 1.5 and about 3.0, wherein the composition is substantially homogeneous, wherein the composition between 0 ppm to about 500 ppm of inorganic residuals, and wherein the composition includes between 0 ppm to about 500 ppm of organic residuals.

15 Claims, 105 Drawing Sheets

(56) References Cited

U.S. PATENT DOCUMENTS

| | | | |
|---|---|---|---|
| 7,635,755 B2 | 12/2009 | Kaplan et al. | |
| 7,674,882 B2 | 3/2010 | Kaplan et al. | |
| 7,727,542 B2 | 6/2010 | DiBenedetto et al. | |
| 8,071,722 B2 | 12/2011 | Kaplan et al. | |
| 8,187,616 B2 | 5/2012 | Wang et al. | |
| 8,288,347 B2 | 10/2012 | Collette et al. | |
| 8,420,077 B2 | 4/2013 | Altman et al. | |
| 8,501,172 B2 | 8/2013 | Kaplan et al. | |
| 8,551,538 B2 | 10/2013 | Qian | |
| 8,614,293 B2 | 12/2013 | Kaplan et al. | |
| 8,623,398 B2 | 1/2014 | Altman et al. | |
| 8,628,791 B2 | 1/2014 | Altman et al. | |
| 8,633,027 B2 | 1/2014 | Altman et al. | |
| 8,685,426 B2 | 4/2014 | Altman et al. | |
| 8,715,740 B2 | 5/2014 | Wang et al. | |
| 8,741,281 B2 | 6/2014 | Van Epps et al. | |
| 8,894,992 B2 | 11/2014 | Van Epps et al. | |
| 8,900,571 B2 | 12/2014 | Van Epps et al. | |
| 8,926,963 B2 | 1/2015 | Van Epps et al. | |
| 2001/0051815 A1 | 12/2001 | Esplin | |
| 2002/0077629 A1 | 6/2002 | Hoffman et al. | |
| 2002/0082220 A1 | 6/2002 | Hoemann et al. | |
| 2002/0111591 A1 | 8/2002 | Mckinnon et al. | |
| 2003/0099630 A1* | 5/2003 | DiBenedetto | A61L 24/0084 424/94.64 |
| 2003/0139752 A1 | 7/2003 | Pasricha et al. | |
| 2003/0206897 A1 | 11/2003 | O'Prey et al. | |
| 2003/0208209 A1 | 11/2003 | Gambale et al. | |
| 2003/0220646 A1 | 11/2003 | Thelen et al. | |
| 2003/0229361 A1 | 12/2003 | Jackson | |
| 2003/0236555 A1 | 12/2003 | Thornes | |
| 2004/0073176 A1 | 4/2004 | Utterberg | |
| 2004/0127907 A1 | 7/2004 | Dakin et al. | |
| 2004/0191199 A1 | 9/2004 | Mougin | |
| 2004/0219630 A1 | 11/2004 | Tsubouchi | |
| 2004/0224406 A1* | 11/2004 | Altman | A61F 2/08 435/395 |
| 2004/0265260 A1 | 12/2004 | Tsubouchi et al. | |
| 2004/0267317 A1 | 12/2004 | Higgins et al. | |
| 2005/0004670 A1 | 1/2005 | Gebhardt et al. | |
| 2005/0021148 A1 | 1/2005 | Gibbs | |
| 2005/0049598 A1 | 3/2005 | West, Jr. et al. | |
| 2005/0090827 A1 | 4/2005 | Gedebou | |
| 2005/0107882 A1 | 5/2005 | Stone et al. | |
| 2005/0130301 A1 | 6/2005 | Mckay et al. | |
| 2005/0149118 A1 | 7/2005 | Koyfman et al. | |
| 2005/0171604 A1 | 8/2005 | Michalow | |
| 2005/0177237 A1 | 8/2005 | Shappley et al. | |
| 2005/0192632 A1 | 9/2005 | Geissler et al. | |
| 2005/0251153 A1 | 11/2005 | Sakamoto et al. | |
| 2005/0251209 A1 | 11/2005 | Saadat et al. | |
| 2005/0261642 A1 | 11/2005 | Weston | |
| 2006/0004364 A1 | 1/2006 | Green et al. | |
| 2006/0178743 A1 | 8/2006 | Carter | |
| 2006/0195106 A1 | 8/2006 | Jones et al. | |
| 2006/0229623 A1 | 10/2006 | Bonutti et al. | |
| 2006/0229676 A1 | 10/2006 | Doll et al. | |
| 2006/0241776 A1 | 10/2006 | Brown et al. | |
| 2006/0241781 A1 | 10/2006 | Brown et al. | |
| 2009/0234026 A1 | 9/2009 | Kaplan et al. | |
| 2011/0076384 A1 | 3/2011 | Cannizzaro et al. | |
| 2011/0105402 A1 | 5/2011 | Kim et al. | |
| 2011/0223153 A1 | 9/2011 | Lu et al. | |
| 2012/0070427 A1 | 3/2012 | Kaplan et al. | |
| 2012/0076771 A1 | 3/2012 | Vepari et al. | |
| 2012/0123519 A1 | 5/2012 | Lovett et al. | |
| 2012/0187591 A1* | 7/2012 | Wang | A61K 9/5169 264/9 |
| 2012/0244143 A1 | 9/2012 | Lo et al. | |
| 2013/0045278 A1 | 2/2013 | Qian | |
| 2013/0165004 A1 | 6/2013 | Kaplan et al. | |
| 2013/0240251 A1 | 9/2013 | Kaplan et al. | |
| 2013/0287742 A1 | 10/2013 | Kaplan et al. | |
| 2014/0134240 A1 | 5/2014 | Kaplan et al. | |
| 2015/0038043 A1 | 2/2015 | Kaplan et al. | |
| 2015/0056293 A1 | 2/2015 | Wang et al. | |

OTHER PUBLICATIONS

Gilbert et al., "Dispersity in Polymer Science", Pure Appl. Chem., 2009, 81(2), pp. 351-353.

Cetinkaya et al., "Silk Fiber Mechanics from Multiscale Force Distribution Analysis", Biophysical Journal, Mar. 2011, 100(5), pp. 1298-1305.

Cho et al., "Molecular Weight Distribution and Solution Properties of Silk Fibroins with Different Dissolution Conditions", International Journal of Biological Macromolecules, Jun. 2012, 51, pp. 336-341.

Fan et al., "Vitamin C-reinforcing Silk Fibroin Nanofibrous Matrices for Skin Care Application", RSC Advances, Mar. 2, 2012, pp. 4110-4119.

Hardy et al., "Polymeric Materials Based on Silk Proteins", Polymer, Aug. 2008, 49(20), pp. 4309-4327.

Hoffman et al., "Silk Fibroin as an Organic Polymer for Controlled Drug Delivery", Journal of Controlled Release, Mar. 2006, 111(1-2), pp. 219-227.

Hyde et al., "Molecular Weight of Silk Fibroin", Journal of Polymer Science, Apr. 1962, 58(166), pp. 1083-1088.

Motta et al., "Stabilization of Bombyx mori Silk Fibroin/Sericin Films by Crosslinking with PEG-DE 600 and Genipin", Journal of Bioactive and Compatible Polymers, Mar. 2011, 26(2), pp. 130-143.

Pandit et al., "Studies on Silk Fibroin I. Molecular Weight, Sedimentation Coefficient, Viscosity and Optical Rotation of Bilk Fibroin from Carbonate-Extracted Silk Fiber", Archives of Biochemistry and Biophysica, 149, Dec. 1972, pp. 259-268.

Paula's Choice, "Jar Packaging: A Waste of Good Antioxidants & Money", http://www.paulaschoice.com/expert-advice/skin-care-basics/_jar-packaging, Aug. 28, 2013, 3 pages.

Preda et al., "Bioengineered Silk Proteins to Control Cell and Tissue Functions" Protein Nanotechnology: Protocols, Instrumentation, and Applications, Methods in Molecular Biology, 2013, 996, Chapter 2, pp. 19-41.

Rockwood et al., "Materials Fabrication from Bombyx Mod Silk Fibroin", Nature Protocols, Sep. 2011, 6(10), pp. 1612-1631.

Bah et al., "Regenerated Silk Fibroin from B. mori Silk Cocoon for Tissue Engineering Applications", International Journal of Environmental Science and Development, Dec. 2010, 1(5), pp. 404-408.

Sielc, "Separation of Potassium", http://www.sielc.com/compound-potassium.html, Aug. 27, 2013, 5 pages.

Nang et al., "Design and Engineering of Silk Fibroin Scaffolds with Biomimetic Hierarchal Structures", Chemical communications, 2013, 49, pp. 1431-1433.

Nang et al., "Effect of Various Dissolution Systems on the Molecular Weight of Regenerated Silk Fibroin", BioMacromolecules, Dec. 2012, 14(1), pp. 285-289.

Wang et al., "Stabilization of Vaccines and Antibiotics in Silk and Eliminating the Cold Chain", PNAS, Jul. 2012, 109 (30), pp. 11981-11986.

Fournier, "Quantitative Data on the Bombym mori L. Silkworm: A Reivew", Biochimie, Feb. 1979, 61(2), pp. 283-320.

Wray et al., "Effect of Processing on Silk-Based Biomaterials: Reproducibility and Biocompatibility", Journal of Biomedical Materials Research Part: Applied Biomaterials, Oct. 2011, 99(1), pp. 89-101 (author manuscript).

International Patent Application No. PCT/US14/58462, International Search Report, dated Mar. 2, 2015, 4 pages.

* cited by examiner

| Time Point | Sericin was extracted at 100° C, 30 min | Sericin was extracted at 100° C, 60 min | Sericin was extracted at 90° C, 30 min | Sericin was extracted at 90° C, 60 min |
|---|---|---|---|---|
| 4 Hours | Some undissolved silk | Some undissolved silk | Significant amount of undissolved silk | Significant amount of undissolved silk |

Fig. 5A    Fig. 5B    Fig. 5C    Fig. 5D

| Time Point | Sericin was extracted at 100° C, 30 min | Sericin was extracted at 100° C, 60 min | Sericin was extracted at 90° C, 30 min | Sericin was extracted at 90° C, 60 min |
|---|---|---|---|---|
| 8 Hours | Small amount of undissolved silk | Little to no undissolved silk | Significant amount of undissolved silk | Some undissolved silk |

Fig. 7A  Fig. 7B  Fig. 7C  Fig. 7D

| Time Point | Sericin was extracted at 100° C, 30 min | Sericin was extracted at 100° C, 60 min | Sericin was extracted at 90° C, 30 min | Sericin was extracted at 90° C, 60 min |
|---|---|---|---|---|
| 4 Hours | Some undissolved silk | Some undissolved silk | Significant amount of undissolved silk, highly viscous | Some undissolved silk |

Fig. 13A  Fig. 13B  Fig. 13C  Fig. 13D

| Time Point | Sericin was extracted at 100° C, 30 min | Sericin was extracted at 100° C, 60 min | Sericin was extracted at 90° C, 30 min | Sericin was extracted at 90° C, 60 min |
|---|---|---|---|---|
| 1 Hour | Small amount of undissolved silk, some precipitate from bubbles | All silk dissolved, some precipitate from bubbles | Some precipitate from bubbles and undissolved silk | Some precipitate from bubbles and undissolved silk |

Fig. 18A    Fig. 18B    Fig. 18C    Fig. 18D

| Time Point | Sericin was extracted at 100° C, 30 min | Sericin was extracted at 100° C, 60 min | Sericin was extracted at 90° C, 30 min | Sericin was extracted at 90° C, 60 min |
|---|---|---|---|---|
| 6 Hours | Some precipitate from bubbles, no undissolved silk | Clear with no precipitate or silk | Some undissolved silk | Clear and no undissolved silk |

Fig. 20A    Fig. 20B    Fig. 20C    Fig. 20D

| Time Point | Sericin was extracted at 100° C, 30 min | Sericin was extracted at 100° C, 60 min | Sericin was extracted at 90° C, 30 min | Sericin was extracted at 90° C, 60 min |
|---|---|---|---|---|
| 1 Hour | Most silk dissolved, some precipitate from bubbles | Most silk dissolved, some slight precipitate from bubbles | Some precipitate from bubbles and significant amount of undissolved silk | Significant amount of undissolved silk |

Fig. 21A    Fig. 21B    Fig. 21C    Fig. 21D

| Time Point | Sericin was extracted at 100° C, 30 min | Sericin was extracted at 100° C, 60 min | Sericin was extracted at 90° C, 30 min | Sericin was extracted at 90° C, 60 min |
|---|---|---|---|---|
| 6 Hours | Slightly cloudy with silk particles on top | Cloudy with precipitate from bubbles | Highly viscous, cloudy, almost solid | Highly viscous, cloudy, almost solid |

Fig. 23A  Fig. 23B  Fig. 23C  Fig. 23D

| Time Point | Sericin was extracted at 100° C, 30 min | Sericin was extracted at 100° C, 60 min | Sericin was extracted at 90° C, 30 min | Sericin was extracted at 90° C, 60 min |
|---|---|---|---|---|
| 1 Hour | Somewhat cloudy with darker color, some silk particles | Completely clear with dark color, slight amount of silk particles | Cloudy, some undissolved silk, highly viscous | Small amount of undissolved silk, partially cloudy, darker color |

Fig. 27A  Fig. 27B  Fig. 27C  Fig. 27D

| Time Point | Sericin was extracted at 100°C, 30 min | Sericin was extracted at 100°C, 60 min | Sericin was extracted at 90°C, 30 min | Sericin was extracted at 90°C, 60 min |
|---|---|---|---|---|
| 4 Hours | Small amount of undissolved silk, highly cloudy | Little to no undissolved silk, deep auburn color | Some undissolved silk, highly cloudy | Slight amount of silk particles, dark color, less viscous |

Fig. 28A  Fig. 28B  Fig. 28C  Fig. 28D

| Time Point | Sericin was extracted at 100° C 30 min | Sericin was extracted at 100° C 60 min | Sericin was extracted at 90° C 30 min | Sericin was extracted at 90° C 60 min |
|---|---|---|---|---|
| 6 Hours | All silk dissolved, cloudy | All silk dissolved, clear | All silk dissolved, cloudy | All silk dissolved, only slightly cloudy |

Fig. 32A  Fig. 32B  Fig. 32C  Fig. 32D

Methods for Silk Film Drying Study

- Diluted silk solution to 2% (m/v%) silk concentration
- Vitamin C added in 5:1 silk:vitC ratio

Film Casting

- Cast 15 samples for each set with 1.85 mL of solution pipetted onto a 1" diameter silicone mold
- Films were cast in drying location and were not moved until testing

Observations and Testing

- Films were observed and massed at 1, 2, 3, 4, 5, 6, 7, 8, 12, 24, and 48 hours after casting
- Tested 5 films from each set at 1, 8, and 48 hours after casting
- Testing procedure consisted of massing, photographing and dissolution of films

Fig. 34

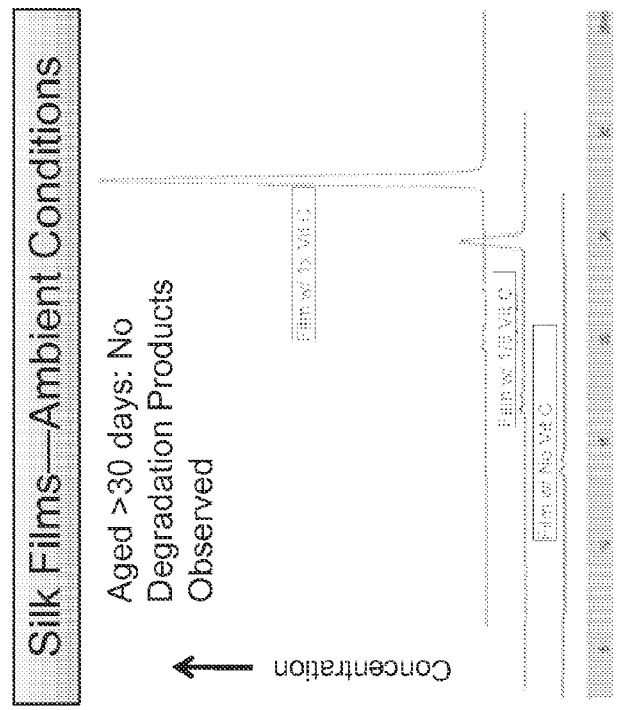
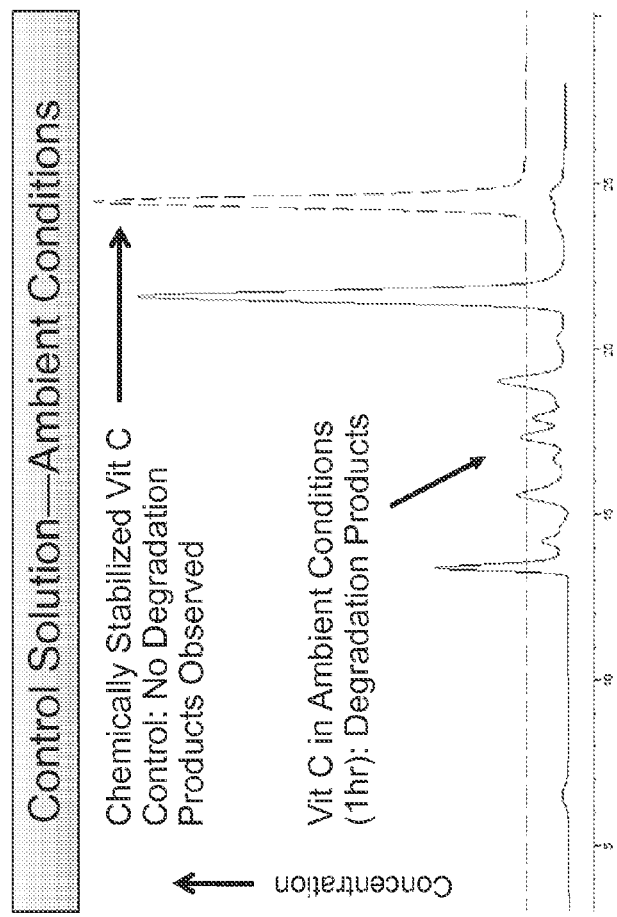
Fig. 36B
Fig. 36A

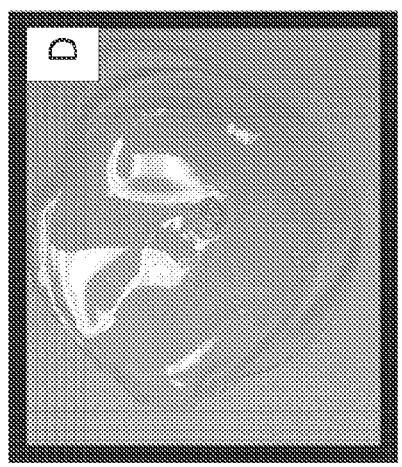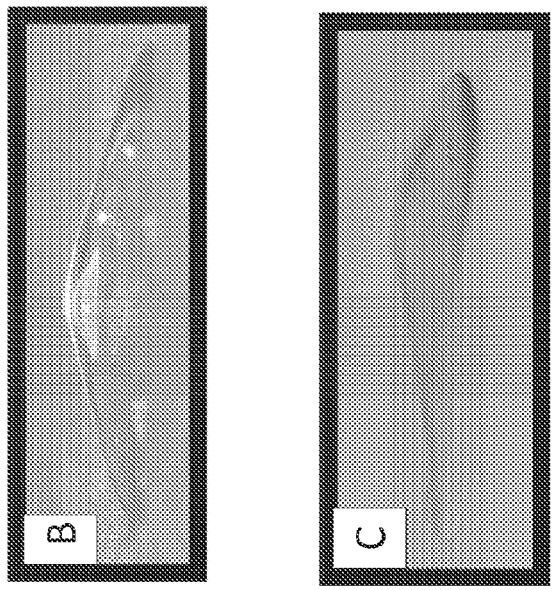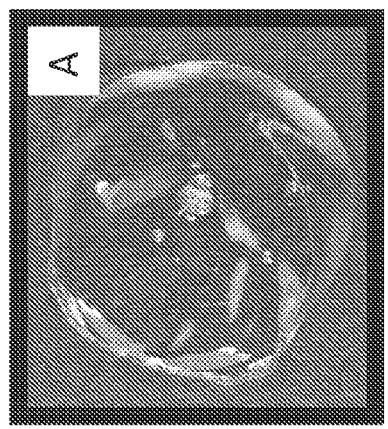
Figs. 40A-40D

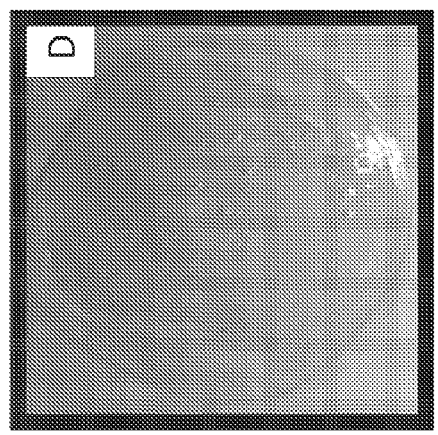
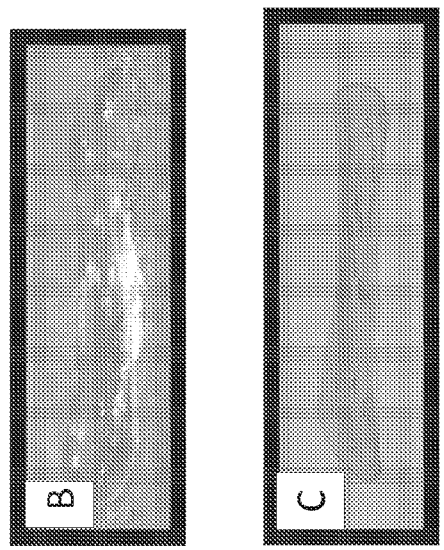
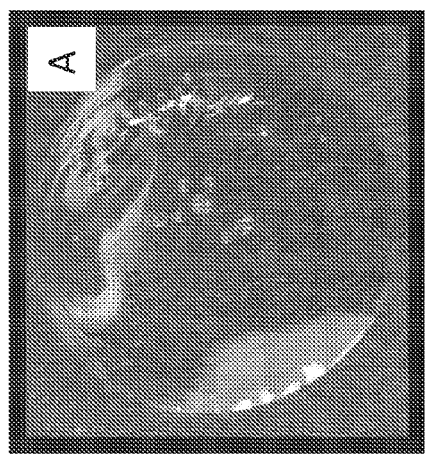
Figs. 42A-42D

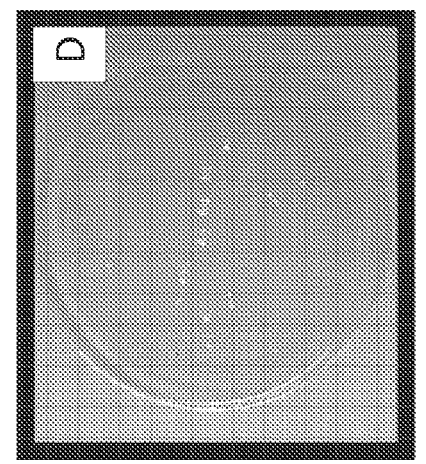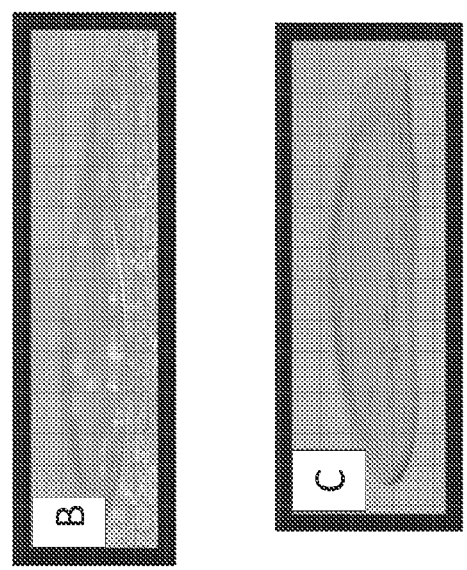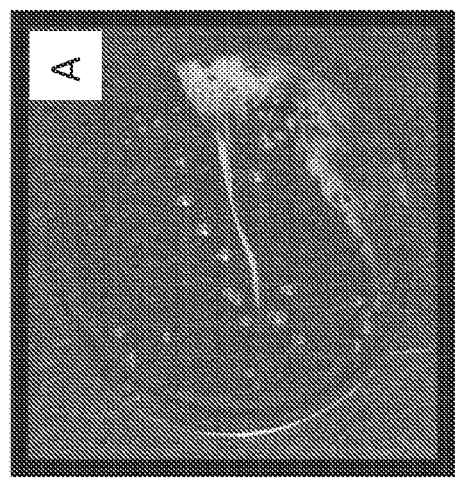
Figs. 44A-44D

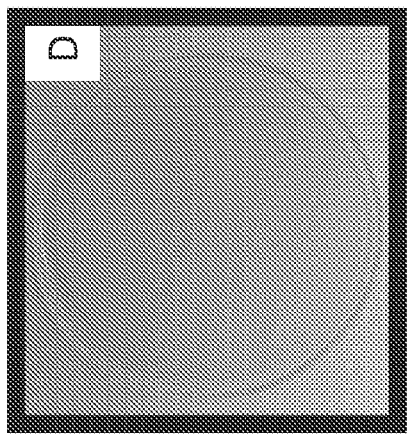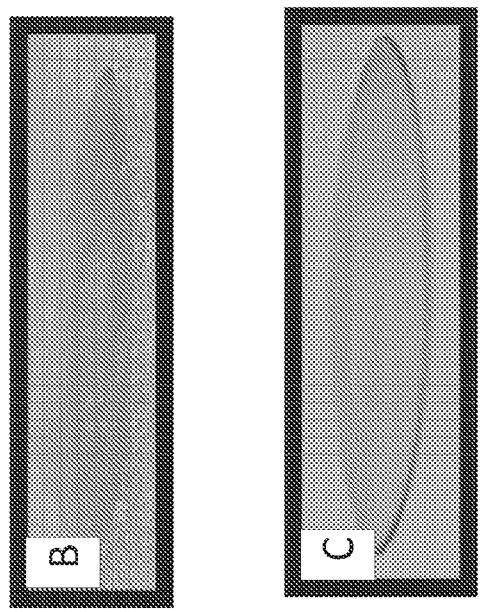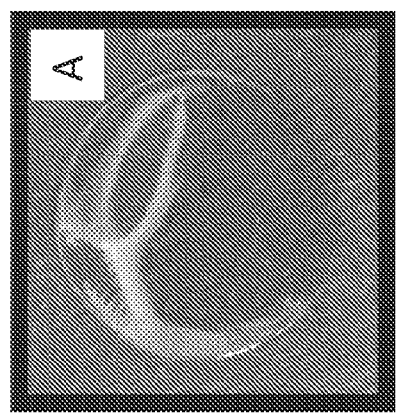
Figs. 45A-45D

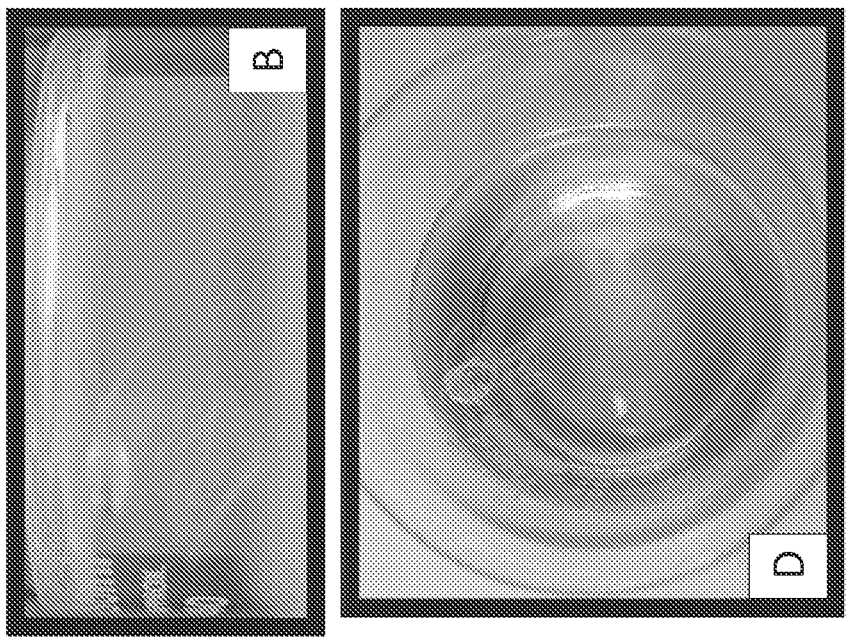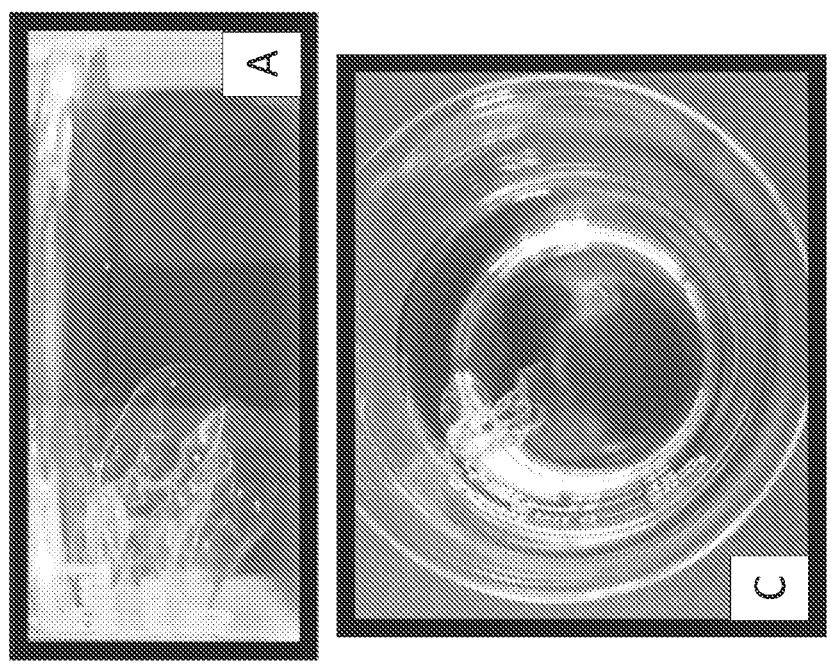
Figs. 50A-50D

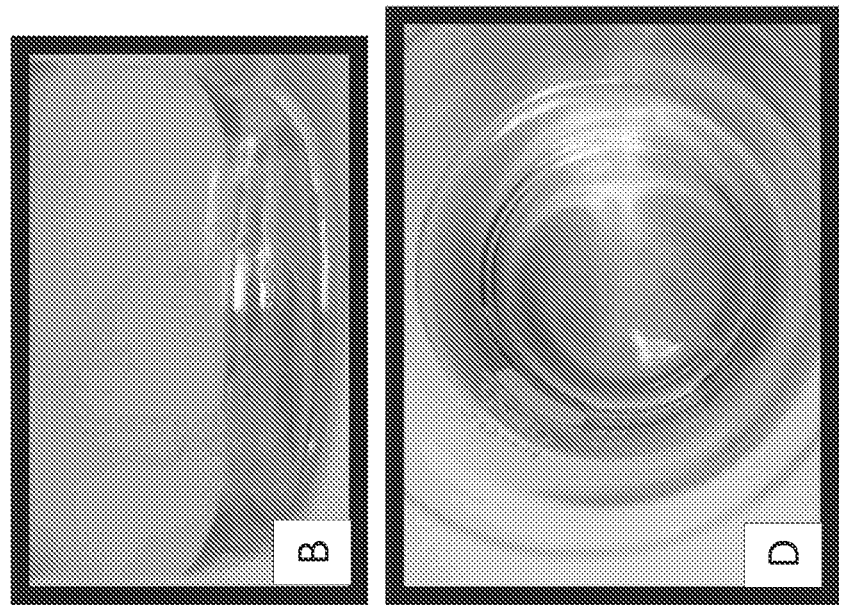
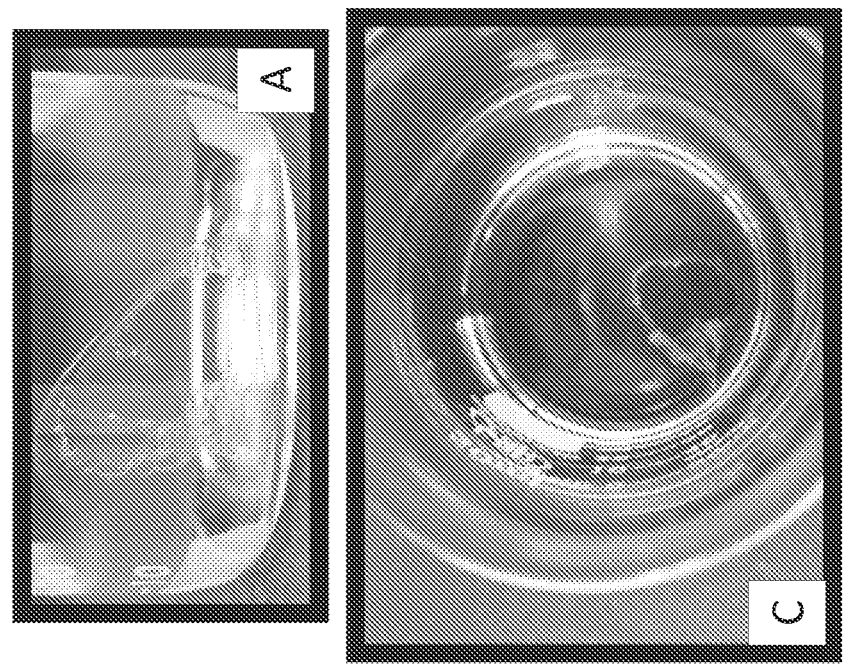
Figs. 53A-53D

Lithium Bromide and Sodium Carbonate Concentration in Silk Protein Solution

| Sample ID | Sample Description | Average Concentration of Na2CO3 (ppm) | Average Concentration of LiBr (ppm) |
|---|---|---|---|
| A | TFF 5kDa | 32.13 | 90.85 |
| B | TFF 10 kDa | 42.91 | 107 |
| C | TFF 10 kDa | 49.06 | 78.55 |
| D | STI 1(TFF-10-0019) | 2.17 | 129.07 |
| E | STI 2(TFF-10-0033) | 2.63 | 196.2 |
| F | STI 3(TFF-10-0034) | 4.18 | 248.93 |

Method: 100C extraction for 60 min, 60C rinse, 100C LiBr in 100C oven for 60 min. Note that TFF could be run for longer and/or at different flow rates (as varied between A-C and D-F) to alter ppm of Na2CO3 and LiBr.

Fig. 55

Sodium Carbonate in Silk Protein Formulations

| Sample ID | Details | Sample Weight (mg) | Conc. of Na$_2$CO$_3$ in Original Film | Std. Dev | Error % |
|---|---|---|---|---|---|
| | | | Average (mg/Film) | | |
| A | Blank Film | ND | NA | NA | NA |
| B | 1:1 film | 30.1 | 0.0141 | 0.0008 | 5.55% |
| C | 5:1 film | 17.3 | 0.0127 | 0.0006 | 4.69% |

Method: 100C extraction for 20 min, RT rinse, LiBr in 60C oven for 4-6 hours. 2% silk films air dried at RT

Fig. 56

Lithium Bromide in Silk Protein Formulations

| Sample ID | Details | Sample Weight (mg) | Conc. of LiBr in Original Film Average (mg/Film) | Std. Dev | Error % |
|---|---|---|---|---|---|
| A | Blank Film | ND | NA | NA | NA |
| B | 1:1 film | 30.1 | 0.0363 | 0.0042 | 11.47% |
| C | 5:1 film | 17.3 | 0.0259 | 0.0005 | 1.82% |

Method: 100C extraction for 20 min, RT rinse, LiBr in 60C oven for 4-6 hours. 2% silk films air dried at RT

Fig. 57

Lithium Bromide and Sodium Carbonate content in Silk Protein Solution

| Sample ID | Solution Volume Equivalent to (X) Films | Sample Weight (mg) | Concentration Na2CO3 | Concentration LiBr |
|---|---|---|---|---|
| 1 | 6 | 0.171 | ND | ND |
| 2 | 8 | 0.228 | ND | ND |
| 3 | 10 | 0.285 | ND | ND |
| 4 | 12 | 0.342 | ND | ND |
| 5 | Neat | - | ND | ND |

*ND=None Detected

Method: 100C boil for 60 min, 60C rinse, LiBr in 60C oven for 4-6 hours

Fig. 58

Vitamin C in Silk Protein Formulations

| Sample ID | Description (Silk:Vit C) | Sample Weight (mg) | Conc. of Vitamin C Average (mg/Film) | Std. Dev | Error % |
|---|---|---|---|---|---|
| A | Blank Film | 4.2 | 0 | 0 | 0.00% |
| B1 | 1:1 film | 7.8 | 3.0974 | 0.0538 | 1.74% |
| B2 | 1:1 film | 7.7 | 3.2534 | 0.0312 | 0.96% |
| C1 | 5:1 film | 4.9 | 0.6194 | 0.0096 | 1.54% |
| C2 | 5:1 film | 4.9 | 0.6454 | 0.0061 | 0.94% |

Method: 100C extraction for 20 min, RT rinse, LiBr in 60C oven for 4-6 hours. 2% silk films air dried at RT

Fig. 59

Stability of Vitamin C in Solution

| Sample ID | Time (hour) | Actual Conc. (µg/mL) | Area | Concentration Vit C (µg/mL) | Recovered (%) | Stability (%) After 24 hrs. |
|---|---|---|---|---|---|---|
| A | 0 | 82.4 | 4277.9 | 80.53 | 97.73 | |
| B | 26 | 82.4 | 4088.94 | 77.62 | 94.2 | |
| Average = | | | 4183.42 | 79.07 | 95.96 | 96.39 |
| Std. Dev. = | | | 133.62 | 2.06 | 2.49 | |
| % Error | | | 3% | 3% | 3% | |

Method: Vitamin C solution (no silk)

Fig. 60

Molecular Weights of Silk Protein Solutions

| Sample ID | Sample Description | Mn | Mw | Polydispersity (PD) (Mw/Mn) |
|---|---|---|---|---|
| A | TFF 5kDa | 14,497 | 33,874 | 2.3366 |
| B | TFF 10 kDa | 14,542 | 33,455 | 2.3006 |
| C | TFF 10 kDa | 14,972 | 34,026 | 2.2726 |
| D | Silk protein solution in water | 12,055 | 26,531 | 2.2008 |

Method:
TFF: 100C extraction for 60 min, 60C rinse, 100C LiBr in 100C oven for 60 min.
Silk Protein: 100C extraction for 20 min, RT rinse, LiBr in 60C oven for 4-6 hours

Fig. 61

| Sample | LiBr (M) | Avg MW | PD |
|---|---|---|---|
| STI 1(TFF-10-0019) | 9.3 | 15727 | 2.033 |
| STI 2(TFF-10-0033) | 9.3 | 24587 | 2.3669 |
| STI 3(TFF-10-0034) | 9.3 | 25273 | 2.338 |
| STI 9.3 M avg | | 21862 | 2.25 |
| STI 1(TFF-10-0031) | ~7.5 | 29645 | 3.0868 |
| STI 2(TFF-10-0030) | ~7.5 | 26856 | 2.9748 |
| STI 7.5M avg | | 28250.5 | 3.0308 |

* TFF-10-0019 from 2 25g extraction/35g dissolution
* TFF-10-0034 from 100g extraction/ 17-35 g dissolution
* TFF-10-0033 from 100g extraction/ 100 g dissolution

Fig. 63

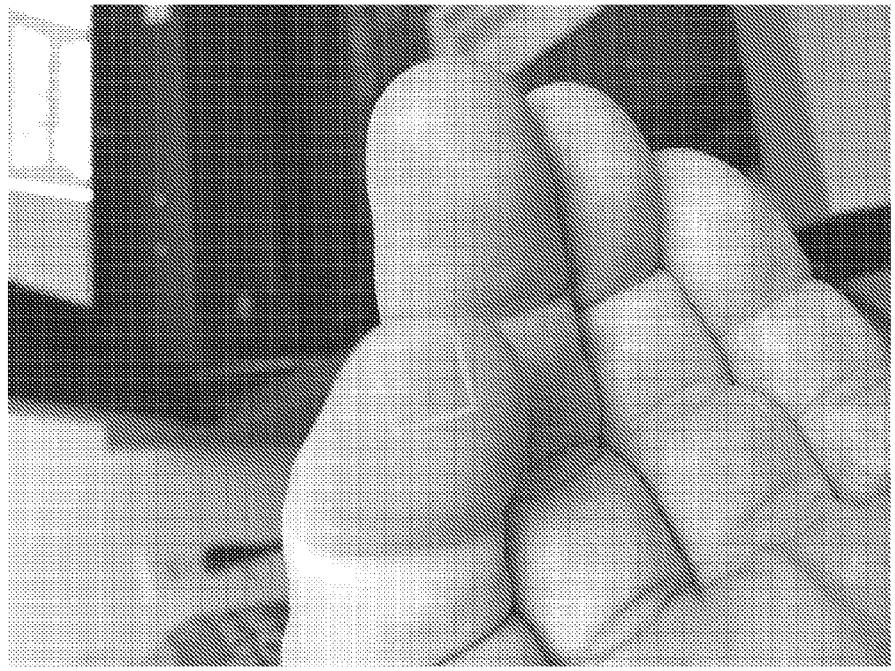
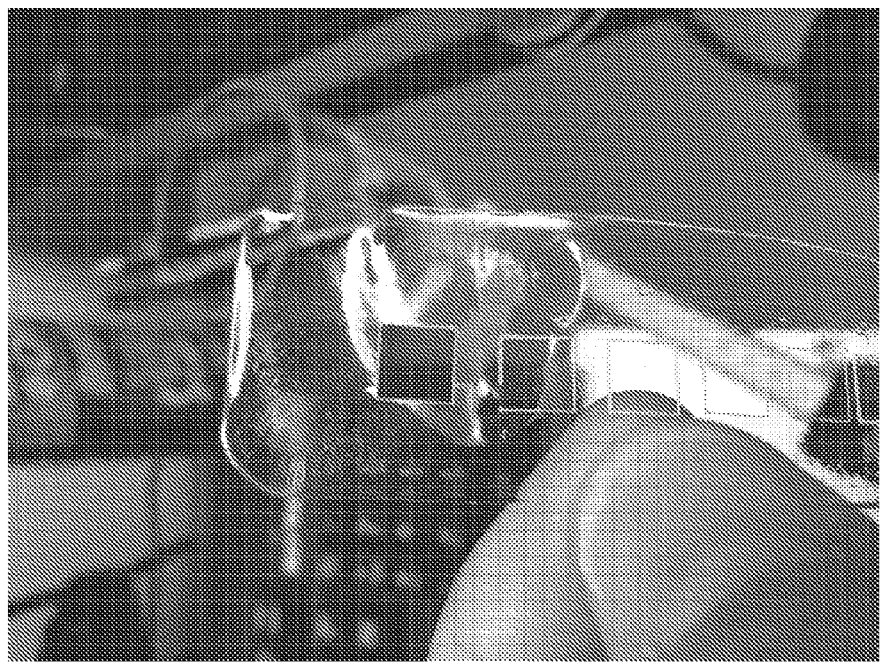
Laser Cutting for Efficiency and Shapes
Fig. 83A
Fig. 83B

- Visible benefits from vitamin C use on the skin are most prevalent after 3-6 months continued use
  - The cells on the skin's surface are replaced by those deep in the dermis approximately once every 28 days
  - Clinical literature has shown vitamin C benefits to be additive with each additional month used as the skin is continually exposed to vitamin C and the cells repeatedly replaced, allowing new collagen to develop and gradually fill fine lines
- Some users saw the initial benefits of their skin feeling better with one month use – longer use will further increase seeing benefits
- User comments:

| After 1 Month Use: | Agree | Not Sure | Disagree |
|---|---|---|---|
| My skin feels better | 63% | 21% | 16% |
| My skin feels firmer | 53% | 34% | 13% |
| My skin looks brighter | 25% | 53% | 22% |
| My skin looks more even | 25% | 47% | 28% |

Fig. 86

Thinking only about the lemongrass gel indicate whether you agree with the following statements about your skin after using it.

Answered: 44  Skipped: 0

| | Agree | Disagree | Not Sure | Total |
|---|---|---|---|---|
| My skin looks brighter. | 25.00% 11 | 13.64% 6 | 61.36% 27 | 44 |
| My skin tone is better. | 34.09% 15 | 15.91% 7 | 50.00% 22 | 44 |
| My skin feels smoother. | 56.82% 25 | 13.64% 6 | 29.55% 13 | 44 |
| My skin feels softer. | 52.27% 23 | 9.09% 4 | 38.64% 17 | 44 |
| My skin feels better. | 50.00% 22 | 13.64% 6 | 36.36% 16 | 44 |
| My skin has improved texture. | 43.18% 19 | 15.91% 7 | 40.91% 18 | 44 |

Fig. 88

| Vitamin C Type | % silk in solution | Solution volume per gel (mL) | Mass of Vitamin C per gel (mg) | % Vitamin C | Other Additive Name | Other Additive Quantity | Notes |
|---|---|---|---|---|---|---|---|
| Sodium Ascorbyl Phosphate (Aromantic) | 2 | 15 | 100 mg | 0.67% | Lemongrass oil | 20 uL | No gelation occurred |
| Sodium Ascorbyl Phosphate (DSM) | 2 | 15 | 100 mg | 0.67% | Lemongrass oil | 20 uL | Gelation at ~28days, normal gel appearance |
| Ascorbyl Tetrapalmitate | 2 | 15 | 100 mg | 0.67% | Lemongrass oil | 20 uL | Ascorbyl Tetrapalmitate is a viscous liquid that did not dissolve, solutions were discarded |
| Ascorbic Acid-2-Glucoside | 2 | 15 | 100 mg | 0.67% | Lemongrass oil | 20 uL | Gelation at 3 days, normal gel appearance |
| l-ascorbic acid and sodium ascorbyl phosphate(DSM) | 2 | 5 | 25 mg l-ascorbic acid, 25 mg sodium ascorbyl phosphate | 1% | Lemongrass oil | 6.67 uL | Gelation in 6 days |

Fig. 89A

| Vitamin C Type | % silk in solution | Solution volume per gel (mL) | Mass of Vitamin C per gel (mg) | % Vitamin C | Other Additive Name | Other Additive Quantity | Notes |
|---|---|---|---|---|---|---|---|
| l-ascorbic acid and ascorbic acid-2-glucoside | 2 | 5 | 500 mg l-ascorbic acid, 500 mg ascorbic acid-2-glucoside | 20% | Lemongrass oil | 6.67 uL | No gelation occurred |
| l-ascorbic acid and magnesium ascorbyl phosphate | 2 | 5 | 25 mg l-ascorbic acid, 25 mg magnesium ascorbyl phosphate | 1% | Lemongrass oil | 6.67 uL | Gelation in 8 days |
| ascorbic acid-2-glucoside and sodium ascorbyl phosphate | 2 | 5 | 25 mg ascorbic acid-2-glucoside, 25 mg sodium ascorbyl phosphate | 1% | Lemongrass oil | 6.67 uL | Gelation in 13 days |
| ascorbic acid-2-glucoside and magnesium ascorbyl phosphate | 2 | 5 | 25 mg ascorbic acid-2-glucoside, 25 mg magnesium ascorbyl phosphate | 1% | Lemongrass oil | 6.67 uL | Gelation in 8 days |
| l-ascorbic acid and ascorbic acid-2-glucoside | 2 | 5 | 25 mg l-ascorbic acid, 25 mg ascorbic acid-2-glucoside | 1% | Lemongrass oil | 6.67 uL | Gelation in 3 days |

Fig. 89B

| Films: | Vitamin C Type | % Silk Solution | Solution per mold | Mold Area | Vitamin C % | Result | Solubility |
|---|---|---|---|---|---|---|---|
| 1 | Sodium Ascorbyl Phosphate (DSM) | 2.2 | 1.56 mL | 5.06 cm^2 | 40 | white/opaque, plastic feel, textured (bumpy) top surface | soluble with insoluble borde, some small insoluble pieces |
| 2 | Magnesium Ascorbyl Phosphate | 2.2 | 1.56 mL | 5.06 cm^2 | 40 | clear/cloudy, plastic feel, textured (rippled) top surface | soluble with insoluble border |
| 3 | Ascorbic Acid-2-Glucoside | 2.2 | 1.56 mL | 5.06 cm^2 | 40 | clear, less pliable than control, subtle textureon top surface | soluble with insoluble border, some small insoluble pieces |
| 4 | L-ascorbic Acid (Control) | 2.2 | 1.56 mL | 5.06 cm^2 | 40 | Clear, pliable, no texture | soluble with insoluble border |

Fig. 90

| % silk in solution | % Vitamin C (l-ascorbic acid) in film | % Caffeine in film | Result |
|---|---|---|---|
| 2.4 | 20 | 20 | dried 19.5 hrs at 24-26C, white crystals on edges, brittle, curled, insoluble in water when applied to skin |
| 2.4 | 25 | 15 | half dried 18 hours at 24-26C: clear, flexible, pliable, insoluble. Half dried 22 hours at 24-26C: clear, brittle, insoluble |
| 2.4 | 25 | 5 | dried 51 hours at 24-29C due to high humidity in lab, insoluble films |
| 2.4 | 25 | 10 | dried 51 hours at 24-29C due to high humidity in lab, insoluble films |

Fig. 91A

| % silk in solution | % Vitamin C (l-ascorbic acid) in film | % Caffeine in film | Result |
|---|---|---|---|
| 2.4 | 25 | 0.5 | unknown drying time, soluble films |
| 2.4 | 25 | 0.5 | dried 46 hours at 24-30C, soluble films |
| 2.4 | 25 | 1 | dried 46 hours at 24-30C, soluble films |
| 2.4 | 25 | 2.5 | dried 46 hours at 24-30C, soluble films |

Fig. 91B

| % silk in solution | Gel Volume | Mass Vitamin C (l-ascorbic acid) in gel | Mass Caffeine in gel | Result |
|---|---|---|---|---|
| 2 | 15 mL | 100 mg | 50 mg | Gelled in 4 days with exact appearance of standard vitamin C gels |

Fig. 92

| Sample | volume of solution (mL) | % Silk | Type of Vitamin C | Additive 1 name/quantity | Additive 2 name/quantity | Mass of vitamin C | Days to gel |
|---|---|---|---|---|---|---|---|
| 1 | 5 | 2 | l-ascorbic acid | Verstatil/75 uL | Dermofeel PA-3/5 uL | 33 | 7 |
| 2 | 5 | 2 | l-ascorbic acid | Verstatil/75 uL | Dermofeel PA-3/5 uL | 33 | 7 |
| 3 | 5 | 2 | l-ascorbic acid | none | none | 33 | 2 |
| 4 | 5 | 2 | ascorbic acid-2-glucoside | none | none | 33 | 5 |

Fig. 93

| Volume of Final Solution | % Silk (Final Solution) | TFF Batch, % Silk | Volume of TFF Batch | Volume of RO/Di water | % HA | Mass HA (mg) | Additive | Additive % | Additive mass (g) | Vitamin C Type | Mass of vitamin C (mg) |
|---|---|---|---|---|---|---|---|---|---|---|---|
| 5 | 1 | TFF-10-0055, 3.98% | 1.25 | 3.75 | 1 | 0.05 | Zinc Oxide | 10 | 0.5 | Sodium Ascorbyl Phosphate | 33 |
| Results | | Zinc Oxide(ZnO) is insoluble but can be dispersed with viscous HA solution. ZnO was mixed with water before HA and became clumpy. Large white residue on skin when applied. | | | | | | | | | |
| 5 | 1 | TFF-10-0055, 3.98% | 1.25 | 3.75 | 1 | 0.05 | Titanium Dioxide | 10 | 0.5 | Sodium Ascorbyl Phosphate | 33 |
| Results | | Titanium Dioxide (TiO2) is insoluble but can be dispersed with viscous HA solution. TiO2 was mixed with water before HA and became clumpy. Large white residue on skin when applied. | | | | | | | | | |
| 5 | 1 | TFF-10-0055, 3.98% | 1.25 | 3.75 | 1 | 0.05 | Zinc Oxide | 5 | 0.25 | Sodium Ascorbyl Phosphate | 33 |
| Results | | ZnO was evenly dispersed after mixing. Solution was low viscosity and ZnO settled to the bottom after a couple days. Minimal white residue on skin when applied. | | | | | | | | | |
| 5 | 1 | TFF-10-0055, 3.98% | 1.25 | 3.75 | 1 | 0.05 | Titanium Dioxide | 5 | 0.25 | Sodium Ascorbyl Phosphate | 33 |
| Results | | TiO2 was evenly dispersed after mixing. Solution was low viscosity and TiO2 settled to the bottom after a couple days. Minimal white residue on skin when applied. | | | | | | | | | |

Fig. 94A

| Volume of Final Solution | % Silk (Final Solution) | TFF Batch, % Silk | Volume of TFF Batch | Volume of RO/DI water | % HA | Mass HA (mg) | Additive | Additive % | Additive mass (g) | Vitamin C Type | Mass of vitamin C (mg) |
|---|---|---|---|---|---|---|---|---|---|---|---|
| 5 | 1 | TFF-10-0055, 3.98% | 1.25 | 3.75 | 2.5 | 0.125 | Zinc Oxide | 5 | 0.25 | Sodium Ascorbyl Phosphate | 33 |
| Results | | | | | | ZnO was evenly dispersed after mixing. Solution was viscosity of syrup and ZnO remained dispersed. Best feel and consistency. Minimal white residue on skin when applied. | | | | | |
| 5 | 1 | TFF-10-0055, 3.98% | 1.25 | 3.75 | 2.5 | 0.125 | Titanium Dioxide | 5 | 0.25 | Sodium Ascorbyl Phosphate | 33 |
| Results | | | | | | TiO2 was evenly dispersed after mixing. Solution was viscosity of syrup and TiO2 remained dispersed. Minimal white residue on skin when applied. | | | | | |
| 5 | 1 | TFF-10-0055, 3.98% | 1.25 | 3.75 | 5 | 0.25 | Zinc Oxide | 5 | 0.25 | Sodium Ascorbyl Phosphate | 33 |
| Results | | | | | | ZnO was evenly dispersed after mixing. Solution was of high viscosity and ZnO remained dispersed. Best feel and consistency. Small white residue on skin when applied. | | | | | |
| 5 | 1 | TFF-10-0055, 3.98% | 1.25 | 3.75 | 5 | 0.25 | Titanium Dioxide | 5 | 0.25 | Sodium Ascorbyl Phosphate | 33 |
| Results | | | | | | TiO2 was evenly dispersed after mixing. Solution was of high viscosity and TiO2 remained dispersed. Small white residue on skin when applied. | | | | | |
| 5 | 1 | TFF-10-0055, 3.98% | 1.25 | 3.75 | 5 | 0.25 | Zinc Oxide | 2.5 | 0.125 | Sodium Ascorbyl Phosphate | 33 |
| Results | | | | | | ZnO was evenly dispersed after mixing. Solution was of high viscosity and ZnO remained dispersed. Small white residue on skin when applied. | | | | | |

Fig. 94B

| Volume of Final Solution | % Silk (Final Solution) | TFF Batch, % Silk | Volume of TFF Batch | Volume of RO/DI water | % HA | Mass HA (mg) | Additive | Additive % | Additive mass (g) | Vitamin C Type | Mass of vitamin C (mg) |
|---|---|---|---|---|---|---|---|---|---|---|---|
| 100 | 1 | TFF-10-0057, 3.8% | 26.3 | 73.7 | 2.5 | 2.5 | Zinc Oxide and Titanium Dioxide | ZnO (3.75%), TiO2 (1.25%) | ZnO (3.75g), TiO2 (1.25g) | Sodium Ascorbyl Phosphate | 666 |
| Results | | | | | | | ZnO and TiO2 was evenly dispersed after mixing. Solution was viscosity of syrup. ZnO and TiO2 remained dispersed. Minimal white residue on skin when applied. Mixed with electric mixer. | | | | |
| 100 | 1 | TFF-10-0057, 3.8% | 26.3 | 73.7 | 2.5 | 2.5 | Zinc Oxide and Titanium Dioxide | ZnO (5.625%), TiO2 (1.875%) | ZnO (5.625g), TiO2 (1.875g) | Sodium Ascorbyl Phosphate | 666 |
| Results | | | | | | | ZnO and TiO2 was evenly dispersed after mixing. Solution was viscosity of syrup. ZnO and TiO2 remained dispersed. Minimal white residue on skin when applied. Mixed with electric mixer. | | | | |
| 110 | 1 | TFF-10-0055, 3.83% | 29 | 81 | 2.5 | 2.75 | Zinc Oxide and Titanium Dioxide | ZnO (12%), TiO2 (3%) | ZnO (13.2g), TiO2 (3.3g) | Sodium Ascorbyl Phosphate | 22000 |
| Results | | | | | | | ZnO and TiO2 was evenly dispersed after mixing. Solution was viscosity of glue. ZnO and TiO2 remained dispersed. Minimal white residue on skin when applied. Mixed with electric mixer. | | | | |
| 110 | 1 | TFF-10-0055, 3.83% | 29 | 81 | 2.5 | 2.75 | Zinc Oxide and Titanium Dioxide | ZnO (15%), TiO2 (5%) | ZnO (16.5g), TiO2 (5.5g) | Sodium Ascorbyl Phosphate | 22000 |
| Results | | | | | | | ZnO and TiO2 was evenly dispersed after mixing. Solution was viscosity of glue. ZnO and TiO2 remained dispersed with some visible particles. Minimal white residue on skin when applied. Mixed with electric mixer. | | | | |

Fig. 94C

| Vit C Type | Volume (ml) | Vit C % | Vit C mass (g) | % silk | lactic acid | lactic acid volume (uL) | Days to gel |
|---|---|---|---|---|---|---|---|
| l-ascobic acid | 5 | 5 | 0.25 | 2 | no | N/A | 10 |
| l-ascobic acid | 5 | 5 | 0.25 | 3 | no | N/A | 7 |
| l-ascobic acid | 5 | 5 | 0.25 | 3.8 | no | N/A | 5 |
| l-ascobic acid | 5 | 10 | 0.5 | 2 | no | N/A | Did not gel at 12 days |
| l-ascobic acid | 5 | 10 | 0.5 | 3 | no | N/A | Did not gel at 12 days |
| l-ascobic acid | 5 | 10 | 0.5 | 3.8 | no | N/A | Did not gel at 12 days |
| l-ascobic acid | 5 | 15 | 0.75 | 2 | no | N/A | Did not gel at 12 days |
| l-ascobic acid | 5 | 15 | 0.75 | 3 | no | N/A | Did not gel at 12 days |
| l-ascobic acid | 5 | 15 | 0.75 | 3.8 | no | N/A | Did not gel at 12 days |
| l-ascobic acid | 5 | 20 | 1 | 2 | no | N/A | Did not gel at 12 days |
| l-ascobic acid | 5 | 20 | 1 | 3 | no | N/A | Did not gel at 12 days |
| l-ascobic acid | 5 | 20 | 1 | 3.8 | no | N/A | Did not gel at 12 days |

Fig. 95A

| Vit C Type | Volume (ml) | Vit C % | Vit C mass (g) | % silk | lactic acid | lactic acid volume (uL) | Days to gel |
|---|---|---|---|---|---|---|---|
| ascorbic acid 2 glucoside | 5 | 5 | | 2 | no | N/A | 4 |
| ascorbic acid 2 glucoside | 5 | 5 | | 3 | no | N/A | 4 |
| ascorbic acid 2 glucoside | 5 | 5 | | 3.8 | no | N/A | 3 |
| ascorbic acid 2 glucoside | 5 | 10 | | 2 | no | N/A | 7 |
| ascorbic acid 2 glucoside | 5 | 10 | | 3 | no | N/A | 7 |
| ascorbic acid 2 glucoside | 5 | 10 | | 3.8 | no | N/A | 5 |
| ascorbic acid 2 glucoside | 5 | 15 | | 2 | no | N/A | Did not gel at 12 days |
| ascorbic acid 2 glucoside | 5 | 15 | | 3 | no | N/A | Did not gel at 12 days |
| ascorbic acid 2 glucoside | 5 | 15 | | 3.8 | no | N/A | 12 |
| ascorbic acid 2 glucoside | 5 | 20 | | 2 | no | N/A | Did not gel at 12 days |
| ascorbic acid 2 glucoside | 5 | 20 | | 3 | no | N/A | Did not gel at 12 days |
| ascorbic acid 2 glucoside | 5 | 20 | | 3.8 | no | N/A | Did not gel at 12 days |

Fig. 95B

| Vit C Type | Volume (ml) | Vit C % | Vit C mass (g) | % silk | lactic acid | lactic acid volume (uL) | Days to gel |
|---|---|---|---|---|---|---|---|
| l-ascobic acid | 5 | 20 | | 3 | yes | 5 | Did not gel at 12 days |
| l-ascobic acid | 5 | 10 | | 3 | yes | 5 | Did not gel at 12 days |
| l-ascobic acid | 5 | 20 | | 5.5 | no | N/A | Did not gel at 12 days |

Fig. 95C

| Test Substance | Microorganism Type | Detection Media | CFU/mL or gram | In Use for (days, if applicable) |
|---|---|---|---|---|
| Water Sample #1 (from 55 gallon tank) | Aerobic Bacteria | Tryptic Soy agar | 1.00E+01 | N/A |
| | Yeast and Mold | Potato Dextrose Agar | <10 | |
| Water Sample #2 (from 5 gallon carboy) | Aerobic Bacteria | Tryptic Soy agar | 5.60E+02 | N/A |
| | Yeast and Mold | Potato Dextrose Agar | 1.25E+02 | |
| Water Sample #3 (tap water) | Aerobic Bacteria | Tryptic Soy agar | <10 | N/A |
| | Yeast and Mold | Potato Dextrose Agar | <10 | |
| Pure ProC Silk Smoothing Gel with Lemon Grass | Aerobic Bacteria | Tryptic Soy agar | 1.00E+01 | 0 |
| | Yeast and Mold | Potato Dextrose Agar | <10 | |
| Pure ProC Silk Smoothing Gel with Rosemary | Aerobic Bacteria | Tryptic Soy agar | <10 | 0 |
| | Yeast and Mold | Potato Dextrose Agar | <10 | |
| Water Sample #1 (5 gallon) | Aerobic Bacteria | Tryptic Soy agar | 1.00E+01 | N/A |
| | Yeast and Mold | Potato Dextrose Agar | <10 | |
| Water Sample #2 (55 gallon tank) | Aerobic Bacteria | Tryptic Soy agar | <10 | N/A |
| | Yeast and Mold | Potato Dextrose Agar | <10 | |
| Water Sample #1 (carboy) | Aerobic Bacteria | Tryptic Soy agar | 2.50E+01 | N/A |
| | Yeast and Mold | Potato Dextrose Agar | <10 | |
| Water Sample #2 (gallon tank) | Aerobic Bacteria | Tryptic Soy agar | <10 | N/A |
| | Yeast and Mold | Potato Dextrose Agar | <10 | |
| Pure ProC Silk Smoothing Gel with Rosemary | Aerobic Bacteria | Tryptic Soy agar | <10 | 26 |
| | Yeast and Mold | Potato Dextrose Agar | <10 | |
| Pure ProC Silk Smoothing Gel with Lemongrass | Aerobic Bacteria | Tryptic Soy agar | <10 | 25 |
| | Yeast and Mold | Potato Dextrose Agar | <10 | |

Fig. 96

STABLE SILK PROTEIN FRAGMENT COMPOSITIONS

RELATED APPLICATIONS

This application is a continuation of U.S. patent application Ser. No. 14/503,021 filed Sep. 30, 2014, which application claims priority to and claims the benefit of U.S. Provisional Application No. 61/884,820, filed Sep. 30, 2013, U.S. Provisional Application No. 62/000,928, filed May 20, 2014, and U.S. Provisional Application No. 62/036,450, filed Aug. 12, 2014. The contents of each of these applications are incorporated herein by reference in their entireties.

BACKGROUND

Silk is a natural polymer produced by a variety of insects and spiders. Silk comprises a filament core protein, silk fibroin, and a glue-like coating consisting of a non-filamentous protein, sericin. Silk has been historically studied for use in the medical field. Silk has been well described in its natural fibrous form and is being studied further for potentially useful secondary forms such as silk gels, sponges, serums, films, powders and composites. Many of these secondary forms can only be created after processing the silk fibers into an aqueous silk solution.

Silk solutions have been generated using a variety of methods with the final solutions having a range of characteristics and varying levels of purity. Silk solutions have not only been used in medical applications, but have also expanded to other areas such as cosmetics and electronics.

SUMMARY

Silk protein fragment compositions and articles manufactured therefrom are disclosed herein. Silk protein fragment compositions are further processed to remove water to varying levels resulting in a range of articles from lyophilized powder to aqueous gels. In an embodiment, an article of the present disclosure is a silk film. In an embodiment, a silk film of the present disclosure can be used to address fine lines and wrinkles of the skin, for example fine lines and wrinkles around the mouth and nose. In an embodiment, a silk film of the present disclosure can be used to address dark spots on the skin. In an embodiment, a silk film of the present disclosure is used for reducing puffy eyes. In an embodiment, an article of the present disclosure is a silk gel. In an embodiment, a silk gel of the present disclosure can be used as a firming eye gel. In an embodiment, a silk gel of the present disclosure can replenish moisture and increase cell renewal while restoring radiance. In an embodiment, a silk gel of the present disclosure is a soothing gel. In an embodiment, a silk gel of the present disclosure is used for reducing puffy eyes. In an embodiment, a silk gel of the present disclosure is used for reducing dark circles around the eyes. In an embodiment, an article of the present disclosure is a silk serum. In an embodiment, a silk serum of the present disclosure can be used as a hydrating serum to restore hydration to the skin. In an embodiment, a silk serum of the present disclosure can be used to treat redness, acne and hyperpigmentation of the skin. In an embodiment, an article of the present disclosure is a silk chemical peel that damages the skin in a controlled manner. In an embodiment, a silk chemical peel of the present disclosure, when applied to the skin, results in healthy vibrant skin. In an embodiment, a silk chemical peel of the present disclosure, when applied to the skin, results in a reduction in fine lines. In an embodiment, a silk chemical peel of the present disclosure, when applied to the skin, results in firming of the skin. In an embodiment, an article of the present disclosure is a silk sunscreen gel.

According to aspects illustrated herein, methods for preparing aqueous solutions of pure silk fibroin-based protein fragments are disclosed. In an embodiment, at least one pure silk fibroin-based protein fragment (SPF) mixture solution having a specific average weight average molecular weight (MW) range and polydispersity is created. In an embodiment, at least SPF mixture solution having a MW range between about 6 kDa and 16 kDa and a polydispersity range between about 1.5 and about 3.0 is created. In an embodiment, at least one SPF mixture solution having a MW between about 17 kDa and 38 kDa and a polydispersity range between about 1.5 and about 3.0 is created. In an embodiment, at least one SPF mixture solution having a MW range between about 39 kDa and 80 kDa and a polydispersity range between about 1.5 and about 3.0 is created.

According to aspects illustrated herein, there is disclosed a composition that includes pure silk fibroin-based protein fragments that are substantially devoid of sericin, wherein the composition has an average weight average molecular weight ranging from about 6 kDa to about 16 kDa, wherein the composition has a polydispersity of between about 1.5 and about 3.0, wherein the composition is substantially homogenous, wherein the composition includes between 0 ppm and about 500 ppm of inorganic residuals, and wherein the composition includes between 0 ppm and about 500 ppm of organic residuals. In an embodiment, the pure silk fibroin-based protein fragments have between about 10 ppm and about 300 ppm of lithium bromide residuals and between about 10 ppm and about 100 ppm of sodium carbonate residuals. In an embodiment, the lithium bromide residuals are measurable using a high-performance liquid chromatography lithium bromide assay, and the sodium carbonate residuals are measurable using a high-performance liquid chromatography sodium carbonate assay. In an embodiment, the composition further includes less than 10% water. In an embodiment, the composition is in the form of a lyophilized structure, such as a lyophilized powder. In an embodiment, the composition is in the form of a solution. In an embodiment, the composition includes from about 0.1 wt % to about 30.0 wt % pure silk fibroin-based protein fragments. The pure silk fibroin-based protein fragments are stable in the solution for at least 30 days. In an embodiment, the term "stable" refers to the absence of spontaneous or gradual gelation, with no visible change in the color or turbidity of the solution. In an embodiment, the term "stable" refers to no aggregation of fragments and therefore no increase in molecular weight over time. In an embodiment, the composition is in the form of an aqueous solution. In an embodiment, the composition is in the form of an organic solution. The composition may be provided in a sealed container. In some embodiments, the composition further includes one or more molecules selected from the group consisting of therapeutic agents, growth factors, antioxidants, proteins, vitamins, carbohydrates, polymers, nucleic acids, salts, acids, bases, biomolecules, glycosamino glycans, polysaccharides, extracellular matrix molecules, metals, metal ion, metal oxide, synthetic molecules, polyanhydrides, cells, fatty acids, fragrance, minerals, plants, plant extracts, preservatives and essential oils. In an embodiment, the added molecule or molecules are stable (i.e., retain activity over time) within the composition and can be released at a desired rate. In an embodiment, the one or more molecules is vitamin C or a derivative thereof. In an embodiment, the composition further includes an alpha hydroxy acid selected from the group consisting of glycolic acid, lactic acid, tartaric acid and citric acid. In an embodiment, the composition further includes hyaluronic acid or its salt form at a concentration of about 0.5% to about 10.0%. In an embodiment, the composition further includes at least one of zinc oxide or titanium dioxide. In an embodiment, the pure silk fibroin-based protein fragments in the composition are hypoallergenic. In an embodiment, the pure silk fibroin-based protein fragments are biocompatible, non-sensitizing, and non-immunogenic. In an embodiment, the pure silk fibroin-based protein fragments are bioresorbable or biodegradable following implantation or application.

According to aspects illustrated herein, there is disclosed a composition that includes pure silk fibroin-based protein fragments that are substantially devoid of sericin, wherein the composition has an average weight average molecular weight ranging from about 17 kDa to about 38 kDa, wherein the composition has a polydispersity of between about 1.5 and about 3.0, wherein the composition is substantially homogenous, wherein the composition includes between 0 ppm and about 500 ppm of inorganic residuals, and wherein the composition includes between 0 ppm and about 500 ppm of organic residuals. In an embodiment, the pure silk fibroin-based protein fragments have between about 10 ppm and about 300 ppm of lithium bromide residuals and between about 10 ppm and about 100 ppm of sodium carbonate residuals. In an embodiment, the lithium bromide residuals are measurable using a high-performance liquid chromatography lithium bromide assay, and the sodium carbonate residuals are measurable using a high-performance liquid chromatography sodium carbonate assay. In an embodiment, the composition further includes less than 10% water. In an embodiment, the composition is in the form of a lyophilized structure, such as a lyophilized powder. In an embodiment, the composition is in the form of a solution. In an embodiment, the composition includes from about 0.1 wt % to about 30.0 wt % pure silk fibroin-based protein fragments. The pure silk fibroin-based protein fragments are stable in the solution for at least 30 days. In an embodiment, the term "stable" refers to the absence of spontaneous or gradual gelation, with no visible change in the color or turbidity of the solution. In an embodiment, the term "stable" refers to no aggregation of fragments and therefore no increase in molecular weight over time. In an embodiment, the composition is in the form of an aqueous solution. In an embodiment, the composition is in the form of an organic solution. The composition may be provided in a sealed container. In some embodiments, the composition further includes one or more molecules selected from the group consisting of therapeutic agents, growth factors, antioxidants, proteins, vitamins, carbohydrates, polymers, nucleic acids, salts, acids, bases, biomolecules, glycosamino glycans, polysaccharides, extracellular matrix molecules, metals, metal ion, metal oxide, synthetic molecules, polyanhydrides, cells, fatty acids, fragrance, minerals, plants, plant extracts, preservatives and essential oils. In an embodiment, the added molecule or molecules are stable (i.e., retain activity over time) within the composition and can be released at a desired rate. In an embodiment, the one or more molecules is vitamin C or a derivative thereof. In an embodiment, the composition further includes an alpha hydroxy acid selected from the group consisting of glycolic acid, lactic acid, tartaric acid and citric acid. In an embodiment, the composition further includes hyaluronic acid or its salt form at a concentration of about 0.5% to about 10.0%. In an embodiment, the composition further includes at least one of zinc oxide or titanium dioxide. In an embodiment, the pure silk fibroin-based protein fragments in the composition are hypoallergenic. In an embodiment, the pure silk fibroin-based protein fragments are biocompatible, non-sensitizing, and non-immunogenic. In an embodiment, the pure silk fibroin-based protein fragments are bioresorbable or biodegradable following implantation or application.

According to aspects illustrated herein, there is disclosed a composition that includes pure silk fibroin-based protein fragments that are substantially devoid of sericin, wherein the composition has an average weight average molecular weight ranging from about 39 kDa to about 80 kDa, wherein the composition has a polydispersity of between about 1.5 and about 3.0, wherein the composition is substantially homogenous, wherein the composition includes between 0 ppm and about 500 ppm of inorganic residuals, and wherein the composition includes between 0 ppm and about 500 ppm of organic residuals. In an embodiment, the pure silk fibroin-based protein fragments have between about 10 ppm and about 300 ppm of lithium bromide residuals and between about 10 ppm and about 100 ppm of sodium carbonate residuals. In an embodiment, the lithium bromide residuals are measurable using a high-performance liquid chromatography lithium bromide assay, and the sodium carbonate residuals are measurable using a high-performance liquid chromatography sodium carbonate assay. In an embodiment, the composition further includes less than 10% water. In an embodiment, the composition is in the form of a lyophilized structure, such as a lyophilized powder. In an embodiment, the composition is in the form of a solution. In an embodiment, the composition includes from about 0.1 wt % to about 30.0 wt % pure silk fibroin-based protein fragments. The pure silk fibroin-based protein fragments are stable in the solution for at least 30 days. In an embodiment, the term "stable" refers to the absence of spontaneous or gradual gelation, with no visible change in the color or turbidity of the solution. In an embodiment, the term "stable" refers to no aggregation of fragments and therefore no increase in molecular weight over time. In an embodiment, the composition is in the form of an aqueous solution. In an embodiment, the composition is in the form of an organic solution. The composition may be provided in a sealed container. In some embodiments, the composition further includes one or more molecules selected from the group consisting of therapeutic agents, growth factors, antioxidants, proteins, vitamins, carbohydrates, polymers, nucleic acids, salts, acids, bases, biomolecules, glycosamino glycans, polysaccharides, extracellular matrix molecules, metals, metal ion, metal oxide, synthetic molecules, polyanhydrides, cells, fatty acids, fragrance, minerals, plants, plant extracts, preservatives and essential oils. In an embodiment, the added molecule or molecules are stable (i.e., retain activity over time) within the composition and can be released at a desired rate. In an embodiment, the one or more molecules is vitamin C or a derivative thereof. In an embodiment, the composition further includes an alpha hydroxy acid selected from the group consisting of glycolic acid, lactic acid, tartaric acid and citric acid. In an embodiment, the composition further includes hyaluronic acid or its salt form at a concentration of about 0.5% to about 10.0%. In an embodiment, the composition further includes at least one of zinc oxide or titanium dioxide. In an embodiment, the pure silk fibroin-based protein fragments in the composition are hypoallergenic. In an embodiment, the pure silk fibroin-based protein fragments are biocompatible, non-sensitizing, and non-immunogenic. In an embodiment, the pure silk fibroin-based protein fragments are bioresorbable or biodegradable following implantation or application.

According to aspects illustrated herein, there is disclosed a film that includes pure silk fibroin-based protein fragments substantially devoid of sericin and comprising: an average weight average molecular weight ranging from about 17 kDa to about 38 kDa; and a polydispersity of between about 1.5 and about 3.0, wherein the film has a water content ranging from about 2.0 wt. % to about 20.0 wt. %, wherein the film includes between 0 ppm and 500 ppm of inorganic residuals, wherein the film includes between 0 ppm and 500 ppm of organic residuals, and wherein the film is sufficiently flexible to conform to anatomical topographies. In an embodiment, the film includes between about 1.0% and about 50.0% crystalline protein domains and being soluble when submersed in water at room temperature. In an embodiment, the film includes from about 30.0 wt. % to about 99.5 wt. % of pure silk fibroin-based protein fragments. In an embodiment, the film has a pH from about 1.0 to about 7.0. In an embodiment, the film further includes from about 0.5 wt. % to about 2.5 wt. % of caffeine. In an embodiment, the film further includes from about 1.0 wt. % to about 50.0 wt. % of vitamin C or a derivative thereof. In an embodiment, the vitamin C or a derivative thereof remains stable within the film for a period of from about 5 days to about 5 years. In an embodiment, the vitamin C or a derivative thereof is stable within the film so as to result in release of the vitamin C in a biologically active form. In an embodiment, the film further includes one or more molecules selected from the group consisting of therapeutic agents, growth factors, antioxidants, proteins, carbohydrates, polymers, nucleic acids, salts, acids, bases, biomolecules, glycosamino glycans, polysaccharides, extracellular matrix molecules, metals, metal ion, metal oxide, synthetic molecules, polyanhydrides, cells, fatty acids, fragrance, minerals, plants, plant extracts, preservatives and essential oils. In an embodiment, the film further includes an alpha hydroxy acid selected from the group consisting of glycolic acid, lactic acid, tartaric acid and citric acid. In an embodiment, the film further includes hyaluronic acid or its salt form at a concentration ranging from about 0.5 wt. % to about 10.0 wt. %. In an embodiment, the film further includes at least one of zinc oxide or titanium dioxide. In an embodiment, the film is packaged in a foil based package that is air tight and light proof. In an embodiment, the film is sufficiently designed for topical application. In an embodiment, the topical application is for cosmetic use. In an embodiment, the topical application is for wound dressing. In an embodiment, the film is sufficiently designed for administration within a body. In an embodiment, the pure silk fibroin-based protein fragments are hypoallergenic. In an embodiment, a method of reducing fine lines and wrinkles includes applying a film of the present disclosure daily to human skin for a period of at least one week and observing a reduction in fine lines and wrinkles on the human skin.

According to aspects illustrated herein, there is disclosed a gel that includes pure silk fibroin-based protein fragments substantially devoid of sericin and comprising: an average weight average molecular weight ranging from about 17 kDa to about 38 kDa; and a polydispersity of between about 1.5 and about 3.0; and water from about 20 wt. % to about 99.9 wt. %, wherein the gel includes between 0 ppm and 500 ppm of inorganic residuals, and wherein the gel includes between 0 ppm and 500 ppm of organic residuals. In an embodiment, the gel includes between about 1.0% and about 50.0% crystalline protein domains. In an embodiment, the gel includes from about 0.1 wt. % to about 6.0 wt. % of pure silk fibroin-based protein fragments. In an embodiment, the gel has a pH from about 1.0 to about 7.0. In an embodiment, the gel further includes from about 0.5 wt. % to about 20.0 wt. % of vitamin C or a derivative thereof. In an embodiment, the vitamin C or a derivative thereof remains stable within the gel for a period of from about 5 days to about 5 years. In an embodiment, the vitamin C or a derivative thereof is stable within the gel so as to result in release of the vitamin C in a biologically active form. In an embodiment, the gel further includes an additive selected from the group consisting of vitamin E, rosemary oil, rose oil, lemon juice, lemon grass oil and caffeine. In an embodiment, the gel is packaged in an airtight container. In an embodiment, the pure silk fibroin-based protein fragments are hypoallergenic. In an embodiment, the gel has less than 10 colony forming units per milliliter. In an embodiment, a method of smoothing and rejuvenating human skin includes applying a gel of the present disclosure daily to human skin for a period of at least one week and observing an improvement in skin texture.

According to aspects illustrated herein, there is disclosed a serum that includes pure silk fibroin-based protein fragments substantially devoid of sericin and comprising: an average weight average molecular weight ranging from about 17 kDa to about 38 kDa; and a polydispersity of between about 1.5 and about 3.0; and hyaluronic acid or its salt form from about 0.5% to about 10.0%, wherein the serum includes between 0 ppm and 500 ppm of inorganic residuals, and wherein the serum includes between 0 ppm and 500 ppm of organic residuals. In an embodiment, the serum includes between about 1.0% and about 50.0% crystalline protein domains. In an embodiment, the serum includes from about 0.1 wt. % to about 6.0 wt. % of pure silk fibroin-based protein fragments. In an embodiment, the serum has a pH from about 1.0 to about 7.0. In an embodiment, the serum further includes an additive selected from the group consisting of vitamin E, rosemary oil, rose oil, lemon juice, lemon grass oil, vanilla, geranium, and green tea. In an embodiment, the serum further includes from about 0.5 wt. % to about 30.0 wt. % of vitamin C or a derivative thereof. In an embodiment, the vitamin C or a derivative thereof remains stable within the serum for a period of from about 5 days to about 5 years. In an embodiment, the vitamin C or a derivative thereof is stable within the serum so as to result in release of the vitamin C in a biologically active form. In an embodiment, the serum is packaged in an airtight container. In an embodiment, the pure silk fibroin-based protein fragments are hypoallergenic. In an embodiment, a method of moisturizing human skin includes applying daily a serum of the present disclosure to human skin for a period of at least one week and observing an improvement in skin hydration.

According to aspects illustrated herein, there is disclosed a skin peel composition that includes pure silk fibroin-based protein fragments that are substantially devoid of sericin, the fragments having an average weight average molecular weight ranging from about 17 kDa to about 38 kDa and a polydispersity of between about 1.5 and about 3.0 in combination with at least one skin exfoliating agent. In an embodiment, the skin peel composition includes at least one skin exfoliating agent selected from the group consisting of glycolic acid and lactic acid. In an embodiment, the skin peel composition includes between about 1.0% and about 50.0% crystalline protein domains. In an embodiment, the skin peel composition has a pH from about 1.0 to about 6.0. In an embodiment, the pure silk fibroin-based protein fragments are hypoallergenic.

According to aspects illustrated herein, there is disclosed a method for preparing an aqueous solution of pure silk fibroin-based protein fragments having an average weight average molecular weight ranging from about 6 kDa to about 16 kDa, the method including the steps of: degumming a silk source by adding the silk source to a boiling (100° C.) aqueous solution of sodium carbonate for a treatment time of between about 30 minutes to about 60 minutes; removing sericin from the solution to produce a silk fibroin extract comprising non-detectable levels of sericin; draining the solution from the silk fibroin extract; dissolving the silk fibroin extract in a solution of lithium bromide having a starting temperature upon placement of the silk fibroin extract in the lithium bromide solution that ranges from about 60° C. to about 140° C.; maintaining the solution of silk fibroin-lithium bromide in an oven having a temperature of about 140° C. for a period of at least 1 hour; removing the lithium bromide from the silk fibroin extract; and producing an aqueous solution of silk protein fragments, the aqueous solution comprising: fragments having an average weight average molecular weight ranging from about 6 kDa to about 16 kDa, and wherein the aqueous solution of pure silk fibroin-based protein fragments comprises a polydispersity of between about 1.5 and about 3.0. In an embodiment, the method includes the step of drying the silk fibroin extract prior to the dissolving step. In an embodiment, the amount of lithium bromide residuals in the aqueous solution can be measured using a high-performance liquid chromatography lithium bromide assay. In an embodiment, the amount of sodium carbonate residuals in the aqueous solution can be measured using a high-performance liquid chromatography sodium carbonate assay. In an embodiment, the method includes the step of adding a therapeutic agent to the aqueous solution of pure silk fibroin-based protein fragments. In an embodiment, the method includes the step of adding a molecule selected from one of an antioxidant or an enzyme to the aqueous solution of pure silk fibroin-based protein fragments. In an embodiment, the method includes the step of adding a vitamin to the aqueous solution of pure silk fibroin-based protein fragments. In an embodiment, the vitamin is selected from one of vitamin C or a derivative thereof. In an embodiment, the method further includes the step of adding an alpha hydroxy acid to the aqueous solution of pure silk fibroin-based protein fragments. In an embodiment, the alpha hydroxy acid is selected from the group consisting of glycolic acid, lactic acid, tartaric acid and citric acid. In an embodiment, the method further includes the step of adding hyaluronic acid at a concentration of about 0.5% to about 10.0% to the aqueous solution of pure silk fibroin-based protein fragments. In an embodiment, the method further includes the step of adding at least one of zinc oxide or titanium dioxide to the aqueous solution of pure silk fibroin-based protein fragments. In an embodiment, the method further includes the step of lyophilizing the aqueous solution of pure silk fibroin-based protein fragments. In an embodiment, a cosmetic film is fabricated from the aqueous solution of silk protein fragments. In an embodiment, a cosmetic gel is fabricated from the aqueous solution of silk protein fragments.

According to aspects illustrated herein, there is disclosed a method for preparing an aqueous solution of pure silk fibroin-based protein fragments having an average weight average molecular weight ranging from about 17 kDa to about 38 kDa, the method including the steps of: adding a silk source to a boiling (100° C.) aqueous solution of sodium carbonate for a treatment time of between about 30 minutes to about 60 minutes so as to result in degumming; removing sericin from the solution to produce a silk fibroin extract comprising non-detectable levels of sericin; draining the solution from the silk fibroin extract; dissolving the silk fibroin extract in a solution of lithium bromide having a starting temperature upon placement of the silk fibroin extract in the lithium bromide solution that ranges from about 80° C. to about 140° C.; maintaining the solution of silk fibroin-lithium bromide in a dry oven having a temperature in the range between about 60° C. to about 100° C. for a period of at least 1 hour; removing the lithium bromide from the silk fibroin extract; and producing an aqueous solution of pure silk fibroin-based protein fragments, wherein the aqueous solution of pure silk fibroin-based protein fragments comprises lithium bromide residuals of between about 10 ppm and about 300 ppm, wherein the aqueous solution of silk protein fragments comprises sodium carbonate residuals of between about 10 ppm and about 100 ppm, wherein the aqueous solution of pure silk fibroin-based protein fragments comprises fragments having an average weight average molecular weight ranging from about 17 kDa to about 38 kDa, and wherein the aqueous solution of pure silk fibroin-based protein fragments comprises a polydispersity of between about 1.5 and about 3.0. In an embodiment, the method includes the step of drying the silk fibroin extract prior to the dissolving step. In an embodiment, the amount of lithium bromide residuals in the aqueous solution can be measured using a high-performance liquid chromatography lithium bromide assay. In an embodiment, the amount of sodium carbonate residuals in the aqueous solution can be measured using a high-performance liquid chromatography sodium carbonate assay. In an embodiment, the method includes the step of adding a therapeutic agent to the aqueous solution of pure silk fibroin-based protein fragments. In an embodiment, the method includes the step of adding a molecule selected from one of an antioxidant or an enzyme to the aqueous solution of pure silk fibroin-based protein fragments. In an embodiment, the method includes the step of adding a vitamin to the aqueous solution of pure silk fibroin-based protein fragments. In an embodiment, the vitamin is selected from one of vitamin C or a derivative thereof. In an embodiment, the method further includes the step of adding an alpha hydroxy acid to the aqueous solution of pure silk fibroin-based protein fragments. In an embodiment, the alpha hydroxy acid is selected from the group consisting of glycolic acid, lactic acid, tartaric acid and citric acid. In an embodiment, the method further includes the step of adding hyaluronic acid at a concentration of about 0.5% to about 10.0% to the aqueous solution of pure silk fibroin-based protein fragments. In an embodiment, the method further includes the step of adding at least one of zinc oxide or titanium dioxide to the aqueous solution of pure silk fibroin-based protein fragments. In an embodiment, the method further includes the step of lyophilizing the aqueous solution of pure silk fibroin-based protein fragments. In an embodiment, a cosmetic film is fabricated from the aqueous solution of silk protein fragments. In an embodiment, a cosmetic gel is fabricated from the aqueous solution of silk protein fragments.

According to aspects illustrated herein, there is disclosed a method for preparing an aqueous solution of pure silk fibroin-based protein fragments having an average weight average molecular weight ranging from about 39 kDa to about 80 kDa, the method including the steps of: adding a silk source to a boiling (100° C.) aqueous solution of sodium carbonate for a treatment time of about 30 minutes so as to result in degumming; removing sericin from the solution to produce a silk fibroin extract comprising non-detectable levels of sericin; draining the solution from the silk fibroin extract; dissolving the silk fibroin extract in a solution of lithium bromide having a starting temperature upon placement of the silk fibroin extract in the lithium bromide solution that ranges from about 80° C. to about 140° C.; maintaining the solution of silk fibroin-lithium bromide in a dry oven having a temperature in the range between about 60° C. to about 100° C. for a period of at least 1 hour; removing the lithium bromide from the silk fibroin extract; and producing an aqueous solution of pure silk fibroin-based protein fragments, wherein the aqueous solution of pure silk fibroin-based protein fragments comprises lithium bromide residuals of between about 10 ppm and about 300 ppm, sodium carbonate residuals of between about 10 ppm and about 100 ppm, fragments having an average weight average molecular weight ranging from about 40 kDa to about 65 kDa, and wherein the aqueous solution of pure silk fibroin-based protein fragments comprises a polydispersity of between about 1.5 and about 3.0. In an embodiment, the method includes the step of drying the silk fibroin extract prior to the dissolving step. In an embodiment, the amount of lithium bromide residuals in the aqueous solution can be measured using a high-performance liquid chromatography lithium bromide assay. In an embodiment, the amount of sodium carbonate residuals in the aqueous solution can be measured using a high-performance liquid chromatography sodium carbonate assay. In an embodiment, the method includes the step of adding a therapeutic agent to the aqueous solution of pure silk fibroin-based protein fragments. In an embodiment, the method includes the step of adding a molecule selected from one of an antioxidant or an enzyme to the aqueous solution of pure silk fibroin-based protein fragments. In an embodiment, the method includes the step of adding a vitamin to the aqueous solution of pure silk fibroin-based protein fragments. In an embodiment, the vitamin is selected from one of vitamin C or a derivative thereof. In an embodiment, the method further includes the step of adding an alpha hydroxy acid to the aqueous solution of pure silk fibroin-based protein fragments. In an embodiment, the alpha hydroxy acid is selected from the group consisting of glycolic acid, lactic acid, tartaric acid and citric acid. In an embodiment, the method further includes the step of adding hyaluronic acid at a concentration of about 0.5% to about 10.0% to the aqueous solution of pure silk fibroin-based protein fragments. In an embodiment, the method further includes the step of adding at least one of zinc oxide or titanium dioxide to the aqueous solution of pure silk fibroin-based protein fragments. In an embodiment, the method further includes the step of lyophilizing the aqueous solution of pure silk fibroin-based protein fragments. In an embodiment, a cosmetic film is fabricated from the aqueous solution of silk protein fragments. In an embodiment, a cosmetic gel is fabricated from the aqueous solution of silk protein fragments.

According to aspects illustrated herein, silk films manufactured from SPF mixture solutions of the present disclosure are disclosed. In an embodiment, at least one molecule or therapeutic agent of interest is physically entrapped into a SPF mixture solution of the present disclosure during processing into films. A silk film of the present disclosure can be used to release at least one molecule or therapeutic agent of interest.

According to aspects illustrated herein, a method is disclosed for producing silk films having entrapped molecules or therapeutic agents.

According to aspects illustrated herein, a method is disclosed for producing silk gels having entrapped molecules or therapeutic agents such as those listed in the following paragraph. In an embodiment, at least one molecule or therapeutic agent of interest is physically entrapped into a SPF mixture solution of the present disclosure during processing into aqueous gels. An aqueous silk gel of the present disclosure can be used to release at least one molecule or therapeutic agent of interest.

According to aspects illustrated herein, a SPF mixture solution of the present disclosure is used to fabricate a silk film or aqueous gel that entraps molecules including, but not limited to, Selenium, Ubiquinone derivatives, Thiol-based antioxidants, Saccharide-containing antioxidants, Polyphenols, Botanical extracts, Caffeic acid, Apigenin, Pycnogenol, Resveratrol, Folic acid, Vitamin b12, Vitamin b6, Vitamin b3, Vitamin E, Vitamin C and derivatives thereof, Vitamin D, Vitamin A, Astaxathin, Lutein, Lycopene, Essential fatty acids (omegas 3 and 6), Iron, Zinc, magnesium, Flavonoids (soy, Curcumin, Silymarin, Pycnongeol), Growth factors, aloe, hyaluronic acid, extracellular matrix proteins, cells, nucleic acids, biomarkers, biological reagents, zinc oxide, benzyol peroxide, retnoids, titanium, caffeine, green tea, allergens in a known dose (for sensitization treatment), essential oils including, but not limited to, lemongrass or rosemary oil, and fragrances. A film of the present disclosure can adhere to the skin when moistened, allowing for easy application and targeted delivery to a treatment area with an ability to be wiped off with water. Molecule loaded films, gels or serums can be used for drug delivery, medical and personal care, including anti-aging, wrinkle and fine line reduction and prevention, crows feet, frown lines and glabella line reduction; acne treatment; UV protection; all types of wound care; topical, intradermal and sub-dermal and implantable medical and pharmaceutical applications; all types and conditions of inflammation, such as eczema or rosacea; creating an even skin tone, pigment reduction, hyperpigmentation treatment, dark spots or age spots resulting from acne, pregnancy, birth control, photodamage; reducing scar and stretch marks, and reducing acne scarring. By stabilizing molecules in a film or gel of the present disclosure, controlled release of the molecule in its active form is achieved. In an embodiment, a film or gel of the present disclosure can deliver its molecule in a time frame relevant to a consumer for daily skin treatment(s). In an embodiment, the pure silk fibroin-based protein composition in an aqueous or organic solution may be used to spin fibers or fabrics for the medical or consumer markets.

BRIEF DESCRIPTION OF THE DRAWINGS

The presently disclosed embodiments will be further explained with reference to the attached drawings. The drawings shown are not necessarily to scale, with emphasis instead generally being placed upon illustrating the principles of the presently disclosed embodiments.

FIGS. 5A-5D are photographs showing dissolved silk in room temperature lithium bromide (LiBr) solutions dissolved in a 60° C. oven for 4 hours (sericin extraction temperature and time were varied).

FIGS. 7A-7D are photographs showing dissolved silk in room temperature LiBr solutions dissolved in a 60° C. oven for 8 hours (sericin extraction temperature and time were varied).

FIGS. 13A-13D are photographs showing dissolved silk in 60° C. LiBr solutions dissolved in a 60° C. oven for 4 hours (sericin extraction temperature and time were varied).

FIGS. 18A-18D are photographs showing dissolved silk in 100° C. LiBr solutions dissolved in a 60° C. oven for 1 hour (sericin extraction temperature and time were varied).

FIGS. 20A-20D are photographs showing dissolved silk in 100° C. LiBr solutions dissolved in a 60° C. oven for 6 hours (sericin extraction temperature and time were varied).

FIGS. 21A-21D are photographs showing dissolved silk in 140° C. (boiling point for LiBr) LiBr solutions dissolved in a 60° C. oven for 1 hour (sericin extraction temperature and time were varied time).

FIGS. 23A-23D are photographs showing dissolved silk in 140° C. (boiling point for LiBr) LiBr solutions dissolved in a 60° C. oven for 6 hours (sericin extraction temperature and time were varied).

FIGS. 27A-27D are photographs showing dissolved silk in 100° C. LiBr solutions dissolved in a 100° C. oven for 1 hour (sericin extraction temperature and time were varied).

FIGS. 28A-28D are photographs showing dissolved silk in 100° C. LiBr solutions dissolved in a 100° C. oven for 4 hours (sericin extraction temperature and time were varied).

FIG. 32A-32D are photographs showing dissolved silk in 140° C. (boiling point for LiBr) LiBr solutions dissolved in a 120° C. oven for 6 hours (sericin extraction temperature and time were varied).

FIG. 34 summarizes an embodiment of parameters for a silk film drying study of the present disclosure.

FIGS. 36A and 36B show HPLC chromatograms from samples comprising vitamin C. FIG. 36A shows peaks from (1) a chemically stabilized sample of vitamin C at ambient conditions and (2) a sample of vitamin C taken after 1 hour at ambient conditions without chemical stabilization to prevent oxidation, where degradation products are visible. FIG. 36B shows peaks from two different embodiments of silk films of the present disclosure that were aged for at least 30 days at room temperature. No degradation products were visible.

FIGS. 40A-40D are photographs showing silk protein fragment-films of the present disclosure dried at 40° C. in a convection oven for 48 hours in closed dish.

FIGS. 42A-42D are photographs showing silk protein fragment-films of the present disclosure dried at 54° C. in a convection oven for 48 hours in open dish.

FIGS. 44A-44D are photographs showing silk protein fragment-films of the present disclosure dried at 54° C. in a film dryer for 48 hours in open dish.

FIGS. 45A-45D are photographs showing silk protein fragment-films of the present disclosure dried at room temperature in a convection oven for 48 hours in open dish.

FIGS. 50A-50D are photographs showing the dissolution, in water, of the formed silk protein fragment-films of the present disclosure dried at 54° C. in a convection oven for 8 hours in open dish.

FIGS. 53A-53D are photographs showing the dissolution, in water, of the formed silk protein fragment-films of the present disclosure dried at 54° C. in a film dryer for 48 hours in open dish.

FIG. 55 is a table summarizing the LiBr and Sodium Carbonate ($Na_2CO_3$) concentration in silk protein solutions of the present disclosure.

FIG. 56 is a table summarizing the $Na_2CO_3$ concentration in silk protein fragment-films of the present disclosure.

FIG. 57 is a table summarizing the LiBr concentration in silk protein fragment-films of the present disclosure.

FIG. 58 is a table summarizing the LiBr and $Na_2CO_3$ concentration in silk protein solutions of the present disclosure.

FIG. 59 is a table summarizing the vitamin C concentration in silk protein fragment-films of the present disclosure.

FIG. 60 is a table summarizing the stability of vitamin C in chemically stabilized solutions.

FIG. 61 is a table summarizing the Molecular Weights of silk protein solutions of the present disclosure.

FIG. 63 is a table summarizing the Molecular Weights of silk dissolved from different concentrations of LiBr and from different extraction and dissolution sizes.

FIGS. 83A and 83B are photographs of a laser cut silk film.

FIG. 86 is a summary of the initial benefits of PureProC™ observed by users and support of consumer knowledge.

FIG. 88 is a summary of the benefits to the skin after using PureProC™ Smoothing Gel: Lemongrass by trial participants.

FIGS. 89A-89B are tables summarizing the effect of vitamin C with or without a vitamin C derivative on gelation.

FIG. 90 is a table summarizing the effect of vitamin C and vitamin C derivatives on the formation of silk films of the present disclosure.

FIGS. 91A-91B are tables summarizing the effect of vitamin C and caffeine on the formation of silk films of the present disclosure.

FIG. 92 is a table summarizing an embodiment of a caffeine gel of the present disclosure.

FIG. 93 is a table summarizing embodiments of preservative gels of the present disclosure.

FIGS. 94A-94C are tables summarizing embodiments of cosmetic serums of the present disclosure with varying additives and concentrations of components suitable for protection against ultraviolet radiation (UV).

FIGS. 95A-95C are tables summarizing embodiments of high concentration vitamin C gels of the present disclosure.

FIG. 96 is a table summarizing the results of various gels of the present disclosure to evaluate the possible microbial contamination in three different states of their use (intact, in-use, ending product).

Figure 1:
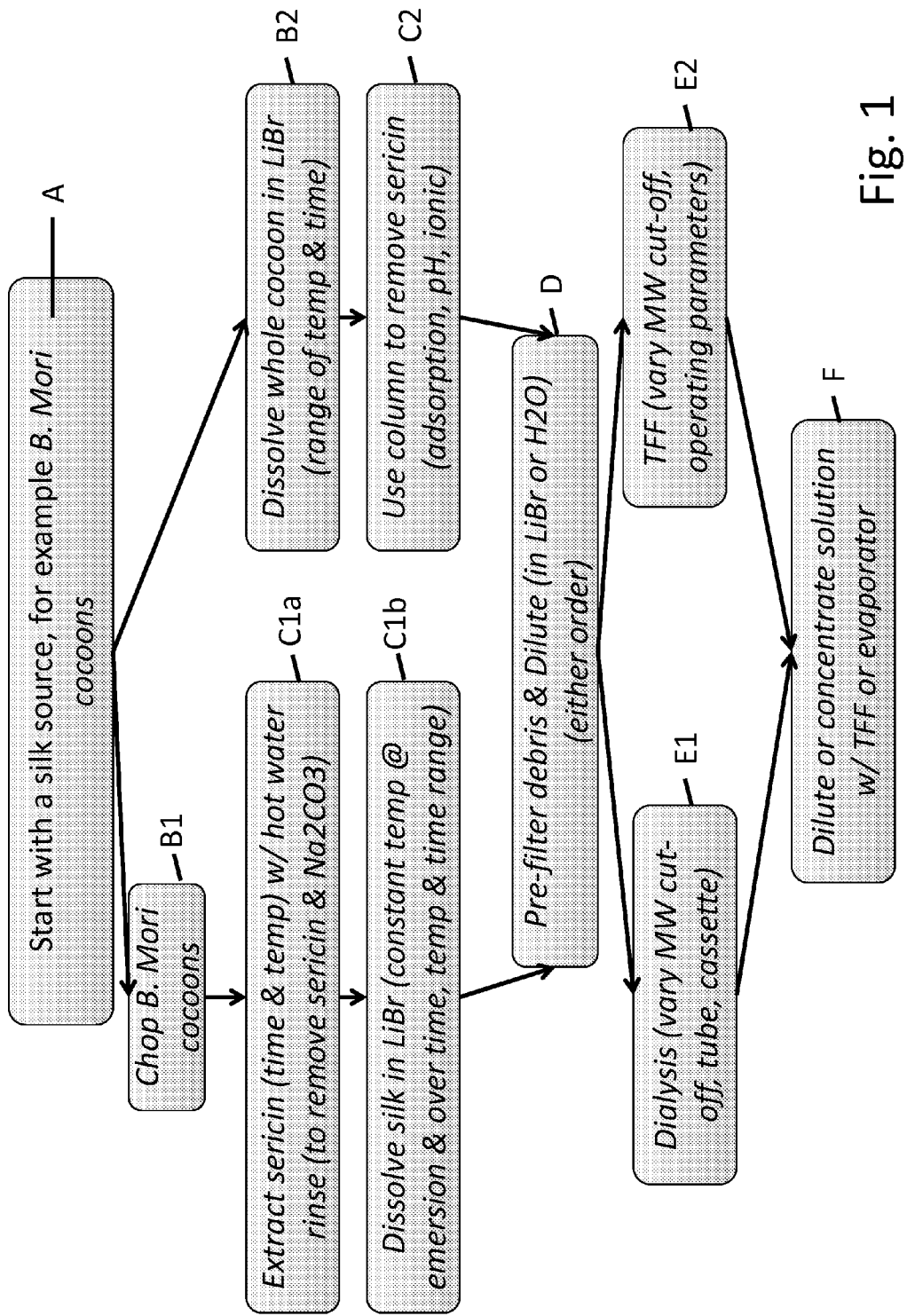
FIG. 1 is a flow chart showing various embodiments for producing pure silk fibroin-based protein fragments (SPFs) of the present disclosure.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Provided herein are methods for producing pure and highly scalable silk protein fragment (SPF) mixture solutions that may be used across multiple industries for a variety of applications. The solutions are generated from raw pure intact silk protein material and processed in order to remove any sericin and achieve the desired weight average molecular weight (MW) and polydispersity of the fragment mixture. Select method parameters may be altered to achieve distinct final silk protein fragment characteristics depending upon the intended use. The resulting final fragment solution is pure silk protein fragments and water with PPM to non-detectable levels of process contaminants, levels acceptable in the pharmaceutical, medical and consumer cosmetic markets. The concentration, size and polydispersity of silk protein fragments in the solution may further be altered depending upon the desired use and performance requirements. In an embodiment, the pure silk fibroin-based protein fragments in the solution are substantially devoid of sericin, have an average weight average molecular weight ranging from about 6 kDa to about 16 kDa, and have a polydispersity ranging from about 1.5 and about 3.0. In an embodiment, the pure silk fibroin-based protein fragments in the solution are substantially devoid of sericin, have an average weight average molecular weight ranging from about 17 kDa to about 38 kDa, and have a polydispersity ranging from about 1.5 and about 3.0. In an embodiment, the pure silk fibroin-based protein fragments in the solution are substantially devoid of sericin, have an average weight average molecular weight ranging from about 39 kDa to about 80 kDa, and have a polydispersity ranging from about 1.5 and about 3.0.

In an embodiment, the silk solutions of the present disclosure may be used to generate articles, such as silk films of various shapes and sizes by varying water content/concentration, or sold as a raw ingredient into the medical, consumer, or electronics markets. In an embodiment, the solutions may be used to generate articles, such as silk gels of varying gel and liquid consistencies by varying water content/concentration, or sold as a raw ingredient into the pharmaceutical, medical, consumer, or electronics markets. Depending on the silk solution utilized and the methods for casting the films or gels, various properties are achieved. The articles may be loaded with at least one therapeutic agent and/or at least one molecule.

As used herein, the terms "substantially sericin free" or "substantially devoid of sericin" refer to silk fibers in which a majority of the sericin protein has been removed. In an embodiment, silk fibroin that is substantially devoid of sericin refers to silk fibroin having between about 0.01% (w/w) and about 10.0% (w/w) sericin. In an embodiment, silk fibroin that is substantially devoid of sericin refers to silk fibroin having between about 0.01% (w/w) and about 9.0% (w/w) sericin. In an embodiment, silk fibroin that is substantially devoid of sericin refers to silk fibroin having between about 0.01% (w/w) and about 8.0% (w/w) sericin. In an embodiment, silk fibroin that is substantially devoid of sericin refers to silk fibroin having between about 0.01% (w/w) and about 7.0% (w/w) sericin. In an embodiment, silk fibroin that is substantially devoid of sericin refers to silk fibroin having between about 0.01% (w/w) and about 6.0% (w/w) sericin. In an embodiment, silk fibroin that is substantially devoid of sericin refers to silk fibroin having between about 0.01% (w/w) and about 5.0% (w/w) sericin. In an embodiment, silk fibroin that is substantially devoid of sericin refers to silk fibroin having between about 0% (w/w) and about 4.0% (w/w) sericin. In an embodiment, silk fibroin that is substantially devoid of sericin refers to silk fibroin having between about 0.05% (w/w) and about 4.0% (w/w) sericin. In an embodiment, silk fibroin that is substantially devoid of sericin refers to silk fibroin having between about 0.1% (w/w) and about 4.0% (w/w) sericin. In an embodiment, silk fibroin that is substantially devoid of sericin refers to silk fibroin having between about 0.5% (w/w) and about 4.0% (w/w) sericin. In an embodiment, silk fibroin that is substantially devoid of sericin refers to silk fibroin having between about 1.0% (w/w) and about 4.0% (w/w) sericin. In an embodiment, silk fibroin that is substantially devoid of sericin refers to silk fibroin having between about 1.5% (w/w) and about 4.0% (w/w) sericin. In an embodiment, silk fibroin that is substantially devoid of sericin refers to silk fibroin having between about 2.0% (w/w) and about 4.0% (w/w) sericin. In an embodiment, silk fibroin that is substantially devoid of sericin refers to silk fibroin having between about 2.5% (w/w) and about 4.0% (w/w) sericin. In an embodiment, silk fibroin that is substantially devoid of sericin refers to silk fibroin having a sericin content between about 0.01% (w/w) and about 0.1% (w/w). In an embodiment, silk fibroin that is substantially devoid of sericin refers to silk fibroin having a sericin content below about 0.1% (w/w). In an embodiment, silk fibroin that is substantially devoid of sericin refers to silk fibroin having a sericin content below about 0.05% (w/w). In an embodiment, when a silk source is added to a boiling (100° C.) aqueous solution of sodium carbonate for a treatment time of between about 30 minutes to about 60 minutes, a degumming loss of about 26 wt. % to about 31 wt. % is obtained.

As used herein, the term "substantially homogeneous" may refer to pure silk fibroin-based protein fragments that are distributed in a normal distribution about an identified molecular weight. As used herein, the term "substantially homogeneous" may refer to an even distribution of additive, for example vitamin C, throughout a composition of the present disclosure.

As used herein, the term "substantially free of inorganic residuals" means that the composition exhibits residuals of 0.1% (w/w) or less. In an embodiment, substantially free of inorganic residuals refers to a composition that exhibits residuals of 0.05% (w/w) or less. In an embodiment, substantially free of inorganic residuals refers to a composition that exhibits residuals of 0.01% (w/w) or less. In an embodiment, the amount of inorganic residuals is between 0 ppm ("non-detectable" or "ND") and 1000 ppm. In an embodiment, the amount of inorganic residuals is ND to about 500 ppm. In an embodiment, the amount of inorganic residuals is ND to about 400 ppm. In an embodiment, the amount of inorganic residuals is ND to about 300 ppm. In an embodiment, the amount of inorganic residuals is ND to about 200 ppm. In an embodiment, the amount of inorganic residuals is ND to about 100 ppm. In an embodiment, the amount of inorganic residuals is between 10 ppm and 1000 ppm.

As used herein, the term "substantially free of organic residuals" means that the composition exhibits residuals of 0.1% (w/w) or less. In an embodiment, substantially free of organic residuals refers to a composition that exhibits residuals of 0.05% (w/w) or less. In an embodiment, substantially free of organic residuals refers to a composition that exhibits residuals of 0.01% (w/w) or less. In an embodiment, the amount of organic residuals is between 0 ppm ("non-detectable" or "ND") and 1000 ppm. In an embodiment, the amount of organic residuals is ND to about 500 ppm. In an embodiment, the amount of organic residuals is ND to about 400 ppm. In an embodiment, the amount of organic residuals is ND to about 300 ppm. In an embodiment, the amount of organic residuals is ND to about 200 ppm. In an embodiment, the amount of organic residuals is ND to about 100 ppm. In an embodiment, the amount of organic residuals is between 10 ppm and 1000 ppm.

Compositions of the present disclosure exhibit "biocompatibility" meaning that the compositions are compatible with living tissue or a living system by not being toxic, injurious, or physiologically reactive and not causing immunological rejection. Such biocompatibility can be evidenced by participants topically applying compositions of the present disclosure on their skin for an extended period of time. In an embodiment, the extended period of time is about 3 days. In an embodiment, the extended period of time is about 7 days. In an embodiment, the extended period of time is about 14 days. In an embodiment, the extended period of time is about 21 days. In an embodiment, the extended period of time is about 30 days. In an embodiment, the extended period of time is selected from the group consisting of about 1 month, about 2 months, about 3 months, about 4 months, about 5 months, about 6 months, about 7 months, about 8 months, about 9 months, about 10 months, about 11 months, about 12 months, and indefinitely.

Compositions of the present disclosure are "hypoallergenic" meaning that they are relatively unlikely to cause an allergic reaction. Such hypoallergenicity can be evidenced by participants topically applying compositions of the present disclosure on their skin for an extended period of time. In an embodiment, the extended period of time is about 3 days. In an embodiment, the extended period of time is about 7 days. In an embodiment, the extended period of time is about 14 days. In an embodiment, the extended period of time is about 21 days. In an embodiment, the extended period of time is about 30 days. In an embodiment, the extended period of time is selected from the group consisting of about 1 month, about 2 months, about 3 months, about 4 months, about 5 months, about 6 months, about 7 months, about 8 months, about 9 months, about 10 months, about 11 months, about 12 months, and indefinitely.

In an embodiment, a solution of the present disclosure is contacted with a therapeutic agent and/or a molecule prior to forming the article. In an embodiment, molecules include, but are not limited to, antioxidants and enzymes. In an embodiment, molecules include, but are not limited to, Selenium, Ubiquinone derivatives, Thiol-based antioxidants, Saccharide-containing antioxidants, Polyphenols, Botanical extracts, Caffeic acid, Apigenin, Pycnogenol, Resveratrol, Folic acid, Vitamin b12, Vitamin b6, Vitamin b3, Vitamin E, Vitamin C and derivatives thereof, Vitamin D, Vitamin A, Astaxathin, Lutein, Lycopene, Essential fatty acids (omegas 3 and 6), Iron, Zinc, magnesium, Flavonoids (soy, Curcumin, Silymarin, Pycnongeol), Growth factors, aloe, hyaluronic acid, extracellular matrix proteins, cells, nucleic acids, biomarkers, biological reagents, zinc oxide, benzyol peroxide, retnoids, titanium, allergens in a known dose (for sensitization treatment), essential oils including, but not limited to, lemongrass or rosemary oil, and fragrances. Therapeutic agents include, but are not limited to, small molecules, drugs, proteins, peptides and nucleic acids. In an embodiment, a silk film of the present disclosure includes a molecule that is a vitamin, such as vitamin C, vitamin A and vitamin E. In an embodiment, a solution of the present disclosure is contacted with an allergen of known quantity prior to forming the article. Allergens include but are not limited to milk, eggs, peanuts, tree nuts, fish, shellfish, soy and wheat. Known doses of allergen loaded within a silk article can be released at a known rate for controlled exposure allergy study, tests and sensitization treatment.

In an embodiment, a solution of the present disclosure is used to create an article with microneedles by standard methods known to one in the art for controlled delivery of molecules or therapeutic agents to or through the skin.

As used herein, the term "fibroin" includes silkworm fibroin and insect or spider silk protein. In an embodiment, fibroin is obtained from Bombyx mori.

Figure 62A:
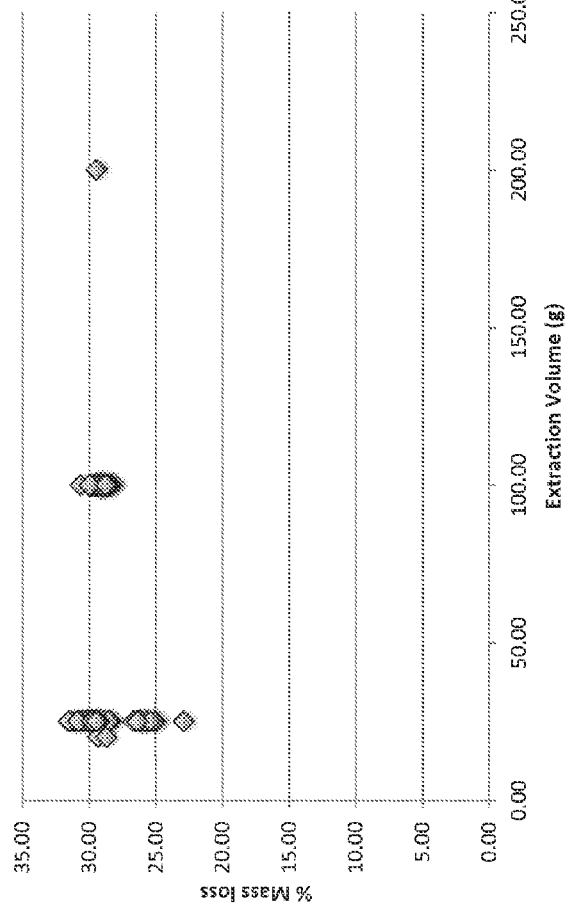
FIGS. 62A and 62B are graphs representing the effect of extraction volume on % mass loss.
Figure 62B:
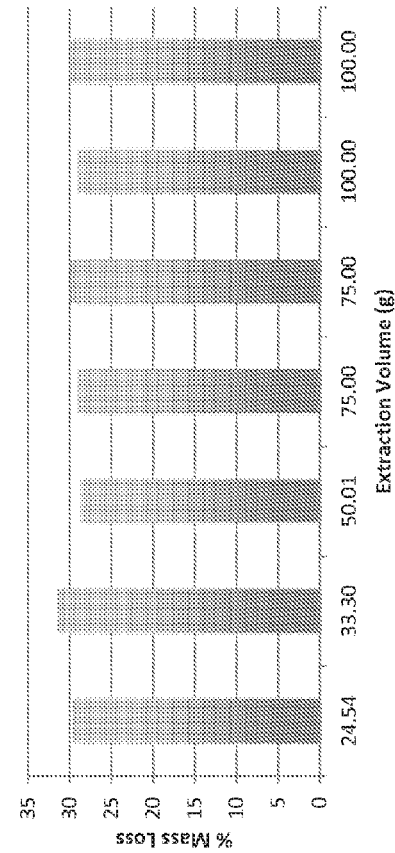
Figure 64:
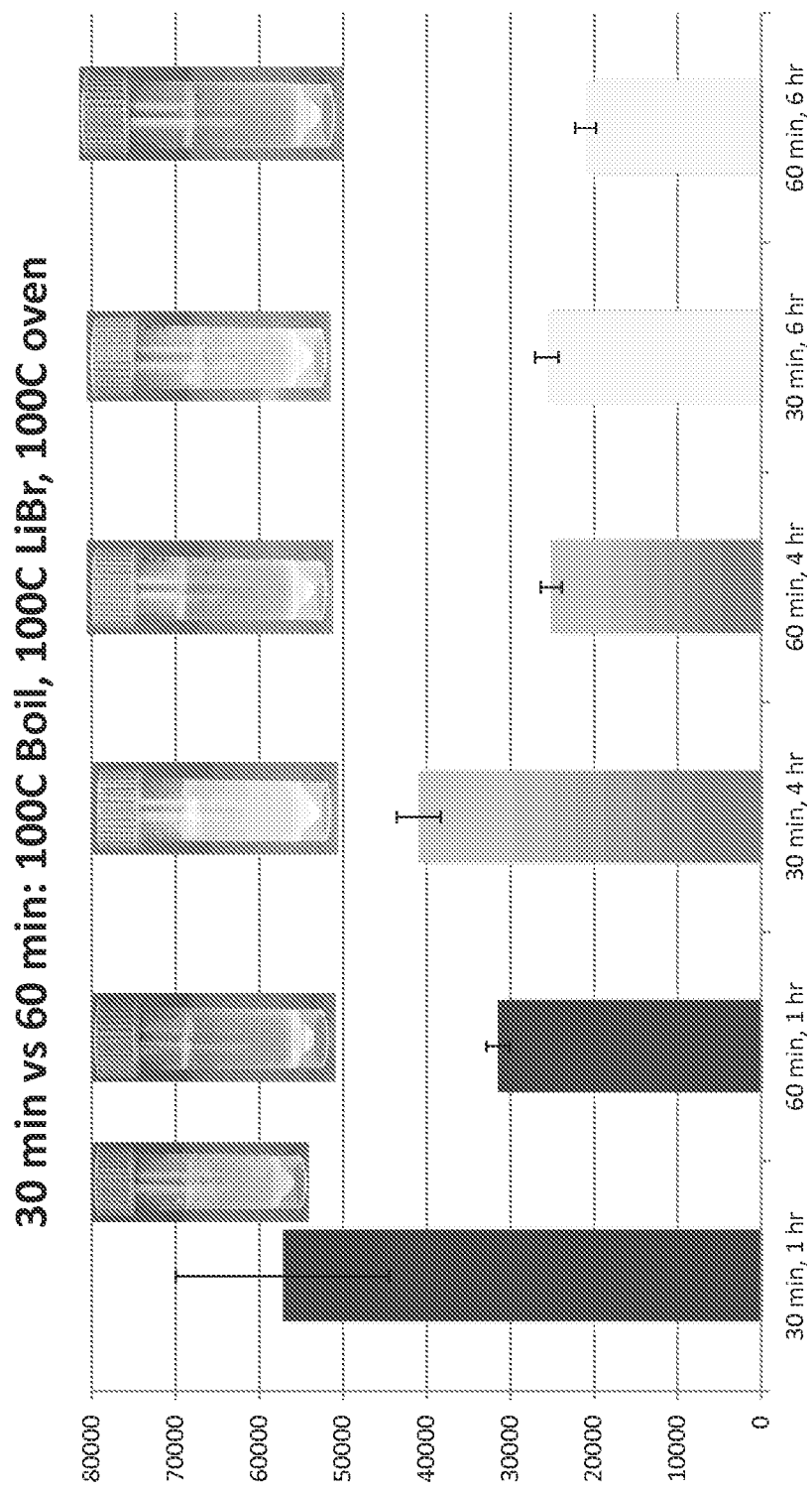
FIG. 64 is a graph summarizing the effect of Extraction Time on Molecular Weight of silk processed under the conditions of 100° C. Extraction Temperature, 100° C. LiBr and 100° C. Oven Dissolution (Oven/Dissolution Time was varied).
Figure 65:
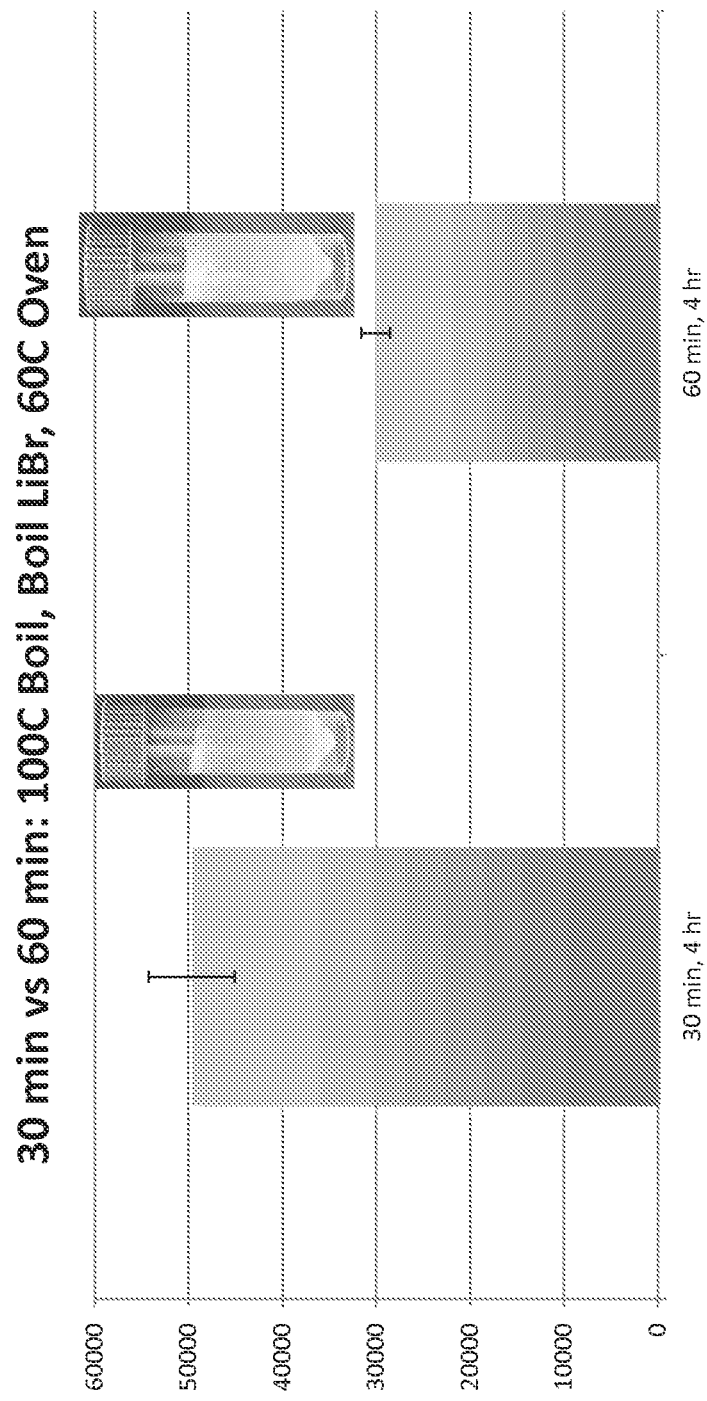
FIG. 65 is a graph summarizing the effect of Extraction Time on Molecular Weight of silk processed under the conditions of 100° C. Extraction Temperature, boiling LiBr and 60° C. Oven Dissolution (Oven/Dissolution Time was varied).
Figure 66:
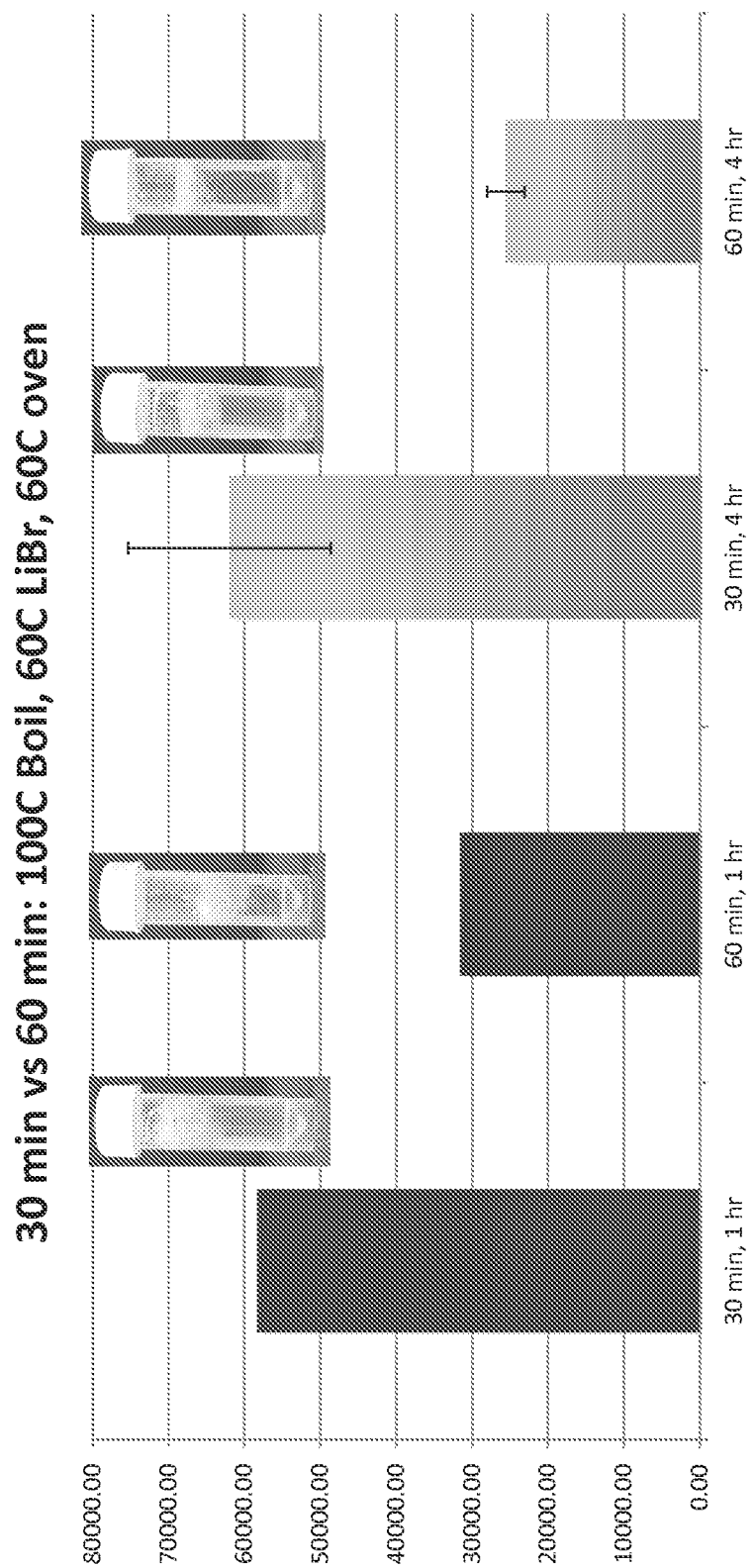
FIG. 66 is a graph summarizing the effect of Extraction Time on Molecular Weight of silk processed under the conditions of 100° C. Extraction Temperature, 60° C. LiBr and 60° C. Oven Dissolution (Oven/Dissolution Time was varied).
Figure 67:
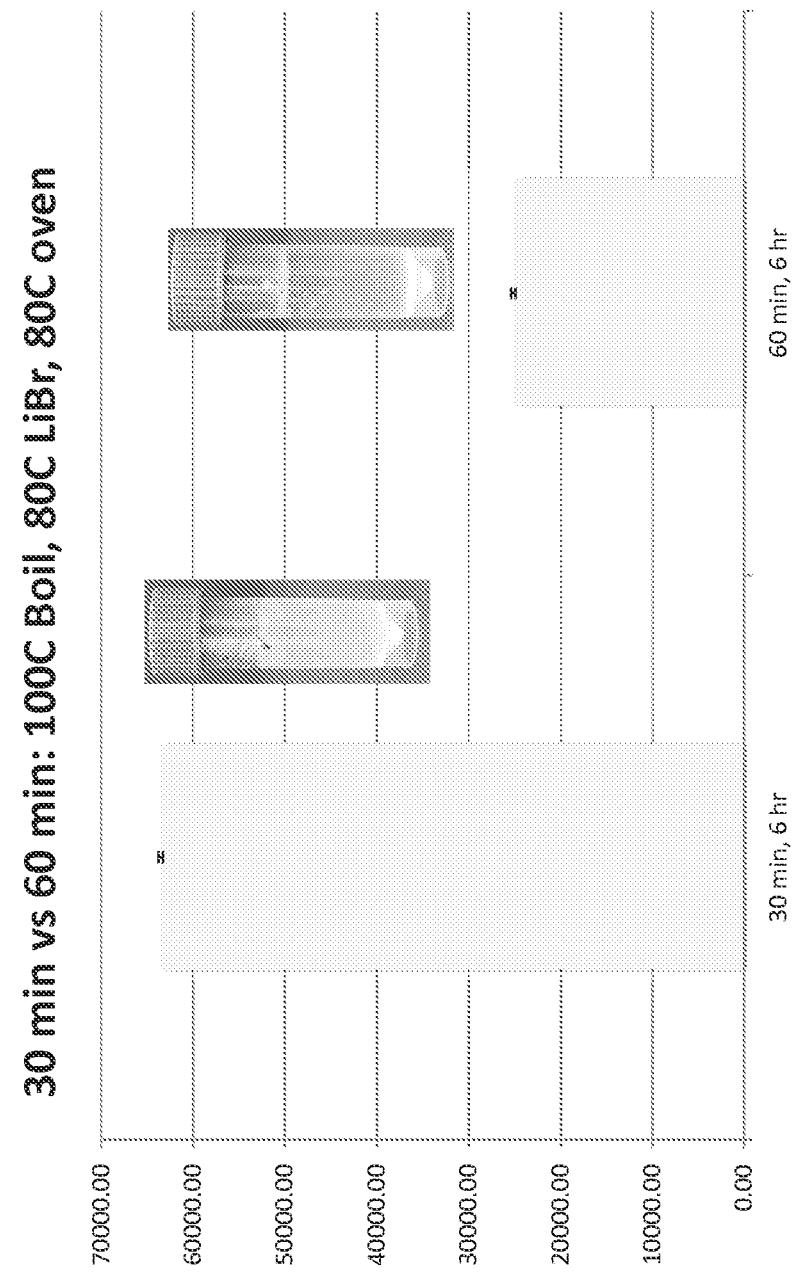
FIG. 67 is a graph summarizing the effect of Extraction Time on Molecular Weight of silk processed under the conditions of 100° C. Extraction Temperature, 80° C. LiBr and 80° C. Oven Dissolution (Oven/Dissolution Time was varied).
Figure 68:
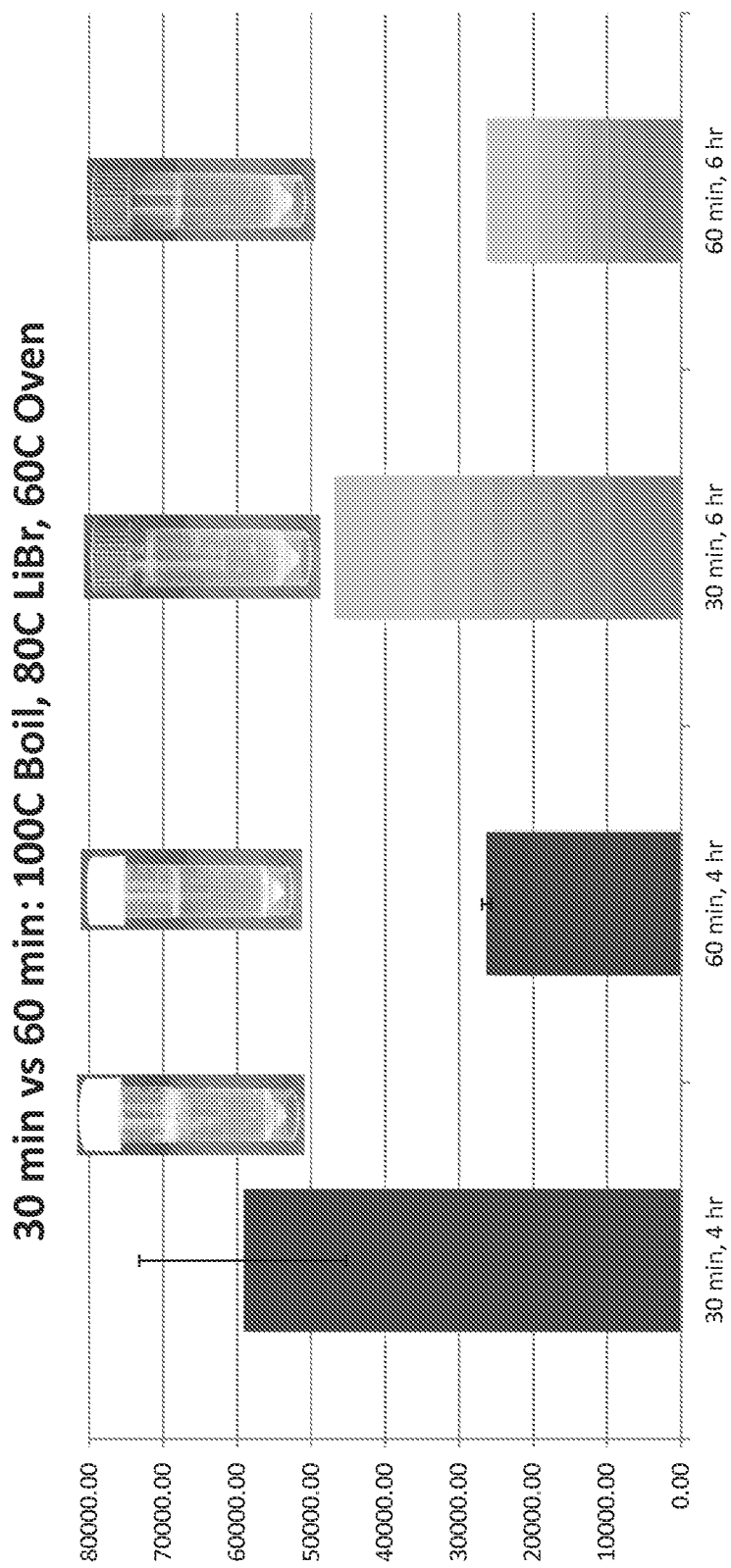
FIG. 68 is a graph summarizing the effect of Extraction Time on Molecular Weight of silk processed under the conditions of 100° C. Extraction Temperature, 80° C. LiBr and 60° C. Oven Dissolution (Oven/Dissolution Time was varied).
Figure 69:
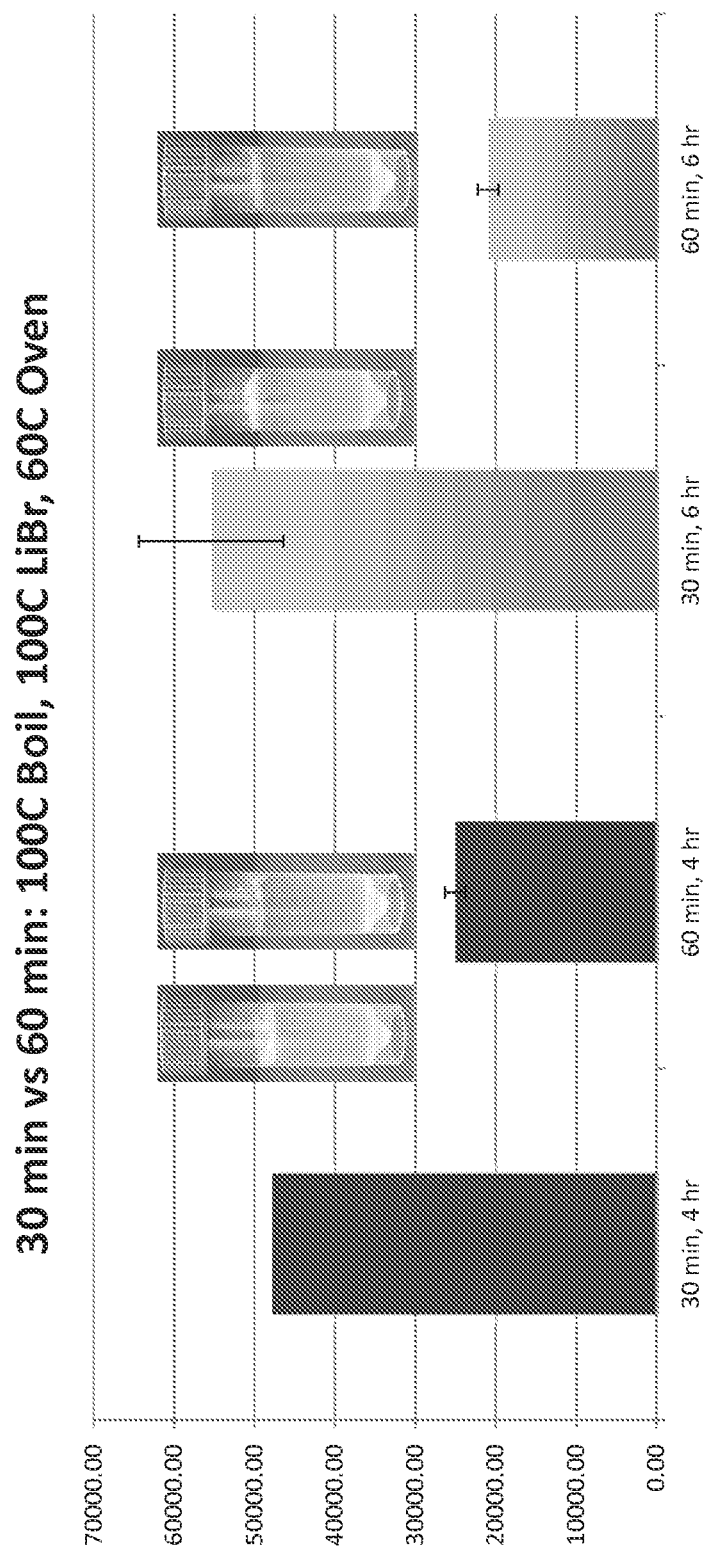
FIG. 69 is a graph summarizing the effect of Extraction Time on Molecular Weight of silk processed under the conditions of 100° C. Extraction Temperature, 100° C. LiBr and 60° C. Oven Dissolution (Oven/Dissolution Time was varied).
Figure 70:
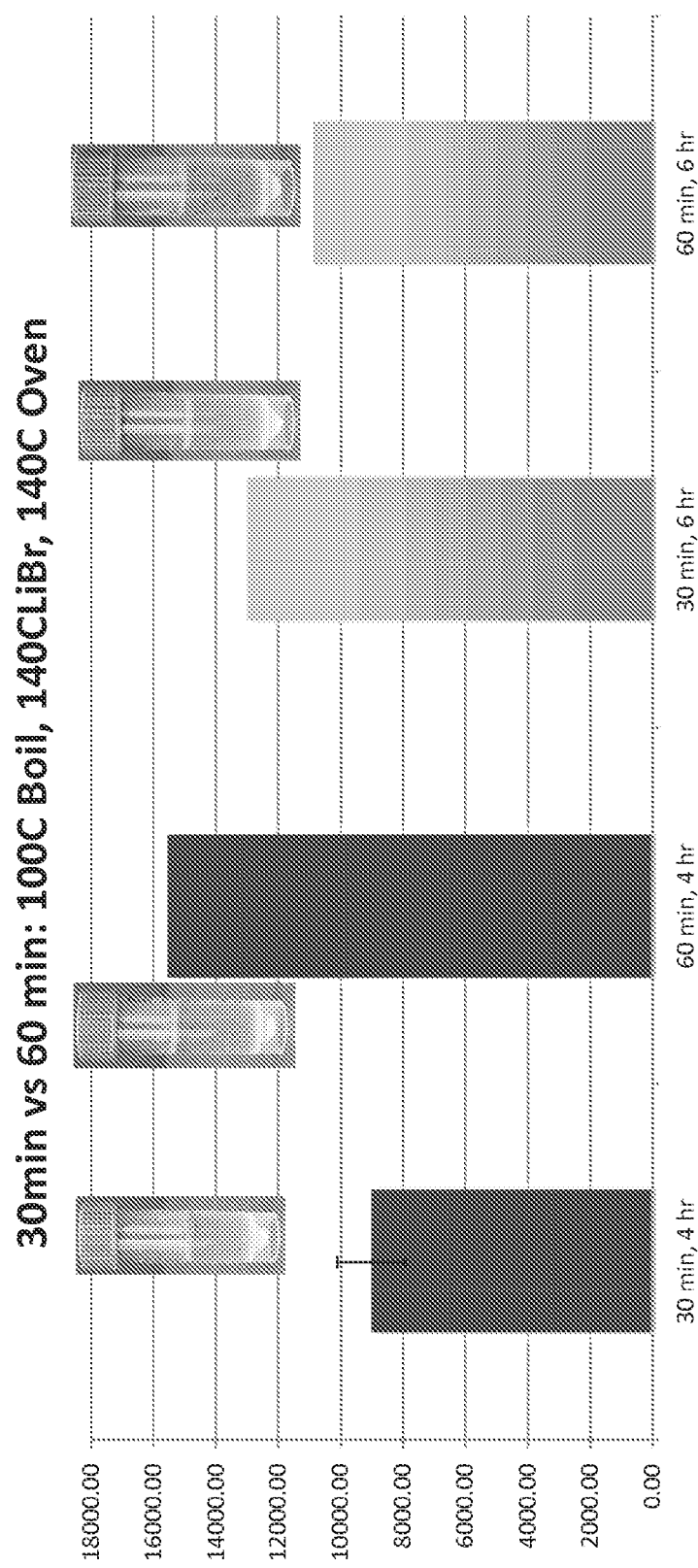
FIG. 70 is a graph summarizing the effect of Extraction Time on Molecular Weight of silk processed under the conditions of 100° C. Extraction Temperature, 140° C. LiBr and 140° C. Oven Dissolution (Oven/Dissolution Time was varied).

FIG. 1 is a flow chart showing various embodiments for producing pure silk fibroin-based protein fragments (SPFs) of the present disclosure. It should be understood that not all of the steps illustrated are necessarily required to fabricate all silk solutions of the present disclosure. As illustrated in FIG. 1, step A, cocoons (heat-treated or non-heat-treated), silk fibers, silk powder or spider silk can be used as the silk source. If starting from raw silk cocoons from Bombyx mori, the cocoons can be cut into small pieces, for example pieces of approximately equal size, step B1. The raw silk is then extracted and rinsed to remove any sericin, step C1a. This results in substantially sericin free raw silk. In an embodiment, water is heated to a temperature between 84° C. and 100° C. (ideally boiling) and then $Na_2CO_3$ (sodium carbonate) is added to the boiling water until the $Na_2CO_3$ is completely dissolved. The raw silk is added to the boiling water/$Na_2CO_3$ (100° C.) and submerged for approximately 15-90 minutes, where boiling for a longer time results in smaller silk protein fragments. In an embodiment, the water volume equals about 0.4× raw silk weight and the $Na_2CO_3$ volume equals about 0.848× raw silk weight. In an embodiment, the water volume equals 0.1× raw silk weight and the $Na_2CO_3$ volume is maintained at 2.12 g/L. This is demonstrated in FIG. 62A and FIG. 62B: silk mass (x-axis) was varied in the same volume of extraction solution (i.e., the same volume of water and concentration of $Na_2CO_3$) achieving sericin removal (substantially sericin free) as demonstrated by an overall silk mass loss of 26 to 31 percent (y-axis). Subsequently, the water dissolved $Na_2CO_3$ solution is drained and excess water/$Na_2CO_3$ is removed from the silk fibroin fibers (e.g., ring out the fibroin extract by hand, spin cycle using a machine, etc.). The resulting silk fibroin extract is rinsed with warm to hot water to remove any remaining adsorbed sericin or contaminate, typically at a temperature range of about 40° C. to about 80° C., changing the volume of water at least once (repeated for as many times as required). The resulting silk fibroin extract is a substantially sericin-depleted silk fibroin. In an embodiment, the resulting silk fibroin extract is rinsed with water at a temperature of about 60° C. In an embodiment, the volume of rinse water for each cycle equals 0.1 L to 0.2 L× raw silk weight. It may be advantageous to agitate, turn or circulate the rinse water to maximize the rinse effect. After rinsing, excess water is removed from the extracted silk fibroin fibers (e.g., ring out fibroin extract by hand or using a machine). Alternatively, methods known to one skilled in the art such as pressure, temperature, or other reagents or combinations thereof may be used for the purpose of sericin extraction. Alternatively, the silk gland (100% sericin free silk protein) can be removed directly from a worm. This would result in liquid silk protein, without any alteration of the protein structure, free of sericin.

Figure 3:
FIG. 3 is a photograph showing dry extracted silk fibroin.

The extracted fibroin fibers are then allowed to dry completely. FIG. 3 is a photograph showing dry extracted silk fibroin. Once dry, the extracted silk fibroin is dissolved using a solvent added to the silk fibroin at a temperature between ambient and boiling, step C1b. In an embodiment, the solvent is a solution of Lithium bromide (LiBr) (boiling for LiBr is 140° C.). Alternatively, the extracted fibroin fibers are not dried but wet and placed in the solvent; solvent concentration can then be varied to achieve similar concentrations as to when adding dried silk to the solvent. The final concentration of LiBr solvent can range from 0.1M to 9.3M. FIG. 63 is a table summarizing the Molecular Weights of silk dissolved from different concentrations of Lithium Bromide (LiBr) and from different extraction and dissolution sizes. Complete dissolution of the extracted fibroin fibers can be achieved by varying the treatment time and temperature along with the concentration of dissolving solvent. Other solvents may be used including, but not limited to, phosphate phosphoric acid, calcium nitrate, calcium chloride solution or other concentrated aqueous solutions of inorganic salts. To ensure complete dissolution, the silk fibers should be fully immersed within the already heated solvent solution and then maintained at a temperature ranging from about 60° C. to about 140° C. for 1-168 hrs. In an embodiment, the silk fibers should be fully immersed within the solvent solution and then placed into a dry oven at a temperature of about 100° C. for about 1 hour.

The temperature at which the silk fibroin extract is added to the LiBr solution (or vice versa) has an effect on the time required to completely dissolve the fibroin and on the resulting molecular weight and polydispersity of the final SPF mixture solution. In an embodiment, silk solvent solution concentration is less than or equal to 20% w/v. In addition, agitation during introduction or dissolution may be used to facilitate dissolution at varying temperatures and concentrations. The temperature of the LiBr solution will provide control over the silk protein fragment mixture molecular weight and polydispersity created. In an embodiment, a higher temperature will more quickly dissolve the silk offering enhanced process scalability and mass production of silk solution. In an embodiment, using a LiBr solution heated to a temperature between 80° C.-140° C. reduces the time required in an oven in order to achieve full dissolution. Varying time and temperature at or above 60° C. of the dissolution solvent will alter and control the MW and polydispersity of the SPF mixture solutions formed from the original molecular weight of the native silk fibroin protein.

Alternatively, whole cocoons may be placed directly into a solvent, such as LiBr, bypassing extraction, step B2. This requires subsequent filtration of silk worm particles from the silk and solvent solution and sericin removal using methods know in the art for separating hydrophobic and hydrophilic proteins such as a column separation and/or chromatography, ion exchange, chemical precipitation with salt and/or pH, and or enzymatic digestion and filtration or extraction, all methods are common examples and without limitation for standard protein separation methods, step C2. Non-heat treated cocoons with the silkworm removed, may alternatively be placed into a solvent such as LiBr, bypassing extraction. The methods described above may be used for sericin separation, with the advantage that non-heat treated cocoons will contain significantly less worm debris.

Dialysis may be used to remove the dissolution solvent from the resulting dissolved fibroin protein fragment solution by dialyzing the solution against a volume of water, step E1. Pre-filtration prior to dialysis is helpful to remove any debris (i.e., silk worm remnants) from the silk and LiBr solution, step D. In one example, a 3 µm or 5 µm filter is used with a flow-rate of 200-300 mL/min to filter a 0.1% to 1.0% silk-LiBr solution prior to dialysis and potential concentration if desired. A method disclosed herein, as described above, is to use time and/or temperature to decrease the concentration from 9.3M LiBr to a range from 0.1M to 9.3M to facilitate filtration and downstream dialysis, particularly when considering creating a scalable process method. Alternatively, without the use of additional time or temperate, a 9.3M LiBr-silk protein fragment solution may be diluted with water to facilitate debris filtration and dialysis. The result of dissolution at the desired time and temperate filtration is a translucent particle-free room temperature shelf-stable silk protein fragment-LiBr solution of a known MW and polydispersity. It is advantageous to change the dialysis water regularly until the solvent has been removed (e.g., change water after 1 hour, 4 hours, and then every 12 hours for a total of 6 water changes). The total number of water volume changes may be varied based on the resulting concentration of solvent used for silk protein dissolution and fragmentation. After dialysis, the final silk solution maybe further filtered to remove any remaining debris (i.e., silk worm remnants).

Alternatively, Tangential Flow Filtration (TFF), which is a rapid and efficient method for the separation and purification of biomolecules, may be used to remove the solvent from the resulting dissolved fibroin solution, step E2. TFF offers a highly pure aqueous silk protein fragment solution and enables scalability of the process in order to produce large volumes of the solution in a controlled and repeatable manner. The silk and LiBr solution may be diluted prior to TFF (20% down to 0.1% silk in either water or LiBr). Pre-filtration as described above prior to TFF processing may maintain filter efficiency and potentially avoids the creation of silk gel boundary layers on the filter's surface as the result of the presence of debris particles. Pre-filtration prior to TFF is also helpful to remove any remaining debris (i.e., silk worm remnants) from the silk and LiBr solution that may cause spontaneous or long-term gelation of the resulting water only solution, step D. TFF, recirculating or single pass, may be used for the creation of water-silk protein fragment solutions ranging from 0.1% silk to 30.0% silk (more preferably, 0.1%-6.0% silk). Different cutoff size TFF membranes may be required based upon the desired concentration, molecular weight and polydispersity of the silk protein fragment mixture in solution. Membranes ranging from 1-100 kDa may be necessary for varying molecular weight silk solutions created for example by varying the length of extraction boil time or the time and temperate in dissolution solvent (e.g., LiBr). In an embodiment, a TFF 5 or 10 kDa membrane is used to purify the silk protein fragment mixture solution and to create the final desired silk-to-water ratio. As well, TFF single pass, TFF, and other methods known in the art, such as a falling film evaporator, may be used to concentrate the solution following removal of the dissolution solvent (e.g., LiBr) (with resulting desired concentration ranging from 0.1% to 30% silk). This can be used as an alternative to standard HFIP concentration methods known in the art to create a water-based solution. A larger pore membrane could also be utilized to filter out small silk protein fragments and to create a solution of higher molecular weight silk with and/or without tighter polydispersity values. FIG. 61 is a table summarizing Molecular Weights for some embodiments of silk protein solutions of the present disclosure. Silk protein solution processing conditions were as follows: 100° C. extraction for 20 min, room temperature rinse, LiBr in 60° C. oven for 4-6 hours. TFF processing conditions for water-soluble films were as follows: 100° C. extraction for 60 min, 60° C. rinse, 100° C. LiBr in 100° C. oven for 60 min. FIGS. 67-78 further demonstrate manipulation of extraction time, LiBr dissolution conditions, and TFF processing and resultant example molecular weights and polydispersities. These examples are not intended to be limiting, but rather to demonstrate the potential of specifying parameters for specific molecular weight silk fragment solutions.

An assay for LiBr and $Na_2CO_3$ detection was performed using an HPLC system equipped with evaporative light scattering detector (ELSD). The calculation was performed by linear regression of the resulting peak areas for the analyte plotted against concentration. More than one sample of a number of formulations of the present disclosure was used for sample preparation and analysis. Generally, four samples of different formulations were weighed directly in a 10 mL volumetric flask. The samples were suspended in 5 mL of 20 mM ammonium formate (pH 3.0) and kept at 2-8° C. for 2 hours with occasional shaking to extract analytes from the film. After 2 hours the solution was diluted with 20 mM ammonium formate (pH 3.0). The sample solution from the volumetric flask was transferred into HPLC vials and injected into the HPLC-ELSD system for the estimation of sodium carbonate and lithium bromide.

The analytical method developed for the quantitation of $Na_2CO_3$ and LiBr in silk protein formulations was found to be linear in the range 10-165 µg/mL, with RSD for injection precision as 2% and 1% for area and 0.38% and 0.19% for retention time for sodium carbonate and lithium bromide respectively. The analytical method can be applied for the quantitative determination of sodium carbonate and lithium bromide in silk protein formulations.

Figure 4:
FIG. 4 is a photograph showing an embodiment of a SPF in the form of a solution of the present disclosure.
Figures 6A, 6B, 6C, 6D:
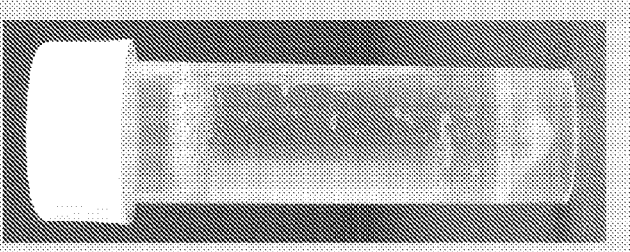
FIGS. 6A-6D are photographs showing dissolved silk in room temperature LiBr solutions dissolved in a 60° C. oven for 6 hours (sericin extraction temperature and time were varied).
Figure 8A:
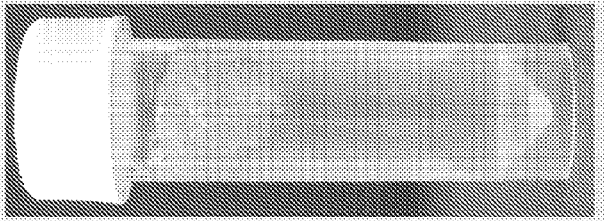
FIGS. 8A-8D are photographs showing dissolved silk in room temperature LiBr solutions dissolved in a 60° C. oven for 12 hours (sericin extraction temperature and time were varied).
Figure 8B:
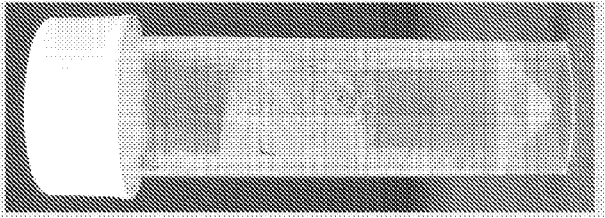
Figure 8C:
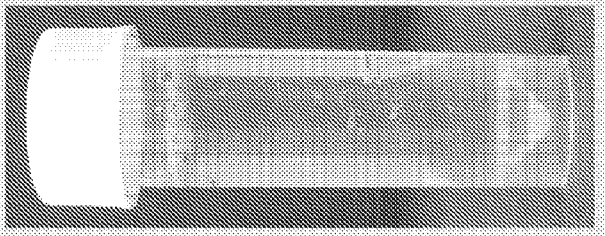
Figure 8D:
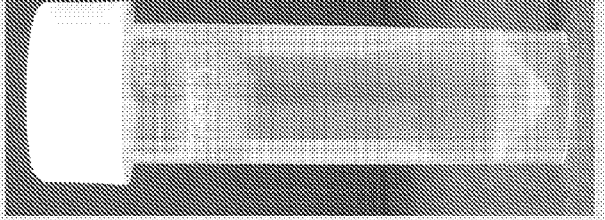
Figure 9A:
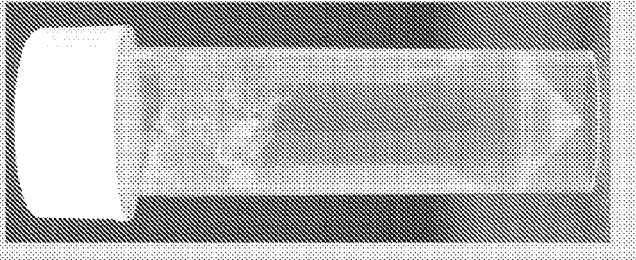
FIGS. 9A-9D are photographs showing dissolved silk in room temperature LiBr solutions dissolved in a 60° C. oven for 24 hours (sericin extraction temperature and time were varied).
Figure 9B:
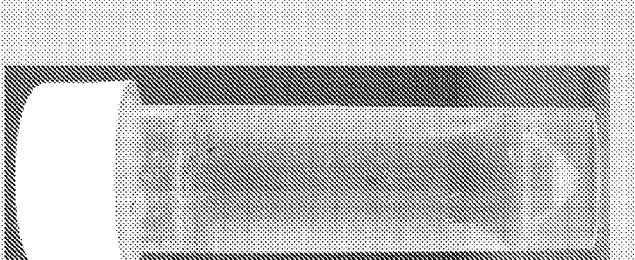
Figure 9C:
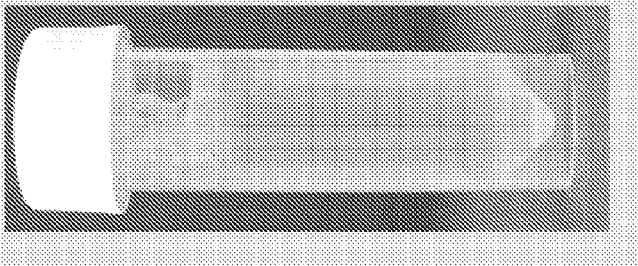
Figure 9D:
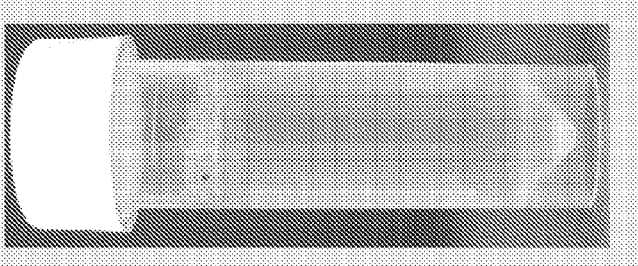
Figures 10A, 10B, 10C, 10D:
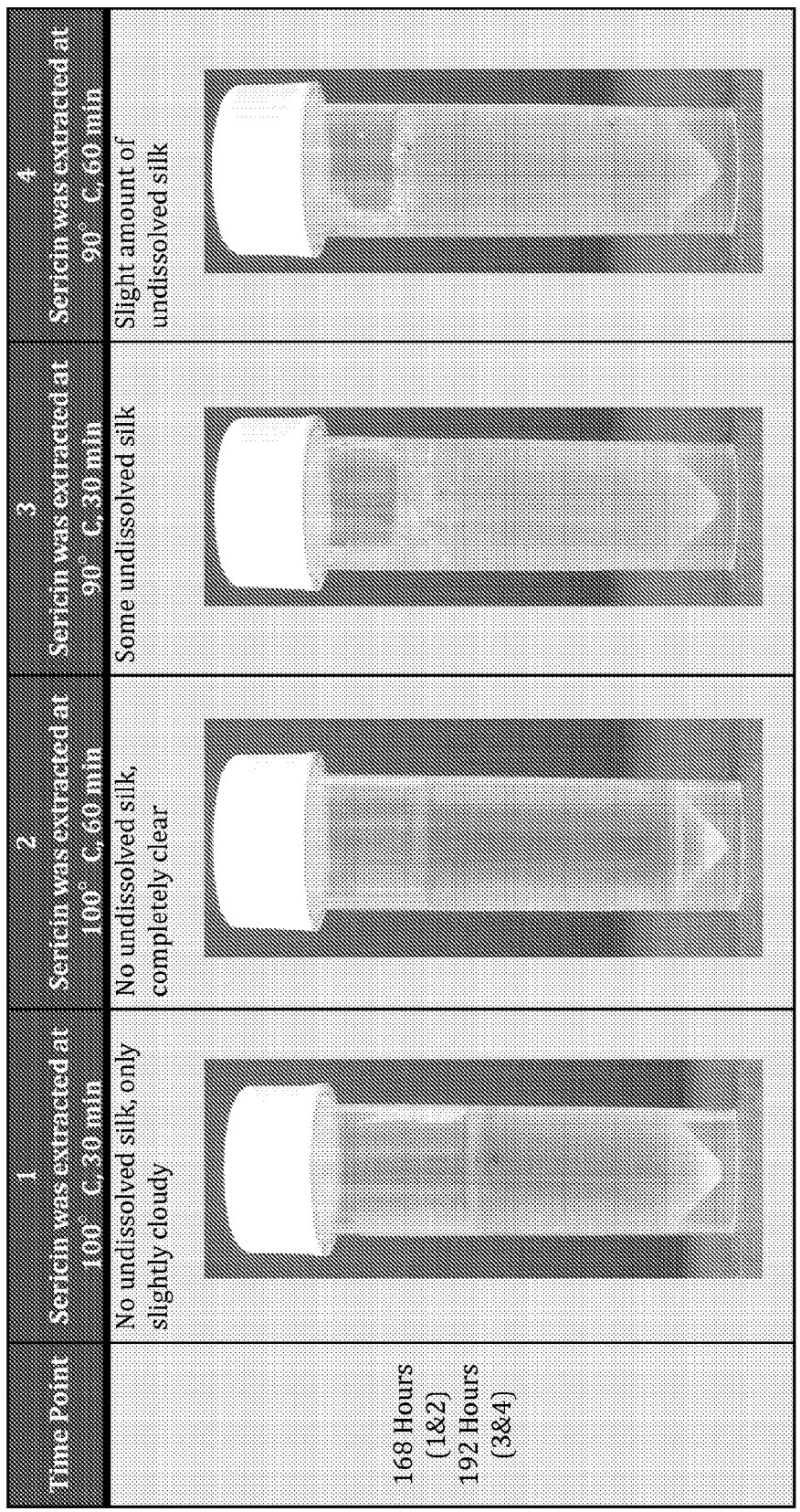
FIGS. 10A-10D are photographs showing dissolved silk in room temperature LiBr solutions dissolved in a 60° C. oven for 168/192 hours (sericin extraction temperature and time were varied).
Figures 11A, 11B, 11C:
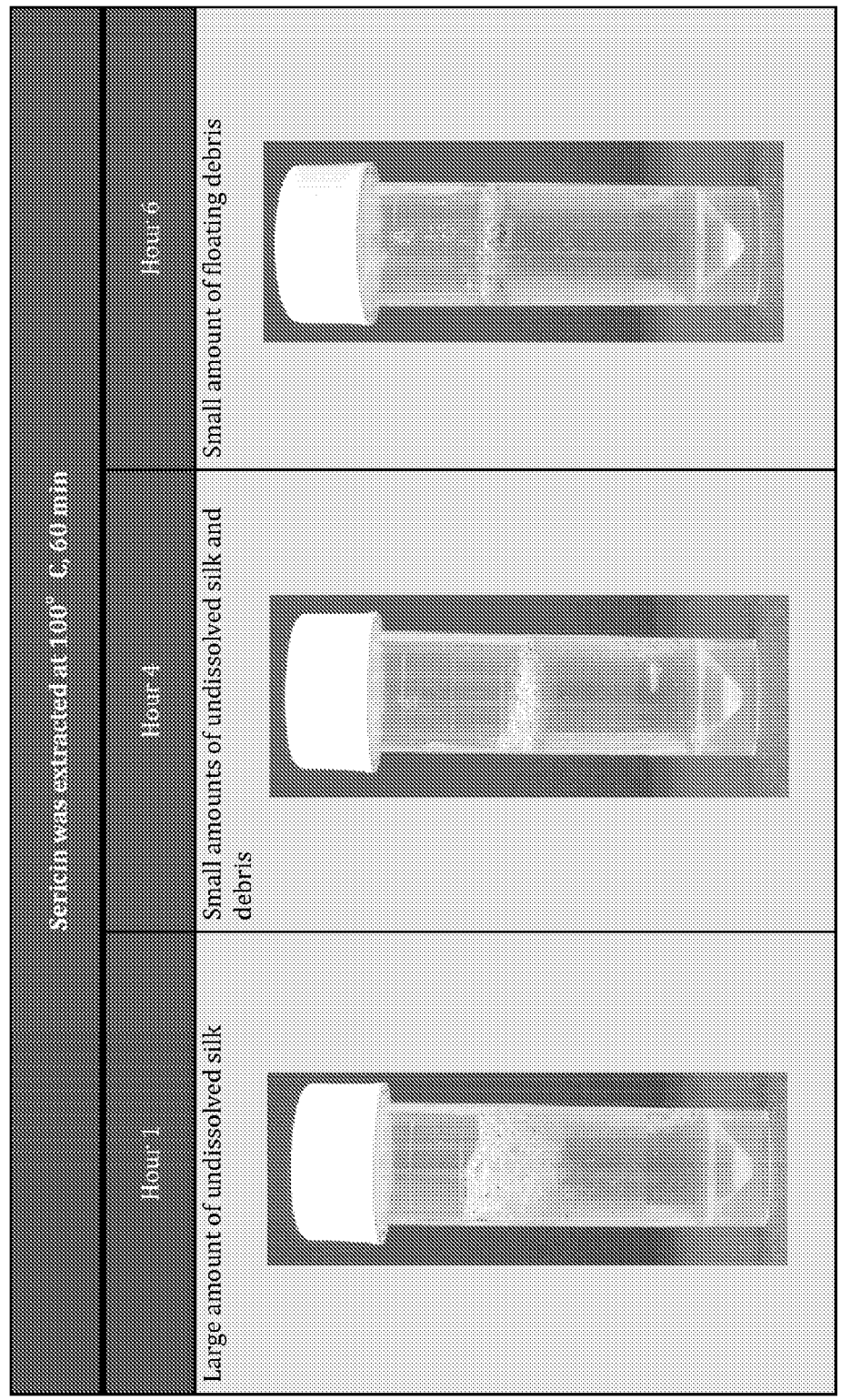
FIGS. 11A-11C are photographs showing dissolved silk in room temperature LiBr solutions dissolved in 60° C. oven for 1, 4, and 6 hours, where sericin extraction was completed at 100° C. for 60 min.
Figures 12A, 12B, 12C, 12D:
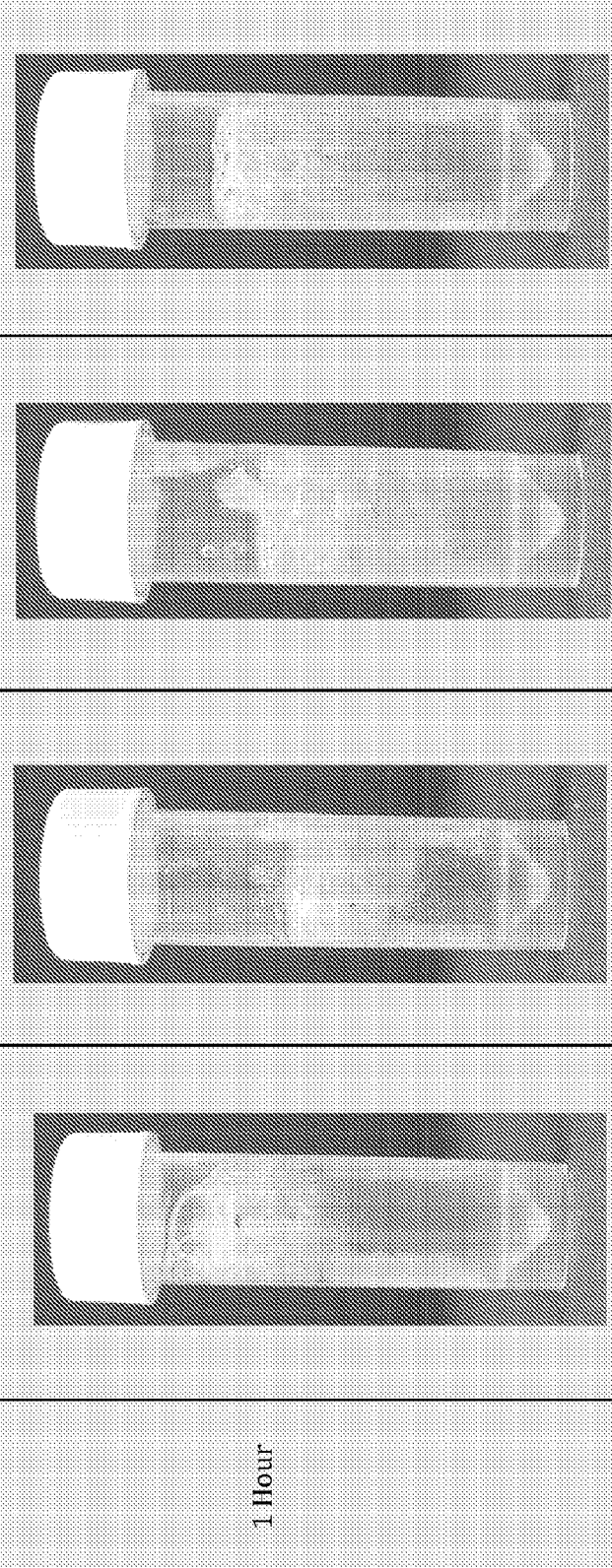
FIGS. 12A-12D are photographs showing dissolved silk in 60° C. LiBr solutions dissolved in a 60° C. oven for 1 hour (sericin extraction temperature and time were varied).
Figures 14, 14A, 14B, 14C, 14D:
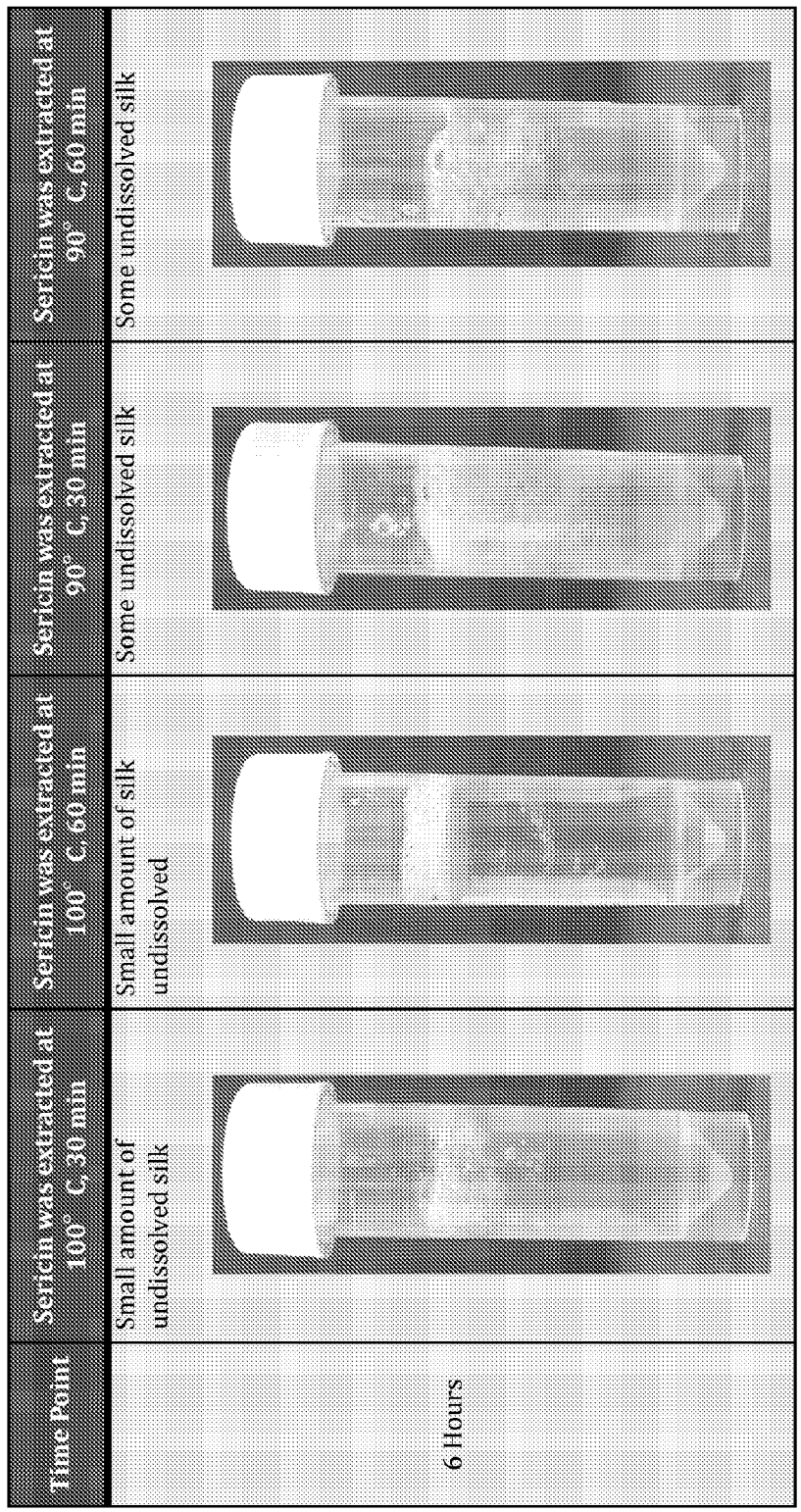
FIGS. 14A-14D are photographs showing dissolved silk in 60° C. LiBr solutions dissolved in a 60° C. oven for 6 hours (sericin extraction temperature and time were varied).
Figure 15A:
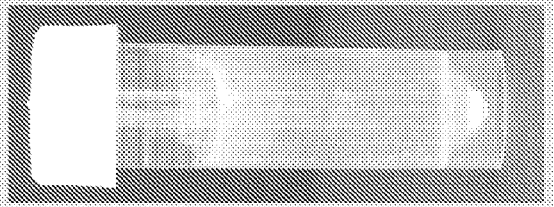
FIGS. 15A-15D are photographs showing dissolved silk in 80° C. LiBr solutions dissolved in a 60° C. oven for 1 hour (sericin extraction temperature and time were varied).
Figure 15B:
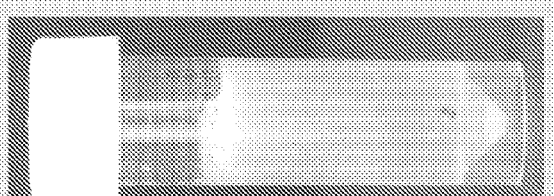
Figure 15C:
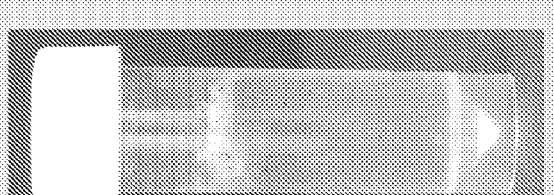
Figure 15D:
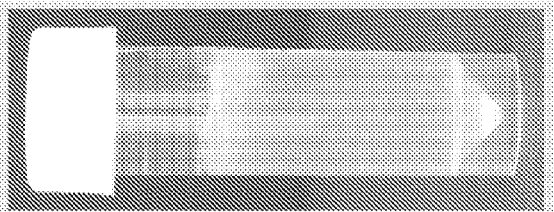
Figures 16A, 16B, 16C, 16D:
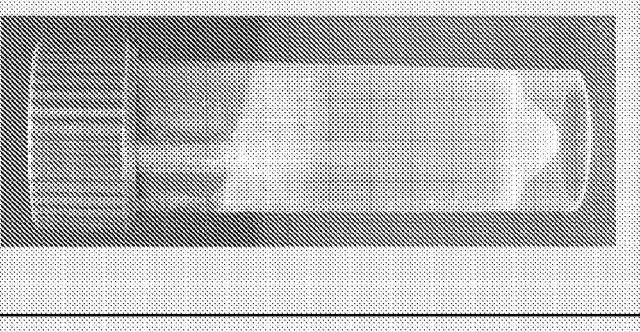
FIGS. 16A-16D are photographs showing dissolved silk in 80° C. LiBr solutions dissolved in a 60° C. oven for 4 hours (sericin extraction temperature and time were varied).
Figure 17A:
FIGS. 17A-17D are photographs showing dissolved silk in 80° C. LiBr solutions dissolved in a 60° C. oven for 4 hours (sericin extraction temperature and time were varied).
Figure 17B:
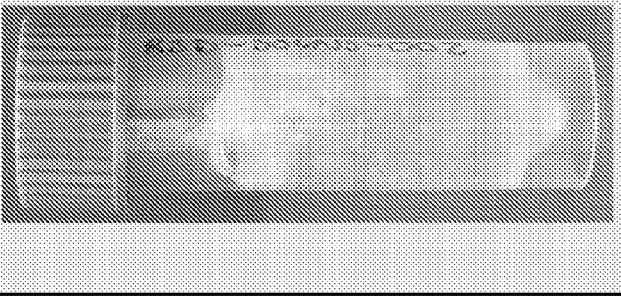
Figure 17C:
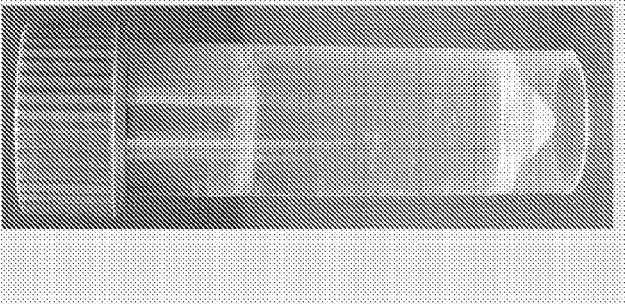
Figure 17D:
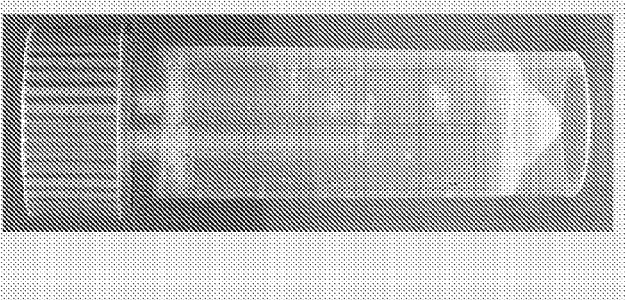
Figures 19A, 19B, 19C, 19D:
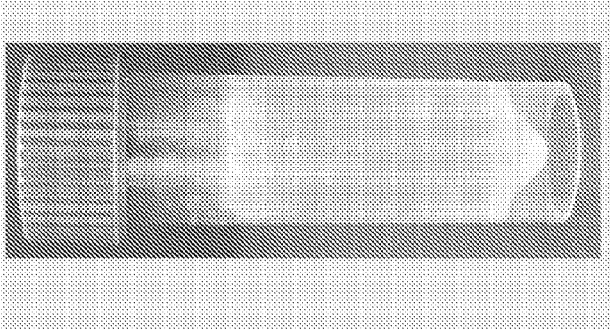
FIGS. 19A-19D are photographs showing dissolved silk in 100° C. LiBr solutions dissolved in a 60° C. oven for 4 hours (sericin extraction temperature and time were varied).
Figures 22A, 22B, 22C, 22D:
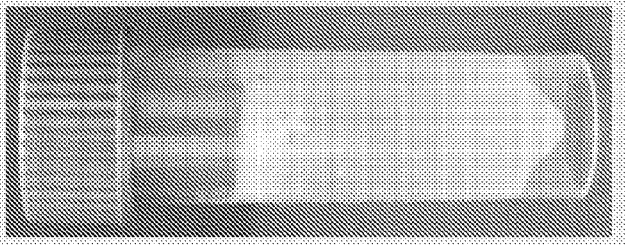
FIGS. 22A-22D are photographs showing dissolved silk in 140° C. (boiling point for LiBr) LiBr solutions dissolved in a 60° C. oven for 4 hours (sericin extraction temperature and time were varied).
Figure 24A:
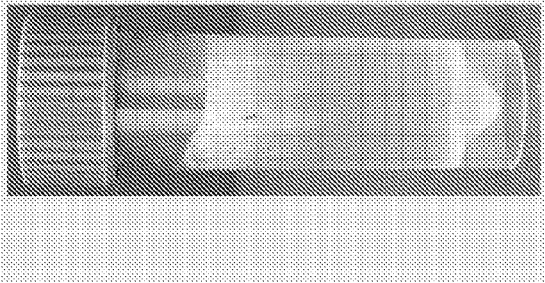
FIGS. 24A-24D are photographs showing dissolved silk in 80° C. LiBr solutions dissolved in a 80° C. oven for 1 hour (sericin extraction temperature and time were varied).
Figure 24B:
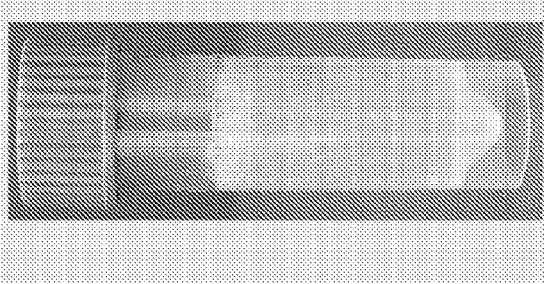
Figure 24C:
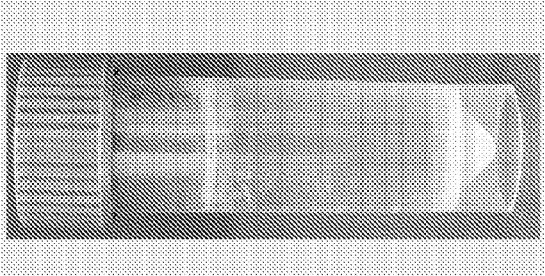
Figure 24D:
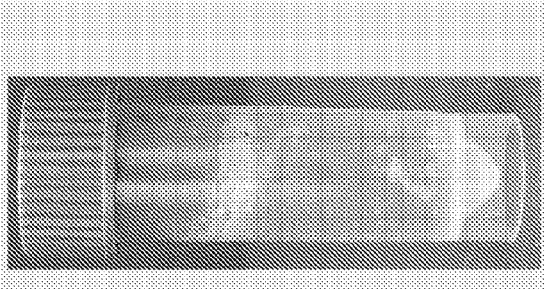
Figures 25A, 25B, 25C, 25D:
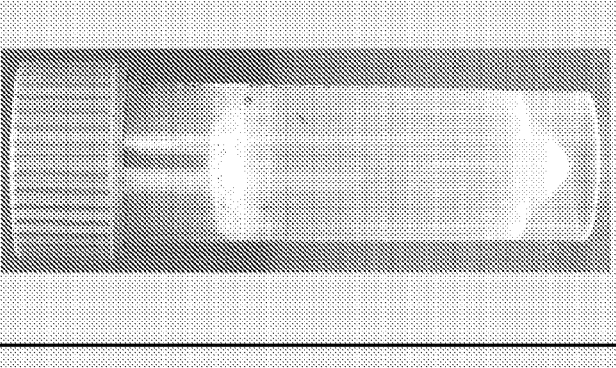
FIGS. 25A-25D are photographs showing dissolved silk in 80° C. LiBr solutions dissolved in a 80° C. oven for 4 hours (sericin extraction temperature and time were varied).
Figure 26A:
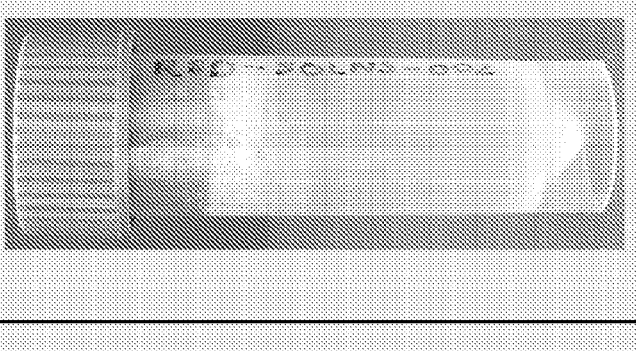
FIGS. 26A-26D are photographs showing dissolved silk in 80° C. LiBr solutions dissolved in a 80° C. oven for 6 hours (sericin extraction temperature and time were varied).
Figure 26B:
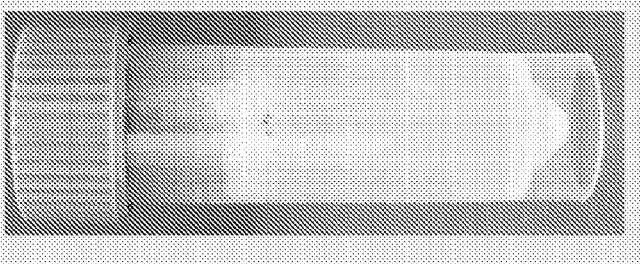
Figure 26C:
Figure 26D:
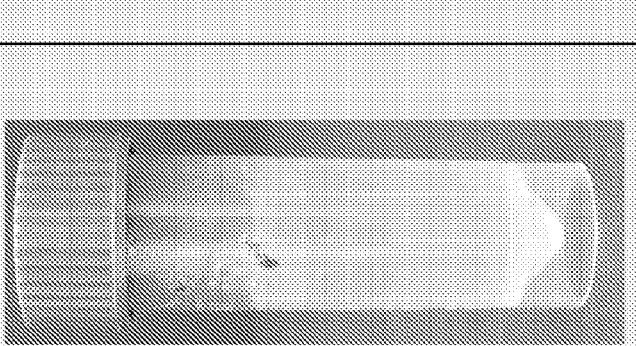
Figure 29D:
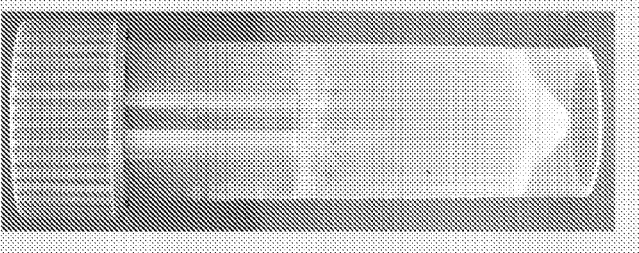
FIGS. 29A-29D are photographs showing dissolved silk in 100° C. LiBr solutions dissolved in a 100° C. oven for 6 hours (sericin extraction temperature and time were varied).
Figure 29C:
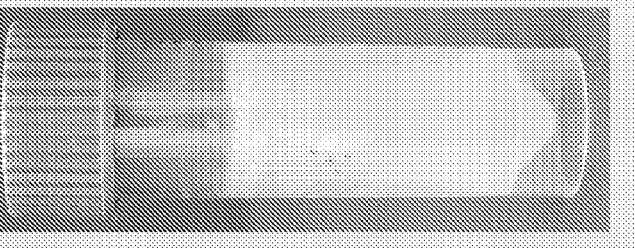
Figure 29B:
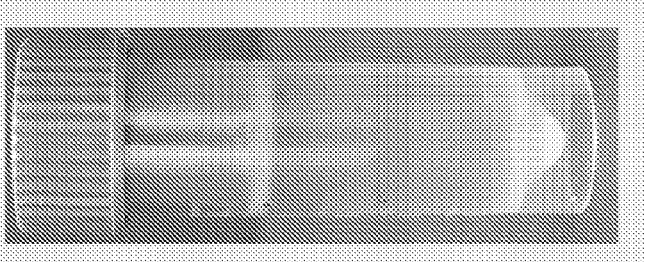
Figure 29A:
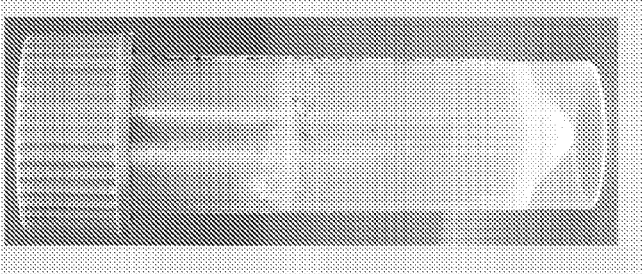
Figures 30A, 30B, 30C, 30D:
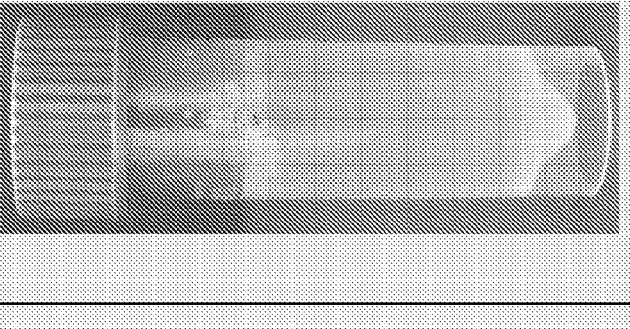
FIGS. 30A-30D are photographs showing dissolved silk in 140° C. (boiling point for LiBr) LiBr solutions dissolved in a 120° C. oven for 1 hour (sericin extraction temperature and time were varied).
Figure 31A:
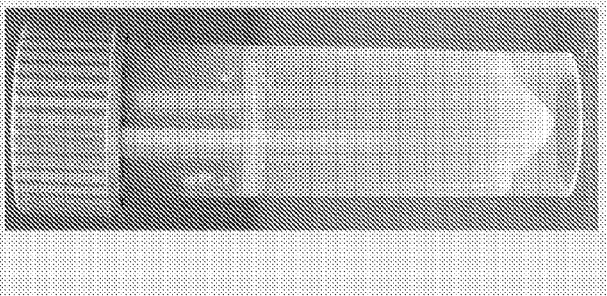
FIGS. 31A-31D are photographs showing dissolved silk in 140° C. (boiling point for LiBr) LiBr solutions dissolved in a 120° C. oven for 4 hours (sericin extraction temperature and time were varied).
Figure 31B:
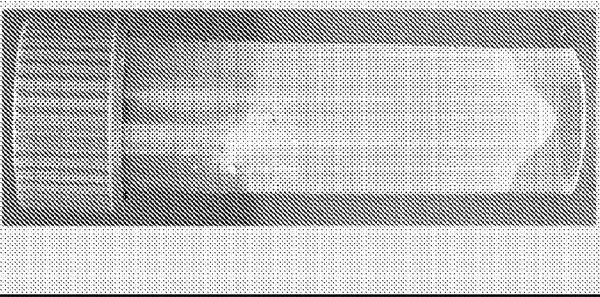
Figure 31C:
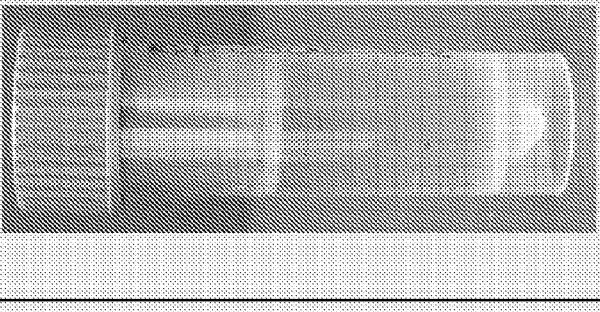
Figure 31D:
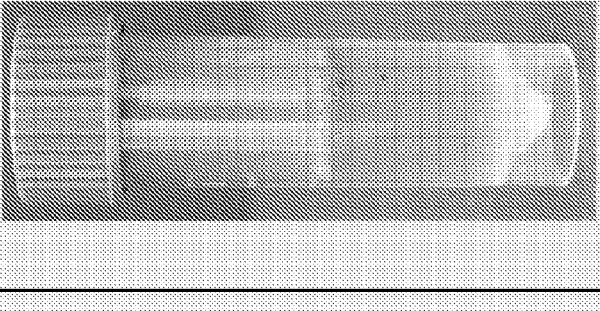

The final silk protein fragment solution, as shown in FIG. 4, is pure silk protein fragments and water with PPM to undetectable levels of particulate debris and/or process contaminants, including LiBr and $Na_2CO_3$. FIG. 55 and FIG. 58 are tables summarizing LiBr and $Na_2CO_3$ concentrations in solutions of the present disclosure. In FIG. 55, the processing conditions included 100° C. extraction for 60 min, 60° C. rinse, 100° C. LiBr in 100° C. oven for 60 min. TFF conditions including pressure differential and number of dia-filtration volumes were varied. In FIG. 58, the processing conditions included 100° C. boil for 60 min, 60° C. rinse, LiBr in 60° C. oven for 4-6 hours. In an embodiment, a SPF composition of the present disclosure is not soluble in an aqueous solution due to the crystallinity of the protein. In an embodiment, a SPF composition of the present disclosure is soluble in an aqueous solution. In an embodiment, the SPFs of a composition of the present disclosure include a crystalline portion of about two-thirds and an amorphous region of about one-third. In an embodiment, the SPFs of a composition of the present disclosure include a crystalline portion of about one-half and an amorphous region of about one-half. In an embodiment, the SPFs of a composition of the present disclosure include a 99% crystalline portion and a 1% amorphous region. In an embodiment, the SPFs of a composition of the present disclosure include a 95% crystalline portion and a 5% amorphous region. In an embodiment, the SPFs of a composition of the present disclosure include a 90% crystalline portion and a 10% amorphous region. In an embodiment, the SPFs of a composition of the present disclosure include a 85% crystalline portion and a 15% amorphous region. In an embodiment, the SPFs of a composition of the present disclosure include a 80% crystalline portion and a 20% amorphous region. In an embodiment, the SPFs of a composition of the present disclosure include a 75% crystalline portion and a 25% amorphous region. In an embodiment, the SPFs of a composition of the present disclosure include a 70% crystalline portion and a 30% amorphous region. In an embodiment, the SPFs of a composition of the present disclosure include a 65% crystalline portion and a 35% amorphous region. In an embodiment, the SPFs of a composition of the present disclosure include a 60% crystalline portion and a 40% amorphous region. In an embodiment, the SPFs of a composition of the present disclosure include a 50% crystalline portion and a 50% amorphous region. In an embodiment, the SPFs of a composition of the present disclosure include a 40% crystalline portion and a 60% amorphous region. In an embodiment, the SPFs of a composition of the present disclosure include a 35% crystalline portion and a 65% amorphous region. In an embodiment, the SPFs of a composition of the present disclosure include a 30% crystalline portion and a 70% amorphous region. In an embodiment, the SPFs of a composition of the present disclosure include a 25% crystalline portion and a 75% amorphous region. In an embodiment, the SPFs of a composition of the present disclosure include a 20% crystalline portion and a 80% amorphous region. In an embodiment, the SPFs of a composition of the present disclosure include a 15% crystalline portion and a 85% amorphous region. In an embodiment, the SPFs of a composition of the present disclosure include a 10% crystalline portion and a 90% amorphous region. In an embodiment, the SPFs of a composition of the present disclosure include a 5% crystalline portion and a 90% amorphous region. In an embodiment, the SPFs of a composition of the present disclosure include a 1% crystalline portion and a 99% amorphous region.

A unique feature of the SPF compositions of the present disclosure are shelf stability (they will not slowly or spontaneously gel when stored in an aqueous solution and there is no aggregation of fragments and therefore no increase in molecular weight over time), from 10 days to 3 years depending on storage conditions, percent silk, and number of shipments and shipment conditions. Additionally pH may be altered to extend shelf-life and/or support shipping conditions by preventing premature folding and aggregation of the silk. In an embodiment, a SPF solution composition of the present disclosure has a shelf stability for up to 2 weeks at room temperature (RT). In an embodiment, a SPF solution composition of the present disclosure has a shelf stability for up to 4 weeks at RT. In an embodiment, a SPF solution composition of the present disclosure has a shelf stability for up to 6 weeks at RT. In an embodiment, a SPF solution composition of the present disclosure has a shelf stability for up to 8 weeks at RT. In an embodiment, a SPF solution composition of the present disclosure has a shelf stability for up to 10 weeks at RT. In an embodiment, a SPF solution composition of the present disclosure has a shelf stability for up to 12 weeks at RT. In an embodiment, a SPF solution composition of the present disclosure has a shelf stability ranging from about 4 weeks to about 52 weeks at RT. Table 1 below shows shelf stability test results for embodiments of SPF compositions of the present disclosure.

TABLE 1

Shelf Stability of SPF Compositions of the Present Disclosure

| % Silk | Temperature | Time to Gelation |
| --- | --- | --- |
| 2 | RT | 4 weeks |
| 2 | 4 C. | >9 weeks |
| 4 | RT | 4 weeks |
| 4 | 4 C. | >9 weeks |
| 6 | RT | 2 weeks |
| 6 | 4 C. | >9 weeks |

A known additive such as a vitamin (e.g., vitamin C) can be added to a SPF composition of the present disclosure to create a gel that is stable from 10 days to 3 years at room temperature (RT). Both examples, a SPF composition and the same with an additive, can be lyophilized for enhanced storage control ranging from 10 days to 10 years depending on storage and shipment conditions. The lyophilized silk powder can also be used as a raw ingredient in the medical, consumer, and electronic markets. Additionally, lyophilized silk powder can be resuspended in water, HFIP, or organic solution following storage to create silk solutions of varying concentrations, including higher concentration solutions than those produced initially. In another embodiment, the silk fibroin-based protein fragments are dried using a rototherm evaporator or other methods known in the art for creating a dry protein form containing less than 10% water by mass.

Either the silk fragment-water solutions or the lyophilized silk protein fragment mixture can be sterilized following standard methods in the art not limited to filtration, heat, radiation or e-beam. It is anticipated that the silk protein fragment mixture, because of its shorter protein polymer length, will withstand sterilization better than intact silk protein solutions described in the art. Additionally, silk articles created from the SPF mixtures described herein may be sterilized as appropriate to application. For example, a silk film loaded with a molecule to be used in medical applications with an open wound/incision, may be sterilized standard methods such as by radiation or e-beam.

Figure 2:
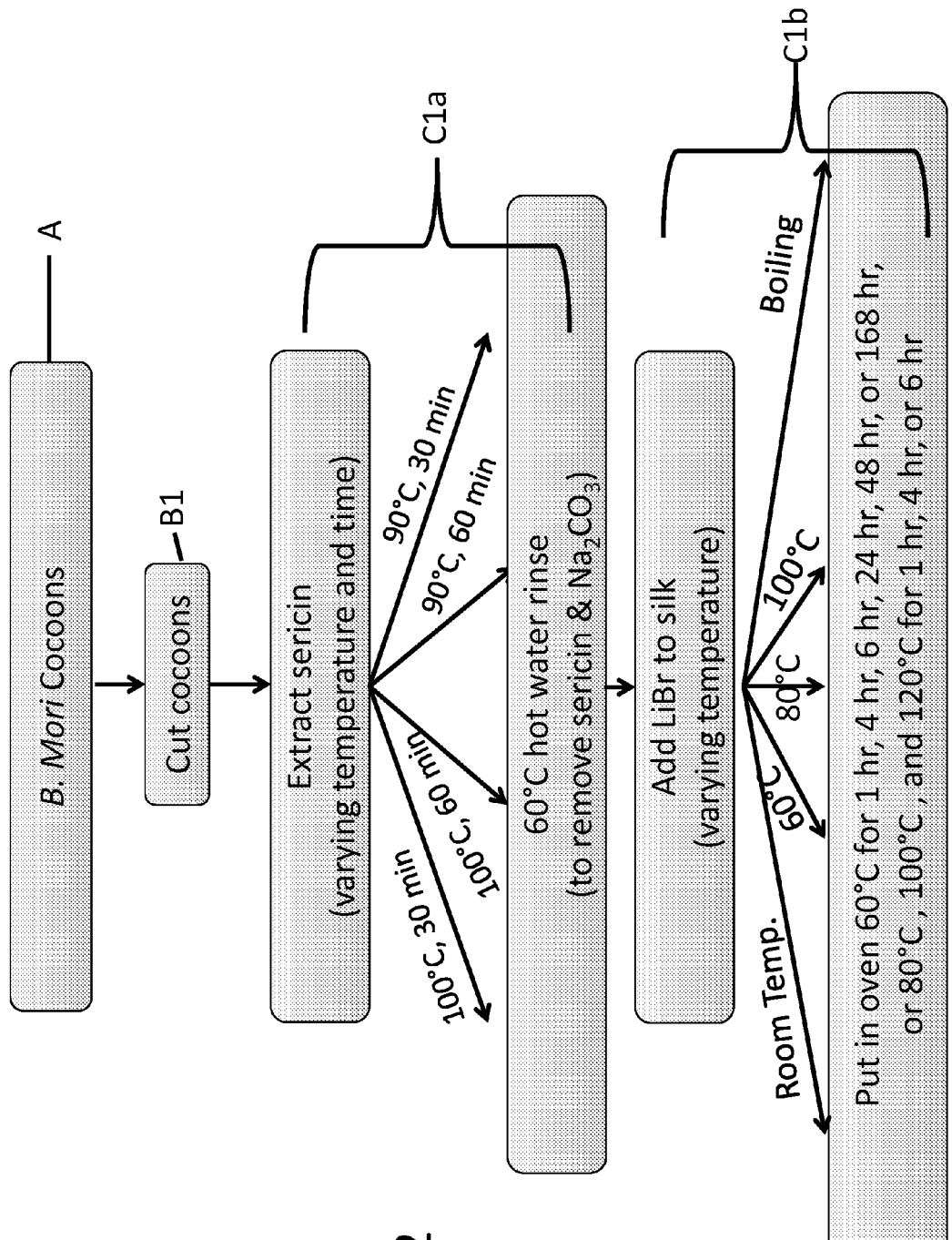
FIG. 2 is a flow chart showing various parameters that can be modified during the process of producing SPFs of the present disclosure during the extraction and the dissolution steps.

FIG. 2 is a flow chart showing various parameters that can be modified during the process of producing a silk protein fragment solution of the present disclosure during the extraction and the dissolution steps. Select method parameters may be altered to achieve distinct final solution characteristics depending upon the intended use, e.g., molecular weight and polydispersity. It should be understood that not all of the steps illustrated are necessarily required to fabricate all silk solutions of the present disclosure.

In an embodiment, a process for producing a silk protein fragment solution of the present disclosure includes forming pieces of silk cocoons from the Bombyx mori silk worm; extracting the pieces at about 100° C. in a solution of water and $Na_2CO_3$ for about 60 minutes, wherein a volume of the water equals about 0.4× raw silk weight and the amount of $Na_2CO_3$ is about 0.848× the weight of the pieces to form a silk fibroin extract; triple rinsing the silk fibroin extract at about 60° C. for about 20 minutes per rinse in a volume of rinse water, wherein the rinse water for each cycle equals about 0.2 L× the weight of the pieces; removing excess water from the silk fibroin extract; drying the silk fibroin extract; dissolving the dry silk fibroin extract in a LiBr solution, wherein the LiBr solution is first heated to about 100° C. to create a silk and LiBr solution and maintained; placing the silk and LiBr solution in a dry oven at about 100° C. for about 60 minutes to achieve complete dissolution and further fragmentation of the native silk protein structure into mixture with desired molecular weight and polydispersity; filtering the solution to remove any remaining debris from the silkworm; diluting the solution with water to result in a 1% silk solution; and removing solvent from the solution using Tangential Flow Filtration (TFF). In an embodiment, a 10 kDa membrane is utilized to purify the silk solution and create the final desired silk-to-water ratio. TFF can then be used to further concentrate the pure silk solution to a concentration of 2% silk to water.

Each process step from raw cocoons to dialysis is scalable to increase efficiency in manufacturing. Whole cocoons are currently purchased as the raw material, but pre-cleaned cocoons or non-heat treated cocoons, where worm removal leaves minimal debris, have also been used. Cutting and cleaning the cocoons is a manual process, however for scalability this process could be made less labor intensive by, for example, using an automated machine in combination with compressed air to remove the worm and any particulates, or using a cutting mill to cut the cocoons into smaller pieces. The extraction step, currently performed in small batches, could be completed in a larger vessel, for example an industrial washing machine where temperatures at or in between 60° C. to 100° C. can be maintained. The rinsing step could also be completed in the industrial washing machine, eliminating the manual rinse cycles. Dissolution of the silk in LiBr solution could occur in a vessel other than a convection oven, for example a stirred tank reactor. Dialyzing the silk through a series of water changes is a manual and time intensive process, which could be accelerated by changing certain parameters, for example diluting the silk solution prior to dialysis. The dialysis process could be scaled for manufacturing by using semi-automated equipment, for example a tangential flow filtration system.

Varying extraction (i.e., time and temperature), LiBr (i.e., temperature of LiBr solution when added to silk fibroin extract or vice versa) and dissolution (i.e., time and temperature) parameters results in solvent and silk solutions with different viscosities, homogeneities, and colors (see FIGS. 5-32). Increasing the temperature for extraction, lengthening the extraction time, using a higher temperature LiBr solution at emersion and over time when dissolving the silk and increasing the time at temperature (e.g., in an oven as shown here, or an alternative heat source) all resulted in less viscous and more homogeneous solvent and silk solutions. While almost all parameters resulted in a viable silk solution, methods that allow complete dissolution to be achieved in fewer than 4 to 6 hours are preferred for process scalability.

FIGS. 5-10 show photographs of four different silk extraction combinations tested: 90° C. 30 min, 90° C. 60 min, 100° C. 30 min, and 100° C. 60 min. Briefly, 9.3 M LiBr was prepared and allowed to sit at room temperature for at least 30 minutes. 5 mL of LiBr solution was added to 1.25 g of silk and placed in the 60° C. oven. Samples from each set were removed at 4, 6, 8, 12, 24, 168 and 192 hours. The remaining sample was photographed.

FIGS. 11-23 show photographs of four different silk extraction combinations tested: 90° C. 30 min, 90° C. 60 min, 100° C. 30 min, and 100° C. 60 min. Briefly, 9.3 M LiBr solution was heated to one of four temperatures: 60° C., 80° C., 100° C. or boiling. 5 mL of hot LiBr solution was added to 1.25 g of silk and placed in the 60° C. oven. Samples from each set were removed at 1, 4 and 6 hours. The remaining sample was photographed.

FIGS. 24-32 show photographs of four different silk extraction combinations tested: Four different silk extraction combinations were used: 90° C. 30 min, 90° C. 60 min, 100° C. 30 min, and 100° C. 60 min. Briefly, 9.3 M LiBr solution was heated to one of four temperatures: 60° C., 80° C., 100° C. or boiling. 5 mL of hot LiBr solution was added to 1.25 g of silk and placed in the oven at the same temperature of the LiBr. Samples from each set were removed at 1, 4 and 6 hours. 1 mL of each sample was added to 7.5 mL of 9.3 M LiBr and refrigerated for viscosity testing. The remaining sample was photographed.

Molecular weight of the silk protein fragments may be controlled based upon the specific parameters utilized during the extraction step, including extraction time and temperature; specific parameters utilized during the dissolution step, including the LiBr temperature at the time of submersion of the silk in to the lithium bromide and time that the solution is maintained at specific temperatures; and specific parameters utilized during the filtration step. By controlling process parameters using the disclosed methods, it is possible to create SPF mixture solutions with polydispersity equal to or lower than 2.5 at a variety of different molecular weight ranging from 5 kDa to 200 kDa, more preferably between 10 kDa and 80 kDA. By altering process parameters to achieve silk solutions with different molecular weights, a range of fragment mixture end products, with desired polydispersity of equal to or less than 2.5 may be targeted based upon the desired performance requirements. For example, a lower molecular weight silk film containing a drug may have a faster release rate compared to a higher molecular weight film making it more ideal for a daily delivery vehicle in consumer cosmetics. Additionally, SPF mixture solutions with a polydispersity of greater than 2.5 can be achieved. Further, two solutions with different average molecular weights and polydispersities can be mixed to create combination solutions. Alternatively, a liquid silk gland (100% sericin free silk protein) that has been removed directly from a worm could be used in combination with any of the SPF mixture solutions of the present disclosure. Molecular weight of the pure silk fibroin-based protein fragment composition was determined using High Pressure Liquid Chromatography (HPLC) with a Refractive Index Detector (RID). Polydispersity was calculated using Cirrus GPC Online GPC/SEC Software Version 3.3 (Agilent).

Parameters were varied during the processing of raw silk cocoons into silk solution. Varying these parameters affected the MW of the resulting silk solution. Parameters manipulated included (i) time and temperature of extraction, (ii) temperature of LiBr, (iii) temperature of dissolution oven, and (iv) dissolution time. Molecular weight was determined with mass spec as shown in FIGS. 64-80.

Experiments were carried out to determine the effect of varying the extraction time. FIGS. 64-70 are graphs showing these results, and Tables 2-8 summarize the results. Below is a summary:

- A sericin extraction time of 30 minutes resulted in larger MW than a sericin extraction time of 60 minutes
- MW decreases with time in the oven
- 140° C. LiBr and oven resulted in the low end of the confidence interval to be below a MW of 9500 Da
- 30 min extraction at the 1 hour and 4 hour time points have undigested silk
- 30 min extraction at the 1 hour time point resulted in a significantly high molecular weight with the low end of the confidence interval being 35,000 Da
- The range of MW reached for the high end of the confidence interval was 18000 to 216000 Da (important for offering solutions with specified upper limit)

TABLE 2

The effect of extraction time (30 min vs 60 min) on molecular weight of silk processed under the conditions of 100° C. Extraction Temperature, 100° C. Lithium Bromide (LiBr) and 100° C. Oven Dissolution Oven/Dissolution Time was varied).

| Boil Time | Oven Time | Average Mw | Std dev | Confidence Interval | | PD |
|---|---|---|---|---|---|---|
| 30 | 1 | 57247 | 12780 | 35093 | 93387 | 1.63 |
| 60 | 1 | 31520 | 1387 | 11633 | 85407 | 2.71 |
| 30 | 4 | 40973 | 2632 | 14268 | 117658 | 2.87 |
| 60 | 4 | 25082 | 1248 | 10520 | 59803 | 2.38 |
| 30 | 6 | 25604 | 1405 | 10252 | 63943 | 2.50 |
| 60 | 6 | 20980 | 1262 | 10073 | 43695 | 2.08 |

TABLE 3

The effect of extraction time (30 min vs 60 min) on molecular weight of silk processed under the conditions of 100° C. Extraction Temperature, boiling Lithium Bromide (LiBr) and 60° C. Oven Dissolution for 4 hr.

| Sample | Boil Time | Average Mw | Std dev | Confidence Interval | | PD |
|---|---|---|---|---|---|---|
| 30 min, 4 hr | 30 | 49656 | 4580 | 17306 | 142478 | 2.87 |
| 60 min, 4 hr | 60 | 30042 | 1536 | 11183 | 80705 | 2.69 |

TABLE 4

The effect of extraction time (30 min vs 60 min) on molecular weight of silk processed under the conditions of 100° C. Extraction Temperature, 60° C. Lithium Bromide (LiBr) and 60° C. Oven Dissolution (Oven/Dissolution Time was varied).

| Sample | Boil Time | Oven Time | Average Mw | Std dev | Confidence Interval | | PD |
|---|---|---|---|---|---|---|---|
| 30 min, 1 hr | 30 | 1 | 58436 | | 22201 | 153809 | 2.63 |
| 60 min, 1 hr | 60 | 1 | 31700 | | 11931 | 84224 | 2.66 |
| 30 min, 4 hr | 30 | 4 | 61956.5 | 13337 | 21463 | 178847 | 2.89 |
| 60 min, 4 hr | 60 | 4 | 25578.5 | 2446 | 9979 | 65564 | 2.56 |

TABLE 5

The effect of extraction time (30 min vs 60 min) on molecular weight of silk processed under the conditions of 100° C. Extraction Temperature, 80° C. Lithium Bromide (LiBr) and 80° C. Oven Dissolution for 6 hr.

| Sample | Boil Time | Average Mw | Std dev | Confidence Interval | | PD |
|---|---|---|---|---|---|---|
| 30 min, 6 hr | 30 | 63510 | | 18693 | 215775 | 3.40 |
| 60 min, 6 hr | 60 | 25164 | 238 | 9637 | 65706 | 2.61 |

TABLE 6

The effect of extraction time (30 min vs 60 min) on molecular weight of silk processed under the conditions of 100° C. Extraction Temperature, 80° C. Lithium Bromide (LiBr) and 60° C. Oven Dissolution (Oven/Dissolution Time was varied).

| Sample | Boil Time | Oven Time | Average Mw | Std dev | Confidence Interval | | PD |
|---|---|---|---|---|---|---|---|
| 30 min, 4 hr | 30 | 4 | 59202 | 14028 | 19073 | 183760 | 3.10 |
| 60 min, 4 hr | 60 | 4 | 26312.5 | 637 | 10266 | 67442 | 2.56 |
| 30 min, 6 hr | 30 | 6 | 46824 | | 18076 | 121293 | 2.59 |
| 60 min, 6 hr | 60 | 6 | 26353 | | 10168 | 68302 | 2.59 |

TABLE 7

The effect of extraction time (30 min vs 60 min) on molecular weight of silk processed under the conditions of 100° C. Extraction Temperature, 100° C. Lithium Bromide (LiBr) and 60° C. Oven Dissolution (Oven/Dissolution Time was varied).

| Sample | Boil Time | Oven Time | Average Mw | Std dev | Confidence Interval | | PD |
|---|---|---|---|---|---|---|---|
| 30 min, 4 hr | 30 | 4 | 47853 | | 19758 | 115900 | 2.42 |
| 60 min, 4 hr | 60 | 4 | 25082 | 1248 | 10520 | 59804 | 2.38 |
| 30 min, 6 hr | 30 | 6 | 55421 | 8992 | 19153 | 160366 | 2.89 |
| 60 min, 6 hr | 60 | 6 | 20980 | 1262 | 10073 | 43694 | 2.08 |

TABLE 8

The effect of extraction time (30 min vs 60 min) on molecular weight of silk processed under the conditions of 100° C. Extraction Temperature, 140° C. Lithium Bromide (LiBr) and 140° C. Oven Dissolution (Oven/Dissolution Time was varied).

| Sample | Boil Time | Oven Time | Average Mw | Std dev | Confidence Interval | | PD |
|---|---|---|---|---|---|---|---|
| 30 min, 4 hr | 30 | 4 | 9024.5 | 1102 | 4493 | 18127 | 2.00865 |
| 60 min, 4 hr | 60 | 4 | 15548 | | 6954 | 34762 | 2.2358 |
| 30 min, 6 hr | 30 | 6 | 13021 | | 5987 | 28319 | 2.1749 |
| 60 min, 6 hr | 60 | 6 | 10888 | | 5364 | 22100 | 2.0298 |

Figure 71:
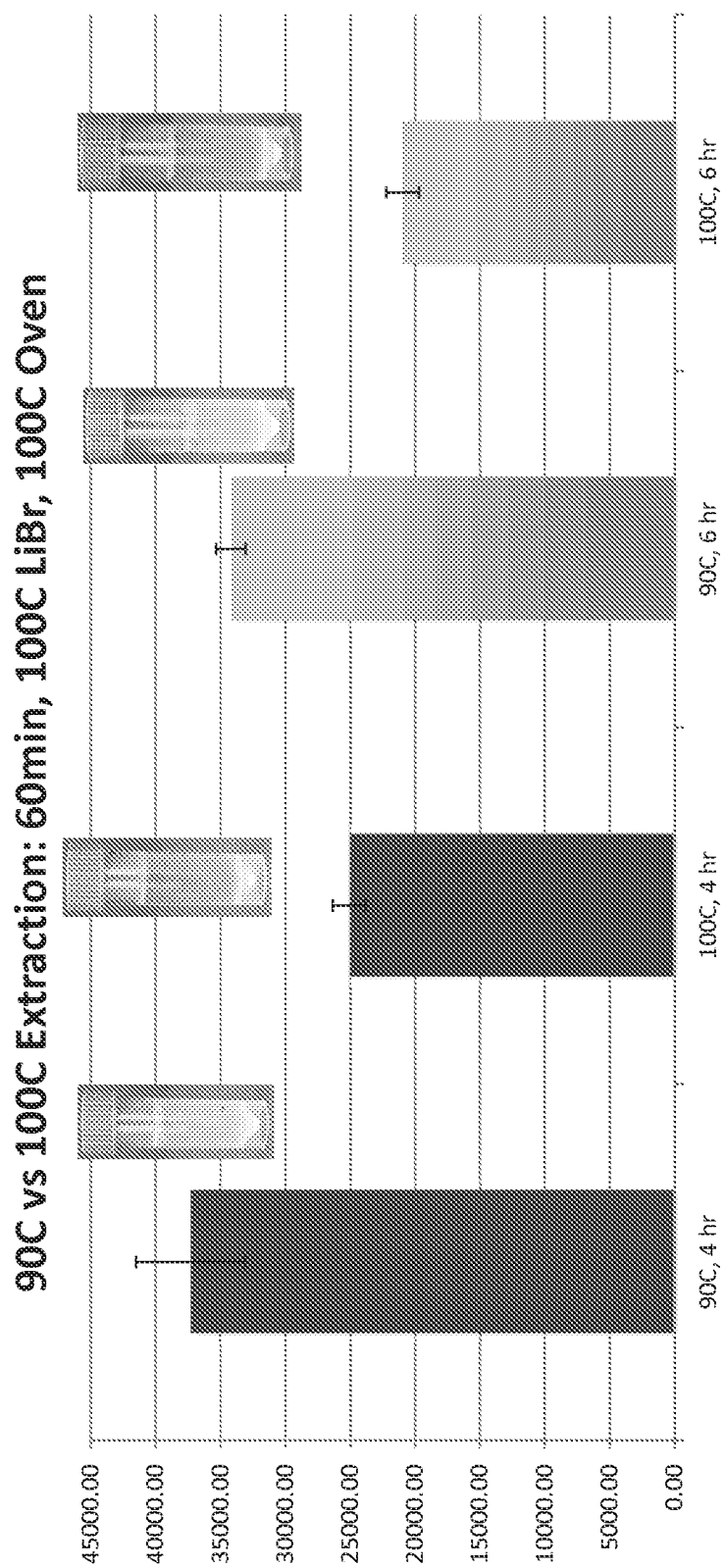
FIG. 71 is a graph summarizing the effect of Extraction Temperature on Molecular Weight of silk processed under the conditions of 60 minute Extraction Time, 100° C. LiBr and 100° C. Oven Dissolution (Oven/Dissolution Time was varied).

Experiments were carried out to determine the effect of varying the extraction temperature. FIG. 71 is a graph showing these results, and Table 9 summarizes the results. Below is a summary:

Sericin extraction at 90° C. resulted in higher MW than sericin extraction at 100° C. extraction Both 90° C. and 100° C. show decreasing MW over time in the oven

TABLE 9

The effect of extraction temperature (90° C. vs. 100° C.) on molecular weight of silk processed under the conditions of 60 min. Extraction Temperature, 100° C. Lithium Bromide (LiBr) and 100° C. Oven Dissolution (Oven/Dissolution Time was varied).

| Sample | Boil Time | Oven Time | Average Mw | Std dev | Confidence Interval | | PD |
|---|---|---|---|---|---|---|---|
| 90 C., 4 hr | 60 | 4 | 37308 | 4204 | 13368 | 104119 | 2.79 |
| 100 C., 4 hr | 60 | 4 | 25082 | 1248 | 10520 | 59804 | 2.38 |
| 90 C., 6 hr | 60 | 6 | 34224 | 1135 | 12717 | 92100 | 2.69 |
| 100 C., 6 hr | 60 | 6 | 20980 | 1262 | 10073 | 43694 | 2.08 |

Figure 72:
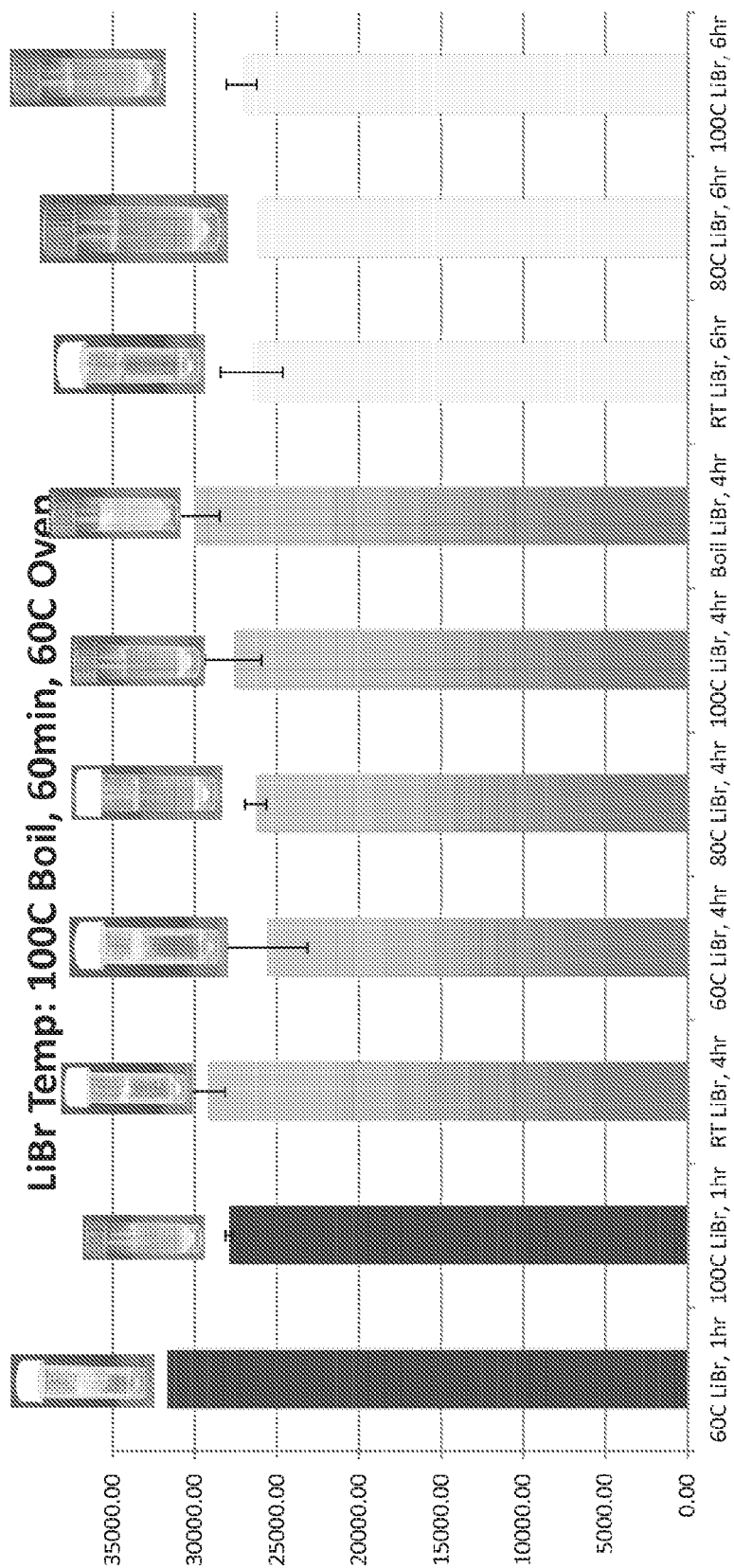
FIG. 72 is a graph summarizing the effect of LiBr Temperature on Molecular Weight of silk processed under the conditions of 60 minute Extraction Time, 100° C. Extraction Temperature and 60° C. Oven Dissolution (Oven/Dissolution Time was varied).
Figure 73:
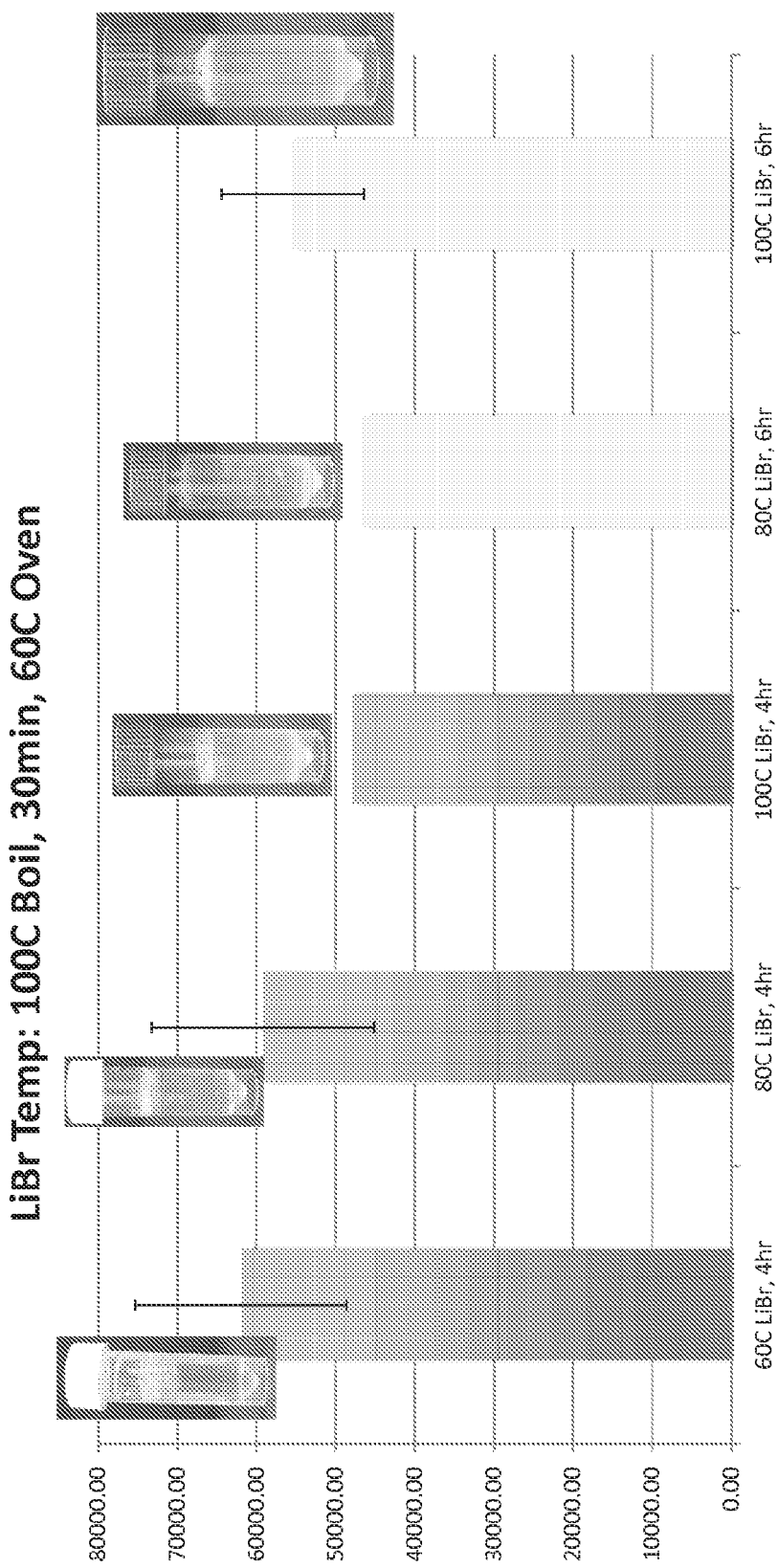
FIG. 73 is a graph summarizing the effect of LiBr Temperature on Molecular Weight of silk processed under the conditions of 30 minute Extraction Time, 100° C. Extraction Temperature and 60° C. Oven Dissolution (Oven/Dissolution Time was varied).
Figure 74:
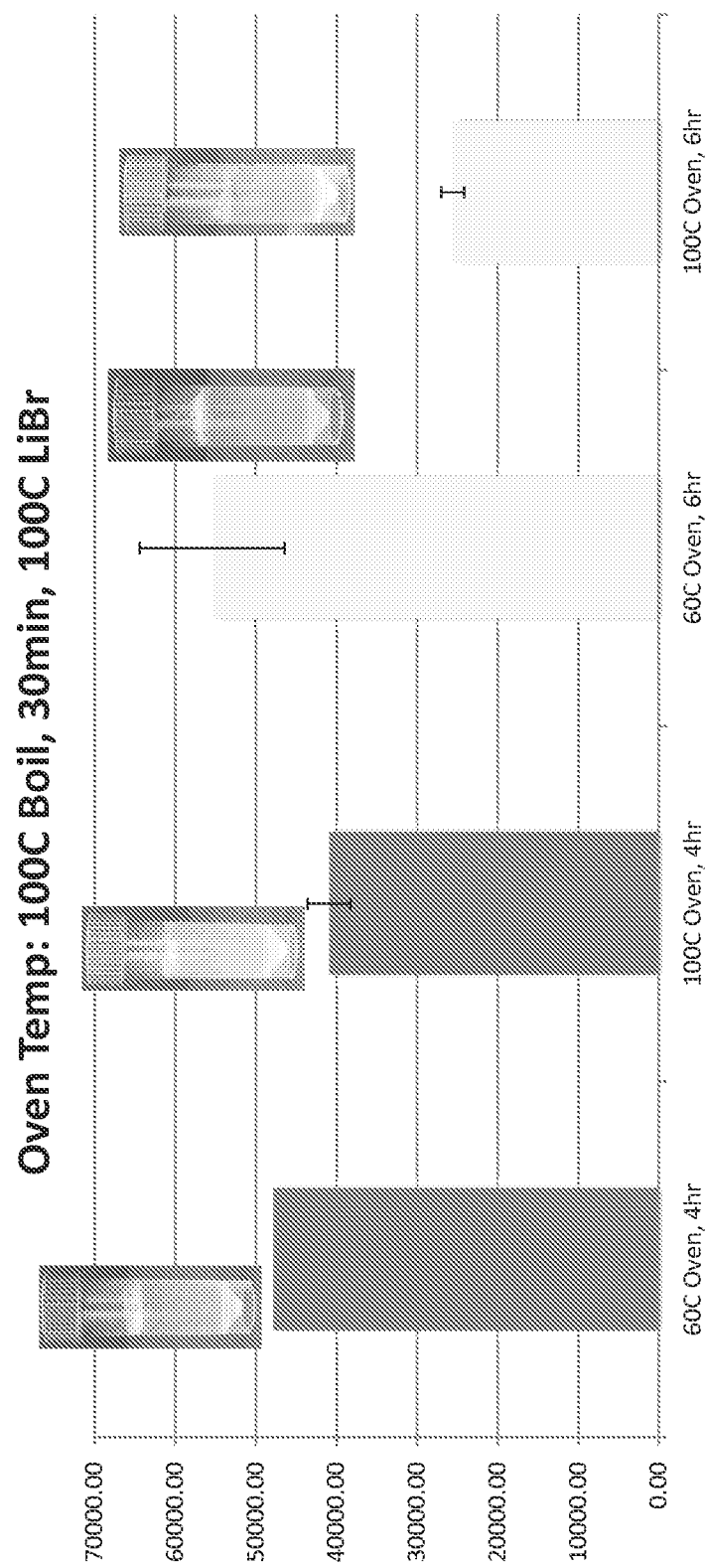
FIG. 74 is a graph summarizing the effect of Oven/Dissolution Temperature on Molecular Weight of silk processed under the conditions of 100° C. Extraction Temperature, 30 minute Extraction Time, and 100° C. Lithium Bromide (Oven/Dissolution Time was varied).
Figure 75:
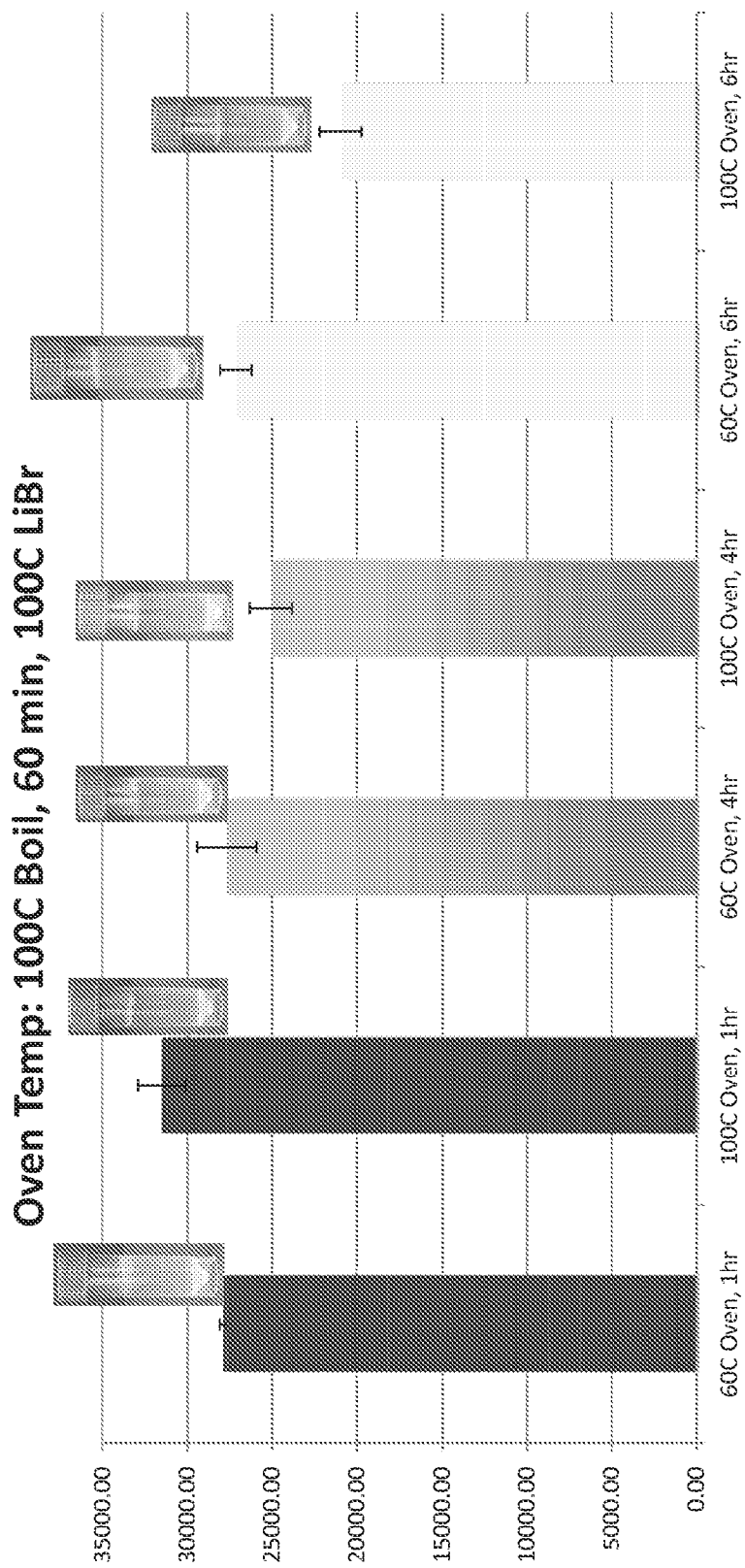
FIG. 75 is a graph summarizing the effect of Oven/Dissolution Temperature on Molecular Weight of silk processed under the conditions of 100° C. Extraction Temperature, 60 minute Extraction Time, and 100° C. Lithium Bromide (Oven/Dissolution Time was varied).
Figure 76:
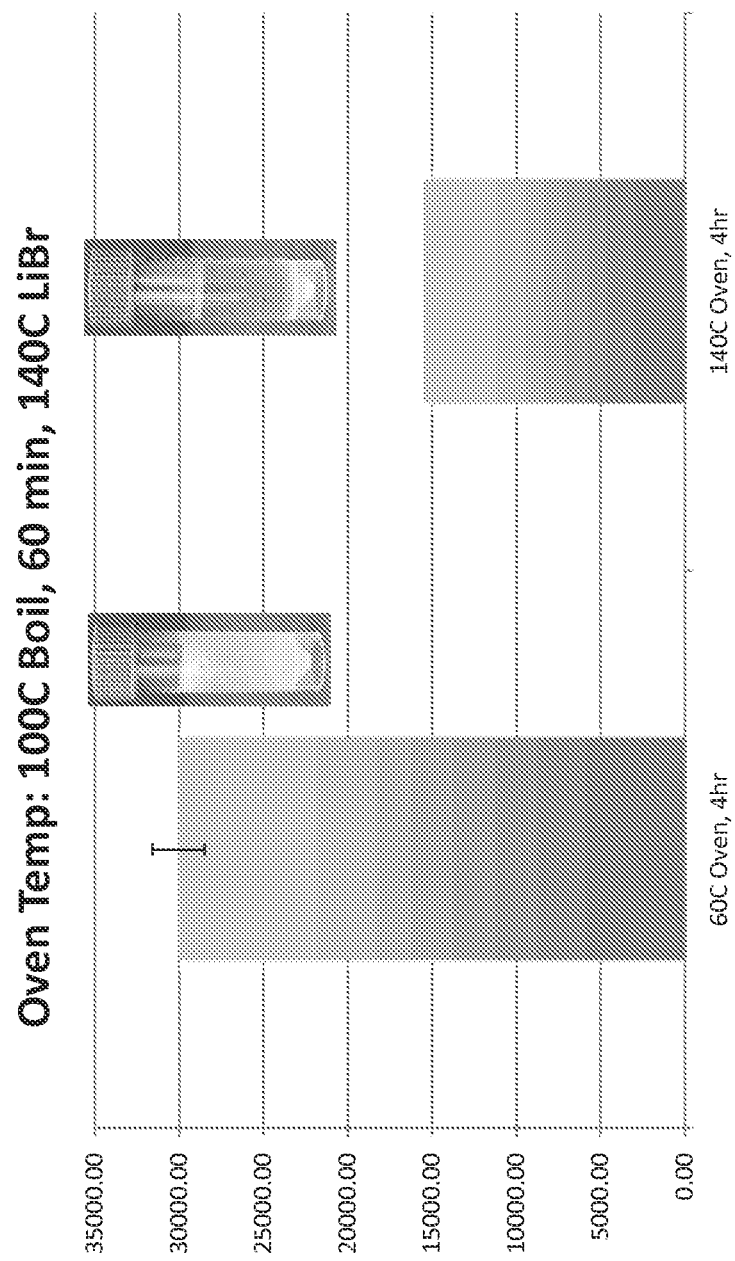
FIG. 76 is a graph summarizing the effect of Oven/Dissolution Temperature on Molecular Weight of silk processed under the conditions of 100° C. Extraction Temperature, 60 minute Extraction Time, and 140° C. Lithium Bromide (Oven/Dissolution Time was varied).
Figure 77:
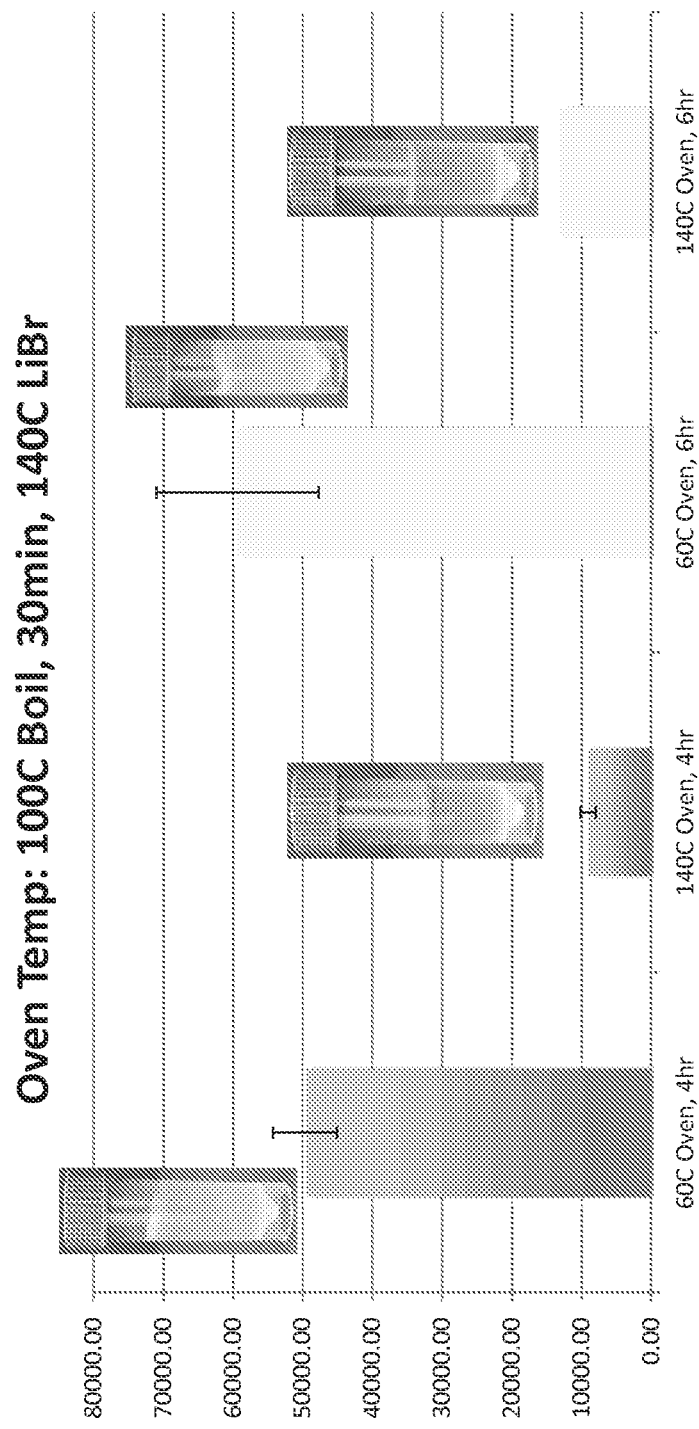
FIG. 77 is a graph summarizing the effect of Oven/Dissolution Temperature on Molecular Weight of silk processed under the conditions of 100° C. Extraction Temperature, 30 minute Extraction Time, and 140° C. Lithium Bromide (Oven/Dissolution Time was varied).
Figure 78:
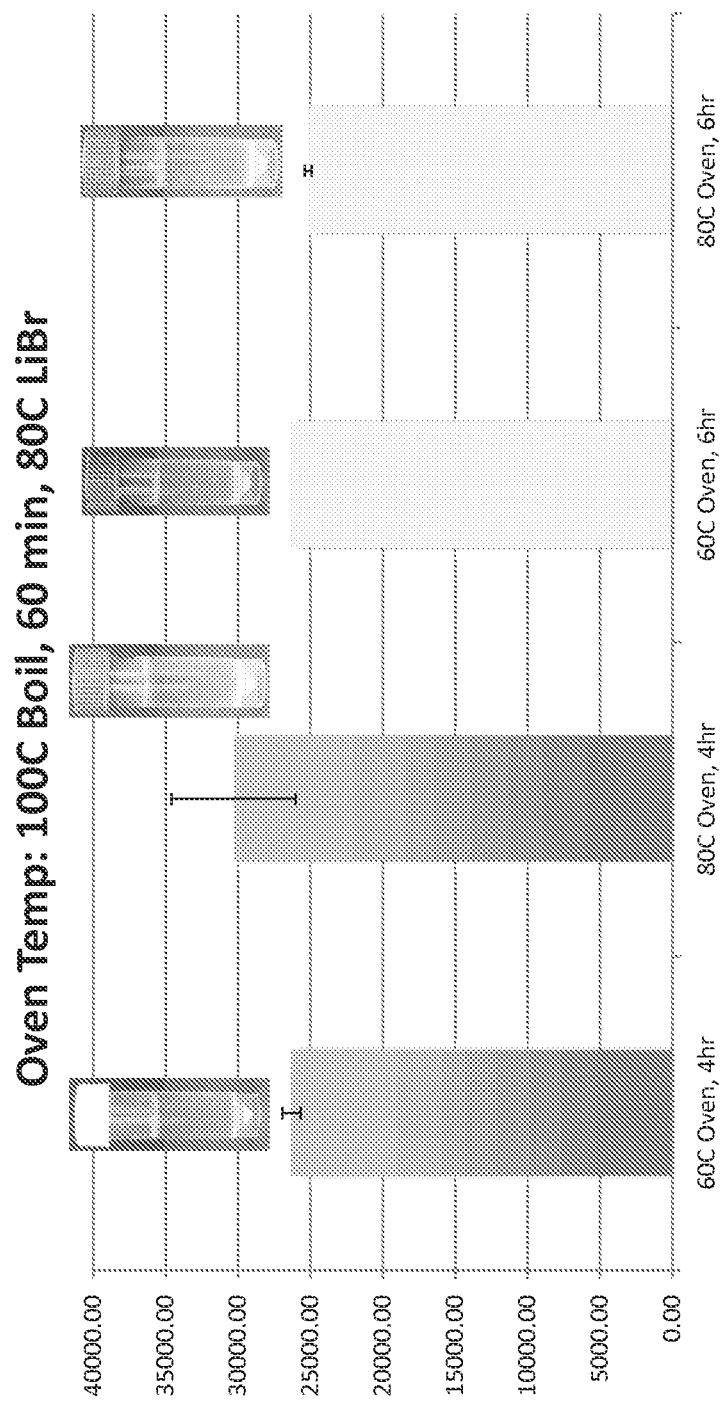
FIG. 78 is a graph summarizing the effect of Oven/Dissolution Temperature on Molecular Weight of silk processed under the conditions of 100° C. Extraction Temperature, 60 minute Extraction Time, and 80° C. Lithium Bromide (Oven/Dissolution Time was varied).
Figure 79:
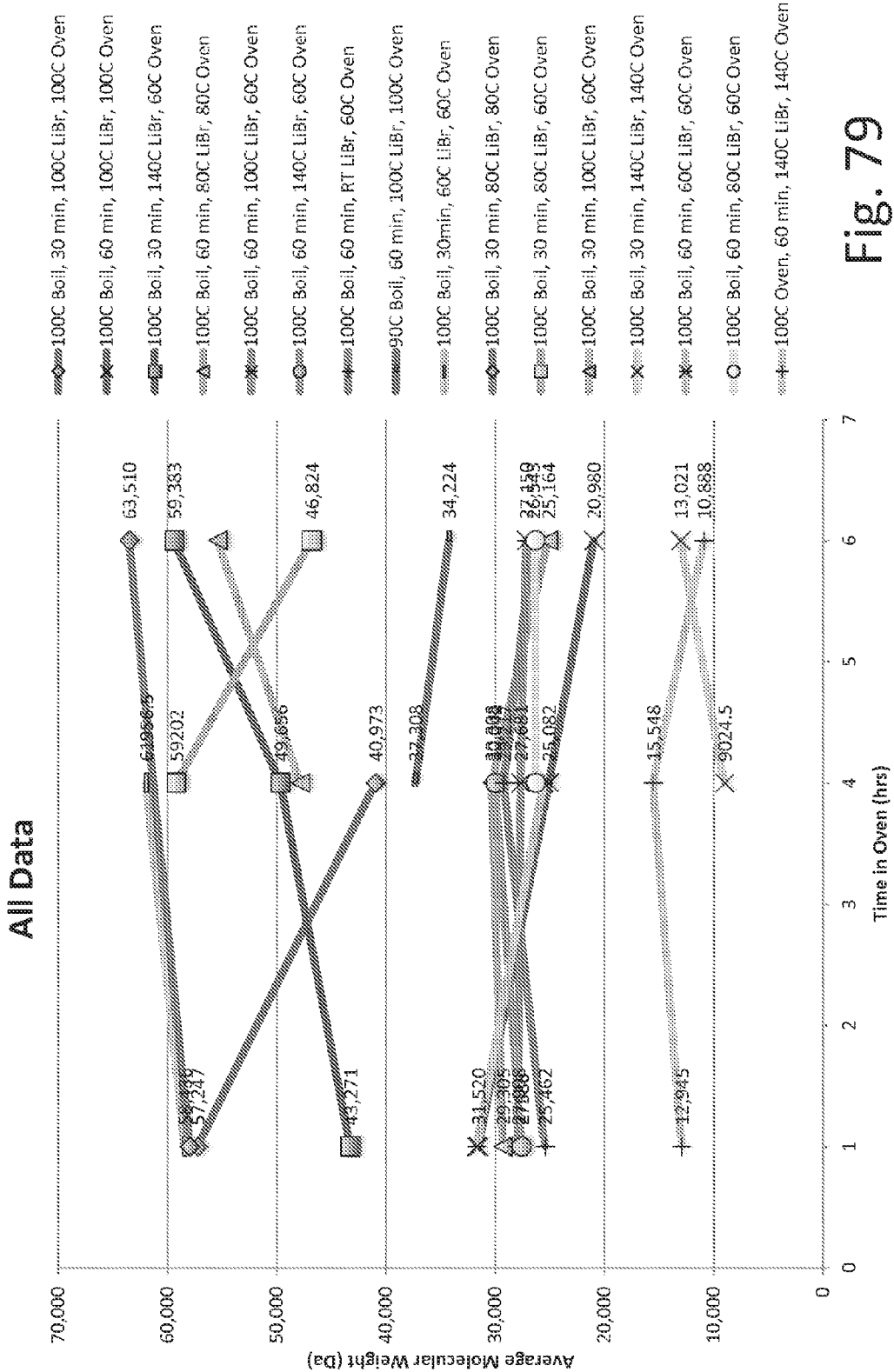
FIG. 79 is a graph summarizing the Molecular Weights of silk processed under varying conditions including Extraction Time, Extraction Temperature, Lithium Bromide (LiBr) Temperature, Oven Temperature for Dissolution, Oven Time for Dissolution.
Figure 80:
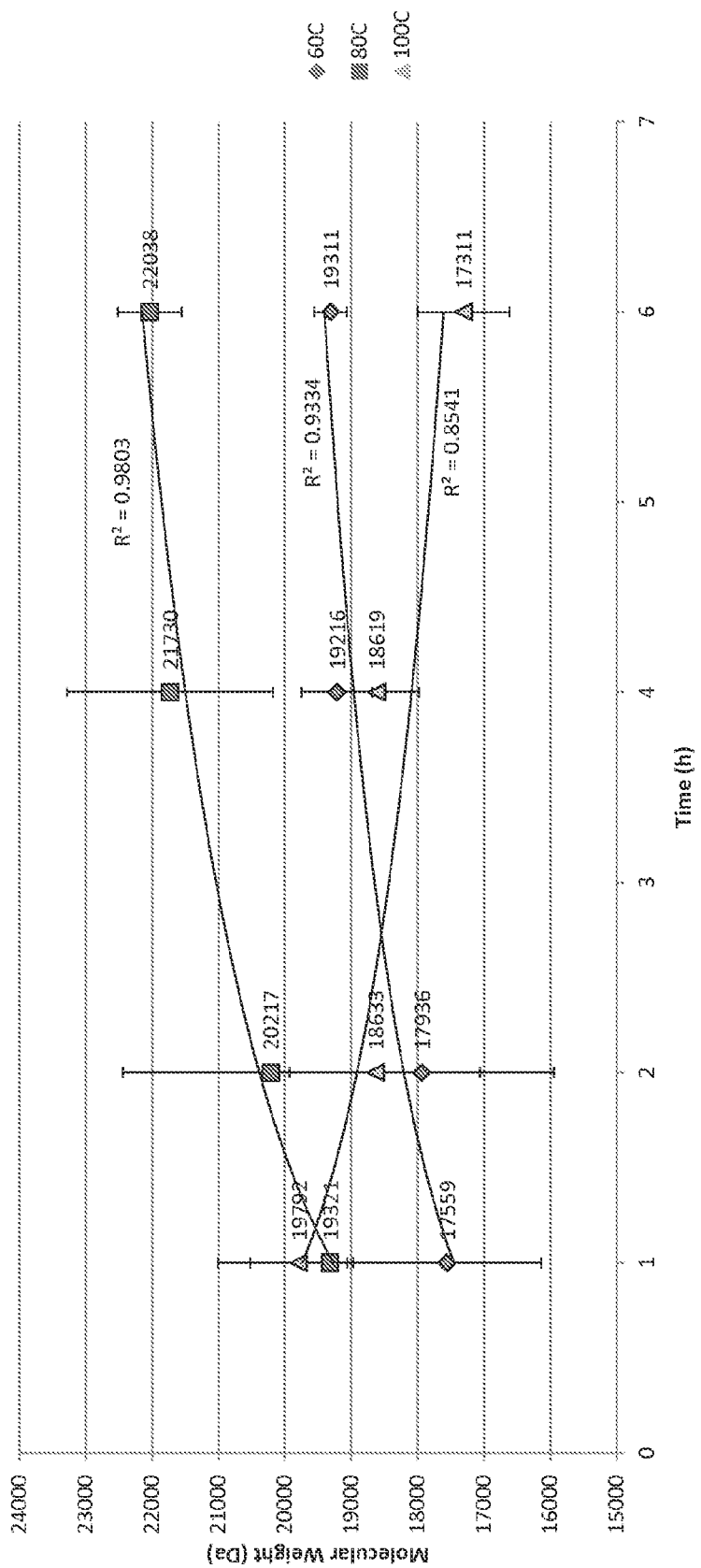
FIG. 80 is a graph summarizing the Molecular Weights of silk processed under conditions in which Oven/Dissolution Temperature is equal to LiBr Temperature.

Experiments were carried out to determine the effect of varying the Lithium Bromide (LiBr) temperature when added to silk. FIGS. 72-73 are graphs showing these results, and Tables 10-11 summarize the results. Below is a summary:

No impact on MW or confidence interval (all CI ~10500-6500 Da)

Studies illustrated that the temperature of LiBr-silk dissolution, as LiBr is added and begins dissolving, rapidly drops below the original LiBr temperature due to the majority of the mass being silk at room temp

TABLE 10

The effect of Lithium Bromide (LiBr) temperature on molecular weight of silk processed under the conditions of 60 min. Extraction Time., 100° C. Extraction Temperature and 60° C. Oven Dissolution (Oven/Dissolution Time was varied).

| Sample | LiBr Temp (° C.) | Oven Time | Average Mw | Std dev | Confidence Interval | | PD |
|---|---|---|---|---|---|---|---|
| 60 C. LiBr, 1 hr | 60 | 1 | 31700 | | 11931 | 84223 | 2.66 |
| 100 C. LiBr, 1 hr | 100 | 1 | 27907 | 200 | 10735 | 72552 | 2.60 |
| RT LiBr, 4 hr | RT | 4 | 29217 | 1082 | 10789 | 79119 | 2.71 |
| 60 C. LiBr, 4 hr | 60 | 4 | 25578 | 2445 | 9978 | 65564 | 2.56 |
| 80 C. LiBr, 4 hr | 80 | 4 | 26312 | 637 | 10265 | 67441 | 2.56 |
| 100 C. LiBr, 4 hr | 100 | 4 | 27681 | 1729 | 11279 | 67931 | 2.45 |
| Boil LiBr, 4 hr | Boil | 4 | 30042 | 1535 | 11183 | 80704 | 2.69 |
| RT LiBr, 6 hr | RT | 6 | 26543 | 1893 | 10783 | 65332 | 2.46 |
| 80 C. LiBr, 6 hr | 80 | 6 | 26353 | | 10167 | 68301 | 2.59 |
| 100 C. LiBr, 6 hr | 100 | 6 | 27150 | 916 | 11020 | 66889 | 2.46 |

TABLE 11

The effect of Lithium Bromide (LiBr) temperature on molecular weight of silk processed under the conditions of 30 min. Extraction Time, 100° C. Extraction Temperature and 60° C. Oven Dissolution (Oven/Dissolution Time was varied).

| Sample | LiBr Temp (° C.) | Oven Time | Average Mw | Std dev | Confidence Interval | | PD |
|---|---|---|---|---|---|---|---|
| 60 C. LiBr, 4 hr | 60 | 4 | 61956 | 13336 | 21463 | 178847 | 2.89 |
| 80 C. LiBr, 4 hr | 80 | 4 | 59202 | 14027 | 19073 | 183760 | 3.10 |
| 100 C. LiBr, 4 hr | 100 | 4 | 47853 | | 19757 | 115899 | 2.42 |
| 80 C. LiBr, 6 hr | 80 | 6 | 46824 | | 18075 | 121292 | 2.59 |
| 100 C. LiBr, 6 hr | 100 | 6 | 55421 | 8991 | 19152 | 160366 | 2.89 |

Experiments were carried out to determine the effect of v oven/dissolution temperature. FIGS. 74-78 are graphs showing these results, and Tables 12-16 summarize the results. Below is a summary:

Oven temperature has less of an effect on 60 min extracted silk than 30 min extracted silk. Without wishing to be bound by theory, it is believed that the 30 min silk is less degraded during extraction and therefore the oven temperature has more of an effect on the larger MW, less degraded portion of the silk.

For 60° C. vs. 140° C. oven the 30 min extracted silk showed a very significant effect of lower MW at higher oven temp, while 60 min extracted silk had an effect but much less The 140° C. oven resulted in a low end in the confidence interval at ~6000 Da

TABLE 12

The effect of oven/dissolution temperature on molecular weight of silk processed under the conditions of 100° C. Extraction Temperature, 30 min. Extraction Time, and 100° C. Lithium Bromide (LiBr) (Oven/Dissolution Time was varied).

| Boil Time | Oven Temp (° C.) | Oven Time | Average Mw | Std dev | Confidence Interval | | PD |
|---|---|---|---|---|---|---|---|
| 30 | 60 | 4 | 47853 | | 19758 | 115900 | 2.42 |
| 30 | 100 | 4 | 40973 | 2632 | 14268 | 117658 | 2.87 |
| 30 | 60 | 6 | 55421 | 8992 | 19153 | 160366 | 2.89 |
| 30 | 100 | 6 | 25604 | 1405 | 10252 | 63943 | 2.50 |

TABLE 13

The effect of oven/dissolution temperature on molecular weight of silk processed under the conditions of 100° C. Extraction Temperature, 60 min. Extraction Time, and 100° C. Lithium Bromide (LiBr) (Oven/Dissolution Time was varied).

| Boil Time | Oven Temp (° C.) | Oven Time | Average Mw | Std dev | Confidence Interval | | PD |
|---|---|---|---|---|---|---|---|
| 60 | 60 | 1 | 27908 | 200 | 10735 | 72552 | 2.60 |
| 60 | 100 | 1 | 31520 | 1387 | 11633 | 85407 | 2.71 |
| 60 | 60 | 4 | 27681 | 1730 | 11279 | 72552 | 2.62 |
| 60 | 100 | 4 | 25082 | 1248 | 10520 | 59803 | 2.38 |
| 60 | 60 | 6 | 27150 | 916 | 11020 | 66889 | 2.46 |
| 60 | 100 | 6 | 20980 | 1262 | 10073 | 43695 | 2.08 |

TABLE 14

The effect of oven/dissolution temperature on molecular weight of silk processed under the conditions of 100° C. Extraction Temperature, 60 min. Extraction Time, and 140° C. Lithium Bromide (LiBr) (Oven/Dissolution Time was varied).

| Boil Time | Oven Temp(° C.) | Oven Time | Average Mw | Std dev | Confidence Interval | | PD |
|---|---|---|---|---|---|---|---|
| 60 | 60 | 4 | 30042 | 1536 | 11183 | 80705 | 2.69 |
| 60 | 140 | 4 | 15548 | | 7255 | 33322 | 2.14 |

TABLE 15

The effect of oven/dissolution temperature on molecular weight of silk processed under the conditions of 100° C. Extraction Temperature, 30 min. Extraction Time, and 140° C. Lithium Bromide (LiBr) (Oven/Dissolution Time was varied).

| Boil Time | Oven Temp (° C.) | Oven Time | Average Mw | Std dev | Confidence Interval | | PD |
|---|---|---|---|---|---|---|---|
| 30 | 60 | 4 | 49656 | 4580 | 17306 | 142478 | 2.87 |
| 30 | 140 | 4 | 9025 | 1102 | 4493 | 18127 | 2.01 |
| 30 | 60 | 6 | 59383 | 11640 | 17641 | 199889 | 3.37 |
| 30 | 140 | 6 | 13021 | | 5987 | 28319 | 2.17 |

TABLE 16

The effect of oven/dissolution temperature on molecular weight of silk processed under the conditions of 100° C. Extraction Temperature, 60 min. Extraction Time, and 80° C. Lithium Bromide (LiBr) (Oven/Dissolution Time was varied).

| Boil Time | Oven Temp (° C.) | Oven Time | Average Mw | Std dev | Confidence Interval | | PD |
|---|---|---|---|---|---|---|---|
| 60 | 60 | 4 | 26313 | 637 | 10266 | 67442 | 2.56 |
| 60 | 80 | 4 | 30308 | 4293 | 12279 | 74806 | 2.47 |
| 60 | 60 | 6 | 26353 | | 10168 | 68302 | 2.59 |
| 60 | 80 | 6 | 25164 | 238 | 9637 | 65706 | 2.61 |

In an embodiment, the methods disclosed herein result in a solution with characteristics that can be controlled during manufacturing, including, but not limited to: MW—may be varied by changing extraction and/or dissolution time and temp (e.g., LiBr temperature), pressure, and filtration (e.g., size exclusion chromatography); Structure—removal or cleavage of heavy or light chain of the fibroin protein polymer; Purity—hot water rinse temperature for improved sericin removal or filter capability for improved particulate removal that adversely affects shelf stability of the silk fragment protein mixture solution; Color—the color of the solution can be controlled with, for example, LiBr temp and time; Viscosity; Clarity; and Stability of solution. The resultant pH of the solution is typically about 7 and can be altered using an acid or base as appropriate to storage requirements.

Figure 33:
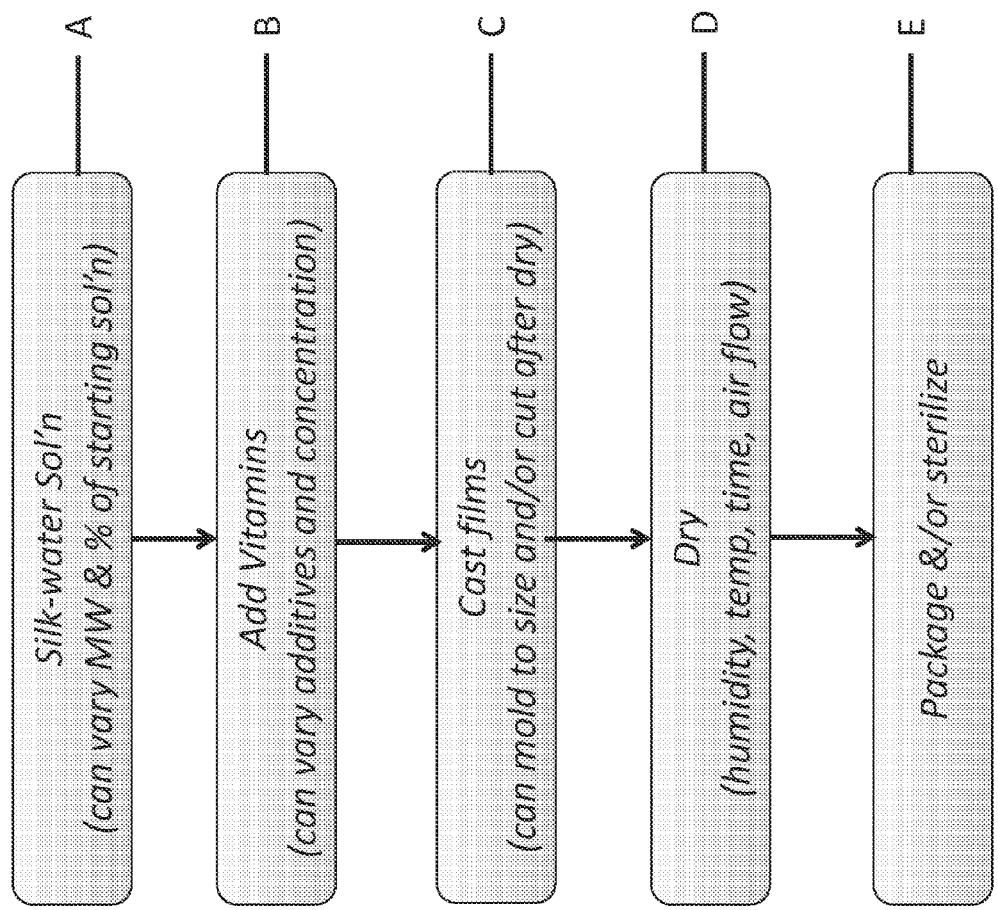
FIG. 33 is a flow chart showing an embodiment for producing a silk film of the present disclosure from a silk solution of the present disclosure.
Figures 82A, 82B, 82C:
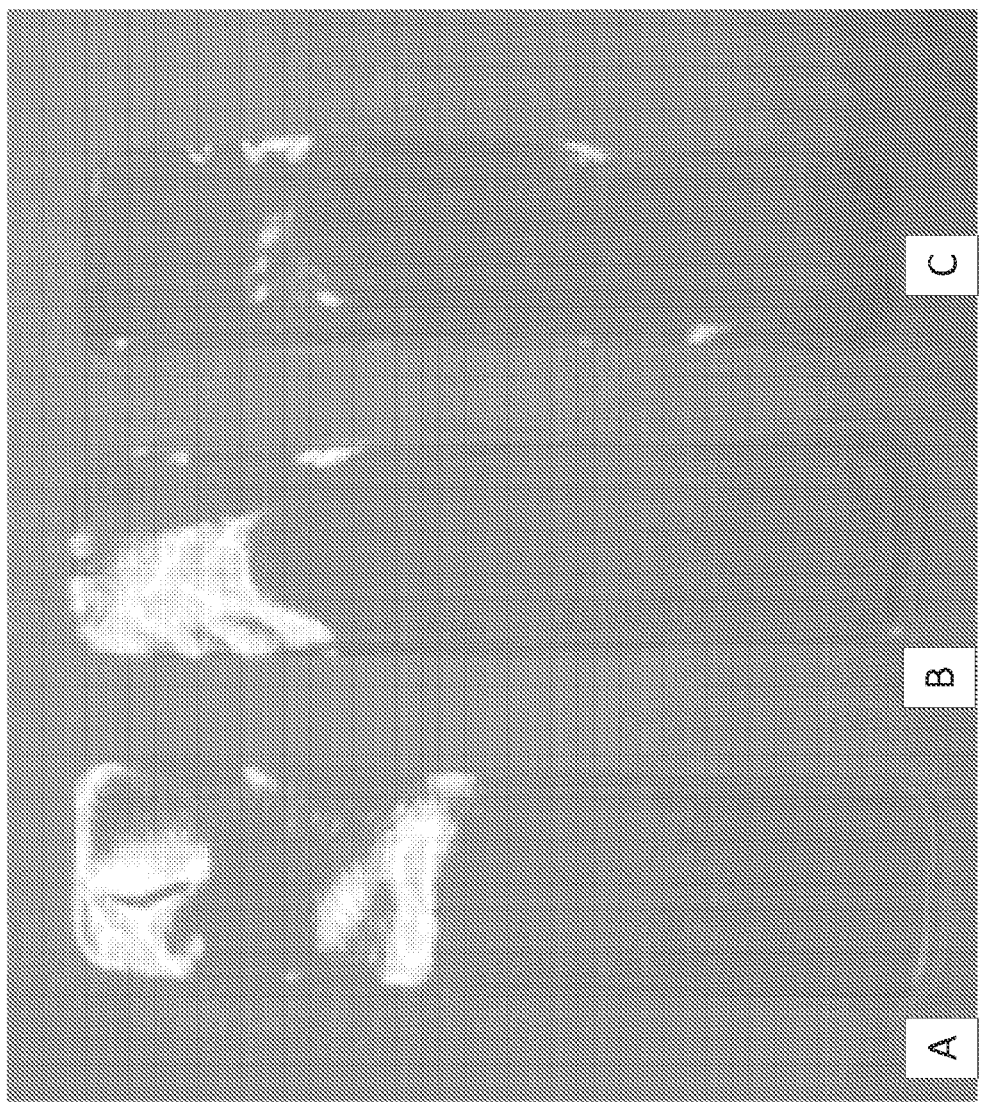
FIGS. 82A-82C are photographs showing the effect of film drying on film color and physical integrity after storage (most dry (FIG. 82A), least dry (FIG. 82C)).

The above-described SPF mixture solutions may be utilized to produce a pure silk protein fragment-film or pure silk protein fragment-gel for numerous applications (e.g., delivery of a drug, vitamin, antioxidant, etc. to the skin). FIG. 33 is a flow chart showing an embodiment for producing a silk film of the present disclosure from a silk solution of the present disclosure. In step A, a silk solution of the present disclosure is chosen, and then at least on molecule or therapeutic agent is added directly to the silk solution prior to gel or film processing, step B. When producing a silk film, the silk solution with additive(s) may be cast directly onto a shaped mold to achieve a unique film shape (e.g., silicone mold) or the silk solution may be cast as a sheet and then subsequently cut or punched into a variety of shapes, with a variety of cutting techniques, including, but not limited to cutting with a rotary blade or laser cutting for example (FIGS. 83A and 83B), depending upon the desired application, step C. If cast on a mold, for example silicone, the silicone mold may be heated on a laser-etched/patterned surface to create an impression that will be transferred to the final film. For example, the product logo could be transferred to the film, visible, but not palpable by hand, and used to show authenticity of the product. The concentration and/or mass of the final silk protein fragment film can be varied to control the film's degree of flexibility and conformity to different anatomical topographies. Altering the drying method for a silk film will also result in different final film characteristics. Applying airflow and/or heat impacts the properties of the film (e.g., brittleness, number of bubbles, curling, solubility, surface appearance), step D. Additionally, the percent moisture within the film at the time of packaging will impact stability over time with too much moisture resulting in yellowing of the films with time (FIGS. 82A-82C). In some embodiments, films ideally may have between about 2 to about 20% water content at completion of drying. It was observed that greater moisture content than 20% in the films will decrease shelf life. If films are not dry enough (that is they have greater than 20% water content) before packaging, they will yellow over time (2+ weeks). It is advised that films are dried in an incubator until the relative humidity in the incubator is less than the relative humidity in the surrounding area and no greater than 36%. Ambient humidity will have an effect on the ability to remove moisture and therefore, a tactile/audio test can be used to determine whether films are ready for packaging. In an embodiment, the test includes removal of a film from the drying system, slightly bending one end of the film and releasing it. If the film feels and sounds similar to a piece of paper or thin plastic, it is considered dry. If the film has not completed drying, it will be pliable and will make no noise upon bending and release. In an embodiment, the film is flexible without the need for process additives such as glycerin, such that a film that is 2.5 cm wide by 10 cm long can be bent in half so that opposite ends of the film can touch one another without the film breaking or cracking. A film of this same size can be bent in half along the length of the film to create a 45-degree angle without breaking or cracking the film.

The final silk protein fragment-film is pure with undetectable levels of particulate debris and/or process contaminants, including LiBr and $Na_2CO_3$. Alternatively, the final SPF mixture solution has less than 500 ppm process contaminants. FIG. 56 and FIG. 57 are tables summarizing LiBr and $Na_2CO_3$ concentrations in films (2% silk films air dried at RT) of the present disclosure. In FIG. 56, the processing conditions included 100° C. extraction for 20 min, RT rinse, LiBr in 60° C. oven for 4-6 hours. In FIG. 57, the processing conditions included 100° C. extraction for 20 min, RT rinse, LiBr in 60° C. oven for 4-6 hours.

In an embodiment, when producing a silk gel, an acid is used to help facilitate gelation. In an embodiment, when producing a silk gel that includes a neutral or a basic molecule and/or therapeutic agent, an acid can be added to facilitate gelation. In an embodiment, when producing a silk gel, increasing the pH (making the gel more basic) increases the shelf stability of the gel. In an embodiment, when producing a silk gel, increasing the pH (making the gel more basic) allows for a greater quantity of an acidic molecule to be loaded into the gel.

In an embodiment, natural additives may be added to the silk gel to further stabilize additives. For example, trace elements such as selenium or magnesium or L-methoinine can be used. Further, light-block containers can be added to further increase stability.

Figure 35:
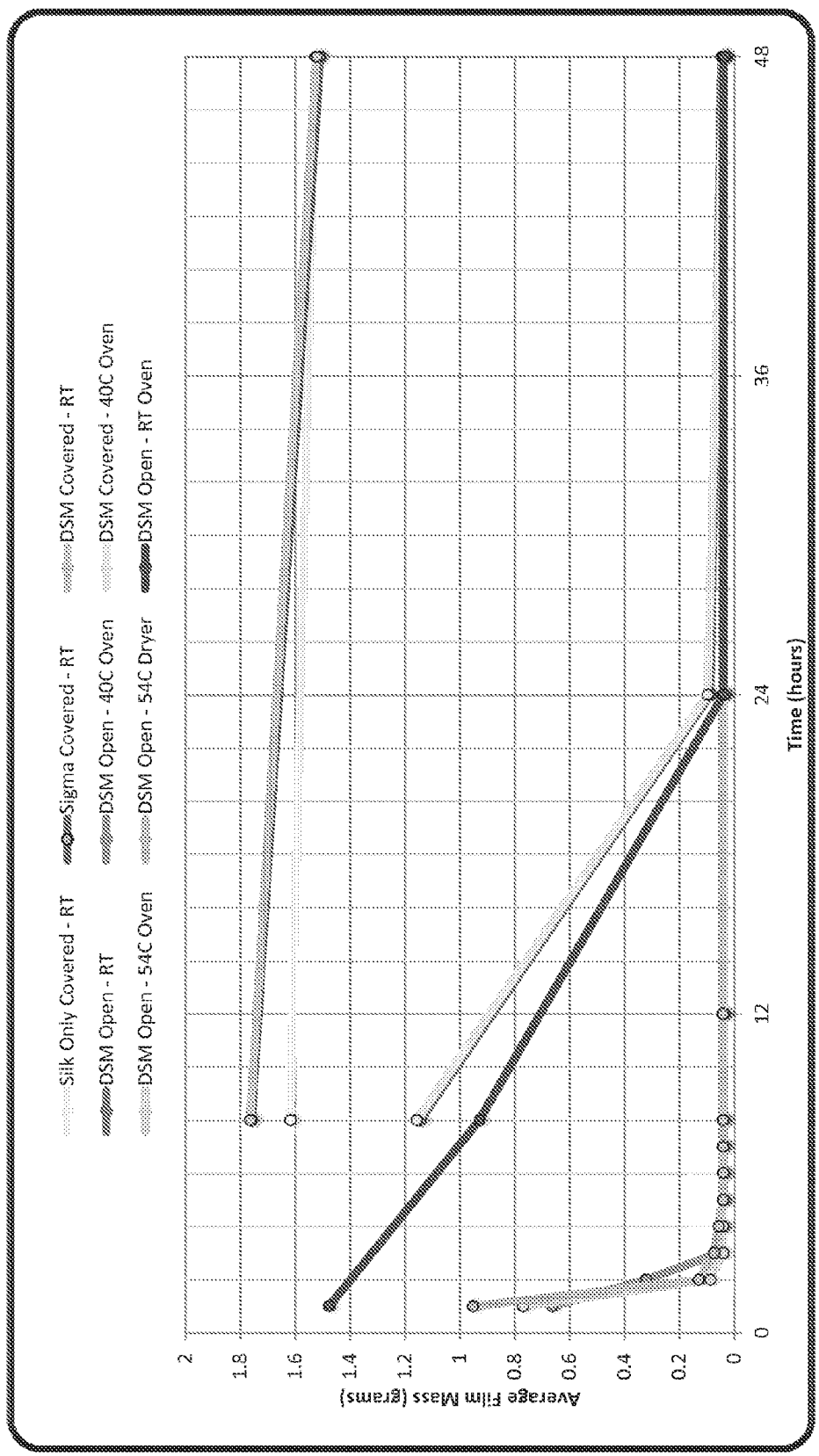
FIG. 35 is a graph showing silk film drying times (under various air flow and temperature conditions).
Figures 37A, 37B, 37C, 37D:
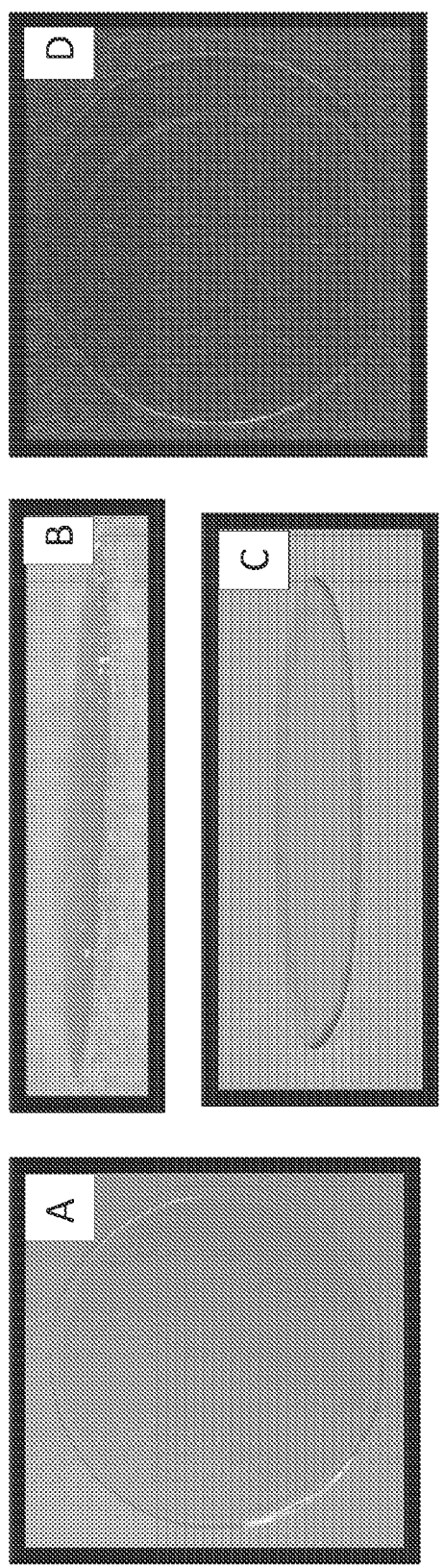
FIGS. 37A-37D are photographs showing silk protein fragment-films of the present disclosure dried at room temperature for 48 hours with open air flow.
Figure 38A:
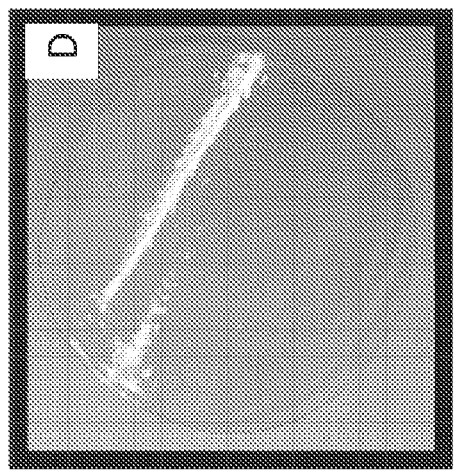
FIGS. 38A-38D are photographs showing silk protein fragment-films of the present disclosure dried at 40° C. in a convection oven for 8 hours with open air flow.
Figure 38B:
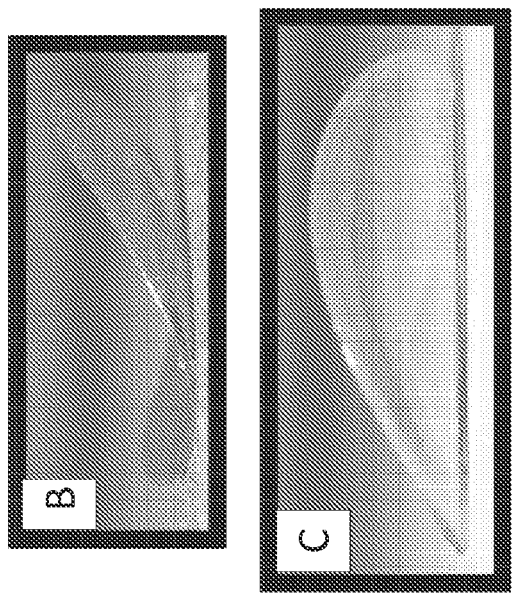
Figure 38C:
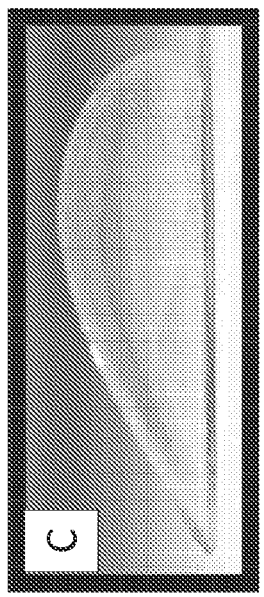
Figure 38D:
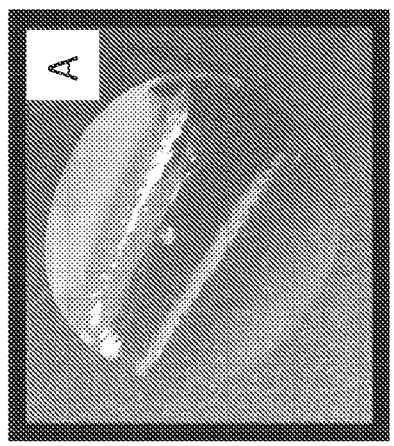
Figures 39A, 39B, 39C, 39D:
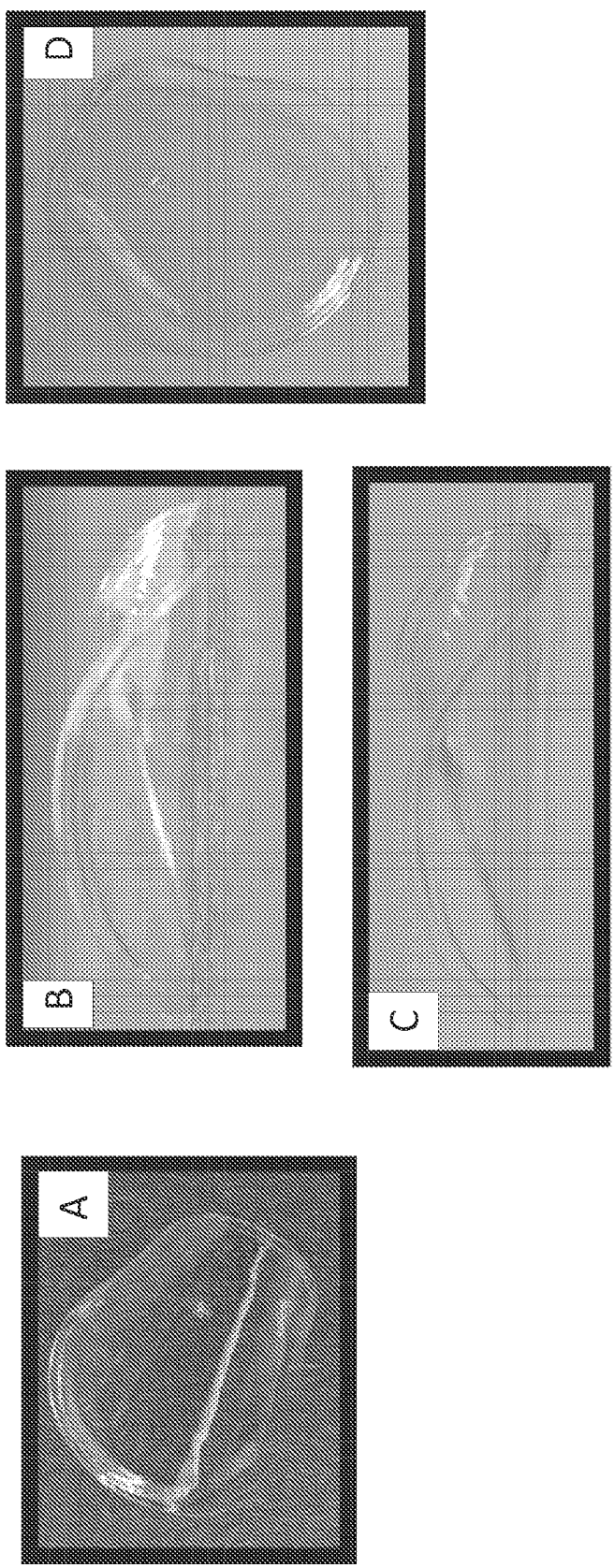
FIGS. 39A-39D are photographs showing silk protein fragment-films of the present disclosure dried at 40° C. in a convection oven for 48 hours with open air flow.
Figures 41A, 41B, 41C, 41D:
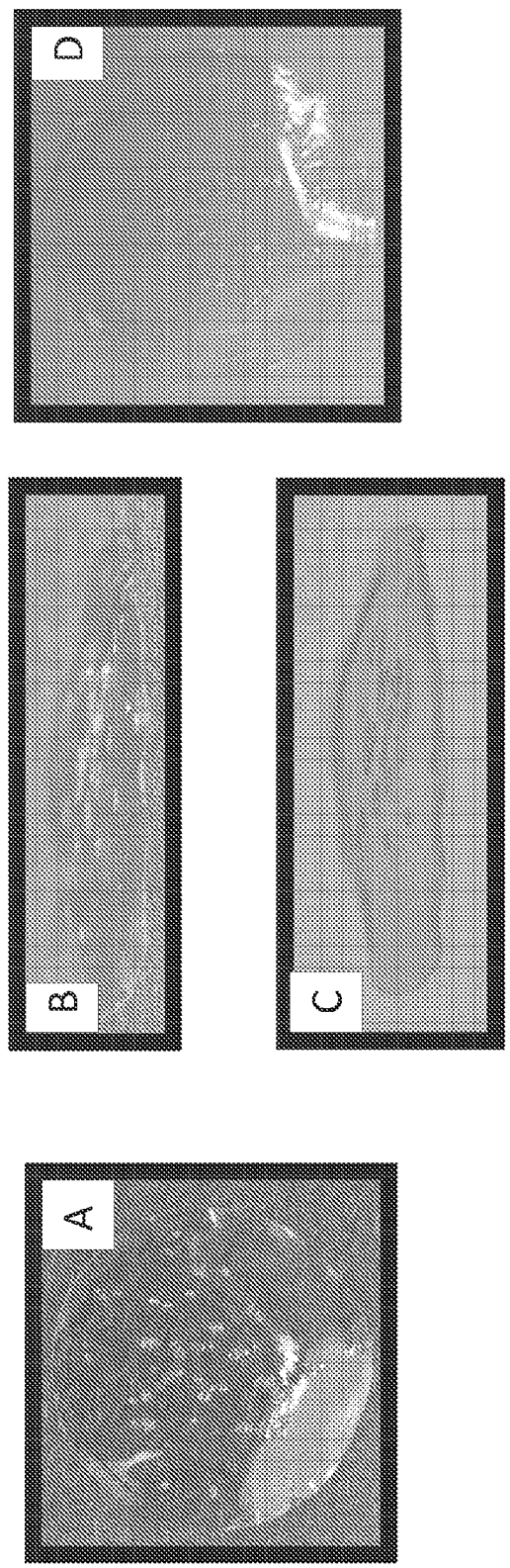
FIGS. 41A-41D are photographs showing silk protein fragment-films of the present disclosure dried at 54° C. in a convection oven for 8 hours in open dish.
Figures 43A, 43B, 43C, 43D:
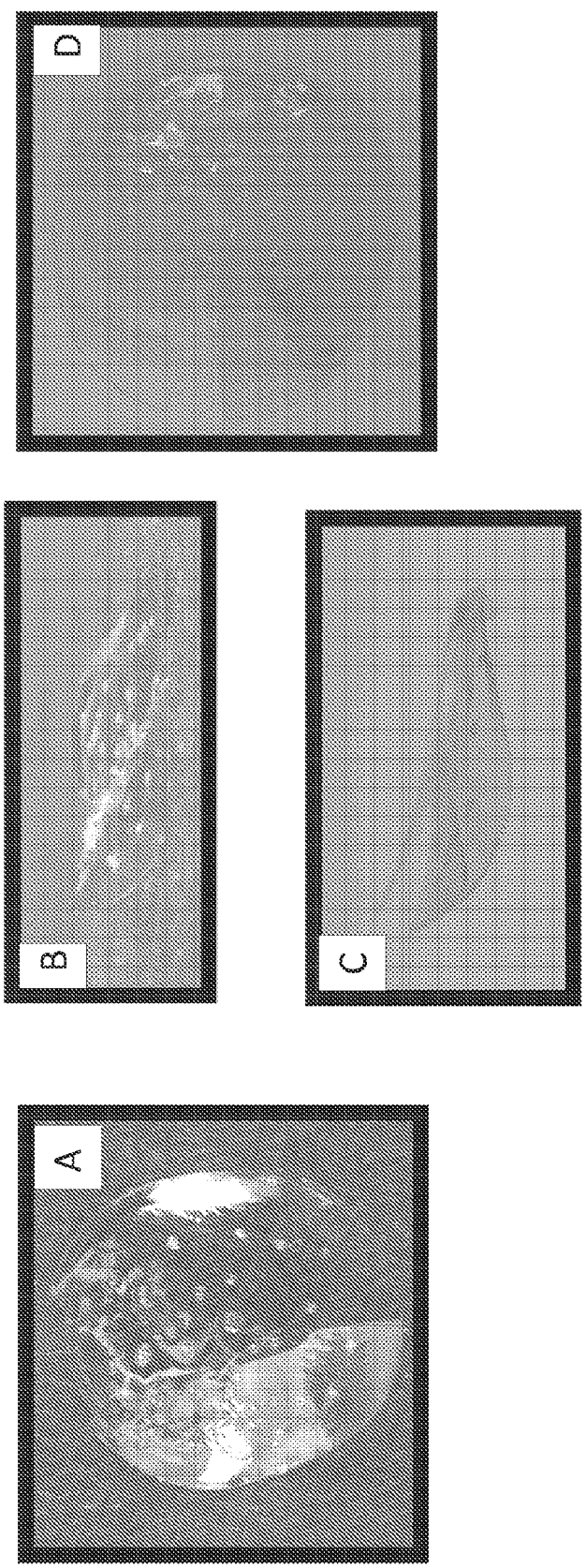
FIGS. 43A-43D are photographs showing silk protein fragment-films of the present disclosure dried at 54° C. in a film dryer for 8 hours in open dish.
Figures 46A, 46B, 46C, 46D:
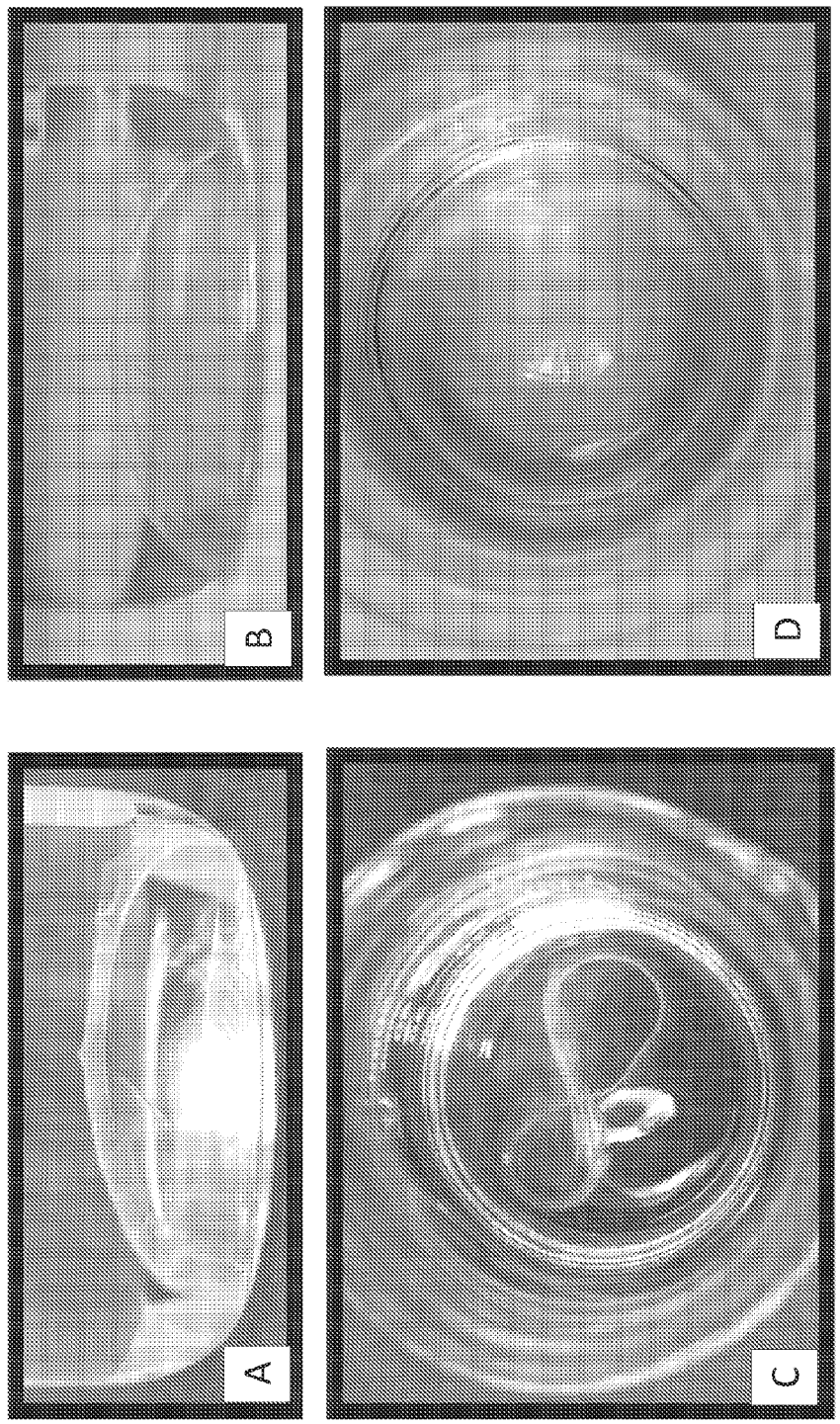
FIGS. 46A-46D are photographs showing the dissolution, in water, of the formed silk protein fragment-films of the present disclosure dried at room temperature for 48 hours with open air flow.
Figures 47A, 47B, 47C, 47D:
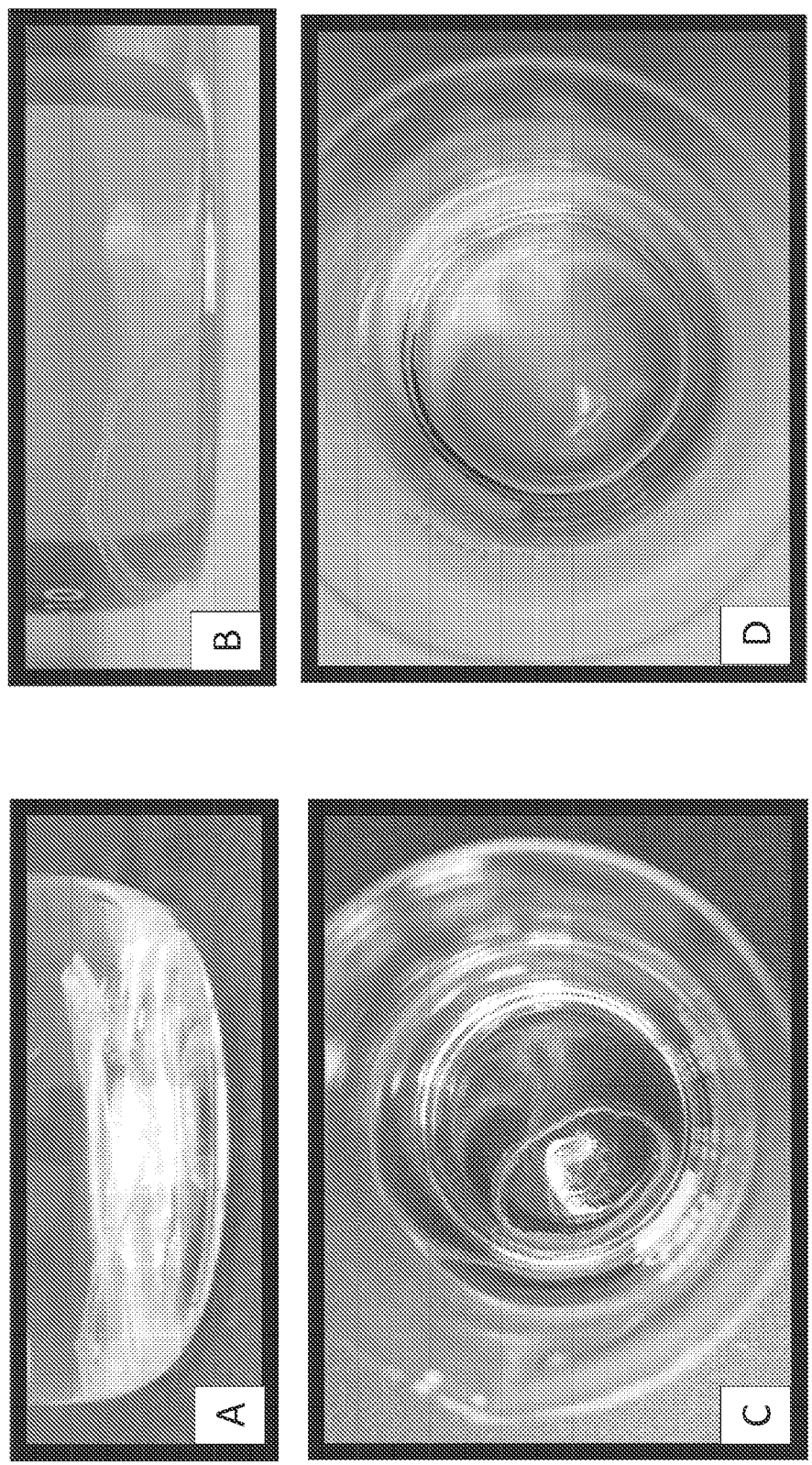
FIGS. 47A-47D are photographs showing the dissolution, in water, of the formed silk protein fragment-films of the present disclosure dried at 40° C. in a convection oven for 8 hours with open air flow.
Figures 48A, 48B, 48C, 48D:
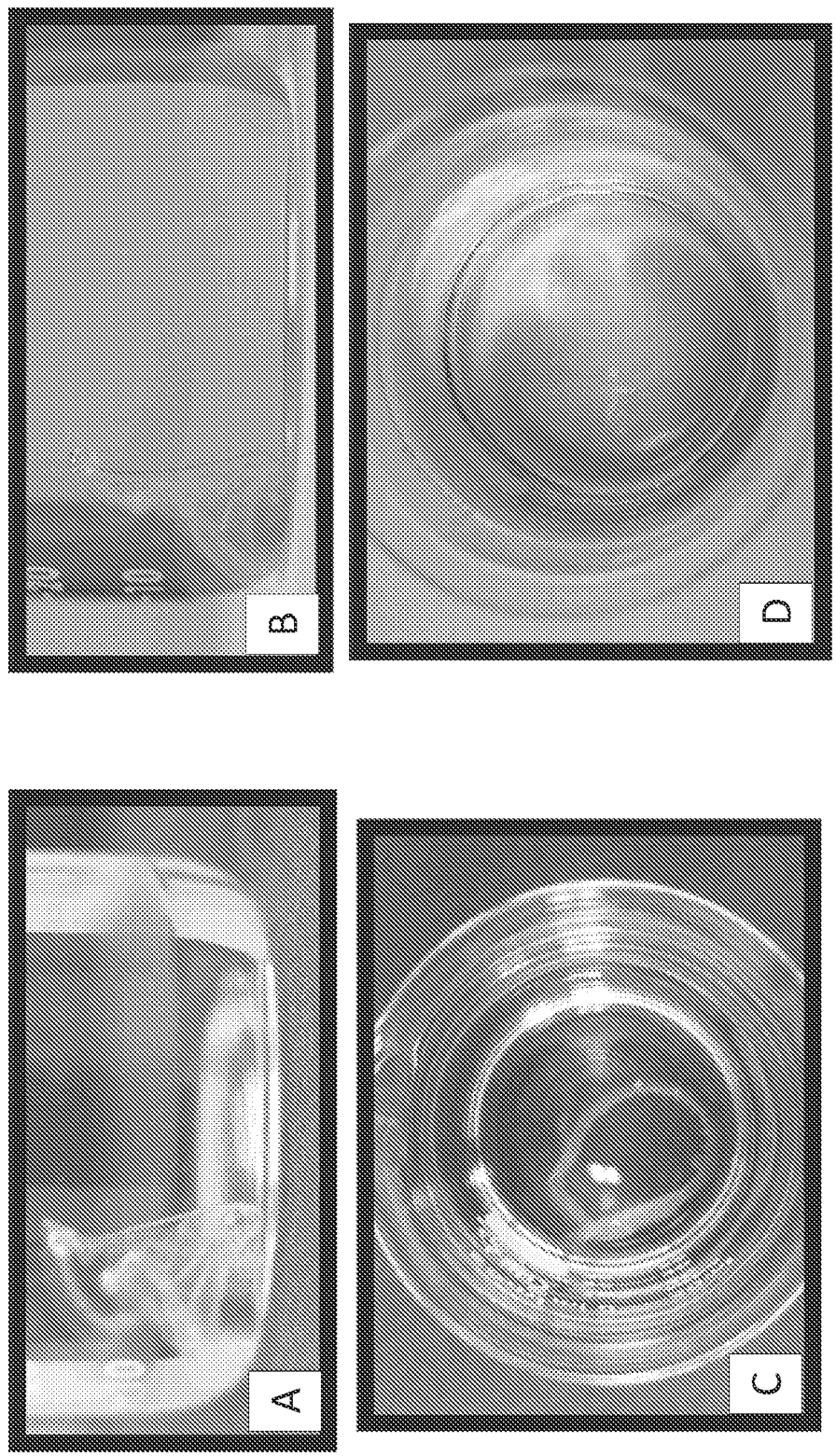
FIGS. 48A-48D are photographs showing the dissolution, in water, of the formed silk protein fragment-films of the present disclosure dried at 40° C. in a convection oven for 48 hours with open air flow.
Figures 49A, 49B, 49C, 49D:
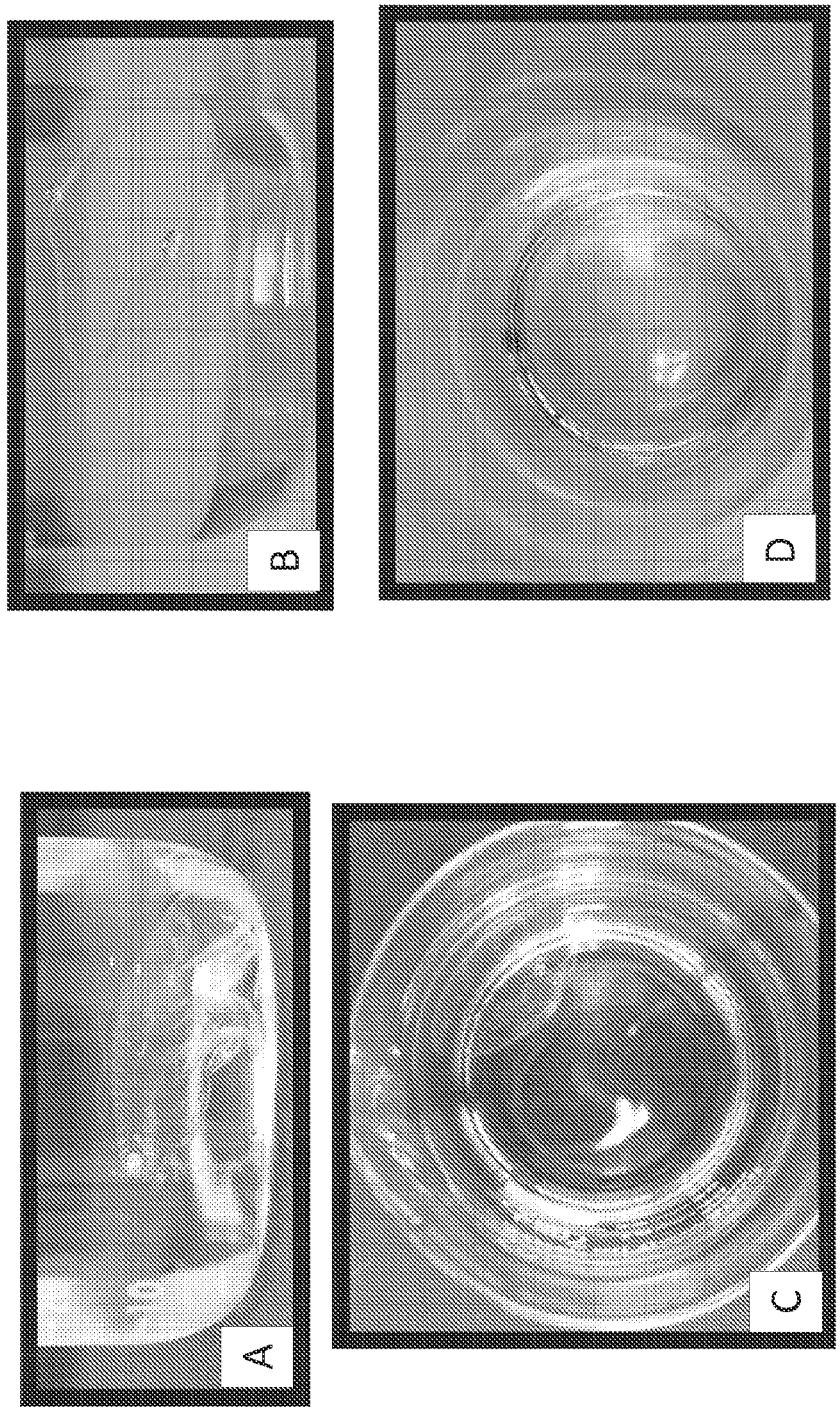
FIGS. 49A-49D are photographs showing the dissolution, in water, of the formed silk protein fragment-films of the present disclosure dried at 40° C. in a convection oven for 48 hours in closed dish.
Figures 51A, 51B, 51C, 51D:
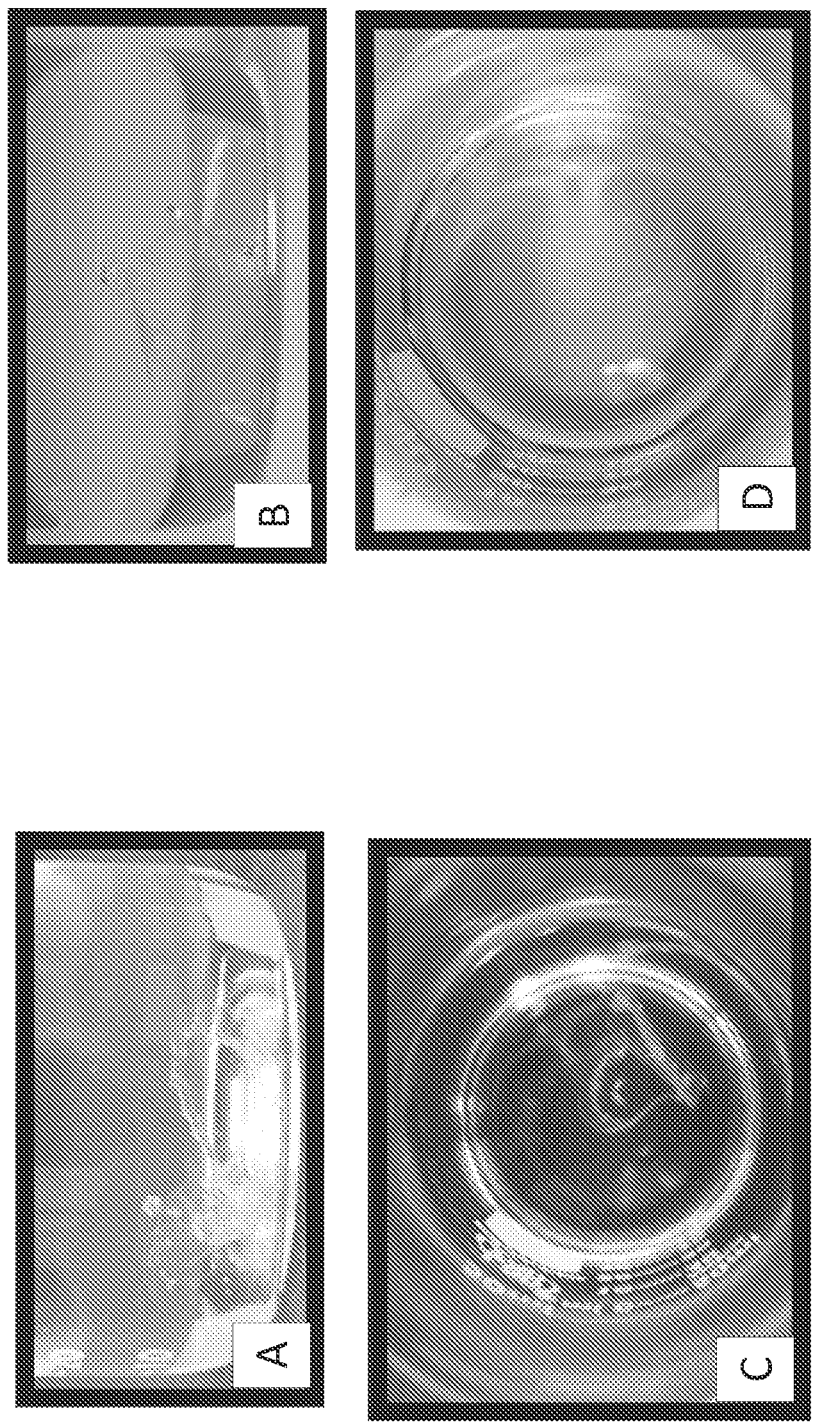
FIGS. 51A-51D are photographs showing the dissolution, in water, of the formed silk protein fragment-films of the present disclosure dried at 54° C. in a convection oven for 48 hours in open dish.
Figures 52A, 52B, 52C, 52D:
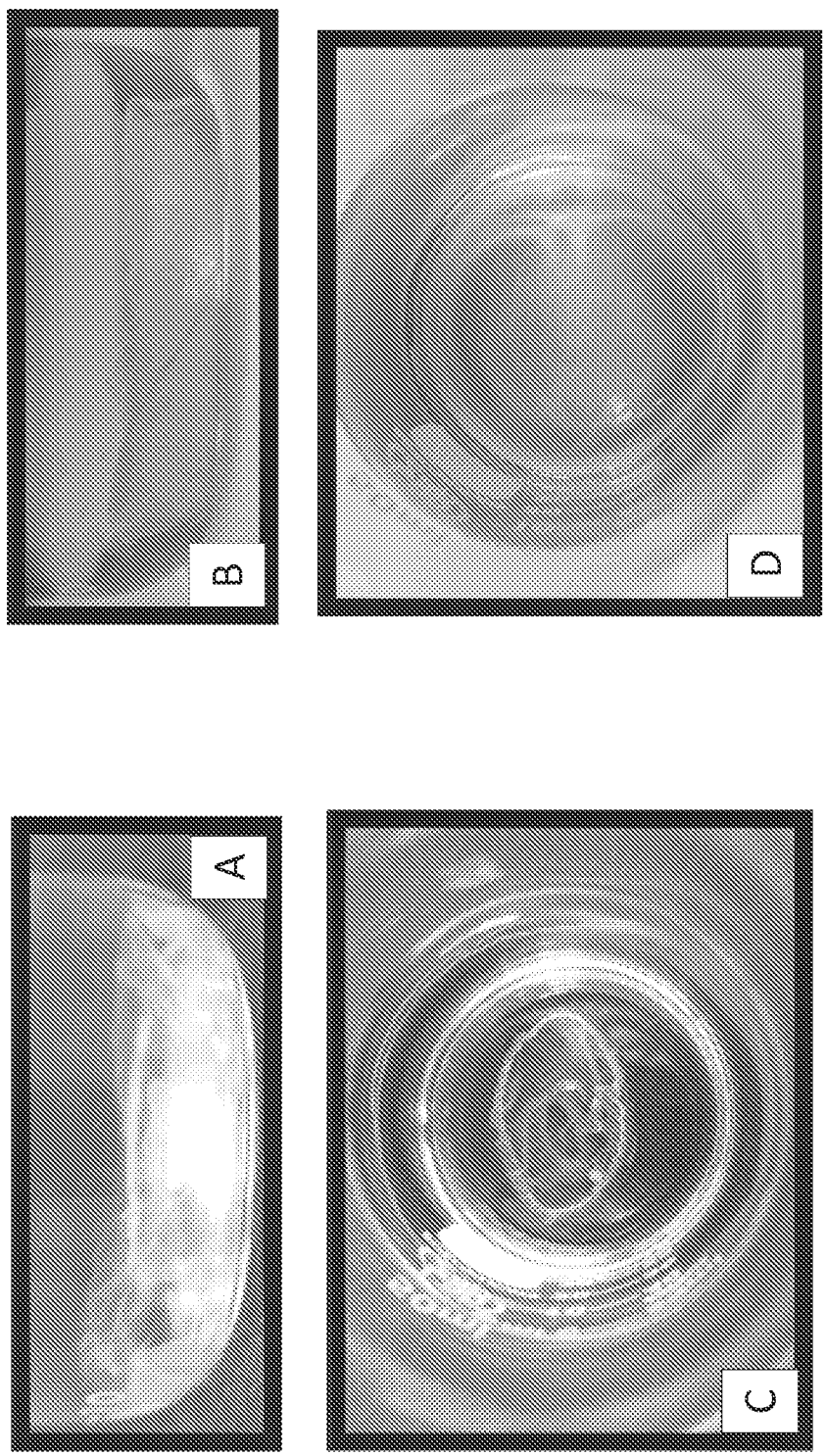
FIGS. 52A-52D are photographs showing the dissolution, in water, of the formed silk protein fragment-films of the present disclosure dried at 54° C. in a film dryer for 8 hours in open dish.
Figures 54A, 54B, 54C, 54D:
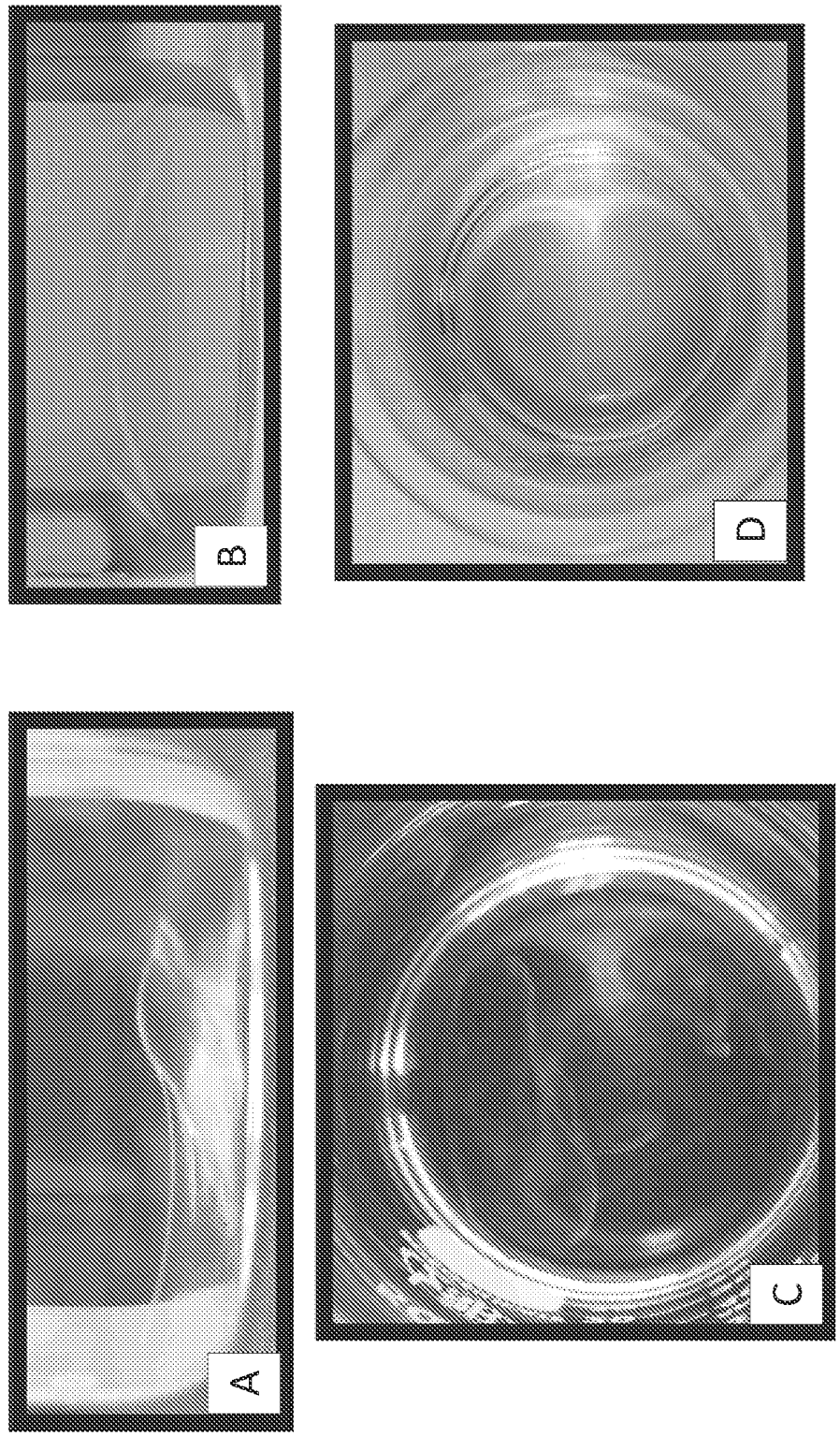
FIGS. 54A-54D are photographs showing the dissolution, in water, of the formed silk protein fragment-films of the present disclosure dried at room temperature in a convection oven for 48 hours in open dish.

FIG. 34 summarizes an embodiment of parameters for a silk fragment-film drying study of the present disclosure. FIG. 35 is a graph showing silk fragment-film drying times (under various air flow and temperature conditions) based on the silk fragment-film drying study of FIG. 34. These studies indicate that airflow is an important parameter to consider for drying (i.e., samples in covered containers did not dry), temperature can be altered to alter drying rate (i.e., increased temperature results in a faster rate of water removal) and that a steady-state of moisture content within the films can be obtained with a variety of parameters (i.e., from 24 to 48 hours, mass is consistent in uncovered samples regardless of temperature). Of note, the final properties of the film, for example brittleness, will vary with drying conditions. Alternatively, film drying rate may be accelerated by the use of an additive in the SPF solution, such as a surfactant or oil. These additives may be used with or without heat to alter drying rate and final film physical properties.

In an embodiment, the drying conditions of the SFP film are 24° C. in a forced air flow incubator for 12 to 48 hours depending on the number of films and ambient humidity. Under these drying conditions, a film that will not shrink more than 5 percent over time when stored in a foil pouch is created. Additionally, the film is homogeneous in composition and physical structure, with no sided-ness and an even distribution of additive, for example vitamin C, throughout.

In an embodiment, the silk protein fragment-film may stabilize vitamin C and derivatives thereof at room temperature when stored in light retaining about 30% to about 100% of its activity after 30 days of storage. In an embodiment, the silk protein fragment-film may stabilize vitamin C and derivatives thereof at room temperature when stored in light retaining about 35% to about 95% of its activity after 30 days of storage. In an embodiment, the silk protein fragment-film may stabilize vitamin C and derivatives thereof at room temperature when stored in light retaining about 40% to about 90% of its activity after 30 days of storage. In an embodiment, the silk protein fragment-film may stabilize vitamin C and derivatives thereof at room temperature when stored in light retaining about 45% to about 85% of its activity after 30 days of storage. In an embodiment, the silk protein fragment-film may stabilize vitamin C and derivatives thereof at room temperature when stored in light retaining about 50% to about 80% of its activity after 30 days of storage. In an embodiment, the silk protein fragment-film may stabilize vitamin C and derivatives thereof at room temperature when stored in light retaining about 55% to about 75% of its activity after 30 days of storage. In an embodiment, the silk protein fragment-film may stabilize vitamin C and derivatives thereof at room temperature when stored in light retaining about 60% to about 70% of its activity after 30 days of storage. In an embodiment, the silk protein fragment-film may stabilize vitamin C and derivatives thereof at room temperature when stored in a sealed airtight container or pouch that prevents light from contacting the film retaining about 80% to about 100% of its activity after 3 to 24 months of storage. In an embodiment, the silk protein fragment-film may stabilize vitamin C and derivatives thereof at room temperature when stored in a sealed airtight container or pouch that prevents light from contacting the film retaining about 80% to about 100% of its activity after about 3 to about 60 months of storage. In an embodiment, the silk protein fragment-film may release between 50% to 90% of active vitamin C and derivatives thereof within 20 mins when adhered to dampened skin. In an embodiment, the silk protein fragment-film may release at least 50% active vitamin C and derivatives thereof within 20 mins when adhered to dampened skin. In an embodiment, the silk protein fragment-film may release at least 60% active vitamin C and derivatives thereof within 20 mins when adhered to dampened skin. In an embodiment, the silk protein fragment-film may release at least 70% active vitamin C and derivatives thereof within 20 mins when adhered to dampened skin. In an embodiment, the silk protein fragment-film may release at least 80% active vitamin C and derivatives thereof within 20 mins when adhered to dampened skin. In an embodiment, the silk protein fragment-film may release at least 90% active vitamin C and derivatives thereof within 20 mins when adhered to dampened skin. In an embodiment, the silk protein fragment-film may release between 10% to 100% of active vitamin C and derivatives thereof within 5 mins to 8 hours when adhered to dampened skin. In an embodiment, the silk protein fragment-film may release at least 10% of active vitamin C and derivatives thereof within 5 mins to 8 hours when adhered to dampened skin. In an embodiment, the silk protein fragment-film may release at least 20% of active vitamin C and derivatives thereof within 5 mins to 8 hours when adhered to dampened skin. In an embodiment, the silk protein fragment-film may release at least 30% of active vitamin C and derivatives thereof within 5 mins to 8 hours when adhered to dampened skin. In an embodiment, the silk protein fragment-film may release at least 40% of active vitamin C and derivatives thereof within 5 mins to 8 hours when adhered to dampened skin. In an embodiment, the silk protein fragment-film may release at least 50% of active vitamin C and derivatives thereof within 5 mins to 8 hours when adhered to dampened skin. In an embodiment, the silk protein fragment-film may release at least 60% of active vitamin C and derivatives thereof within 5 mins to 8 hours when adhered to dampened skin. In an embodiment, the silk protein fragment-film may release at least 70% of active vitamin C and derivatives thereof within 5 mins to 8 hours when adhered to dampened skin. In an embodiment, the silk protein fragment-film may release at least 80% of active vitamin C and derivatives thereof within 5 mins to 8 hours when adhered to dampened skin. In an embodiment, the silk protein fragment-film may release at least 90% of active vitamin C and derivatives thereof within 5 mins to 8 hours when adhered to dampened skin. It is believed that exposure to higher temperatures for a longer period of time may break down the silk protein into more versatile silk protein fragment mixtures and/or disrupt any silk protein tertiary and/or secondary silk protein structure that could adversely affect shelf stability and/or performance of resulting structures (e.g., gels, films, foams, etc.) as well as reduces the number of heavy chains within the silk protein.

FIGS. 36A and 36B show two HPLC chromatograms from samples comprising vitamin C. The chromatogram on the left shows peaks from (1) a chemically stabilized sample of vitamin C at ambient conditions and (2) a sample of vitamin C taken after 1 hour at ambient conditions without chemical stabilization to prevent oxidation, where degradation products are visible. The chromatogram on the right shows peaks from two different embodiments of silk films of the present disclosure that were aged for at least 30 days at room temperature. No degradation products were visible. FIG. 59 is a table summarizing the vitamin C concentration in silk protein fragment-films (2% silk films air dried at RT) of the present disclosure. In FIG. 59 processing conditions included 100° C. extraction for 20 min, RT rinse, LiBr in 60° C. oven for 4-6 hours. FIG. 60 is a table summarizing the stability of vitamin C in chemically stabilized solutions. FIGS. 89A-89B are tables summarizing vitamin C stability in SPF gels without chemical stabilizers as compared to chemically stabilized vitamin C in competitive anti-aging skincare products. A gel cast at 20% total vitamin C additive concentration did not gel. Without wishing to be bound by theory, it appears there is a relationship between vitamin C concentration, silk concentration, and gelation. An increase in vitamin C at a given concentration of silk will result in a longer time to gelation or inhibit gelation. This may be due to the vitamin C molecule physically blocking interaction between silk protein fragments or cross-linking of silk protein.

In an embodiment, the molecule or molecules are stable and can be released over an extended time period. In an embodiment, release rate is controlled by the specific weight average molecular weight of the silk fibroin-based protein fragments used. In another embodiment, release rate is controlled by creation of a multi-layer structure. For example, multiple films can be cast and dried upon each other. Additionally, each layer can be formed using the same or different molecular weight compositions. In an embodiment, the degree of crystallinity of the protein structure is altered through film drying conditions, thereby controlling the release rate. The molecule or molecules may be released topically on the skin, subcutaneously following implantation, or locally or systemically through oral administration or implantation. In an embodiment, the molecule or molecules is released between 1 minutes and 20 minutes. In an embodiment, the molecule or molecules is released between 20 minutes and 60 minutes. In an embodiment, the molecule or molecules is released between 1 hour and 4 hours. In an embodiment, the molecule or molecules is released between 4 hours and 8 hours. In an embodiment, the molecule or molecules is released between 8 hours and 24 hours. In an embodiment, the molecule or molecules is released between 1 day and 7 days. In an embodiment, the molecule or molecules is released between 1 week and 4 weeks. In an embodiment, the molecule or molecules is released between 1 month and 3 months. In an embodiment, the molecule or molecules is released between 3 months and 6 months. In an embodiment, the molecule or molecules is released between 20 minutes and 6 months. In an embodiment, the molecule or molecules are stable at extreme temperature and humidity conditions.

Films of the present disclosure comprised of about 20 kDA average weight average molecular weight silk fibroin-based protein fragments and containing about 20% vitamin C by mass, were stored individually within foil pouches and exposed to temperature extremes. Foil pouches containing films were exposed to:

Ambient conditions (time 0 films)
"Extreme Cold" (−29° C.±2° C. for 72 hours), followed by "Hot Humid" (38° C.±2° C. at 85% Humidity±5% for 72 hours), and subsequently "Extreme Heat, Moderate Humidity" (60° C.±2° C. at 30% Humidity±5% for 6 hours)

The amount of active vitamin C was measured using HPLC. All films were observed to support maintenance of vitamin C activity with exposure to extremes, as summarized in Table 17.

TABLE 17

Amount of active vitamin C in films under varying conditions

| N | Conditions | Average Conc of vit C in sample (mg/g) | Std. Dev |
|---|---|---|---|
| 4 | Time 0, ambient conditions | 184.90 | 15.15 |
| 16 | 1) −29° C. ± 2° C. for 72 hours<br>2) 38° C. ± 2° C. at 85% Humidity ± 5% for 72 hours<br>3) 60° C. ± 2° C. at 30% Humidity ± 5% for 6 hours | 193.97 | 10.25 |

FIGS. 37-45 are photographs showing silk protein fragment-films of the present disclosure dried under various temperature, time and drying conditions.

FIGS. 46-54 are photographs showing the dissolution, in water, of the formed silk protein fragment-films of the present disclosure under various temperature, time and drying conditions. The water solubility of films of the present disclosure may be varied by altering drying conditions. For example, drying a film to 20% humidity in a forced air incubator and then increasing ambient humidity to 50% for a period of hours and subsequently drying the film back to 20% humidity will result in an insoluble film. Under ordinary conditions where the humidity is steadily decreased, a water-soluble silk film is created. It is anticipated that the increase in humidity allowed the protein structure to be further mobilized in the film and further crystallized, resulting in a non-soluble film. Alternative methods in the art to create non-soluble films include the introduction of methanol. The films of the present disclosure are clearly differentiated from those films due to their solubility in water. The SFP gel articles described herein range from a hydrogel which can be injected or spread topically to a film-gel article that appears as a film and contains a minimal but controlled water content, thereby preventing crystallinity and allowing water solubility.

In some embodiments, a composition of the present disclosure can further include skin penetration enhancers, including, but not limited to, sulfoxides (such as dimethylsulfoxide), pyrrolidones (such as 2-pyrrolidone), alcohols (such as ethanol or decanol), azones (such as laurocapram and 1-dodecylazacycloheptan-2-one), surfactants (including alkyl carboxylates and their corresponding acids such as oleic acid, fluoroalkylcarboxylates and their corresponding acids, alkyl sulfates, alkyl ether sulfates, docusates such as dioctyl sodium sulfosuccinate, alkyl benzene sulfonates, alkyl ether phosphates, and alkyl aryl ether phosphates), glycols (such as propylene glycol), terpenes (such as limonene, p-cymene, geraniol, farnesol, eugenol, menthol, terpineol, carveol, carvone, fenchone, and verbenone), and dimethyl isosorbide.

Following are non-limiting examples of suitable ranges for various parameters in and for preparation of the silk solutions of the present disclosure. The silk solutions of the present disclosure may include one or more, but not necessarily all, of these parameters and may be prepared using various combinations of ranges of such parameters.

In an embodiment, the percent silk in the solution is less than 30%. In an embodiment, the percent silk in the solution is less than 25%. In an embodiment, the percent silk in the solution is less than 20%. In an embodiment, the percent silk in the solution is less than 19%. In an embodiment, the percent silk in the solution is less than 18%. In an embodiment, the percent silk in the solution is less than 17%. In an embodiment, the percent silk in the solution is less than 16%. In an embodiment, the percent silk in the solution is less than 15%. In an embodiment, the percent silk in the solution is less than 14%. In an embodiment, the percent silk in the solution is less than 13%. In an embodiment, the percent silk in the solution is less than 12%. In an embodiment, the percent silk in the solution is less than 11%. In an embodiment, the percent silk in the solution is less than 10%. In an embodiment, the percent silk in the solution is less than 9%. In an embodiment, the percent silk in the solution is less than 8%. In an embodiment, the percent silk in the solution is less than 7%. In an embodiment, the percent silk in the solution is less than 6%. In an embodiment, the percent silk in the solution is less than 5%. In an embodiment, the percent silk in the solution is less than 4%. In an embodiment, the percent silk in the solution is less than 3%. In an embodiment, the percent silk in the solution is less than 2%. In an embodiment, the percent silk in the solution is less than 1%. In an embodiment, the percent silk in the solution is less than 0.9%. In an embodiment, the percent silk in the solution is less than 0.8%. In an embodiment, the percent silk in the solution is less than 0.7%. In an embodiment, the percent silk in the solution is less than 0.6%. In an embodiment, the percent silk in the solution is less than 0.5%. In an embodiment, the percent silk in the solution is less than 0.4%. In an embodiment, the percent silk in the solution is less than 0.3%. In an embodiment, the percent silk in the solution is less than 0.2%. In an embodiment, the percent silk in the solution is less than 0.1%. In an embodiment, the percent silk in the solution is greater than 0.1%. In an embodiment, the percent silk in the solution is greater than 0.2%. In an embodiment, the percent silk in the solution is greater than 0.3%. In an embodiment, the percent silk in the solution is greater than 0.4%. In an embodiment, the percent silk in the solution is greater than 0.5%. In an embodiment, the percent silk in the solution is greater than 0.6%. In an embodiment, the percent silk in the solution is greater than 0.7%. In an embodiment, the percent silk in the solution is greater than 0.8%. In an embodiment, the percent silk in the solution is greater than 0.9%. In an embodiment, the percent silk in the solution is greater than 1%. In an embodiment, the percent silk in the solution is greater than 2%. In an embodiment, the percent silk in the solution is greater than 3%. In an embodiment, the percent silk in the solution is greater than 4%. In an embodiment, the percent silk in the solution is greater than 5%. In an embodiment, the percent silk in the solution is greater than 6%. In an embodiment, the percent silk in the solution is greater than 7%. In an embodiment, the percent silk in the solution is greater than 8%. In an embodiment, the percent silk in the solution is greater than 9%. In an embodiment, the percent silk in the solution is greater than 10%. In an embodiment, the percent silk in the solution is greater than 11%. In an embodiment, the percent silk in the solution is greater than 12%. In an embodiment, the percent silk in the solution is greater than 13%. In an embodiment, the percent silk in the solution is greater than 14%. In an embodiment, the percent silk in the solution is greater than 15%. In an embodiment, the percent silk in the solution is greater than 16%. In an embodiment, the percent silk in the solution is greater than 17%. In an embodiment, the percent silk in the solution is greater than 18%. In an embodiment, the percent silk in the solution is greater than 19%. In an embodiment, the percent silk in the solution is greater than 20%. In an embodiment, the percent silk in the solution is greater than 25%. In an embodiment, the percent silk in the solution is between 0.1% and 30%. In an embodiment, the percent silk in the solution is between 0.1% and 25%. In an embodiment, the percent silk in the solution is between 0.1% and 20%. In an embodiment, the percent silk in the solution is between 0.1% and 15%. In an embodiment, the percent silk in the solution is between 0.1% and 10%. In an embodiment, the percent silk in the solution is between 0.1% and 9%. In an embodiment, the percent silk in the solution is between 0.1% and 8%. In an embodiment, the percent silk in the solution is between 0.1% and 7%. In an embodiment, the percent silk in the solution is between 0.1% and 6.5%. In an embodiment, the percent silk in the solution is between 0.1% and 6%. In an embodiment, the percent silk in the solution is between 0.1% and 5.5%. In an embodiment, the percent silk in the solution is between 0.1% and 5%. In an embodiment, the percent silk in the solution is between 0.1% and 4.5%. In an embodiment, the percent silk in the solution is between 0.1% and 4%. In an embodiment, the percent silk in the solution is between 0.1% and 3.5%. In an embodiment, the percent silk in the solution is between 0.1% and 3%. In an embodiment, the percent silk in the solution is between 0.1% and 2.5%. In an embodiment, the percent silk in the solution is between 0.1% and 2.0%. In an embodiment, the percent silk in the solution is between 0.1% and 2.4%. In an embodiment, the percent silk in the solution is between 0.5% and 5%. In an embodiment, the percent silk in the solution is between 0.5% and 4.5%. In an embodiment, the percent silk in the solution is between 0.5% and 4%. In an embodiment, the percent silk in the solution is between 0.5% and 3.5%. In an embodiment, the percent silk in the solution is between 0.5% and 3%. In an embodiment, the percent silk in the solution is between 0.5% and 2.5%. In an embodiment, the percent silk in the solution is between 1 and 4%. In an embodiment, the percent silk in the solution is between 1 and 3.5%. In an embodiment, the percent silk in the solution is between 1 and 3%. In an embodiment, the percent silk in the solution is between 1 and 2.5%. In an embodiment, the percent silk in the solution is between 1 and 2.4%. In an embodiment, the percent silk in the solution is between 1 and 2%. In an embodiment, the percent silk in the solution is between 20% and 30%. In an embodiment, the percent silk in the solution is between 0.1% and 6%. In an embodiment, the percent silk in the solution is between 6% and 10%. In an embodiment, the percent silk in the solution is between 6% and 8%. In an embodiment, the percent silk in the solution is between 6% and 9%. In an embodiment, the percent silk in the solution is between 10% and 20%. In an embodiment, the percent silk in the solution is between 11% and 19%. In an embodiment, the percent silk in the solution is between 12% and 18%. In an embodiment, the percent silk in the solution is between 13% and 17%. In an embodiment, the percent silk in the solution is between 14% and 16%. In an embodiment, the percent silk in the solution is 2.4%. In an embodiment, the percent silk in the solution is 2.0%.

In an embodiment, the percent sericin in the solution is non-detectable to 30%. In an embodiment, the percent sericin in the solution is non-detectable to 5%. In an embodiment, the percent sericin in the solution is 1%. In an embodiment, the percent sericin in the solution is 2%. In an embodiment, the percent sericin in the solution is 3%. In an embodiment, the percent sericin in the solution is 4%. In an embodiment, the percent sericin in the solution is 5%. In an embodiment, the percent sericin in the solution is 10%. In an embodiment, the percent sericin in the solution is 30%.

In an embodiment, the stability of the LiBr-silk fragment solution is 0 to 1 year. In an embodiment, the stability of the LiBr-silk fragment solution is 0 to 2 years. In an embodiment, the stability of the LiBr-silk fragment solution is 0 to 3 years. In an embodiment, the stability of the LiBr-silk fragment solution is 0 to 4 years. In an embodiment, the stability of the LiBr-silk fragment solution is 0 to 5 years. In an embodiment, the stability of the LiBr-silk fragment solution is 1 to 2 years. In an embodiment, the stability of the LiBr-silk fragment solution is 1 to 3 years. In an embodiment, the stability of the LiBr-silk fragment solution is 1 to 4 years. In an embodiment, the stability of the LiBr-silk fragment solution is 1 to 5 years. In an embodiment, the stability of the LiBr-silk fragment solution is 2 to 3 years. In an embodiment, the stability of the LiBr-silk fragment solution is 2 to 4 years. In an embodiment, the stability of the LiBr-silk fragment solution is 2 to 5 years. In an embodiment, the stability of the LiBr-silk fragment solution is 3 to 4 years. In an embodiment, the stability of the LiBr-silk fragment solution is 3 to 5 years. In an embodiment, the stability of the LiBr-silk fragment solution is 4 to 5 years.

In an embodiment, the stability of a composition of the present disclosure is 10 days to 6 months. In an embodiment, the stability of a composition of the present disclosure is 6 months to 12 months. In an embodiment, the stability of a composition of the present disclosure is 12 months to 18 months. In an embodiment, the stability of a composition of the present disclosure is 18 months to 24 months. In an embodiment, the stability of a composition of the present disclosure is 24 months to 30 months. In an embodiment, the stability of a composition of the present disclosure is 30 months to 36 months. In an embodiment, the stability of a composition of the present disclosure is 36 months to 48 months. In an embodiment, the stability of a composition of the present disclosure is 48 months to 60 months.

In an embodiment, a composition of the present disclosure includes pure silk fibroin-based protein fragments having an average weight average molecular weight ranging from 6 kDa to 16 kDa. In an embodiment, a composition of the present disclosure includes pure silk fibroin-based protein fragments having an average weight average molecular weight ranging from 17 kDa to 38 kDa. In an embodiment, a composition of the present disclosure includes pure silk fibroin-based protein fragments having an average weight average molecular weight ranging from 39 kDa to 80 kDa. In an embodiment, a composition of the present disclosure includes pure silk fibroin-based protein fragments having an average weight average molecular weight ranging from 1 to 5 kDa. In an embodiment, a composition of the present disclosure includes pure silk fibroin-based protein fragments having an average weight average molecular weight ranging from 5 to 10 kDa. In an embodiment, a composition of the present disclosure includes pure silk fibroin-based protein fragments having an average weight average molecular weight ranging from 10 to 15 kDa. In an embodiment, a composition of the present disclosure includes pure silk fibroin-based protein fragments having an average weight average molecular weight ranging from 15 to 20 kDa. In an embodiment, a composition of the present disclosure includes pure silk fibroin-based protein fragments having an average weight average molecular weight ranging from 20 to 25 kDa. In an embodiment, a composition of the present disclosure includes pure silk fibroin-based protein fragments having an average weight average molecular weight ranging from 25 to 30 kDa. In an embodiment, a composition of the present disclosure includes pure silk fibroin-based protein fragments having an average weight average molecular weight ranging from 30 to 35 kDa. In an embodiment, a composition of the present disclosure includes pure silk fibroin-based protein fragments having an average weight average molecular weight ranging from 35 to 40 kDa. In an embodiment, a composition of the present disclosure includes pure silk fibroin-based protein fragments having an average weight average molecular weight ranging from 40 to 45 kDa. In an embodiment, a composition of the present disclosure includes pure silk fibroin-based protein fragments having an average weight average molecular weight ranging from 45 to 50 kDa. In an embodiment, a composition of the present disclosure includes pure silk fibroin-based protein fragments having an average weight average molecular weight ranging from 50 to 55 kDa. In an embodiment, a composition of the present disclosure includes pure silk fibroin-based protein fragments having an average weight average molecular weight ranging from 55 to 60 kDa. In an embodiment, a composition of the present disclosure includes pure silk fibroin-based protein fragments having an average weight average molecular weight ranging from 60 to 65 kDa. In an embodiment, a composition of the present disclosure includes pure silk fibroin-based protein fragments having an average weight average molecular weight ranging from 65 to 70 kDa. In an embodiment, a composition of the present disclosure includes pure silk fibroin-based protein fragments having an average weight average molecular weight ranging from 70 to 75 kDa. In an embodiment, a composition of the present disclosure includes pure silk fibroin-based protein fragments having an average weight average molecular weight ranging from 75 to 80 kDa. In an embodiment, a composition of the present disclosure includes pure silk fibroin-based protein fragments having an average weight average molecular weight ranging from 80 to 85 kDa. In an embodiment, a composition of the present disclosure includes pure silk fibroin-based protein fragments having an average weight average molecular weight ranging from 85 to 90 kDa. In an embodiment, a composition of the present disclosure includes pure silk fibroin-based protein fragments having an average weight average molecular weight ranging from 90 to 95 kDa. In an embodiment, a composition of the present disclosure includes pure silk fibroin-based protein fragments having an average weight average molecular weight ranging from 95 to 100 kDa. In an embodiment, a composition of the present disclosure includes pure silk fibroin-based protein fragments having an average weight average molecular weight ranging from 100 to 105 kDa. In an embodiment, a composition of the present disclosure includes pure silk fibroin-based protein fragments having an average weight average molecular weight ranging from 105 to 110 kDa. In an embodiment, a composition of the present disclosure includes pure silk fibroin-based protein fragments having an average weight average molecular weight ranging from 110 to 115 kDa. In an embodiment, a composition of the present disclosure includes pure silk fibroin-based protein fragments having an average weight average molecular weight ranging from 115 to 120 kDa. In an embodiment, a composition of the present disclosure includes pure silk fibroin-based protein fragments having an average weight average molecular weight ranging from 120 to 125 kDa. In an embodiment, a composition of the present disclosure includes pure silk fibroin-based protein fragments having an average weight average molecular weight ranging from 125 to 130 kDa. In an embodiment, a composition of the present disclosure includes pure silk fibroin-based protein fragments having an average weight average molecular weight ranging from 130 to 135 kDa. In an embodiment, a composition of the present disclosure includes pure silk fibroin-based protein fragments having an average weight average molecular weight ranging from 135 to 140 kDa. In an embodiment, a composition of the present disclosure includes pure silk fibroin-based protein fragments having an average weight average molecular weight ranging from 140 to 145 kDa. In an embodiment, a composition of the present disclosure includes pure silk fibroin-based protein fragments having an average weight average molecular weight ranging from 145 to 150 kDa. In an embodiment, a composition of the present disclosure includes pure silk fibroin-based protein fragments having an average weight average molecular weight ranging from 150 to 155 kDa. In an embodiment, a composition of the present disclosure includes pure silk fibroin-based protein fragments having an average weight average molecular weight ranging from 155 to 160 kDa. In an embodiment, a composition of the present disclosure includes pure silk fibroin-based protein fragments having an average weight average molecular weight ranging from 160 to 165 kDa. In an embodiment, a composition of the present disclosure includes pure silk fibroin-based protein fragments having an average weight average molecular weight ranging from 165 to 170 kDa. In an embodiment, a composition of the present disclosure includes pure silk fibroin-based protein fragments having an average weight average molecular weight ranging from 170 to 175 kDa. In an embodiment, a composition of the present disclosure includes pure silk fibroin-based protein fragments having an average weight average molecular weight ranging from 175 to 180 kDa. In an embodiment, a composition of the present disclosure includes pure silk fibroin-based protein fragments having an average weight average molecular weight ranging from 180 to 185 kDa. In an embodiment, a composition of the present disclosure includes pure silk fibroin-based protein fragments having an average weight average molecular weight ranging from 185 to 190 kDa. In an embodiment, a composition of the present disclosure includes pure silk fibroin-based protein fragments having an average weight average molecular weight ranging from 190 to 195 kDa. In an embodiment, a composition of the present disclosure includes pure silk fibroin-based protein fragments having an average weight average molecular weight ranging from 195 to 200 kDa. In an embodiment, a composition of the present disclosure includes pure silk fibroin-based protein fragments having an average weight average molecular weight ranging from 200 to 205 kDa. In an embodiment, a composition of the present disclosure includes pure silk fibroin-based protein fragments having an average weight average molecular weight ranging from 205 to 210 kDa. In an embodiment, a composition of the present disclosure includes pure silk fibroin-based protein fragments having an average weight average molecular weight ranging from 210 to 215 kDa. In an embodiment, a composition of the present disclosure includes pure silk fibroin-based protein fragments having an average weight average molecular weight ranging from 215 to 220 kDa. In an embodiment, a composition of the present disclosure includes pure silk fibroin-based protein fragments having an average weight average molecular weight ranging from 220 to 225 kDa. In an embodiment, a composition of the present disclosure includes pure silk fibroin-based protein fragments having an average weight average molecular weight ranging from 225 to 230 kDa. In an embodiment, a composition of the present disclosure includes pure silk fibroin-based protein fragments having an average weight average molecular weight ranging from 230 to 235 kDa. In an embodiment, a composition of the present disclosure includes pure silk fibroin-based protein fragments having an average weight average molecular weight ranging from 235 to 240 kDa. In an embodiment, a composition of the present disclosure includes pure silk fibroin-based protein fragments having an average weight average molecular weight ranging from 240 to 245 kDa. In an embodiment, a composition of the present disclosure includes pure silk fibroin-based protein fragments having an average weight average molecular weight ranging from 245 to 250 kDa. In an embodiment, a composition of the present disclosure includes pure silk fibroin-based protein fragments having an average weight average molecular weight ranging from 250 to 255 kDa. In an embodiment, a composition of the present disclosure includes pure silk fibroin-based protein fragments having an average weight average molecular weight ranging from 255 to 260 kDa. In an embodiment, a composition of the present disclosure includes pure silk fibroin-based protein fragments having an average weight average molecular weight ranging from 260 to 265 kDa. In an embodiment, a composition of the present disclosure includes pure silk fibroin-based protein fragments having an average weight average molecular weight ranging from 265 to 270 kDa. In an embodiment, a composition of the present disclosure includes pure silk fibroin-based protein fragments having an average weight average molecular weight ranging from 270 to 275 kDa. In an embodiment, a composition of the present disclosure includes pure silk fibroin-based protein fragments having an average weight average molecular weight ranging from 275 to 280 kDa. In an embodiment, a composition of the present disclosure includes pure silk fibroin-based protein fragments having an average weight average molecular weight ranging from 280 to 285 kDa. In an embodiment, a composition of the present disclosure includes pure silk fibroin-based protein fragments having an average weight average molecular weight ranging from 285 to 290 kDa. In an embodiment, a composition of the present disclosure includes pure silk fibroin-based protein fragments having an average weight average molecular weight ranging from 290 to 295 kDa. In an embodiment, a composition of the present disclosure includes pure silk fibroin-based protein fragments having an average weight average molecular weight ranging from 295 to 300 kDa. In an embodiment, a composition of the present disclosure includes pure silk fibroin-based protein fragments having an average weight average molecular weight ranging from 300 to 305 kDa. In an embodiment, a composition of the present disclosure includes pure silk fibroin-based protein fragments having an average weight average molecular weight ranging from 305 to 310 kDa. In an embodiment, a composition of the present disclosure includes pure silk fibroin-based protein fragments having an average weight average molecular weight ranging from 310 to 315 kDa. In an embodiment, a composition of the present disclosure includes pure silk fibroin-based protein fragments having an average weight average molecular weight ranging from 315 to 320 kDa. In an embodiment, a composition of the present disclosure includes pure silk fibroin-based protein fragments having an average weight average molecular weight ranging from 320 to 325 kDa. In an embodiment, a composition of the present disclosure includes pure silk fibroin-based protein fragments having an average weight average molecular weight ranging from 325 to 330 kDa. In an embodiment, a composition of the present disclosure includes pure silk fibroin-based protein fragments having an average weight average molecular weight ranging from 330 to 335 kDa. In an embodiment, a composition of the present disclosure includes pure silk fibroin-based protein fragments having an average weight average molecular weight ranging from 35 to 340 kDa. In an embodiment, a composition of the present disclosure includes pure silk fibroin-based protein fragments having an average weight average molecular weight ranging from 340 to 345 kDa. In an embodiment, a composition of the present disclosure includes pure silk fibroin-based protein fragments having an average weight average molecular weight ranging from 345 to 350 kDa.

In an embodiment, a composition of the present disclosure having pure silk fibroin-based protein fragments has a polydispersity ranging from about 1 to about 5.0. In an embodiment, a composition of the present disclosure having pure silk fibroin-based protein fragments has a polydispersity ranging from about 1.5 to about 3.0. In an embodiment, a composition of the present disclosure having pure silk fibroin-based protein fragments has a polydispersity ranging from about 1 to about 1.5. In an embodiment, a composition of the present disclosure having pure silk fibroin-based protein fragments has a polydispersity ranging from about 1.5 to about 2.0. In an embodiment, a composition of the present disclosure having pure silk fibroin-based protein fragments has a polydispersity ranging from about 2.0 to about 2.5. In an embodiment, a composition of the present disclosure having pure silk fibroin-based protein fragments, has a polydispersity ranging from about is 2.0 to about 3.0. In an embodiment, a composition of the present disclosure having pure silk fibroin-based protein fragments, has a polydispersity ranging from about is 2.5 to about 3.0.

In an embodiment, a composition of the present disclosure having pure silk fibroin-based protein fragments has non-detectable levels of LiBr residuals. In an embodiment, the amount of the LiBr residuals in a composition of the present disclosure is between 10 ppm and 1000 ppm. In an embodiment, the amount of the LiBr residuals in a composition of the present disclosure is between 10 ppm and 300 ppm. In an embodiment, the amount of the LiBr residuals in a composition of the present disclosure is less than 25 ppm. In an embodiment, the amount of the LiBr residuals in a composition of the present disclosure is less than 50 ppm. In an embodiment, the amount of the LiBr residuals in a composition of the present disclosure is less than 75 ppm. In an embodiment, the amount of the LiBr residuals in a composition of the present disclosure is less than 100 ppm. In an embodiment, the amount of the LiBr residuals in a composition of the present disclosure is less than 200 ppm. In an embodiment, the amount of the LiBr residuals in a composition of the present disclosure is less than 300 ppm. In an embodiment, the amount of the LiBr residuals in a composition of the present disclosure is less than 400 ppm. In an embodiment, the amount of the LiBr residuals in a composition of the present disclosure is less than 500 ppm. In an embodiment, the amount of the LiBr residuals in a composition of the present disclosure is less than 600 ppm. In an embodiment, the amount of the LiBr residuals in a composition of the present disclosure is less than 700 ppm. In an embodiment, the amount of the LiBr residuals in a composition of the present disclosure is less than 800 ppm. In an embodiment, the amount of the LiBr residuals in a composition of the present disclosure is less than 900 ppm. In an embodiment, the amount of the LiBr residuals in a composition of the present disclosure is less than 1000 ppm. In an embodiment, the amount of the LiBr residuals in a composition of the present disclosure is non-detectable to 500 ppm. In an embodiment, the amount of the LiBr residuals in a composition of the present disclosure is non-detectable to 450 ppm. In an embodiment, the amount of the LiBr residuals in a composition of the present disclosure is non-detectable to 400 ppm. In an embodiment, the amount of the LiBr residuals in a composition of the present disclosure is non-detectable to 350 ppm. In an embodiment, the amount of the LiBr residuals in a composition of the present disclosure is non-detectable to 300 ppm. In an embodiment, the amount of the LiBr residuals in a composition of the present disclosure is non-detectable to 250 ppm. In an embodiment, the amount of the LiBr residuals in a composition of the present disclosure is non-detectable to 200 ppm. In an embodiment, the amount of the LiBr residuals in a composition of the present disclosure is non-detectable to 150 ppm. In an embodiment, the amount of the LiBr residuals in a composition of the present disclosure is non-detectable to 100 ppm. In an embodiment, the amount of the LiBr residuals in a composition of the present disclosure is 100 ppm to 200 ppm. In an embodiment, the amount of the LiBr residuals in a composition of the present disclosure is 200 ppm to 300 ppm. In an embodiment, the amount of the LiBr residuals in a composition of the present disclosure is 300 ppm to 400 ppm. In an embodiment, the amount of the LiBr residuals in a composition of the present disclosure is 400 ppm to 500 ppm.

In an embodiment, a composition of the present disclosure having pure silk fibroin-based protein fragments, has non-detectable levels of $Na_2CO_3$ residuals. In an embodiment, the amount of the $Na_2CO_3$ residuals in a composition of the present disclosure is less than 100 ppm. In an embodiment, the amount of the $Na_2CO_3$ residuals in a composition of the present disclosure is less than 200 ppm. In an embodiment, the amount of the $Na_2CO_3$ residuals in a composition of the present disclosure is less than 300 ppm. In an embodiment, the amount of the $Na_2CO_3$ residuals in a composition of the present disclosure is less than 400 ppm. In an embodiment, the amount of the $Na_2CO_3$ residuals in a composition of the present disclosure is less than 500 ppm. In an embodiment, the amount of the $Na_2CO_3$ residuals in a composition of the present disclosure is less than 600 ppm. In an embodiment, the amount of the $Na_2CO_3$ residuals in a composition of the present disclosure is less than 700 ppm. In an embodiment, the amount of the $Na_2CO_3$ residuals in a composition of the present disclosure is less than 800 ppm. In an embodiment, the amount of the $Na_2CO_3$ residuals in a composition of the present disclosure is less than 900 ppm. In an embodiment, the amount of the $Na_2CO_3$ residuals in a composition of the present disclosure is less than 1000 ppm. In an embodiment, the amount of the $Na_2CO_3$ residuals in a composition of the present disclosure is non-detectable to 500 ppm. In an embodiment, the amount of the $Na_2CO_3$ residuals in a composition of the present disclosure is non-detectable to 450 ppm. In an embodiment, the amount of the $Na_2CO_3$ residuals in a composition of the present disclosure is non-detectable to 400 ppm. In an embodiment, the amount of the $Na_2CO_3$ residuals in a composition of the present disclosure is non-detectable to 350 ppm. In an embodiment, the amount of the $Na_2CO_3$ residuals in a composition of the present disclosure is non-detectable to 300 ppm. In an embodiment, the amount of the $Na_2CO_3$ residuals in a composition of the present disclosure is non-detectable to 250 ppm. In an embodiment, the amount of the $Na_2CO_3$ residuals in a composition of the present disclosure is non-detectable to 200 ppm. In an embodiment, the amount of the $Na_2CO_3$ residuals in a composition of the present disclosure is non-detectable to 150 ppm. In an embodiment, the amount of the $Na_2CO_3$ residuals in a composition of the present disclosure is non-detectable to 100 ppm. In an embodiment, the amount of the $Na_2CO_3$ residuals in a composition of the present disclosure is 100 ppm to 200 ppm. In an embodiment, the amount of the $Na_2CO_3$ residuals in a composition of the present disclosure is 200 ppm to 300 ppm. In an embodiment, the amount of the $Na_2CO_3$ residuals in a composition of the present disclosure is 300 ppm to 400 ppm. In an embodiment, the amount of the $Na_2CO_3$ residuals in a composition of the present disclosure is 400 ppm to 500 ppm.

In an embodiment, the water solubility of pure silk fibroin-based protein fragments of the present disclosure is 50 to 100%. In an embodiment, the water solubility of pure silk fibroin-based protein fragments of the present disclosure is 60 to 100%. In an embodiment, the water solubility of pure silk fibroin-based protein fragments of the present disclosure is 70 to 100%. In an embodiment, the water solubility of pure silk fibroin-based protein fragments of the present disclosure is 80 to 100%. In an embodiment, water solubility is 90 to 100%. In an embodiment, the silk fibroin-based fragments of the present disclosure are non-soluble in aqueous solutions.

In an embodiment, the solubility of pure silk fibroin-based protein fragments of the present disclosure in organic solutions is 50 to 100%. In an embodiment, the solubility of pure silk fibroin-based protein fragments of the present disclosure in organic solutions is 60 to 100%. In an embodiment, the solubility of pure silk fibroin-based protein fragments of the present disclosure in organic solutions is 70 to 100%. In an embodiment, the solubility of pure silk fibroin-based protein fragments of the present disclosure in organic solutions is 80 to 100%. In an embodiment, the solubility of pure silk fibroin-based protein fragments of the present disclosure in organic solutions is 90 to 100%. In an embodiment, the silk fibroin-based fragments of the present disclosure are non-soluble in organic solutions.

In an embodiment, the percent water content in gels of the present disclosure is 20% to 99.9%. In an embodiment, the percent water content in gels of the present disclosure is 20% to 25%. In an embodiment, the percent water content in gels of the present disclosure is 25% to 30%. In an embodiment, the percent water content in gels of the present disclosure is 30% to 35%. In an embodiment, the percent water content in gels of the present disclosure is 35% to 40%. In an embodiment, the percent water content in gels of the present disclosure is 40% to 45%. In an embodiment, the percent water content in gels of the present disclosure is 45% to 50%. In an embodiment, the percent water content in gels of the present disclosure is 50% to 55%. In an embodiment, the percent water content in gels of the present disclosure is 55% to 60%. In an embodiment, the percent water content in gels of the present disclosure is 60% to 65%. In an embodiment, the percent water in gel cosmetic gels of the present disclosure s is 65% to 70%. In an embodiment, the percent water content in gels of the present disclosure is 70% to 75%. In an embodiment, the percent water content in gels of the present disclosure is 75% to 80%. In an embodiment, the percent water content in gels of the present disclosure is 80% to 85%. In an embodiment, the percent water content in gels of the present disclosure is 85% to 90%. In an embodiment, the percent water content in gels of the present disclosure is 90% to 95%. In an embodiment, the percent water content in gels of the present disclosure is 95% to 99%.

In an embodiment, the percent water content in films of the present disclosure is 20%. In an embodiment, the percent water content in films of the present disclosure is less than 20%. In an embodiment, the percent water content in films of the present disclosure is less than 18%. In an embodiment, the percent water content in films of the present disclosure is less than 16%. In an embodiment, the percent water content in films of the present disclosure is less than 14%. In an embodiment, the percent water content in films of the present disclosure is less than 12%. In an embodiment, the percent water content in films of the present disclosure is less than 10%. In an embodiment, the percent water content in films of the present disclosure is between about 2% and about 20%.

In an embodiment, the extraction temperature during a method of preparing a composition of the present disclosure is greater than 84° C. In an embodiment, the extraction temperature during a method of preparing a composition of the present disclosure is less than 100° C. In an embodiment, the extraction temperature during a method of preparing a composition of the present disclosure is 84° C. to 100° C. In an embodiment, the extraction temperature during a method of preparing a composition of the present disclosure is 84° C. to 94° C. In an embodiment, the extraction temperature during a method of preparing a composition of the present disclosure is 94° C. to 100° C.

The following examples are put forth so as to provide those of ordinary skill in the art with a complete disclosure and description of how to make and use the described embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLES

Example 1

Development of a Silk Film of the Present Disclosure for Use in Fine Line Lifting Applications

TABLE 18

| Film Recipe for Fine Line Lifting Film - FIG. 82A | |
|---|---|
| % SPF Mixture Solution of the Present Disclosure | 2.4% |
| Quantity Vitamin C | 4:1 (silk:Vit C) (0.006 g/mL 2.4% solution) 20% |
| mL per film (2.5 cm by 10 cm) | 7.08 mL |
| Mass of silk per film: | 170 mg |
| Mass of l-ascorbic acid per film: | 42.5 mg |
| pH | 4.0 (when water is applied) |

Figure 84:
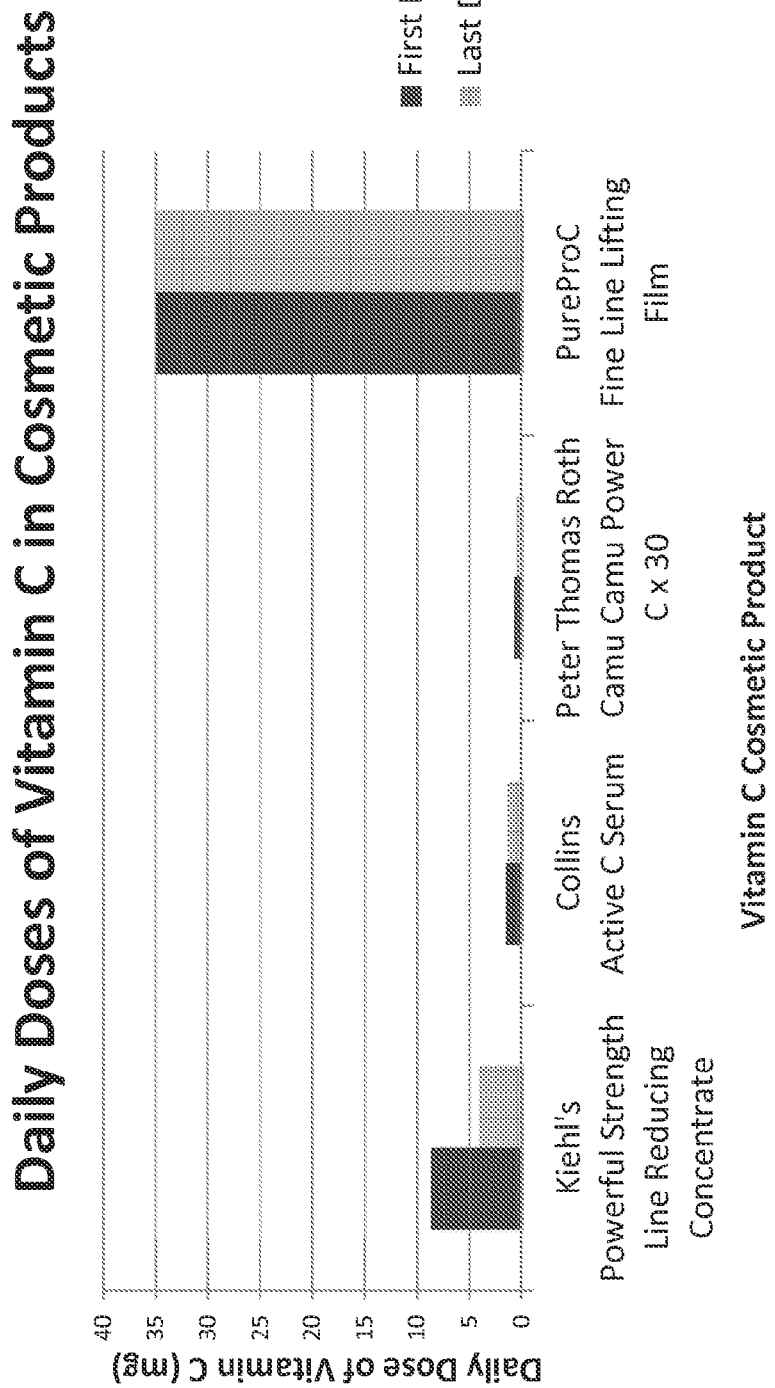
FIG. 84 is a graph summarizing the quantity of vitamin C in a daily dose (i.e., the average amount of product used to cover a 25 cm² area of skin) of PureProC™ and competitor products over a 30 day period.
Figure 85:
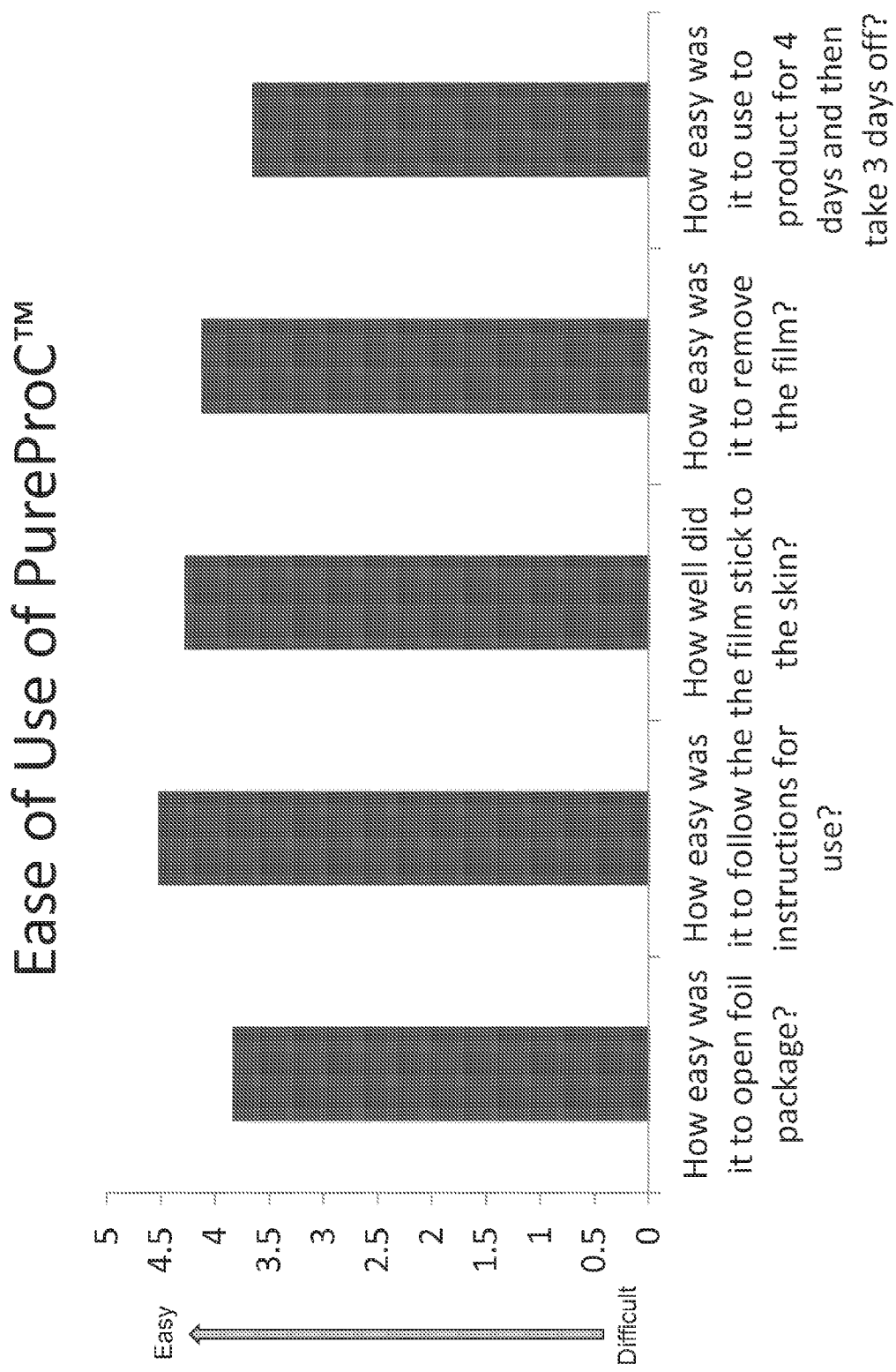
FIG. 85 is a graph summarizing the ease of use of PureProC™ collected in a user experience.

Silk films (2.5 cm×10 cm) were manufactured according to methods disclosed herein varying process parameters so as to result in fine line lifting films. The silk films were given the name "PureProC™ film", and can be packaged in a foil based package that is air tight and light proof. Table 18 provides details of the PureProC™ films used in a study of 32 individuals using the films for four (4) weeks. Biocompatibility and hypo-allergenicity of the films was observed. Further, no sensitization, toxicity, or immune response was observed. FIG. 84 is a graph summarizing the quantity of vitamin C in a daily dose (i.e., the average amount of product used to cover a 25 $cm^2$ area of skin) of PureProC™ and competitor products over a 30 day period. FIGS. 85 and 86 summarize resultant ease of use data and observed benefits within the first month of use.

In an embodiment, PureProC™ films were removed by peeling the films off. In an embodiment, PureProC™ films were removed by using a wet cotton ball or similar removal pad. In an embodiment, PureProC™ films were removed by washing the area where the film is placed with a wash cloth. In an embodiment, PureProC™ film PureProC™ films were removed using water. The PureProC™ films can be shaped into strips for multiple areas of the face or larger pieces can be cut to fit target areas. In an embodiment, grips or backing(s) on the PureProC™ films can be included for ease of application. In an embodiment, a PureProC™ film of the present disclosure includes silk and vitamin C (20%).

In an embodiment, a film of the present disclosure is soluble in water (insoluble border). In an embodiment, a film of the present disclosure is clear/transparent. In an embodiment, a film of the present disclosure has a pH=4 when water is applied. Films of the present disclosure can be made with different combinations of % silk and volume to produce films with silk quantities of 3 mg/cm^2 to 10 mg/cm^2. Films of the present disclosure can be made with from about 1% to about 50% l-ascorbic acid. Films of the present disclosure can adhere to skin with water. Films of the present disclosure can be spread on skin once water is applied. Films of the present disclosure can dry when humidity of drying equipment is 16-40% and below the humidity of the lab Example 2

Development of Silk Gels of the Present Disclosure

Temperature Treatment

Samples 1, 3, 6, 8, O-1, O-2, O-3, and O-4 were used to examine the effect of temperature treatment on serum gelation time. Samples 1, 6, O-1, and O-2 were identical other than temperature treatment. Samples 3, 8, O-3, and O-4 were identical other than temperature treatment. The two groups differed in silk to vitamin C ratio. Time to serum gelation was directly related to temperature treatment with a higher temperature resulting in quicker serum gelation.

Solution Volume

Samples 1, M and D were used to examine the effect of solution volume on serum gelation time. Samples M and D varied from sample 1 only by an increased solution volume.

TABLE 19

Gel Samples - Silk gel formulations including additives, concentration of silk and additive, gelation conditions and gelation times.

| Sample Name | mL 2% silk solution | Mass Vit C (g) | Ratio silk:VitC | Additive | Amount of additive | Temp/ Treatment | Days to Gelation |
|---|---|---|---|---|---|---|---|
| 1 | 10 | 0.04 | 5:01 | None | None | RT | 8 |
| 2 | 10 | 0.08 | 2.5:1 | None | None | RT | 8 |
| 3 | 10 | 0.2 | 1:01 | None | None | RT | 8 |
| 4 | 10 | 0.4 | 1:02 | None | None | RT | 14 |
| 5 | 10 | 0.8 | 1:04 | None | None | RT | None |
| 6 | 10 | 0.04 | 5:01 | None | None | Fridge | ~39 |
| 7 | 10 | 0.08 | 2.5:1 | None | None | Fridge | ~39 |
| 8 | 10 | 0.2 | 1:01 | None | None | Fridge | ~39 |
| 9 | 10 | 0.4 | 1:02 | None | None | Fridge | None |
| 10 | 10 | 0.8 | 1:04 | None | None | Fridge | None |
| 11 | 10 | 0.2 | 1:01 | None | None | RT/Shake vigorously | 8 |
| O-1 | 10 | 0.04 | 5:01 | None | None | 37 C. Oven | 3 |
| O-2 | 10 | 0.04 | 5:01 | None | None | 50 C. Oven | 2 |
| O-3 | 10 | 0.2 | 1:01 | None | None | 37 C. Oven | 4 |
| O-4 | 10 | 0.2 | 1:01 | None | None | 50 C. Oven | 3 |
| M | 40 | 0.16 | 5:01 | None | None | RT | 5 |
| D | 40 | 0.16 | 5:01 | None | None | RT | 5 |
| E1 | 10 | 0.04 | 5:01 | Vit E | 1 drop | RT | 7 |
| E2 | 10 | 0.04 | 5:01 | Vit E | 3 drops | RT | 7 |
| E3 | 10 | 0 | None | Vit E | 1 drop | RT | None |
| E4 | 10 | 0 | None | Vit E | 3 drops | RT | None |
| L1 | 10 | 0.04 | 5:01 | Lemon | 300 uL | RT | 6 |
| L2 | 10 | 0.04 | 5:01 | Lemon Juice | 300 uL | RT | 6 |
| L3 | 10 | 0.04 | 5:01 | Lemon Juice | 1000 uL | RT | 5 |
| L4 | 10 | 0 | None | Lemon | 300 uL | RT | 6 |
| L5 | 10 | 0 | None | Lemon Juice | 300 uL | RT | 7 |
| Jar 1 | 20 | 0.08 | 5:01 | Lemon Juice | 2000 uL | RT | 5-7 |
| Jar 2 | 5 | 0.02 | 5:01 | Lemongrass Oil | 1 drop | RT | 2-3 |
| R-1 | 10 | 0.04 | 5:01 | Rosemary Oil | 1 drop | RT | 7 |
| T-1 | 10 | 0.04 | 5:01 | None | None | RT/Tube | 7 |
| RO-1 | 10 | 0.04 | 5:01 | Rose Oil | 1 drop | RT | 6 |
| RO-2 | 10 | None | None | Rose Oil | 1 drop | RT | None |

Ratio of Silk to Vitamin C

Samples 1-10 were used to examine the effect of silk to vitamin C ratio on serum gelation. Samples 1-3 with less vitamin C gelled quicker than samples 4 and 5. All other conditions were kept constant. Samples 6-8 with less vitamin C gelled quicker than samples 9 and 10. All other conditions were kept constant. It is concluded that decreasing the ratio of silk to vitamin C (increasing the amount of vitamin C), will lengthen the time to gel creation. At ratios with small amounts of vitamin C, days to gel creation did not vary greatly.

Physical Stimulation

Samples 3 and 11 were used to examine the effect of physical stimulation on serum gelation. Each sample was prepared under the same conditions. Sample 11 was vigorously shaken for about 3 minutes after addition of vitamin C. Treatment of 3 and 11 was otherwise the same. The shaking resulted in bubbles but did not significantly change gel creation time.

Samples M and D gelled in 5 days while sample 1 gelled in 8 days. Samples M and D were definitively noticed to be gelled on the day of gelling while sample 1 gelled over a weekend.

Additives

Samples E1, E2, E3, E4, L1, L2, L3, L4, L5, Jar 2, R1, RO-1 and RO-2 were used to examine the effect of additives on serum gelation time. Samples E1-4 contained Vitamin E. Only samples E1 and E2 contained vitamin C and only these two samples gelled. Vitamin E can be added to a solution to become a gel but it appears that another additive may be needed to create a gel. Samples L1-5 contained a form of lemon juice. Samples L1 and L4 had juice directly from a lemon while samples L2, L3 and L5 contained lemon juice from a plastic lemon container. Samples L4 and L5 did not have vitamin C while all others did. All samples gelled showing that lemon juice can create gel on its own. Amount of lemon juice and type of lemon juice had little effect on gelation time. Sample Jar 2 contained lemon grass oil which formed an albumen like substance when initially added. This sample also had vitamin C but gelation time was significantly quicker than with other vitamin C samples. Sample R1 contained rosemary oil, which seemed to be soluble, as well as vitamin C. The sample gelled in a similar time frame to other samples with only vitamin C. Samples RO-1 and RO-2 contained rose oil while only RO-1 had vitamin C. Only RO-1 gelled showing that rose oil will not create a gel quickly on its own. In both cases the rose oil was immiscible and visible as yellow bubbles.

Aqueous silk fibroin-based fragment solution and essential oils are immiscible liquids. In an embodiment, to increase the fragrance of the silk fibroin-based fragment solution, without entrapping oils within the solution, the solution is mixed with the essential oil with the use of a stir bar. The stir bar is rotated at a speed such that some turbulence is observed in the mixture, thus causing contact between the fragrant essential oil and the molecules in solution, adding a scent to the solution. Before casting of product from the solution, mixing may be stopped and the oil allowed to separate to the top of the solution. Dispensing from the bottom fraction of the solution into the final product allows for fragrance without visible essential oil within the final product.

Alternatively, the silk fibroin-based solution and essential oil can be combined with or without additional ingredients and/or an emulsifier to create a composition containing both ingredients.

In an embodiment, mixing of the solution as described above can reduce gelation time if the solution is used to create a gel formulation.

Vessel

Samples T1 and Jar 1 were used to examine the effect of casting vessel on serum gelation time. Jar 1 was cast in a glass jar while T1 was cast in an aluminum tube. Both samples gelled and did not affect serum gel time.

SUMMARY

Figure 81:
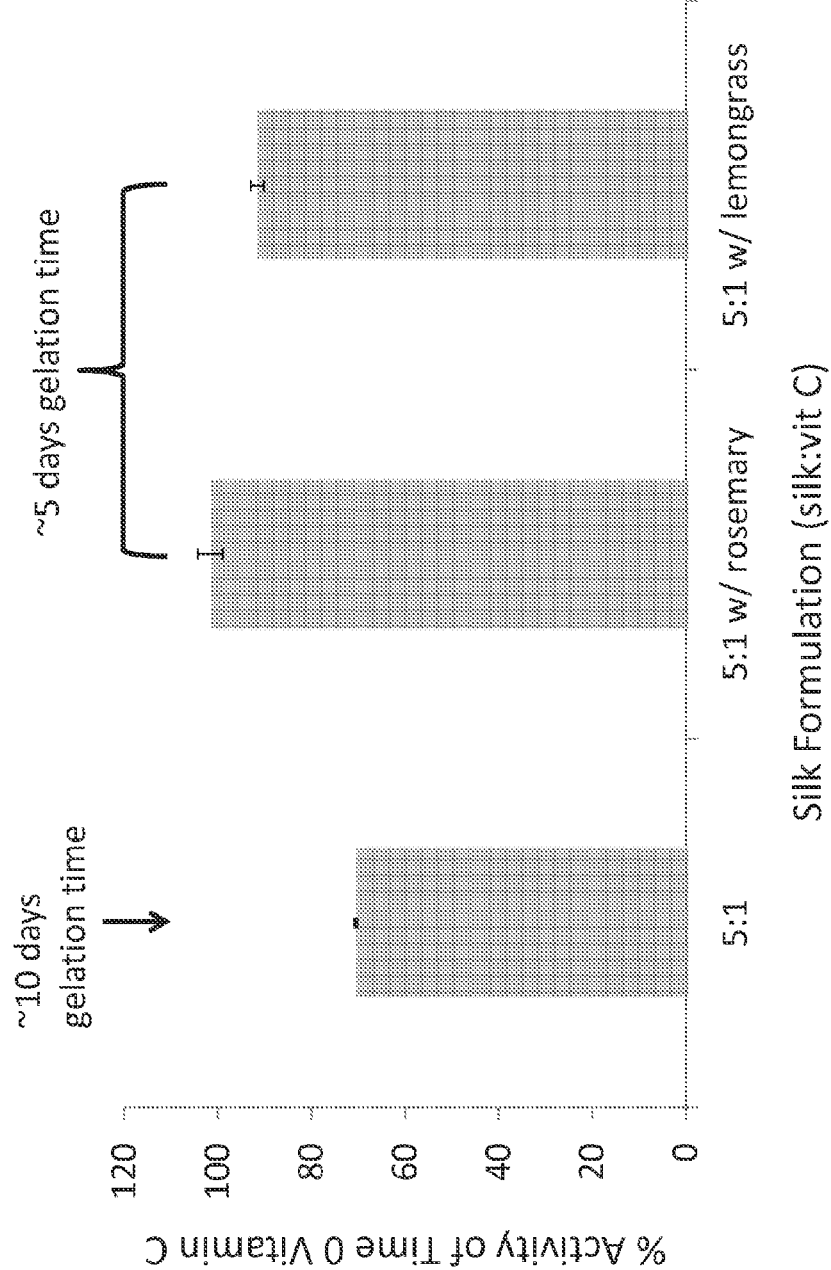
FIG. 81 is a graph representing the % Activity of Vitamin C in PureProC™ Gel.

All treatments of silk solution for gel solution were in a conical tube at room temperature unless otherwise stated. The ratio of silk to vitamin C did affect the ability of a solution to gel as ratios above 1:2 did not gel and a 1:2 ratio took twice as long as other lower ratios (5:1, 2.5:1, 1:1). Temperature affected gel creation time with higher temperatures resulting in quicker gel times. 50° C. treatment gelled in as quick as 2 days, 37° C. treatment gelled in as quick as 3 days, room temperature treatment gelled in 5-8 days and storage in a refrigerator took at least 39 days to gel. The effects of additives on gel creation were dependent on the additive. Vitamin E, Rosemary Oil and Rose Oil all had no effect on gel creation. Each of these additives did not prevent gelation or affect the time to gelation. Each also required the presence of vitamin C to gel. Lemon juice from a fresh lemon, pre-squeezed lemon juice from a plastic lemon container and lemon grass oil did affect gel creation. Without wishing to be bound by theory, it is believed that the lower pH as a result of these additives is the reason the additives had an impact on decreasing gelation time. Both lemon juice types were able to cause gelation without the presence of vitamin C. This occurred in the same number of days as with vitamin C. The lemongrass oil was able to decrease the number of days to gelation to 2-3 days. All additives appeared soluble other than lemongrass oil and rose oil. Rose oil remained in yellow bubbles while the lemongrass oil was partially soluble and formed an albumen like chunk. In an embodiment, oils that are not fully soluble, can still be suspended within the gel as an additive. Physical stimulation by shaking, vessel the solution was cast into and solution volume did not affect gelation time. FIG. 81 is a graph representing the % Activity of Vitamin C in gels of the present disclosure.

TABLE 20

Concentration of vitamin C in various gel formulations.

| Sample Info | Sample Weight (mg) | Concentration of Vitamin C (mg/g) In Sample | Average |
|---|---|---|---|
| Rosemary (Room Temperature storage) | 685.7 | 3.2511 3.2804 | 3.2657 |
| | 638 | 3.3336 3.3332 | 3.3334 |
| Lemongrass (Room Temperature storage) | 646 | 2.8672 2.8868 | 2.877 |
| | 645.5 | 2.9051 2.9052 | 2.9051 |
| Rosemary (Room Temperature; Foil Covered storage) | 645.2 | 3.9063 3.923 | 3.9147 |
| | 649 | 3.9443 3.9305 | 3.9374 |
| Lemongrass (Room Temperature; Foil Covered storage) | 630.1 | 3.8253 3.8295 | 3.8274 |
| | 660.4 | 3.8283 3.8222 | 3.8253 |
| Rosemary (Fridge, Foil Covered storage) | 672.4 | 5.1616 5.1352 | 5.1484 |
| | 616.5 | 5.1984 5.2036 | 5.201 |
| Lemongrass (Fridge, Foil Covered storage) | 640.5 | 5.1871 5.1776 | 5.1824 |
| | 627.7 | 5.2098 5.2154 | 5.2126 |

Example 3

Development of Silk Gels of the Present Disclosure for Use as Smoothing Gel

TABLE 21

Lemongrass Gel

| | |
|---|---|
| % Silk Solution | 2% |
| Quantity Vitamin C | 100 mg/15 mL solution |
| Quantity Lemongrass Oil | 20 uL/15 mL solution |

TABLE 22

Rosemary Gel

| | |
|---|---|
| % Silk Solution | 2% |
| Quantity Vitamin C | 100 mg/15 mL solution |
| Quantity Rosemary Oil | 20 uL/50 mL solution |

TABLE 23

Lemongrass Gel (50 mL)

| | |
|---|---|
| % Silk Solution (60 minute boil, 25 kDA) | 2% |
| Quantity Vitamin C (ascorbyl glucoside) | 12.82 mg/mL solution (641 mg total) |

TABLE 23-continued

Lemongrass Gel (50 mL)

| | |
|---|---|
| Quantity Lemongrass Oil | 1.33 uL/mL solution |
| pH | 4 |

TABLE 24

Rosemary Gel (50 mL)

| | |
|---|---|
| % Silk Solution (60 minute boil, 25 kDA) | 2% |
| Quantity Vitamin C (ascorbyl glucoside) | 12.82 mg/mL solution (641 mg total) |
| Quantity Rosemary Oil | 0.8 uL/mL solution |
| pH | 4 |

Gels of the present disclosure can be made with about 0.5% to about 8% silk solutions. Gels of the present disclosure can be made with ascorbyl glucoside at concentrations of about 0.67% to about 15% w/v. Gels of the present disclosure be clear/white in color. Gels of the present disclosure can have a consistency that is easily spread and absorbed by the skin. Gels of the present disclosure can produce no visual residue or oily feel after application. Gels of the present disclosure do not brown over time.

Silk gels with essential oils were prepared by diluting a silk solution of the present disclosure to 2%. Vitamin C was added to the solution and allowed to dissolve. The essential oil was added, stirred and dissolved. The solution was aliquot into jars.

Figure 87:
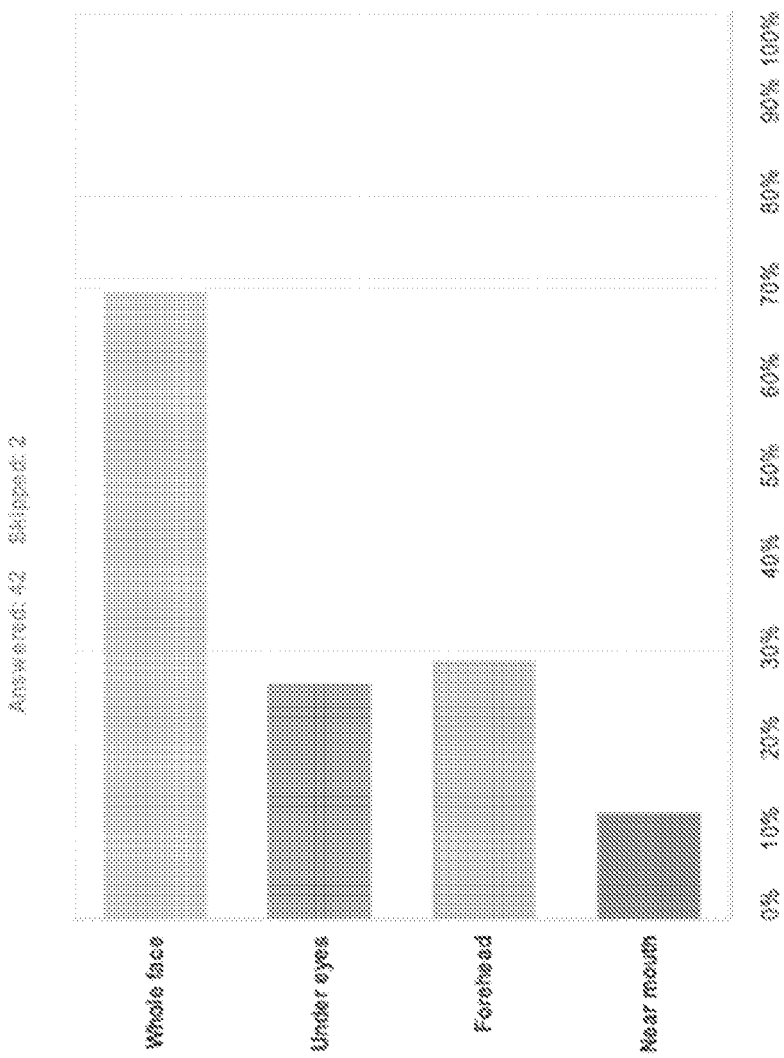
FIG. 87 is a graph summarizing where trial participants used PureProC™ Smoothing Gel.

A trial was conducted with 44 people on two formulations of the present disclosure, PureProC™ Rosemary Gel and PureProC™ Lemongrass Gel (FIGS. 87 and 88). Respondents were asked to use each sample once a day for a week each. The majority of respondents applied the gel to the whole face. Other areas where it was most commonly applied included the forehead, under eyes and near mouth.

The majority of respondents applied the gel during the morning (67%) with the balance 33% applying the gel in the evening. Ninety-eight (98%) of participants used the gel once a day during the test. Respondents were asked to describe in their own words how the gel felt when it was applied and how it felt during the 24 hours until the next application. Smooth, cool, and soft were the most often mentioned adjectives used to describe how the gel felt. Eighty percent (80%) of test participants gave a high score to interest in continuing to use the gel.

Respondents were asked about what they did with their other products that were usually used on their face during the trial. The majority applied the gel first and then added the other products or applied the gel at night with no additional products. Only 14% of participants indicated that they eliminated one of their normal products while testing the gel. PureProC™ can be used in conjunction with or in replacement of other products. Additionally, sunscreen can be added to the gel or it may be dispensed from a pump instead of a jar. With repeated topical use, no skin irritation, rash, or signs of non-compatibility was observed. Biocompatibility and hypo-allergenicity of the gels was observed. Further, no sensitization, toxicity, or immune response was observed.

Example 4

Silk Articles of the Present Disclosure Made from Silk Solutions of the Present Disclosure Silk solutions of various molecular weights and/or combinations of molecular weights can be optimized for specific applications. The following provides an example of this process but it not intended to be limiting in application or formulation.

Three (3) silk solutions were utilized in standard silk structures in accordance with standard methods in the literature with the following results:

Solution #1 is a silk concentration of 5.9%, average MW of 19.8 kDa and 2.2 PD (made with a 60 min boil extraction, 100 degree LiBr dissolution for 1 hr)

Solution #2 is a silk concentration of 6.4% (made with a 30 min boil extraction, 60 degree LiBr dissolution for 4 hrs)

Solution #3 is a silk concentration of 6.17% (made with a 30 min boil extraction, 100 C LiBr dissolution for 1 hour)

Films:

Films were made in accordance with Rockwood et al (Nature Protocols; Vol. 6; No. 10; published on-line Sep. 22, 2011; doi:10.1038/nprot.2011.379). Briefly, 4 mL of 1% or 2% (wt/vol) aqueous silk solution was added into 100 mm Petri dish (Volume of silk can be varied for thicker or thinner films and is not critical) and allowed to dry overnight uncovered. The bottom of a vacuum desiccator was filled with water. Dry films were placed in the desiccator and vacuum applied, allowing the films to water anneal for 4 hours prior to removal from the dish. Films cast from solution #1 did not result in a structurally continuous film; the film was cracked in several pieces. These pieces of film dissolved in water in spite of the water annealing treatment.

Egel:

"Egel" is an electrogelation process as described in Rockwood et al. Briefly, 10 ml of aqueous silk solution is added to a 50 ml conical tube and a pair of platinum wire electrodes immersed into the silk solution. A 20 volt potential was applied to the platinum electrodes for 5 minutes, the power supply turned off and the gel collected. Solution #1 did not form an EGEL over the 5 minutes of applied electric current.

Gelation:

Solutions #2 and #3 were gelled in accordance with the published horseradish peroxidase (HRP) protocol. Behavior seemed typical of published solutions.

Sonicated Gels:

Gels were made following the sonication process in Rockwood et al. Briefly, 5 ml of silk solution was added to a 15 ml conical tube. The sonicating horn was immersed in the solution and the solution sonicated at 50% amplitude (21 W). Silk gels were made with 2%, 4% and 6% silk solutions. As compared to standard literature silk, Solutions #2 and #3 formed gels after a longer time, for example:

Standard literature silk: 5-8 min
Solution #2: 20 min
Solution #3: 120 min

Porous 3D Scaffolds:

Water based, salt leached scaffolds were made in accordance with the published methods of Rockwood. Salt with particle sizes of interest was prepared by stacking the sieves with the largest mesh on top and the smallest mesh on the bottom. Salt was added and sieves shaken vigorously collecting the salt. With a 5-ml syringe, 6% (wt/vol) fibroin solution was aliquoted into plastic containers, 2 ml per mold and 5-600 micron salt particles were slowly added on top of the fibroin solution in the mold while rotating the container so that the salt was uniform. The ratio of salt to silk in solution was maintained at 25:1.

The container was gently tapped on the bench top to remove air bubbles, the cap closed and the solution allowed to settle overnight at room temperature. Once gelled, the lids were removed and the molds placed in a 2-liter beaker with ultrapure water (three containers per 2 liters of water). The beakers were transferred to a stir plate and stirred, changing the water 2-3 times per day for 2 d (4-6 washes in total). The scaffolds were removed from the molds and placed them in fresh water for an additional day.

Solution #1 did not form a scaffold; it did not gel. Both solution #2 & #3 formed scaffolds. The scaffolds made with Solution #3 appear softer than the ones made with Solution #2, but both scaffolds were homogeneous.

Example 5

Tangential Flow Filtration (TFF) to Remove Solvent from Dissolved Silk Solutions of the Present Disclosure A variety of % silk concentrations have been produced through the use of Tangential Flow Filtration (TFF). In all cases a 1% silk solution was used as the input feed. A range of 750-18,000 mL of 1% silk solution was used as the starting volume. Solution is diafiltered in the TFF to remove lithium bromide. Once below a specified level of residual LiBr, solution undergoes ultrafiltration to increase the concentration through removal of water. See examples below.
7.30% Silk Solution:
A 7.30% silk solution was produced beginning with 30 minute extraction batches of 100 g silk cocoons per batch. Extracted silk fibers were then dissolved using 100 C 9.3M LiBr in a 100 C oven for 1 hour. 100 g of silk fibers were dissolved per batch to create 20% silk in LiBr. Dissolved silk in LiBr was then diluted to 1% silk and filtered through a 5 um filter to remove large debris. 15,500 mL of 1%, filtered silk solution was used as the starting volume/diafiltration volume for TFF. Once LiBr was removed, the solution was ultrafiltered to a volume around 1300 mL. 1262 mL of 7.30% silk was then collected. Water was added to the feed to help remove the remaining solution and 547 mL of 3.91% silk was then collected.
6.44% Silk Solution:
A 6.44% silk solution was produced beginning with 60 minute extraction batches of a mix of 25, 33, 50, 75 and 100 g silk cocoons per batch. Extracted silk fibers were then dissolved using 100 C 9.3M LiBr in a 100 C oven for 1 hour. 35, 42, 50 and 71 g per batch of silk fibers were dissolved to create 20% silk in LiBr and combined. Dissolved silk in LiBr was then diluted to 1% silk and filtered through a 5 um filter to remove large debris. 17,000 mL of 1%, filtered silk solution was used as the starting volume/diafiltration volume for TFF. Once LiBr was removed, the solution was ultrafiltered to a volume around 3000 mL. 1490 mL of 6.44% silk was then collected. Water was added to the feed to help remove the remaining solution and 1454 mL of 4.88% silk was then collected
2.70% Silk Solution:
A 2.70% silk solution was produced beginning with 60 minute extraction batches of 25 g silk cocoons per batch. Extracted silk fibers were then dissolved using 100 C 9.3M LiBr in a 100 C oven for 1 hour. 35.48 g of silk fibers were dissolved per batch to create 20% silk in LiBr. Dissolved silk in LiBr was then diluted to 1% silk and filtered through a 5 um filter to remove large debris. 1000 mL of 1%, filtered silk solution was used as the starting volume/diafiltration volume for TFF. Once LiBr was removed, the solution was ultrafiltered to a volume around 300 mL. 312 mL of 2.7% silk was then collected.

Example 6

Gel Vitamin C Derivatives of the Present Disclosure

The purest form of vitamin C is L-ascorbic acid. There are a number of other derivatives of vitamin C that function like pure vitamin C after they are converted to L-ascorbic acid in the body. Vitamin C derivatives are being utilized to extend shelf life. Derivatives are stable forms of L-ascorbic acid and will not oxidize or lose stability. Table 25 below summarizes some vitamin C derivatives tested in the skin care products of the present disclosure:

TABLE 25

| Derivatives Explored |
| --- |
| Sodium Ascorbyl Phosphate (Aromantic) |
| Sodium Ascorbyl Phosphate (DSM) |
| Magnesium Ascorbyl Phosphate |
| Ascorbic Acid-2-Glucoside |
| Ascorbyl Tetraisopalmitate |

The Tables in FIGS. 89A-89B summarize embodiments of gels of the present disclosure. Ascorbic acid-2-glucoside was the most successful vitamin C derivative at gel formation with gel being formed in a 2% silk solution in 3 days. Sodium ascorbyl phosphate from DSM supplier formed a gel in a 2% silk solution after 28 days while the same molecule from Aromantic failed to create a gel. In all cases 100 mg of vitamin C derivative was mixed in 15 mL of 2% silk solution, and all gels had the same appearance as gels created with ascorbic acid.

Gels were also cast with combinations of two vitamin C options. In each case, at least one of the vitamin C options was known to cause gelation (L-ascorbic acid or ascorbic acid-2-glucoside). All combination gels were able to gel at 1% total vitamin C additive concentration. A gel cast at 20% total vitamin C additive concentration did not gel. Without wishing to be bound by theory, it appears there is a relationship between vitamin C concentration, silk concentration, and gelation. An increase in vitamin C at a given concentration of silk will result in a longer time to gelation or inhibit gelation. This may be due to the vitamin C molecule physically blocking interaction between silk protein fragments or cross-linking of silk protein. Modification to pH may allow additional concentrations of vitamin C and derivatives thereof to be added.

Ascorbyl tetraisopalmitate was not used in any gel forming formulation, as it was unable to dissolve or be dispersed in an aqueous silk solution. Ascorbyl tetraisopalmitate is a highly viscous, oil soluble liquid that might need the help of an emulsifier to possible dissolve in aqueous silk solution.

Example 7

Film Vitamin C Derivatives of the Present Disclosure

FIG. 90 is a table summarizing embodiments of films of the present disclosure. Sodium ascorbyl phosphate, magnesium ascorbyl phosphate and ascorbic acid-2-glucoside could be cast in films with varying appearance. Sodium ascorbyl phosphate films were opaque and white with a textured top surface similar to plastic. Magnesium ascorbyl phosphate films were clear and cloudy with a textured top surface similar to plastic. Ascorbic acid-2-glucoside films were most similar to L-ascorbic acid films although slightly less pliable and slightly textured. All films were soluble with an insoluble border. In an embodiment, a film with an insoluble border can be made completely spreadable by punching a shape from the region contained within the soluble section.

Example 8

Caffeine Films with Vitamin C of the Present Disclosure

FIGS. 91A-91B are tables summarizing embodiments of caffeine films of the present disclosure. Films were cast with 0.5%, 1%, 2.5%, 5%, 10%, 15% and 20% caffeine and 20% or 25% vitamin C. All combinations formed films. 20% caffeine films had caffeine precipitate out. Films with 0.5%-2.5% were soluble. In an embodiment, a caffeine film of the present disclosure is used for reducing puffy eyes.

Example 9

Caffeine Gels with Vitamin C of the Present Disclosure

A silk gel with 2% silk and 100 mg L-ascorbic acid/15 mL solution was created with the addition of 50 mg caffeine/15 mL solution. The gel has the exact appearance of standard L-ascorbic acid gels. In an embodiment, a caffeine gel of the present disclosure is used for reducing puffy eyes. A range of essential oils can be used including, but not limited to, lemongrass, vanilla, geranium, and green tea.

Example 10

Green Tea Gels with Vitamin C of the Present Disclosure

Steps:

| | |
|---|---|
| Green Tea Prep | Heat 250 mL water to boil<br>Steep tea bag 2-3 minutes with occasional stir<br>remove tea bag and let cool |
| Gel Solution Prep | Use TFF-10-0047 (3.71% silk)<br>dilute to 3% silk with water<br>dilute to 2% with green tea<br>add L-ascorbic acid |
| Gel | Gelation occurred like standard gel at room temperature<br>Green/yellow color<br>Green Tea scent |
| Solution Spec: | 2% silk solution<br>65 mL (35 ml of 3.71% silk, 8.3 mL water, 21.66 mL green tea)<br>0.43 g L-ascorbic acid |

FIG. 92 is a table summarizing an embodiment of a caffeine gel of the present disclosure. A silk gel with 2% silk and 100 mg L-ascorbic acid/15 mL solution was created with the addition of 50 mg caffeine/15 mL solution. The gel has the exact appearance of standard L-ascorbic acid gels.

Example 11

Preservative Gels with Vitamin C of the Present Disclosure

FIG. 93 is a table summarizing embodiments of preservative gels of the present disclosure. Silk gels were cast with standard 2% silk solution and 100 mg L-ascorbic acid/15 mL solution with the addition of a preservative and chelating agent. The preservative added was Verstatil SL by Kinetic (Water, Sodium Levulinate, Potassium Sorbate) at 1.5% and the chelating agent was Dermofeel-PA3 by Kinetic (Sodium Phytate) at 0.1%. The addition of preservatives extended gelation time to 7 days. Gel is being observed for discoloration and integrity with L-ascorbic acid and ascorbic acid-2-glucoside gel comparisons.

Example 12

Chemical Peels of the Present Disclosure

The primary variable investigated was the concentration of lactic acid and/or glycolic acid necessary to create a silk solution of a desired pH. In order to determine the relationship between concentration in silk and pH, 2% silk solutions (60 minute boil, 25 kDA) were titrated with glycolic and lactic acid and tested for pH with pH strips. See the following titrations/formulations below:

TABLE 26

Lactic Acid Peel 1: Initial solution:
25 mL of 2% silk solution, pH = 7-8

| Quantity of Lactic Acid Added | Total Lactic Acid | pH |
|---|---|---|
| 100 μL | 100 μL | 3 |
| 100 μL | 200 μL | 2 |
| 100 μL | 300 μL | 1-2 |

Time to gel: 3 days

TABLE 27

Lactic Acid Peel 2: Initial solution:
25 mL of 2% silk solution, pH = 7-8

| Quantity of Lactic Acid Added | Total Lactic Acid | pH |
|---|---|---|
| 25 μL | 25 μL | 4 |

Time to gel: >5 days

TABLE 28

Glycolic Acid Peel 1: Initial solution:
25 mL of 2% silk solution, pH = 7-8

| Quantity of Glycolic Acid Added | Total Glycolic Acid | pH |
|---|---|---|
| 41 mg | 41 mg | 4 |
| 43.25 mg | 84.25 mg | 3 |
| 30.7 mg | 114.95 mg | 3 |
| 56.4 mg | 171.35 mg | 2-3 |
| 91.66 mg | 263.01 mg | 2 |
| 171.35 mg | 434.4 mg | 1-2 |

Time to gel: 3 days

TABLE 29

Glycolic Acid Peel 2: Initial solution:
25 mL of 2% silk solution, pH = 7-8

| Quantity of Lactic Acid Added | Total Lactic Acid | pH |
|---|---|---|
| 41 mg | 41 mg | 4 |

Time to gel: >5 days

TABLE 30

Lactic/Glycolic Acid Peel: Initial solution:
25 mL of 2% silk solution, pH = 7-8

| Total Lactic Acid | Total Glycolic Acid | Lemongrass | pH |
|---|---|---|---|
| 150 μL | 200 mg | 33.3 μL | 2 |

Time to gel: 3 days

TABLE 31

Lactic/Glycolic Acid Peel: Initial solution:
30 mL of 2% silk solution, pH = 7-8

| | |
|---|---|
| % Silk Solution (60 minute boil, 25 kDA) | 2% |
| Lactic Acid Concentration | 6 μL/mL |
| Glycolic Acid Concentration | 8 mg/mL |
| pH | 2 |
| Lemongrass Concentration | 1.33 μL/mL |

A peel of the present disclosure can have a % silk ranging from about 0.5% to about 8%. The pH of a peel of the present disclosure can be adjusted with varying quantities of lactic and glycolic acid. Peels can also be made with lactic acid only or glycolic acid only. A peel of the present disclosure can be clear/white in color. A peel of the present disclosure can have a gel consistency that is easily spread and absorbed by the skin. A peel of the present disclosure does not brown or change colors.

In an embodiment, a chemical peel of the present disclosure can be applied weekly to reveal healthy, vibrant skin. In an embodiment, a chemical peel of the present disclosure can be applied weekly to diminish fine lines. In an embodiment, a chemical peel of the present disclosure can be applied weekly to firm the skin.

Each formulation (after titration, if applicable) was applied as a liquid and as a gel and observed for look and feel. Peels of pH=4 (Lactic Acid Peel 2, Glycolic Acid peel 2) resulted in a minimal burning feeling after a few minutes of application, while peels of pH=~2 (Lactic Acid Peel 1, Glycolic Acid Peel 1, Lactic/Glycolic Acid Peel) caused a slightly more intense burning feel. Little difference in degree of burning was felt between liquid and gel other than that the burning sensation was more delayed in the gel form. PH was maintained in the gel form and was confirmed by using a pH strip.

Glycolic acid and lactic acid are both alpha hydroxy acids (AHA's) that are among the most commonly used peels for superficial peeling (outermost skin layer peeling). Chemical peels are intended to burn the top layers of the skin in a controlled manner, to remove superficial dermal layers and dead skin in order to improve appearance. AHAs are common in chemical peels due to low risk of adverse reactions and high control of strength (control pH and time applied). Glycolic acid is most commonly used and has a very small molecular size, enabling deep penetration into the epidermis. Lactic acid is another commonly used AHA and offers a more gentle peel with higher control due to its larger molecular size. Any number of chemicals known in the art that lower pH and are physical exfoliates can be used in place of AHAs.

Example 13

Hydrating Serums of the Present Disclosure

Variables include: concentration of silk in solution, concentration of HA, addition of vitamin C, and serum preparation method. Table 32 is a list of samples that were evaluated:

TABLE 32

Embodiments of serums of the present disclosure containing HA and Silk (60 minute boil, 25 kDA), with or without vitamin C, and with 20 uL/15 mL lemongrass essential oil (30 mL solution)

| Method | HA (%) | Silk (%) | Vit C (mg) | Observation |
|---|---|---|---|---|
| HA added to water before dilution of silk | 0.5 | 2 | 0 | White, slightly opaque, viscous liquid |
| | 1 | | | White/yellow, slightly opaque, viscous liquid |
| | 0.5 | 2 | 0 | Low viscosity, clear-white opaque with film on top, some white residue when applied topically to skin |
| | 1 | | | Slightly viscous, clear liquid with film on top |
| | 0.5 | 1 | 0 | Slightly viscous, clear liquid with film on top |
| | 1 | | | Smooth viscous liquid, no white residue when applied topically to skin |
| | 0.5 | 0.5 | 0 | Moderately viscous liquid, clear |
| | 1 | | | Smooth, clear, no white residue when applied topically to skin |
| | 0.5 | 2 | 35 | Non homogeneous mix of hard gel and viscous liquid |
| | 1 | | | Non homogeneous mix of hard gel and viscous liquid |
| | 1 | 1 | 35 | Non homogeneous mix of hard gel and viscous liquid |
| | | 0.5 | | Opaque, white liquid/non-viscous |
| | 1 | 4 | 35 | Separated mixture of hard gel and viscous liquid |
| | | | 0 | Non homogeneous mix of hard gel and viscous liquid |
| | 5 | 2 | 0 | Yellow, gel |
| HA added to water before dilution of silk, stirred vigorously | 10 | 2 | 0 | Viscous jelly upon stirring with undissolved HA |
| | 5 | | | Very viscous jelly upon stirring |
| | 1 | | | Viscous jelly upon stirring |
| | 0.5 | | | |

TABLE 32-continued

Embodiments of serums of the present disclosure containing HA and Silk (60 minute boil, 25 kDA), with or without vitamin C, and with 20 uL/15 mL lemongrass essential oil (30 mL solution)

| Method | HA (%) | Silk (%) | Vit C (mg) | Observation |
|---|---|---|---|---|
| HA added to water before dilution of silk, shaken | 1 | 2 | 0 | Non homogeneous thick, viscous jelly/gel |
|  | 5 | 1 | 0 |  |
| HA added to water and let sit for 1 day before dilution of silk | 1 | 1 | 0 | Clear/slightly opaque, viscous liquid, smooth feel, little to no white residue when applied topically to skin |
| HA added to diluted silk solution, stirred | 0.5 | 2 | 0 | Viscous, clear/white liquid varying in consistency |
|  | 1 |  |  |  |
|  | 0.5 | 1 |  | Clear viscous liquid varying in consistency |
|  | 1 |  |  |  |
|  | 0.5 | 6 |  | White, opaque jelly varying in consistency |
|  | 1 |  |  |  |
| HA added to diluted silk solution, stirred | 0.5 | 3.9 | 0 | White, slightly opaque, viscous liquid |
|  | 1 |  |  |  |
|  | 0.5 | 2 | 35 | White gel varying in consistency |
|  | 1 |  |  |  |

In an embodiment, a hydrating serum of the present disclosure protects the skin and seals in moisture with the power of silk fibroin-based fragment proteins. In an embodiment, a hydrating serum of the present disclosure delivers moisture for immediate and long-term hydration throughout the day with concentrated hyaluronic acid. A range of essential oils can be used in a hydrating serum of the present disclosure including, but not limited to, lemongrass, vanilla, geranium, and green tea. In an embodiment, one or two drops of a hydrating serum of the present disclosure can be smoothed over the face and neck. In an embodiment, a hydrating serum of the present disclosure includes water, aqueous silk fibroin-based fragment solution, hyaluronic acid, and lemongrass oil. In an embodiment, the silk fibroin-based fragment protein in a hydrating serum of the present disclosure has the ability to stabilize and protect skin while sealing in moisture, all without the use of harsh chemical preservatives or synthetic additives. In an embodiment, the hyaluronic acid in a hydrating serum of the present disclosure nourishes skin and delivers moisture for lasting hydration. In an embodiment, the lemongrass essential oil in a hydrating serum of the present disclosure yields antioxidant and anti-inflammatory properties that support skin rejuvenation. In an embodiment, a hydrating serum of the present disclosure has a pH of about 6.0.

Silk Fibroin-Based Fragment Solution

Because silk fibroin-based fragment solution is both aqueous and able to entrap and deliver small molecules, the solution is able to deliver both water and hygroscopic HA molecules to the skin for hydration. A range in concentration of silk fibroin-based fragment compositions in solution from 0.5%-6.0% was tested for feasibility and product outcome. All concentrations tested were found to be feasible.

Hyaluronic Acid

Hyaluronic acid (Sodium Hyaluronate) was tested as an ingredient in the hydrating serum due to its hygroscopic properties and ability to promote soft, hydrated skin. A range in concentration of hyaluronic acid in solution from 0.5%-10.0% was tested for feasibility and product outcome. All concentrations tested, with the exception of 10.0%, were found to be feasible. Feasibility was determined based on the ability to dissolve hyaluronic acid.

Vitamin C and Derivatives Thereof

Vitamin C (L-ascorbic acid) was tested as an ingredient in the hydrating serum. Initial vitamin C samples became a non-homogeneous mixture of gel and liquid. A follow-up trial with vitamin C resulted in a homogeneous, white, opaque, non-viscous liquid that was not quickly absorbed by the skin. In an embodiment, a vitamin C derivative that does not readily cause gelation, such as sodium ascorbyl phosphate, could be added up to the concentration at which it would no longer be soluble (for example, 0% to about 40%). In an embodiment, 20% sodium ascorbyl phosphate could be added. Vitamin C options that do cause gelation (L-ascorbic acid and ascorbyl glucoside) could be added at high concentrations (for example greater than about 10% up to about 50%) at which gelation is inhibited.

Serum Creation Method

Initial serums were created by the addition of HA to a silk fibroin-based fragment solution followed by stirring. The HA appeared to stick together and was not dissolved until forcefully stirred. The mixing process was then changed so that HA was first dissolved in water and then immediately used to dilute a high concentration silk fibroin-based fragment solution (>4%) to the desired concentrations. The resulting serums were more homogeneous and had a desirable smooth, clear look and feel. Upon application to the skin, a white residue briefly appeared that could be rubbed in. In an alternate method formulations were created by dissolving HA in water and allowing it to sit for 1 day until complete dissolution was observed. The HA and water solution was then used to dilute a high concentration silk fibroin-based fragment solution to the desired concentrations. The resulting serum was clear, smooth, homogeneous and left little to no white residue when applied.

Example 14

UV Hydrating Serums of the Present Disclosure

Variables tested include: concentration of HA, concentration of zinc oxide, concentration of titanium dioxide, addition of vitamin C, and serum preparation method.

FIGS. 94A-94C are tables summarizing embodiments of cosmetic serums of the present disclosure with varying additives and concentrations of components suitable for protection against ultraviolet radiation (UV). Table 33 provides an embodiment of a hydrating serum of the present disclosure with vitamin C.

TABLE 33

Embodiment of Hydrating serum of the present disclosure with vitamin C

| | |
|---|---|
| % Silk Solution (60 minute boil, 25 kDA) | 1.0% w/v |
| Hyaluronic Acid (sodium hyaluronate) | 0.75% w/v |
| Lemongrass Oil | 20 uL/15 mL silk solution |
| Sodium Ascorbyl Phosphate | 6 g |
| Lactic Acid | 1.2 mL |

A serum of the present disclosure can be made with from about 0.25% to about 10% sodium hyaluronate (increasing % results in more viscous serum). 0.5% to about 10% silk solutions can be used to prepare a serum of the present disclosure. A serum of the present disclosure can be clear and have a yellow tinted color. A serum of the present disclosure can have a pH=6. A serum of the present disclosure can have a lubricious texture that is rubbed in easily without residue.

Concentration of HA:

Hyaluronic acid (Sodium Hyaluronate) was tested as an ingredient in the UV silk serum due to its hygroscopic properties and widely accepted use in cosmetic products to promote hydration of skin. 1%, 2.5% and 5% HA solutions were tested. With increasing HA %, the serum became more viscous and gel like. 1% HA was not feasible for the UV serum due to the fact that the UV additives (zinc oxide, titanium dioxide) are not water soluble and need to be dispersed. 1% HA was not viscous enough for dispersion and the UV additives precipitated out. 2.5% gave the best consistency based on preferred feel, texture and viscosity and was able to disperse the UV additives. 5% was a very thick, viscous serum.

Concentration of Mineral Filters: Zinc Oxide and Titanium Dioxide:

Zinc oxide and titanium dioxide were explored as UV additives that are considered safe. These additives mechanically protect from UV radiation by forming a physical reflective barrier on the skin. Both are not soluble in water and must be dispersed for the current aqueous solution. Zinc oxide concentration varied from 2.5%, 3.75%, 5%, 5.625%, 10%, 12% and 15%. Titanium dioxide concentrations varied from 1.25%, 1.875%, 3%, 5% and 10%. Increasing the concentration of UV additives resulted in minor increases of white residue and how well dispersed the additives were, however if mixed well enough the effects were negligible. Zinc oxide and titanium dioxide were mixed together into serums in order to achieve broad spectrum protection. Zinc oxide is a broad spectrum UV additive capable of protecting against long and short UV A and UV B rays. However titanium dioxide is better at UV B protection and often added with zinc oxides for best broad spectrum protection. Combinations included 3.75%/1.25% ZnO/TiO2, 5.625%/1.875% ZnO/TiO2, 12%/3% ZnO/TiO2, 15%/5% ZnO/TiO2. The 3.75%/1.25% ZnO/TiO2 resulted in spf 5 and the 5.625%/1.875% ZnO/TiO2 produced spf 8.

Vitamin C:

Sodium ascorbyl phosphate was used as a vitamin C source. Formulations were created with the vitamin C concentration equal to that in the silk gel (0.67%). Formulations were also created with 20% sodium ascorbyl phosphate which is soluble in water.

Serum Preparation:

The vitamin C (sodium ascorbyl phosphate) must first be dissolved in water. Sodium hyaluronate is then added to the water, mixed vigorously and left to fully dissolve. The result is a viscous liquid (depending on HA %). The viscosity of the HA solution allows even dispersion of the zinc oxide and titanium dioxide and therefore HA must be mixed before addition of UV additives. The zinc oxide and titanium dioxide are then added to the solution and mixed vigorously with the use of an electric blender. Silk solution is then added and mixed to complete the serum formulation.

Chemical Filters:

A UV serum of the present disclosure can include one, or a combination of two or more, of these active chemical filter ingredients: oxybenzone, avobenzone, octisalate, octocrylene, homosalate and octinoxate. A UV serum of the present disclosure can also include a combination of zinc oxide with chemical filters.

In an embodiment, a UV serum of the present disclosure can be applied approximately 15 minutes before sun exposure to all skin exposed to sun, and can be reapplied at least every 2 hours. In an embodiment, a UV serum of the present disclosure includes water, zinc oxide, sodium hyaluronate, titanium dioxide, silk, and vitamin C or a vitamin C derivative such as sodium ascorbyl phosphate. In an embodiment, a UV serum of the present disclosure protects skin and seals in moisture with the power of silk protein. In an embodiment, a UV serum of the present disclosure improves skin tone, promotes collagen production and diminishes the appearance of wrinkles and fine lines with the antioxidant abilities of vitamin C. In an embodiment, a UV serum of the present disclosure delivers moisture for immediate and long-term hydration throughout the day with concentrated hyaluronic acid. In an embodiment, a UV serum of the present disclosure helps prevent sunburn with the combined action of zinc oxide and titanium dioxide. In an embodiment, a UV serum of the present disclosure is designed to protect, hydrate, and diminish fine lines while shielding skin from harsh UVA and UVB rays. In an embodiment, the silk protein in a UV serum of the present disclosure stabilizes and protects skin while sealing in moisture, without the use of harsh chemical preservatives or synthetic additives. In an embodiment, the vitamin C/derivative in a UV serum of the present disclosure acts as a powerful antioxidant that supports skin rejuvenation. In an embodiment, the sodium hyaluronate in a UV serum of the present disclosure nourishes the skin and delivers moisture for long-lasting hydration. In an embodiment, the zinc oxide and titanium dioxide in a UV serum of the present disclosure shields skin from harmful UVA and UVB rays. The silk protein stabilization matrix in a UV serum of the present disclosure protects the active ingredients from the air, to deliver their full benefits without the use of harsh chemicals or preservatives. The silk matrix also traps moisture within the skin furthering the hydrating effect of the sodium hyaluronate.

Example 15

Dark Spot Films of the Present Disclosure

To reduce the appearance of dark spots, a high concentration of vitamin C may be necessary to reverse the overproduction of melanin. In this example, a 40% vitamin C (1.5:1 silk to vitamin C) was studied. The size and shape of the film can be made appropriate to a targeted area, for example to a small circular film of diameter 1 in (2.54 cm).

The dark spot film, or a similar film of the present disclosure, of varying vitamin C concentration (0-50%) can be applied as a hydrofilm. Skin can be wetted with water. The film is then applied to the wet area. Water is then applied to the top surface of the film to turn it into a gel. The gel can then be spread and gently massaged into the application area. Table 34 provides details of an embodiment of a hydrofilm of the present disclosure (with no insoluble border).

TABLE 34

An Embodiment of a hydrofilm of the present disclosure

| | |
|---|---|
| % Silk Solution (60 minute boil, 25 kDA) | 2.56% |
| Quantity Vitamin C (l-ascorbic acid) | 15.62 mg total (10 mg in 1 in circle punch out) |
| Volume of solution per mold | 2.44 mL |
| Film Size | 1.25 in diameter circle (7.917 cm$^2$) |

A film of the present disclosure can be made with different combinations of % silk and volume to produce films with silk quantities of 3 mg/cm$^2$ to 10 mg/cm$^2$. A film of the present disclosure can be made with from about 1% to about 50% l-ascorbic acid. A film of the present disclosure is soluble in water (insoluble border is removed by punching out the center of the film). A film of the present disclosure can adhere to skin with water. A film of the present disclosure can be spread on skin once water is applied. A film of the present disclosure can be dried when the humidity of drying equipment is 16-40% and below the humidity of the lab. A film of the present disclosure can be clear/transparent.

In an embodiment, a dark spot film of the present disclosure includes water, silk, and vitamin C (L-ascorbic acid). In an embodiment, a dark spot film of the present disclosure includes 40% vitamin C. In an embodiment, a dark spot film of the present disclosure reduces skin pigmentation and evens skin tone in a targeted area with daily use. Vitamin C can inhibit pigment transfer from pigment producing cells, called melanocytes, to skin surface cells with continual application. In an embodiment, a dark spot film of the present disclosure can be applied to clean, dampened skin for 20 minutes. In an embodiment, additional water can be applied to an adhered film. The silk protein stabilization matrix in a dark spot film of the present disclosure protects the active ingredients from the air, to deliver their full benefits without the use of harsh chemicals or preservatives, such as paraben and phthalate. Thus, a dark spot film of the present disclosure is paraben and phthalate-free. Table 35 provides details of an embodiment of a film of the present disclosure.

TABLE 35

An Embodiment of a Film of the Present Disclosure

| | |
|---|---|
| % Silk Solution (60 minute boil, 25 kDA) | 2.2% |
| Surface area | 5.07 cm$^2$ |
| Volume of silk solution for casting | 1.56 mL |
| Mass of silk per film: | 34 mg |
| Mass of l-ascorbic acid per film: | 23 mg |
| Concentration of l-ascorbic acid in film: | 40% |
| pH | 3 |

A 2.1% silk solution of the present disclosure (0.321 mL/cm$^2$) to 2.4% silk solution of the present disclosure (0.282 mL/cm$^2$) can been used to create dark spot films of the present disclosure with 34 mg of silk (6.7 mg/cm$^2$). In an embodiment, a 2.2% silk solution of the present disclosure (60 minute boil, 25 kDA) is used to produce a film of the present disclosure. The % silk and volume of solution can vary to produce equivalent films. A dark spot film of the present disclosure can be made with different combinations of % silk and volume to produce films with silk quantities of 3 mg/cm$^2$ to 10 mg/cm$^2$. A dark spot film of the present disclosure can be made with from about 15 to about 50% l-ascorbic acid. A dark spot film of the present disclosure is soluble in water (insoluble border). A dark spot film of the present disclosure is clear/transparent. A dark spot film of the present disclosure has a pH=3 when water is applied. A dark spot film of the present disclosure can adhere to skin with water. A dark spot film of the present disclosure can dry when humidity of drying equipment is 16-40% and below the humidity of the lab Example 16

High Concentration Vitamin C Gels of the Present Disclosure

High concentration vitamin C gels were pursued up to 20%. Vitamin C type, vitamin C concentration, % silk and pH were varied to increase the quantity of vitamin C in a gel.

FIGS. 95A-95C are tables summarizing embodiments of high concentration vitamin C gels of the present disclosure. The highest concentration of vitamin C to gel was a 15% ascorbic acid 2 glucoside gel with 3.8% silk solution after 12 days. 5 and 10% ascorbic acid-2-glucoside formulations with 2, 3 and 3.8% silk all gelled. For each group of % vitamin C, gelation first occurred in the 3.8% silk followed by the 3% and lastly the 2%. It appears that there is a relationship between vitamin C concentration, silk concentration and gelation. If a solution has too much vitamin C in relation to silk, gelation will be prevented. Therefore, in order to produce high concentration vitamin C gels, higher concentration silk is necessary. One sample was cast at 5.5% silk and 20% vitamin C but gelation did not occur and a higher % silk may be necessary. Samples were also brought to a pH of 2 with lactic acid in order to help induce gelation in 3% silk solutions with 10 or 20% vitamin C, however gelation did not occur in 12 days.

Example 17

Microbiological Study of Gels of the Present Disclosure

Contaminating micro-organisms in cosmetics may cause a spoilage of the product and, when pathogenic, they represent a serious health risk for consumers worldwide. The United States Pharmacopoeia (USP) Microbial Limits Test provides several methods for the determination of total microbial count for bacteria, yeast and mold. Various gels of the present disclosure were tested to evaluate the possible microbial contamination in three different states of their use (intact, in-use, ending product). FIG. 96 is a table summarizing the results of such testing.

The samples of gel and water samples from carboys were analyzed for determination of CFU/mL (colony-forming units per milliliter) of aerobic bacteria as well as yeast and mold. Samples were exposed to growth medium of Tryptic Soy Agar (TSA) for bacteria and Potato Dextrose Agar (PDA) for fungi (yeast/mold) at an exposure temperature of 23±3° C. Samples were incubated at 30.0±2° C. for 3 days (bacteria) and 5 days (Fungi). Samples were then observed for determination of colony-forming units/mL.

The limit of detection for the assays was 10 CFU/ml or g for bacteria and fungi, and the values of <10 indicate that microorganisms could not be detected in the samples. Values of >1.00E+04 indicate that the microbial colonies are Too Numerous to Count in the dilutions plated.

Example 18

UV Silk Foams and Liquids of the Present Disclosure

In an embodiment, the vitamin C derivative sodium ascorbyl phosphate (DSM) was dissolved in water. Sodium hyaluronate ("HA") was then added to the water, mixed vigorously, and left to fully dissolve. The result is a viscous liquid (depending on HA %). The viscosity of the HA solution allows even dispersion of the zinc oxide and titanium dioxide and therefore HA is typically mixed before addition of UV additives. The zinc oxide and titanium dioxide are added to the HA solution and mixed vigorously, for example with the use of an electric blender. 60 minute boiled (~25 kDa) silk solution is then added and mixed to create a 1% silk formulation.

Figure 97:
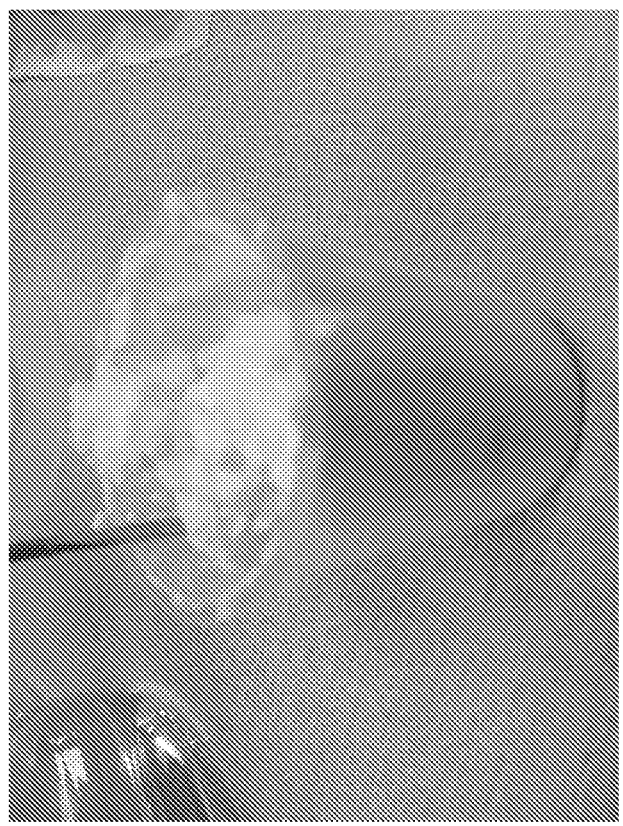
FIG. 97 is a photograph of an embodiment of a foam product of the present disclosure suitable for protection against UV.
Figure 98:
FIG. 98 is a photograph of an embodiment of a viscous liquid of the present disclosure suitable for protection against UV.
Figure 99:
FIG. 99 is a photograph of an embodiment of a viscous liquid of the present disclosure suitable for protection against U.
Figure 100:
FIG. 100 is a photograph an embodiment of a foam product of the present disclosure suitable for protection against UV.

Two formulations were created without the addition of sodium ascorbyl phosphate (samples "HU2" and "HU4"). For sample HU2, zinc oxide and titanium dioxide were added and mixed by blending with an electric blender and whisk. The result was a viscous white liquid (FIG. 98 and FIG. 99). Silk was then added and blended with an electric blender and whisk. The solution became a creamy foam similar to shaving cream (FIG. 97 and FIG. 100). Vitamin E in the form of dl-alpha tocopheryl acetate can be added to the solution to recover a viscous liquid texture that can be applied with a smooth even texture (FIG. 98). With increasing the quantity of dl-alpha tocopheryl acetate, the formulation will become less foam-like and more of a smooth liquid or lotion texture.

HU4 was split into two batches: FIG. 99, batch 2 and FIG. 100, batch 1. The first batch followed the same procedures to HU2 and became a foam. For the second batch of HU4, sodium ascorbyl phosphate was added and dissolved before adding any zinc, titanium or silk. The UV additives were then added by blending with an electric blender and whisk and created a standard white viscous liquid. Silk was then added with an electric blender and whisk. The result was slightly thicker viscous liquid than normally seen. Without wishing to be bound by theory, it appears the addition of sodium ascorbyl phosphate inhibits foaming. Without wishing to be bound by theory, it appears that whisking, as opposed to mixing or blending, creates a silk foam.

Example 19

Lyophilized Silk Powders of the Present Disclosure

TABLE 37

Embodiments of lyophilized silk powders

| Silk Solution | Treatment | Soluble |
|---|---|---|
| ~60 kDa silk, 6% silk, pH = 7-8 | lyopholize and cut with blender | no |
| ~60 kDa silk, 6% silk, pH = 10 | lyopholize and cut with blender | no |
| ~25 kDa silk, 6% silk, pH = 7-8 | lyopholize and cut with blender | yes |
| ~25 kDa silk, 6% silk, pH = 10 | lyopholize and cut with blender | yes |

The above silk solutions were transformed to a silk powder through lyophilization to remove bulk water and chopping to small pieces with a blender. pH was adjusted with sodium hydroxide. Low molecular weight silk (~25 kDa) was soluble while high molecular weight silk (~60 kDa) was not.

The lyophilized silk powder can be advantageous for enhanced storage control ranging from 10 days to 10 years depending on storage and shipment conditions. The lyophilized silk powder can also be used as a raw ingredient in the pharmaceutical, medical, consumer, and electronic markets. Additionally, lyophilized silk powder can be re-suspended in water, HFIP, or an organic solution following storage to create silk solutions of varying concentrations, including higher concentration solutions than those produced initially.

In an embodiment, aqueous pure silk fibroin-based protein fragment solutions of the present disclosure comprising 1%, 3%, and 5% silk by weight were each dispensed into a 1.8 L Lyoguard trays, respectively. All 3 trays were placed in a 12 ft$^2$ lyophilizer and a single run performed. The product was frozen with a shelf temperature of ≤−40° C. and held for 2 hours. The compositions were then lyophilized at a shelf temperature of −20° C., with a 3 hour ramp and held for 20 hours, and subsequently dried at a temperature of 30° C., with a 5 hour ramp and held for about 34 hours. Trays were removed and stored at ambient conditions until further processing. Each of the resultant lyophilized silk fragment compositions were able to dissolve in aqueous solvent and organic solvent to reconstitute silk fragment solutions between 0.1 wt % and 8 wt %. Heating and mixing were not required but were used to accelerate the dissolving rate. All solutions were shelf-stable at ambient conditions.

In an embodiment, an aqueous pure silk fibroin-based protein fragment solution of the present disclosure, fabri-

TABLE 36

Embodiments of UV Silk Foams and Liquids of the Present Disclosure

| Sample | Total Volume | % silk | % HA (sodium hyaluronate) | Mass HA (g) | % ZnO | Mass ZnO (g) | % TiO$_2$ | Mass TiO$_2$ (g) | Sodium Ascorbyl Phosphate (g) |
|---|---|---|---|---|---|---|---|---|---|
| HU2 | 55 | 1 | 2.5 | 1.375 | 12 | 6.6 | 3 | 1.65 | N/A |
| HU4 Batch 1 | 27.5 | 1 | 3.5 | 0.9625 | 12 | 3.3 | 3 | 0.825 | 5.5 |
| HU4 Batch 2 | 27.5 | 1 | 3.5 | 0.9625 | 12 | 3.3 | 3 | 0.825 | N/A | cated using a method of the present disclosure with a 30 minute boil, has a molecular weight of about 57 kDa, a polydispersity of about 1.6, inorganic and organic residuals of less than 500 ppm, and a light amber color.

In an embodiment, an aqueous pure silk fibroin-based protein fragment solution of the present disclosure, fabricated using a method of the present disclosure with a 60 minute boil, has a molecular weight of about 25 kDa, a polydispersity of about 2.4, inorganic and organic residuals of less than 500 ppm, and a light amber color.

A method for preparing an aqueous solution of pure silk fibroin-based protein fragments having an average weight average molecular weight ranging from about 6 kDa to about 16 kDa includes the steps of: degumming a silk source by adding the silk source to a boiling (100° C.) aqueous solution of sodium carbonate for a treatment time of between about 30 minutes to about 60 minutes; removing sericin from the solution to produce a silk fibroin extract comprising non-detectable levels of sericin; draining the solution from the silk fibroin extract; dissolving the silk fibroin extract in a solution of lithium bromide having a starting temperature upon placement of the silk fibroin extract in the lithium bromide solution that ranges from about 60° C. to about 140° C.; maintaining the solution of silk fibroin-lithium bromide in an oven having a temperature of about 140° C. for a period of at least 1 hour; removing the lithium bromide from the silk fibroin extract; and producing an aqueous solution of silk protein fragments, the aqueous solution comprising: fragments having an average weight average molecular weight ranging from about 6 kDa to about 16 kDa, and wherein the aqueous solution of pure silk fibroin-based protein fragments comprises a polydispersity of between about 1.5 and about 3.0. The method may further comprise drying the silk fibroin extract prior to the dissolving step. The aqueous solution of pure silk fibroin-based protein fragments may comprise lithium bromide residuals of less than 300 ppm as measured using a high-performance liquid chromatography lithium bromide assay. The aqueous solution of pure silk fibroin-based protein fragments may comprise sodium carbonate residuals of less than 100 ppm as measured using a high-performance liquid chromatography sodium carbonate assay. The method may further comprise adding a therapeutic agent to the aqueous solution of pure silk fibroin-based protein fragments. The method may further comprise adding a molecule selected from one of an antioxidant or an enzyme to the aqueous solution of pure silk fibroin-based protein fragments. The method may further comprise adding a vitamin to the aqueous solution of pure silk fibroin-based protein fragments. The vitamin may be vitamin C or a derivative thereof. The aqueous solution of pure silk fibroin-based protein fragments may be lyophilized. The method may further comprise adding an alpha hydroxy acid to the aqueous solution of pure silk fibroin-based protein fragments. The alpha hydroxy acid may be selected from the group consisting of glycolic acid, lactic acid, tartaric acid and citric acid. The method may further comprise adding hyaluronic acid or its salt form at a concentration of about 0.5% to about 10.0% to the aqueous solution of pure silk fibroin-based protein fragments. The method may further comprise adding at least one of zinc oxide or titanium dioxide. A film may be fabricated from the aqueous solution of pure silk fibroin-based protein fragments produced by this method. The film may comprise from about 1.0 wt. % to about 50.0 wt. % of vitamin C or a derivative thereof. The film may have a water content ranging from about 2.0 wt. % to about 20.0 wt. %. The film may comprise from about 30.0 wt. % to about 99.5 wt. % of pure silk fibroin-based protein fragments. A gel may be fabricated from the aqueous solution of pure silk fibroin-based protein fragments produced by this method. The gel may comprise from about 0.5 wt. % to about 20.0 wt. % of vitamin C or a derivative thereof. The gel may have a silk content of at least 2% and a vitamin content of at least 20%.

A method for preparing an aqueous solution of pure silk fibroin-based protein fragments having an average weight average molecular weight ranging from about 17 kDa to about 38 kDa includes the steps of: adding a silk source to a boiling (100° C.) aqueous solution of sodium carbonate for a treatment time of between about 30 minutes to about 60 minutes so as to result in degumming; removing sericin from the solution to produce a silk fibroin extract comprising non-detectable levels of sericin; draining the solution from the silk fibroin extract; dissolving the silk fibroin extract in a solution of lithium bromide having a starting temperature upon placement of the silk fibroin extract in the lithium bromide solution that ranges from about 80° C. to about 140° C.; maintaining the solution of silk fibroin-lithium bromide in a dry oven having a temperature in the range between about 60° C. to about 100° C. for a period of at least 1 hour; removing the lithium bromide from the silk fibroin extract; and producing an aqueous solution of pure silk fibroin-based protein fragments, wherein the aqueous solution of pure silk fibroin-based protein fragments comprises lithium bromide residuals of between about 10 ppm and about 300 ppm, wherein the aqueous solution of silk protein fragments comprises sodium carbonate residuals of between about 10 ppm and about 100 ppm, wherein the aqueous solution of pure silk fibroin-based protein fragments comprises fragments having an average weight average molecular weight ranging from about 17 kDa to about 38 kDa, and wherein the aqueous solution of pure silk fibroin-based protein fragments comprises a polydispersity of between about 1.5 and about 3.0. The method may further comprise drying the silk fibroin extract prior to the dissolving step. The aqueous solution of pure silk fibroin-based protein fragments may comprise lithium bromide residuals of less than 300 ppm as measured using a high-performance liquid chromatography lithium bromide assay. The aqueous solution of pure silk fibroin-based protein fragments may comprise sodium carbonate residuals of less than 100 ppm as measured using a high-performance liquid chromatography sodium carbonate assay. The method may further comprise adding a therapeutic agent to the aqueous solution of pure silk fibroin-based protein fragments. The method may further comprise adding a molecule selected from one of an antioxidant or an enzyme to the aqueous solution of pure silk fibroin-based protein fragments. The method may further comprise adding a vitamin to the aqueous solution of pure silk fibroin-based protein fragments. The vitamin may be vitamin C or a derivative thereof. The aqueous solution of pure silk fibroin-based protein fragments may be lyophilized. The method may further comprise adding an alpha hydroxy acid to the aqueous solution of pure silk fibroin-based protein fragments. The alpha hydroxy acid may be selected from the group consisting of glycolic acid, lactic acid, tartaric acid and citric acid. The method may further comprise adding hyaluronic acid or its salt form at a concentration of about 0.5% to about 10.0% to the aqueous solution of pure silk fibroin-based protein fragments. The method may further comprise adding at least one of zinc oxide or titanium dioxide. A film may be fabricated from the aqueous solution of pure silk fibroin-based protein fragments produced by this method. The film may comprise from about 1.0 wt. % to about 50.0 wt. % of vitamin C or a derivative thereof. The film may have a water content ranging from about 2.0 wt. % to about 20.0 wt. %. The film may comprise from about 30.0 wt. % to about 99.5 wt. % of pure silk fibroin-based protein fragments. A gel may be fabricated from the aqueous solution of pure silk fibroin-based protein fragments produced by this method. The gel may comprise from about 0.5 wt. % to about 20.0 wt. % of vitamin C or a derivative thereof. The gel may have a silk content of at least 2% and a vitamin content of at least 20%.

According to aspects illustrated herein, there is disclosed a method for preparing an aqueous solution of pure silk fibroin-based protein fragments having an average weight average molecular weight ranging from about 39 kDa to about 80 kDa, the method including the steps of: adding a silk source to a boiling (100° C.) aqueous solution of sodium carbonate for a treatment time of about 30 minutes so as to result in degumming; removing sericin from the solution to produce a silk fibroin extract comprising non-detectable levels of sericin; draining the solution from the silk fibroin extract; dissolving the silk fibroin extract in a solution of lithium bromide having a starting temperature upon placement of the silk fibroin extract in the lithium bromide solution that ranges from about 80° C. to about 140° C.; maintaining the solution of silk fibroin-lithium bromide in a dry oven having a temperature in the range between about 60° C. to about 100° C. for a period of at least 1 hour; removing the lithium bromide from the silk fibroin extract; and producing an aqueous solution of pure silk fibroin-based protein fragments, wherein the aqueous solution of pure silk fibroin-based protein fragments comprises lithium bromide residuals of between about 10 ppm and about 300 ppm, sodium carbonate residuals of between about 10 ppm and about 100 ppm, fragments having an average weight average molecular weight ranging from about 40 kDa to about 65 kDa, and wherein the aqueous solution of pure silk fibroin-based protein fragments comprises a polydispersity of between about 1.5 and about 3.0. The method may further comprise drying the silk fibroin extract prior to the dissolving step. The aqueous solution of pure silk fibroin-based protein fragments may comprise lithium bromide residuals of less than 300 ppm as measured using a high-performance liquid chromatography lithium bromide assay. The aqueous solution of pure silk fibroin-based protein fragments may comprise sodium carbonate residuals of less than 100 ppm as measured using a high-performance liquid chromatography sodium carbonate assay. The method may further comprise adding a therapeutic agent to the aqueous solution of pure silk fibroin-based protein fragments. The method may further comprise adding a molecule selected from one of an antioxidant or an enzyme to the aqueous solution of pure silk fibroin-based protein fragments. The method may further comprise adding a vitamin to the aqueous solution of pure silk fibroin-based protein fragments. The vitamin may be vitamin C or a derivative thereof. The aqueous solution of pure silk fibroin-based protein fragments may be lyophilized. The method may further comprise adding an alpha hydroxy acid to the aqueous solution of pure silk fibroin-based protein fragments. The alpha hydroxy acid may be selected from the group consisting of glycolic acid, lactic acid, tartaric acid and citric acid. The method may further comprise adding hyaluronic acid or its salt form at a concentration of about 0.5% to about 10.0% to the aqueous solution of pure silk fibroin-based protein fragments. The method may further comprise adding at least one of zinc oxide or titanium dioxide. A film may be fabricated from the aqueous solution of pure silk fibroin-based protein fragments produced by this method. The film may comprise from about 1.0 wt. % to about 50.0 wt. % of vitamin C or a derivative thereof. The film may have a water content ranging from about 2.0 wt. % to about 20.0 wt. %. The film may comprise from about 30.0 wt. % to about 99.5 wt. % of pure silk fibroin-based protein fragments. A gel may be fabricated from the aqueous solution of pure silk fibroin-based protein fragments produced by this method. The gel may comprise from about 0.5 wt. % to about 20.0 wt. % of vitamin C or a derivative thereof. The gel may have a silk content of at least 2% and a vitamin content of at least 20%.

All patents, patent applications, and published references cited herein are hereby incorporated by reference in their entirety. While the methods of the present disclosure have been described in connection with the specific embodiments thereof, it will be understood that it is capable of further modification. Further, this application is intended to cover any variations, uses, or adaptations of the methods of the present disclosure, including such departures from the present disclosure as come within known or customary practice in the art to which the methods of the present disclosure pertain.

What is claimed is:

1. A composition comprising:
    pure silk fibroin-based protein fragments having about 0.01% (w/w) to about 10% (w/w) sericin,
    wherein the fragments have an average weight average molecular weight ranging from about 6 kDa to about 16 kDa,
    wherein the fragments have a polydispersity of from about 1.5 to about 3.0,
    wherein the composition is substantially homogeneous,
    wherein the composition includes between 0 ppm to 500 ppm of inorganic residuals,
    wherein the composition includes between 0 ppm to 500 ppm of organic residuals, and
    wherein the composition does not spontaneously or gradually gelate and does not visibly change in color or turbidity when in a solution for at least 10 days.

2. The composition of claim 1 wherein the inorganic residuals include lithium bromide residuals and wherein the organic residuals include sodium carbonate residuals.

3. The composition of claim 2 wherein the lithium bromide residuals are measurable using a high-performance liquid chromatography lithium bromide assay, and the sodium carbonate residuals are measurable using a high-performance liquid chromatography sodium carbonate assay.

4. The composition of claim 1 wherein the solution is an aqueous solution.

5. The composition of claim 1 in a sealed container.

6. The composition of claim 1 further comprising polyanhydrides.

7. The composition of claim 1 further comprising vitamin C or a derivative thereof.

8. The composition of claim 1 further comprising an alpha hydroxy acid selected from the group consisting of glycolic acid, lactic acid, tartaric acid, and citric acid.

9. The composition of claim 1 further comprising hyaluronic acid or its salt form at a concentration of about 0.5 wt. % to about 10.0 wt. %.

10. The composition of claim 1 further comprising at least one of zinc oxide or titanium dioxide.

11. The composition of claim 1 wherein the pure silk fibroin-based protein fragments are hypoallergenic.

12. The composition of claim 1 having less than 10 colony forming units per gram.

13. The composition of claim 1, wherein the composition does not spontaneously or gradually gelate and does not visibly change in color or turbidity when in a solution for at least 30 days.

14. The composition of claim 1 wherein the average weight average molecular weight range and the polydispersity are measurable using a high-performance liquid chromatography assay.

15. The composition of claim 1, wherein the fragments have an average weight average molecular weight ranging from 10 kDa to 15 kDa.

* * * * *